US012642910B2

(12) United States Patent
Diaz et al.

(10) Patent No.: US 12,642,910 B2
(45) Date of Patent: Jun. 2, 2026

(54) SYSTEM AND METHOD FOR SAFETY SYRINGE

(71) Applicant: CREDENCE MEDSYSTEMS, INC., Menlo Park, CA (US)

(72) Inventors: Stephen H. Diaz, Palo Alto, CA (US); Conor Edward Shanley, Emerald Hills, CA (US); Mina M. Leung, Mountain View, CA (US); Alan E. Shluzas, San Carlos, CA (US); Jeff Tillack, Foster City, CA (US)

(73) Assignee: CREDENCE MEDSYSTEMS, INC., Menlo Park, CA (US)

( * ) Notice: Subject to any disclaimer, the term of this patent is extended or adjusted under 35 U.S.C. 154(b) by 318 days.

(21) Appl. No.: 17/364,546

(22) Filed: Jun. 30, 2021

(65) Prior Publication Data

US 2021/0402094 A1 Dec. 30, 2021

Related U.S. Application Data

(60) Provisional application No. 63/193,466, filed on May 26, 2021, provisional application No. 63/156,264, (Continued)

(51) Int. Cl.
*A61M 5/19* (2006.01)
*A61M 5/315* (2006.01)
(Continued)

(52) U.S. Cl.
CPC .......... *A61M 5/19* (2013.01); *A61M 5/31511* (2013.01); *A61M 5/3294* (2013.01); (Continued)

(58) Field of Classification Search
CPC .. A61M 5/19; A61M 5/3129; A61M 5/31511; A61M 5/322; A61M 5/31596; (Continued)

(56) References Cited

U.S. PATENT DOCUMENTS 5,373,855 A * 12/1994 Skrabal ............... A61M 5/1582
604/164.11
10,173,010 B2 1/2019 Shluzas et al.
(Continued)

OTHER PUBLICATIONS

PCT International Search Report and Written Opinion for International Appln. No. PCT/US2021/039996, Applicant Credence Medsystems, Inc., dated Dec. 7, 2021 (19 pages).
(Continued)

*Primary Examiner* — Michael J Tsai
*Assistant Examiner* — Justin L Zamory
(74) *Attorney, Agent, or Firm* — Vista IP Law Group, LLP

(57) ABSTRACT

A system for serially injecting liquids includes a syringe body defining a syringe proximal opening and a distal needle interface, proximal and distal stopper members, forming proximal and distal chambers. The system also includes a first liquid in the distal chamber and a second liquid in the proximal chamber, and a plunger configured to be manually manipulated to insert the proximal stopper member distally. Moreover, the system includes a needle hub assembly coupled to the syringe body, the needle assembly including a needle. The needle defines a needle interior, and distal, middle and proximal openings. The distal, middle and proximal openings are fluidly coupled through the needle interior. Manipulating the plunger member to insert the proximal stopper member initially expels the first liquid from the distal chamber, then serially expels the second liquid from the proximal chamber.

22 Claims, 135 Drawing Sheets

Related U.S. Application Data filed on Mar. 3, 2021, provisional application No. 63/046,517, filed on Jun. 30, 2020.

(51) Int. Cl.
 *A61M 5/32* (2006.01)
 *A61M 5/178* (2006.01)

(52) U.S. Cl.
 CPC ............... *A61M 2005/1787* (2013.01); *A61M 2005/3231* (2013.01); *A61M 2005/3241* (2013.01); *A61M 2202/064* (2013.01)

(58) Field of Classification Search
 CPC ........... A61M 2005/1787; A61M 2005/31598; A61M 2005/287; A61M 2005/3234; A61M 2005/3241
 See application file for complete search history.

(56) References Cited

U.S. PATENT DOCUMENTS

| | | | | |
|---|---|---|---|---|
| 2002/0107483 | A1* | 8/2002 | Cook ................ | A61M 25/0618 604/164.01 |
| 2018/0117261 | A1 | 5/2018 | Steese-Bradley et al. | |
| 2019/0374716 | A1* | 12/2019 | Diaz ................... | A61M 5/3221 |

OTHER PUBLICATIONS

Foreign OA for JP Patent Appln. No. 2022-580337 dated Mar. 18, 2025.

Foreign Response to OA for JP Patent Appln. No. 2022-580337 dated Jun. 12, 2025.

Foreign Voluntary amendment for CA Patent Appln. No. 3187589 dated Jun. 24, 2025.

Foreign OA for CN Patent Appln. No. 202180053186.5 dated Oct. 20, 2025 (with English translation).

Foreign Response for JP Patent Appln. No. 2022-580337 dated Oct. 28, 2025.

Foreign OA for JP Patent Appln. No. 2022-580337 dated Jul. 29, 2025 (with English translation).

Foreign Examination Report for EP Patent Appln. No. 21 745 658.1 dated Sep. 11, 2025.

Foreign NOA for JP Patent Appln. No. 2022-580337 dated Nov. 25, 2025 (with English translation).

Foreign OA for IN Patent Appln. No. 202347005606 dated Jan. 13, 2026.

Foreign Response for CN Patent Appln. No. 202180053186.5 dated Mar. 16, 2026.

Foreign Response for CN Patent Appln. No. 202180053186.5 dated Feb. 24, 2026.

* cited by examiner

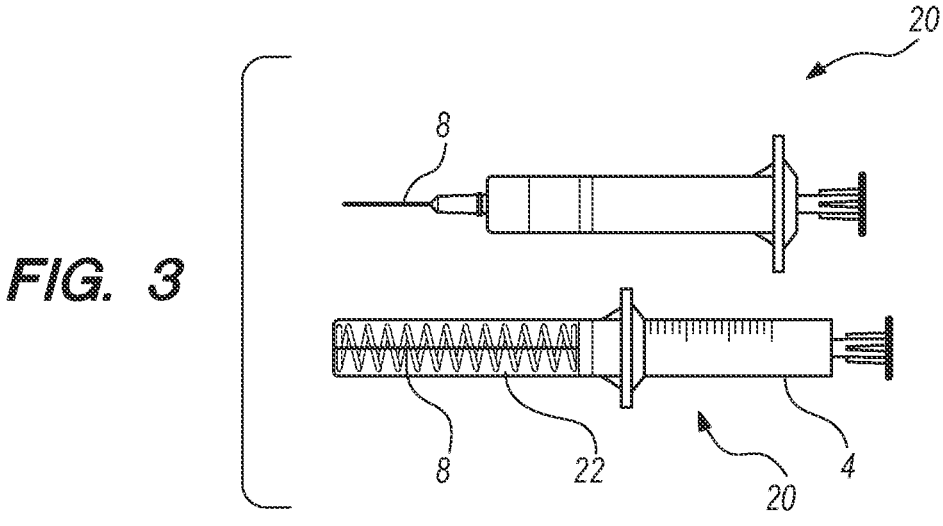
*FIG. 3*
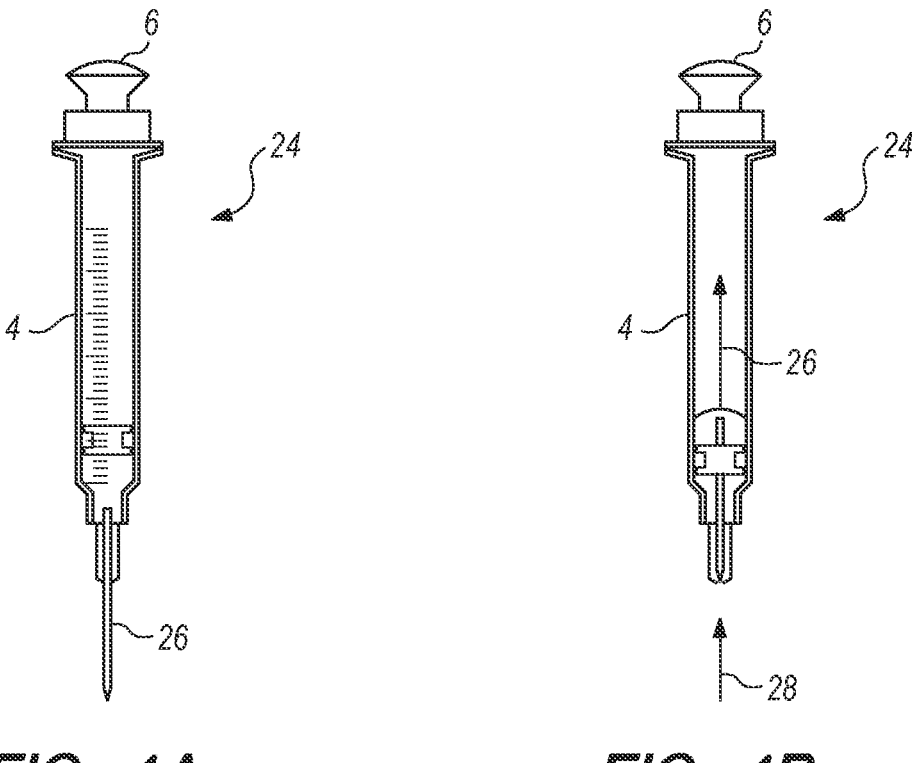
*FIG. 4A*            *FIG. 4B*

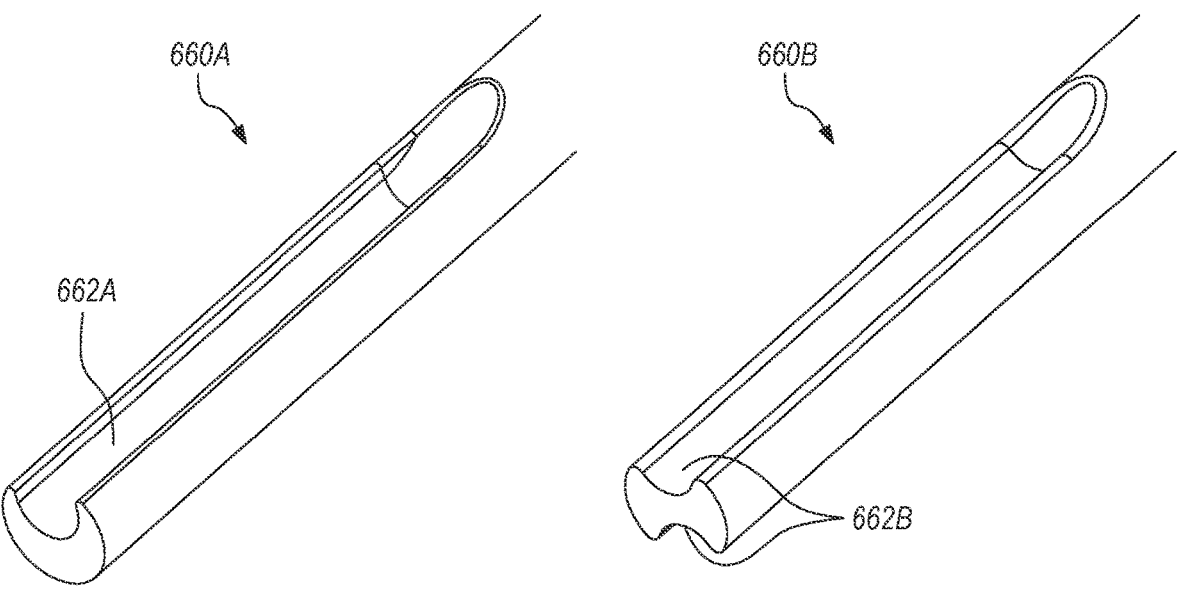
660A
662A
660B
662B
FIG. 49A        FIG. 49B
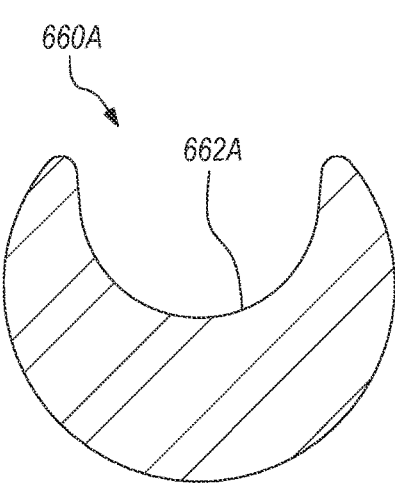
660A
662A
FIG. 50A
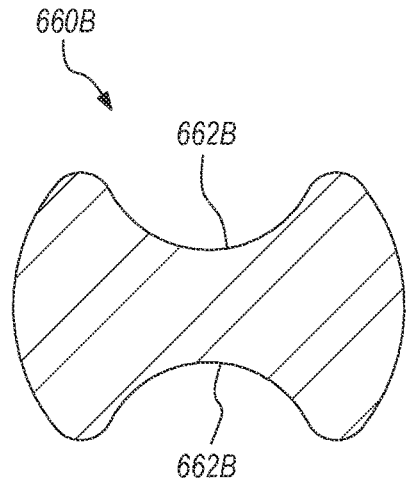
660B
662B
662B
FIG. 50B

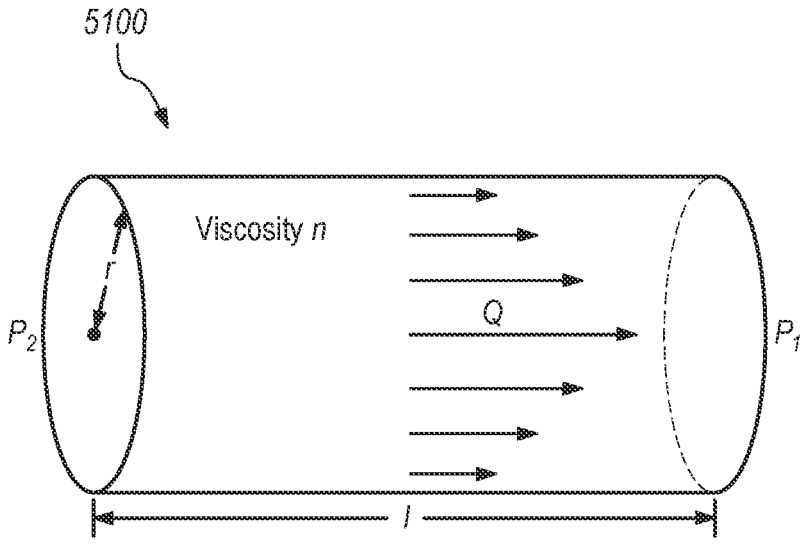
*FIG. 51*
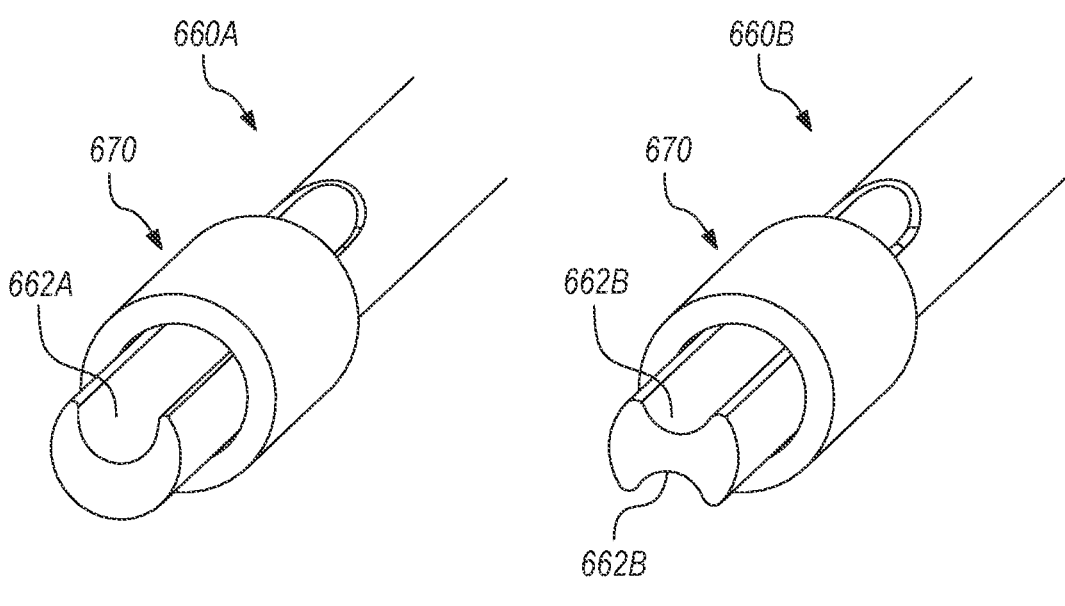
*FIG. 52A*                    *FIG. 52B*

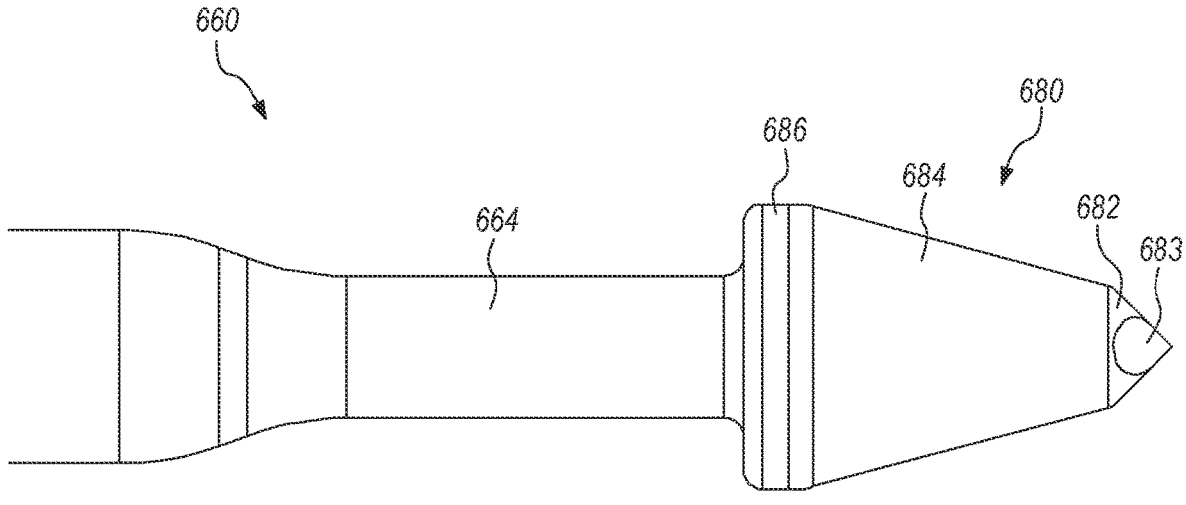
FIG. 53
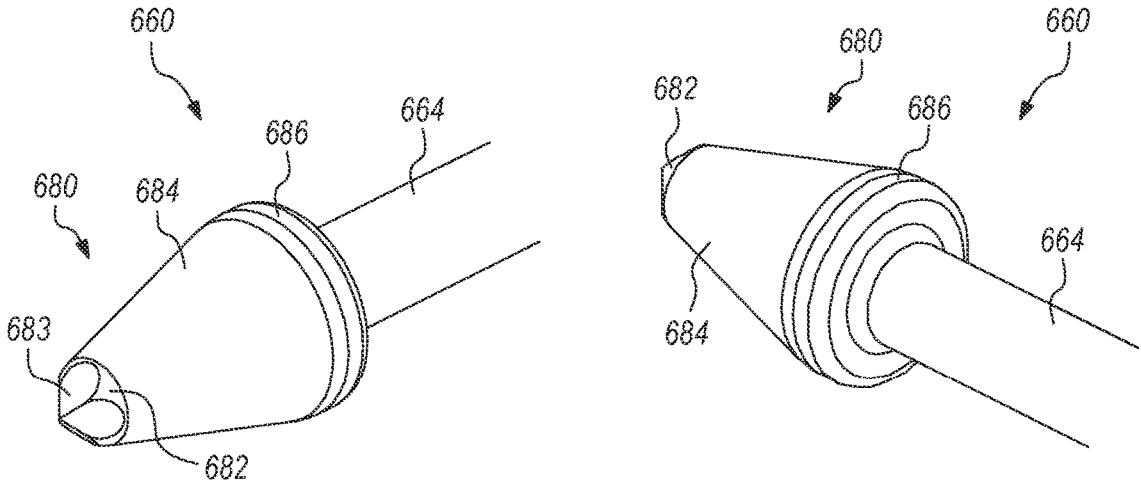
FIG. 54A                    FIG. 54B

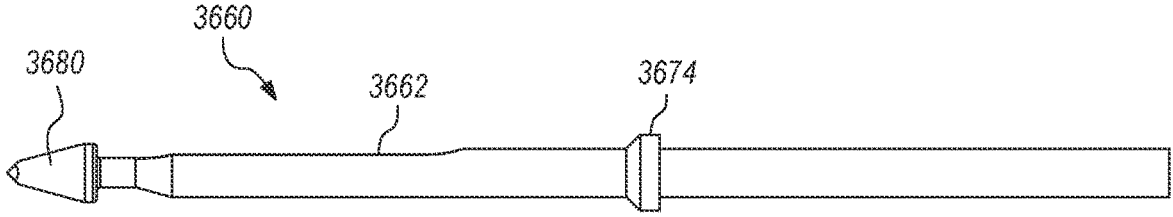
FIG. 70
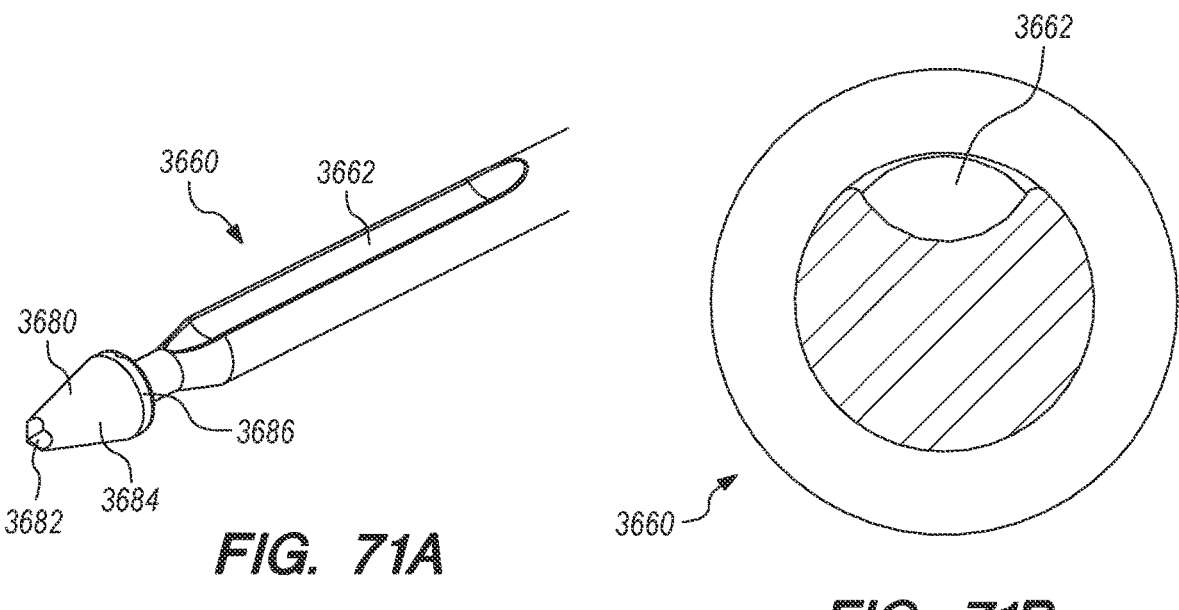
FIG. 71A
FIG. 71B
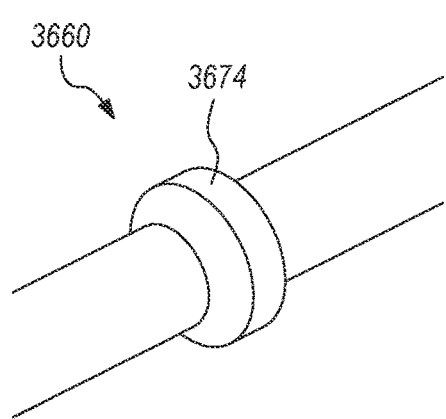
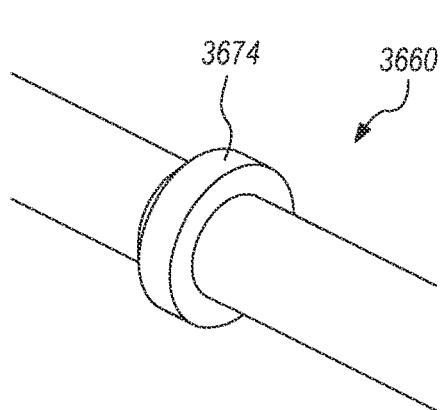
FIG. 71C
FIG. 71D

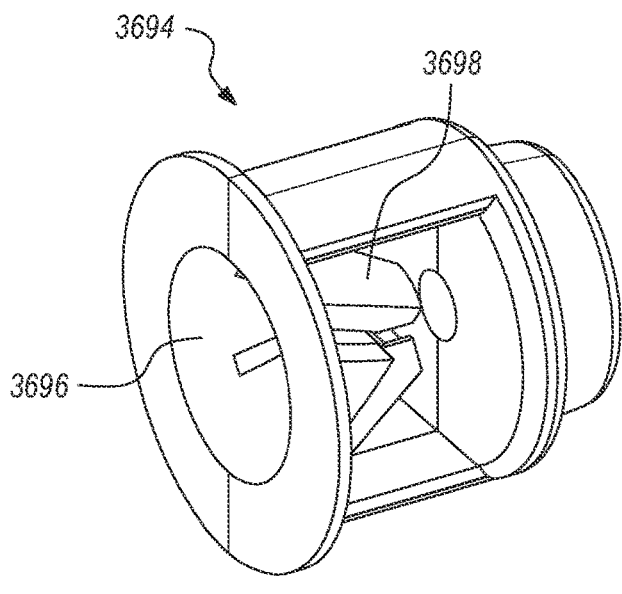
FIG. 76A
FIG. 76B
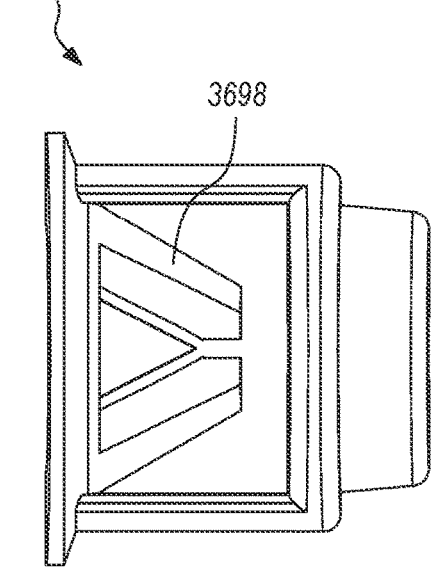
FIG. 76C

4560

4562B

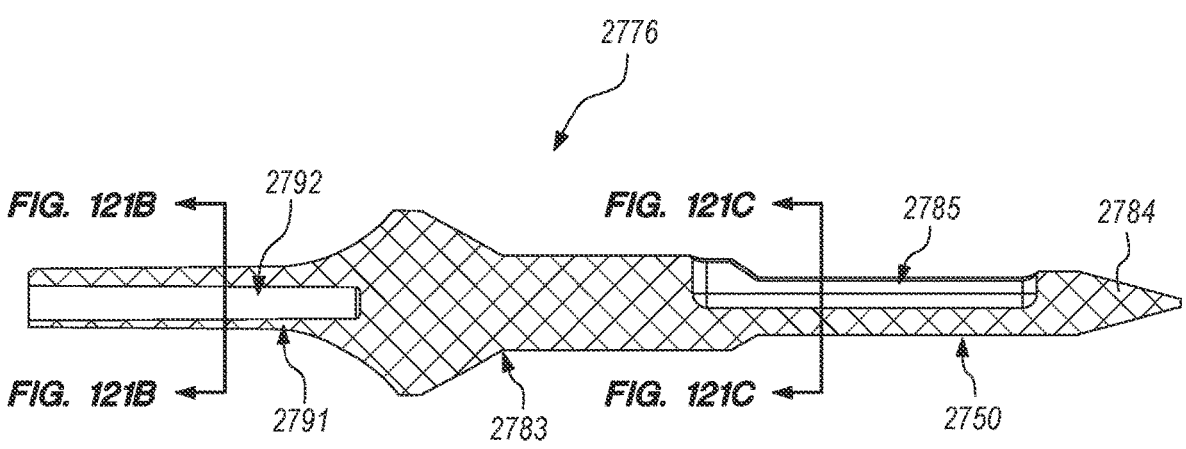
FIG. 121A
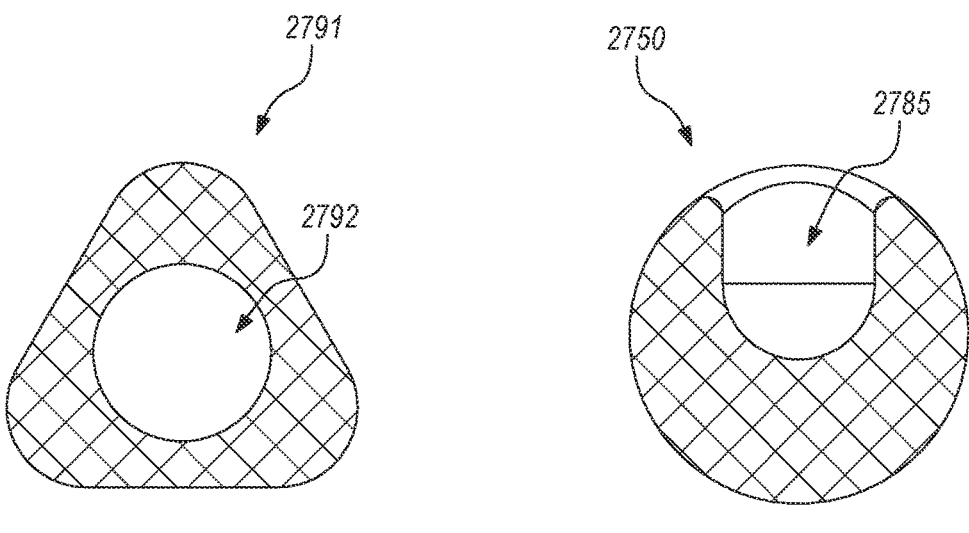
FIG. 121B          FIG. 121C

3983

3993

3991

3995

3991

3993

3995

3995

3994

3994

4683

4691

4683

4691

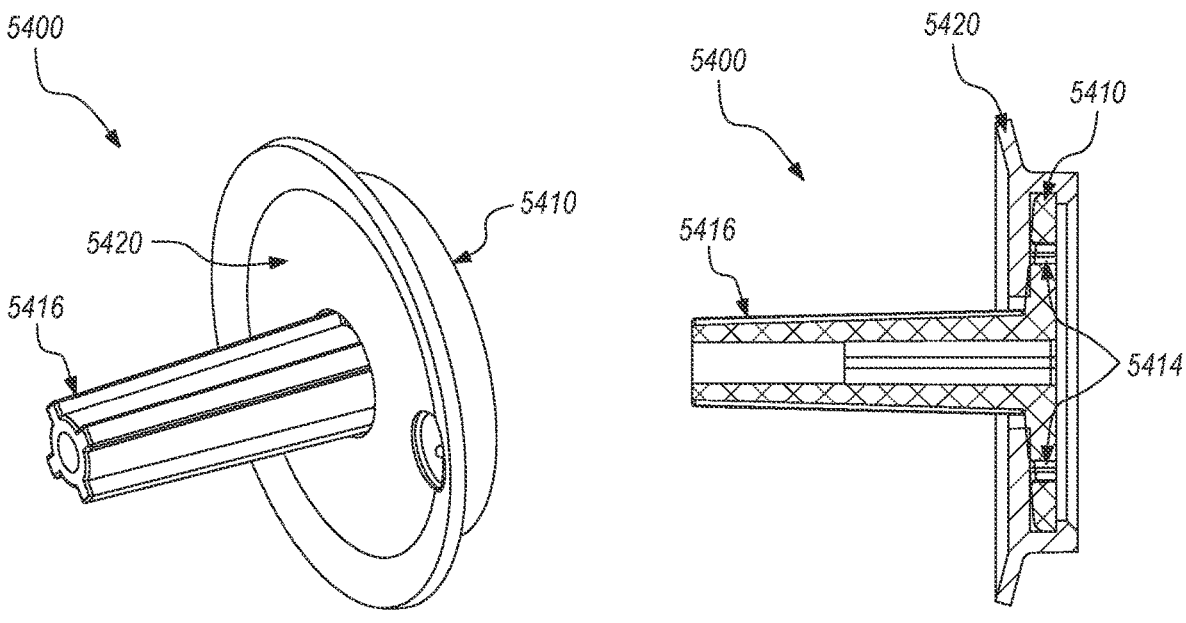
FIG. 148A
FIG. 148B
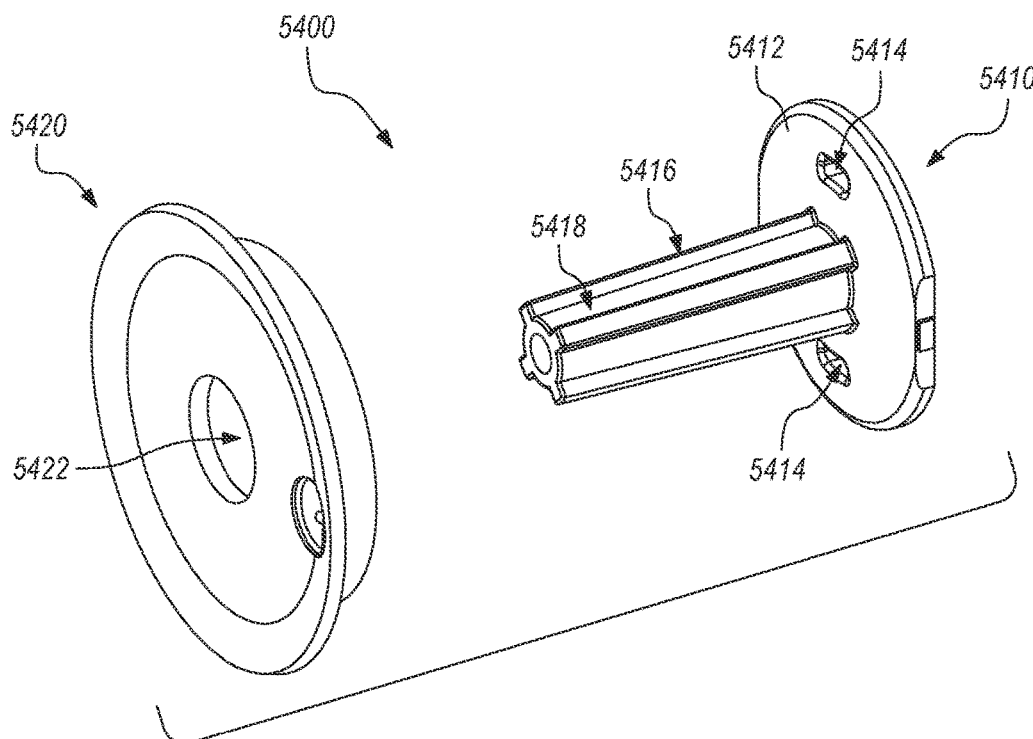
FIG. 148C

SYSTEM AND METHOD FOR SAFETY SYRINGE

The present application claims priority to (1) U.S. Provisional Patent Application Ser. No. 63/046,517, filed on Jun. 30, 2020 and entitled "SYSTEM AND METHOD FOR SAFETY SYRINGE"; (2) U.S. Provisional Patent Application Ser. No. 63/156,264, filed on Mar. 3, 2021 and entitled "SYSTEM AND METHOD FOR SAFETY SYRINGE"; and (3) U.S. Provisional Patent Application Ser. No. 63/193,466, filed on May 26, 2021 and entitled "SYSTEM AND METHOD FOR SAFETY SYRINGE". This application includes subject matter similar to the subject matter described in the following co-owned U.S. patent applications: (1) U.S. Utility patent application Ser. No. 14/321,706, filed Jul. 1, 2014 and issued as U.S. Utility Pat. No. 9,814,842 on Nov. 14, 2017 and entitled "SAFETY SYRINGE"; (2) U.S. Utility patent application Ser. No. 14/543,787, filed Nov. 17, 2014 and issued as U.S. Utility Pat. No. 10,300,217 on May 28, 2019 and entitled "SYSTEM AND METHOD FOR DRUG DELIVERY WITH A SAFETY SYRINGE"; (3) U.S. Utility patent application Ser. No. 14/696,342, filed Apr. 24, 2015, and issued as U.S. Utility Pat. No. 10,010,677 on Jul. 7, 2018 and entitled "SYSTEM AND METHOD FOR SAFETY SYRINGE"; (4) U.S. Utility patent application Ser. No. 15/801,239, filed on Nov. 1, 2017 and issued as U.S. Utility Pat. No. 10,926,038 on Feb. 23, 2021 and entitled "SYSTEM AND METHOD FOR SAFETY SYRINGE"; (5) U.S. Utility patent application Ser. No. 15/801,259, filed on Nov. 1, 2017, and issued as U.S. Utility Pat. No. 10,864,330 on Dec. 15, 2020 and entitled "SYSTEM AND METHOD FOR SAFETY SYRINGE"; (6) U.S. Utility patent application Ser. No. 15/801,281 filed on Nov. 1, 2017 and issued as U.S. Utility Pat. No. 10,912,894 on Feb. 9, 2021 and entitled "CARTRIDGE SAFETY INJECTION SYSTEM AND METHODS"; (7) U.S. Utility patent application Ser. No. 15/801,304 filed on Nov. 1, 2017 and issued as U.S. Utility Pat. No. 10,960,144 on Mar. 30, 2021 and entitled "SYSTEM AND METHOD FOR SAFETY SYRINGE"; (8) U.S. Provisional Patent Application Ser. No. 62/809,369, filed on Feb. 22, 2019 and entitled "SYSTEM AND METHOD FOR SAFETY SYRINGE"; (9) U.S. Utility patent application Ser. No. 16/435,429 filed on Jun. 7, 2019 and entitled "SYSTEM AND METHOD FOR SAFETY SYRINGE"; (10) U.S. Utility patent application Ser. No. 16/837,835, filed Apr. 1, 2020 and entitled "POLYMERIC INJECTION SYSTEMS"; (11) U.S. Provisional Patent Application Ser. No. 62/864,509 filed on Jun. 21, 2019 and entitled "SYSTEM AND METHOD FOR SAFETY SYRINGE"; (12) U.S. Provisional Patent Application Ser. No. 62/904,988 filed on Sep. 24, 2019 and entitled "SYSTEM AND METHOD FOR SAFETY SYRINGE"; (13) U.S. Provisional Patent Application Ser. No. 63/094,313 filed on Oct. 20, 2020 and entitled "RETRACTION MECHANISM FOR SAFE INJECTION SYSTEM"; (14) U.S. Provisional Patent Application Ser. No. 62/682,381, filed on Jun. 8, 2018 and entitled "SYSTEM AND METHOD FOR SAFETY SYRINGE"; and (15) U.S. Provisional Patent Application Ser. No. 62/729,880, filed on Sep. 11, 2018 and entitled "SYSTEM AND METHOD FOR SAFETY SYRINGE"; (16) U.S. Provisional Patent Application Ser. No. 63/094,313 filed on Oct. 20, 2020 and entitled "RETRACTION MECHANISM FOR SAFE INJECTION SYSTEM." The contents of the applications and patents identified herein are fully incorporated herein by reference as though set forth in full.

FIELD OF THE INVENTION

The present invention relates generally to injection systems, devices, and processes for facilitating various levels of control over fluid infusion, and more particularly to systems and methods related to serial injection in healthcare environments.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs.

Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during assembly of a Luer coupling.

The use of needle injection configurations, on the other hand, carries with it the risk of a sharp needle contacting or stabbing a person or structure that is not desired. For this reason, so called "safety syringes" have been developed. One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety. Other "safety syringes" are described in U.S. patent application Ser. Nos. 14/696,342, 14/543,787, 14/321,706, 15/801,239, 15/801,259, 15/801,281, 15/801, 304, 16/908,531, 17/031,108, and 63/094,313, the contents of which are fully incorporated herein by reference as though set forth in full.

Further complicating the syringe marketplace is an increasing demand for prefilled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface 14). Liquid medicine may reside in the volume, or medicine reservoir, (40) between the distal seal and the distal end (37) of the plunger tip (36). The plunger tip (36) may comprise a standard butyl rubber material and may be coated, such as with a biocompatible lubricious coating (e.g., polytetrafluoroethylene ("PTFE")), to facilitate preferred sealing and relative motion characteristics against the associated syringe body structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the chamber or reservoir (40), and to assist with expulsion of the associated fluid through the needle, a plunger tip (36) may be positioned within the syringe body (34). The syringe body (34) may define a substantially cylindrical shape (i.e., so that a plunger tip 36 having a circular cross-sectional shape may establish a seal against the syringe body (34)), or be configured to have other cross-sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

Moreover, an increasing number of injectable liquids (e.g., medicines) have an additional requirement that two or more components are preferably injected serially (e.g., into a patient) within a short time (e.g., seconds) of each other. Multiple components can be injected serially using separate injection devices (e.g., pre-loaded syringes) or using the same injection device to serially draw the multiple components from separate open containers and serially inject them. However, such serial injection using separate injection devices or serially drawing and injecting the multiple components necessarily results in multiple needle insertions into a patient, and can be inaccurate and lead to loss of components. Further, serial injection using separate injection devices or serially drawing the multiple components into a syringe can lead to unnecessary exposure of a user to one or more uncapped needles. Moreover, serial injection using separate injection devices or serially drawing and injecting the multiple components can cause an unacceptable lag between injections of the multiple components.

In some cases there may be a chemical reaction that takes place between the components of a multi-component injection. The use of traditional style dual chamber syringes, such as disclosed in U.S. Utility patent application Ser. No. 14/696,342, which was previously incorporated by reference herein, where the components are mixed together inside of the syringe, may not be compatible with these reactive components as the mixed components may not be suitable for injection. Some illustrative examples of this phenomenon include when the components are mixed together, the viscosity of the combined medicine increases such that the medicine cannot be easily injected through a needle. Also, other reactions such as exothermic, endothermic, etc. may take place that could prevent the use of a traditional dual chamber injection system.

Existing dual chamber injection systems (see e.g., U.S. Pat. No. 4,874,381) utilize an external bypass channel formed into the outer wall of the syringe body. The external bypass channel is positioned such that with distally directed motion of the plunger the distal stopper moves distally exposing the external bypass channel to both the proximal and distal chambers to allow liquid to travel from the proximal chamber around the distal stopper into the distal chamber, to be mixed with the medicine component in the distal chamber. If the needle or syringe is capped for drug storage, these external bypass channel style dual chamber injection systems experience an increase in pressure in the distal chamber during transfer and mixing. This increase in pressure causes resistance to transfer and difficulty in transferring all the liquid from the proximal chamber to the distal chamber. Additionally, the increase in pressure increases force the must be maintained on the plunger rod during mixing. To minimize the effects of the increase in pressure, external bypass dual chamber injection systems require the removal of a needle cap before fluid transfer and mixing, or to open the syringe and install the needle after mixing has occurred to allow for venting of the pressure in the distal chamber during transfer and mixing. These requirements increase the risk of needle stick injury, and/or require additional steps by the user. It would be beneficial to incorporate a shielded and vented pre-attached needle with integrated needle retraction to dual chamber injection systems. The shielded and vented needle shield inventions disclosed herein are applicable to external bypass style dual chamber injection systems. Additionally, it would be beneficial to integrate plunger position control methodologies to maintain precise control of the position of the distal stopper during transfer and mixing.

In addition, an increasing number of injectable liquids (e.g., medicines) have yet another requirement that time of exposure of the injectable liquid to metals (e.g., stainless steel of a needle) be minimized. Still another requirement is the desirability of systems suitable for patient self-injection.

It is also desirable to incorporate needle stick prevention technology into the injection system. The ability to retract the sharp end of the needle at least partially inside of the syringe protects the person giving the injection and the patient from inadvertent needle stick injuries.

There is a need for injection systems which address the shortcomings of currently-available configurations. In particular, there is a need for multiple chamber safety injection solutions which may utilize the existing and relatively well-controlled supply chain of conventionally delivered prefilled syringe assemblies such as those described in reference to FIGS. 5A and 5B.

Exemplary safe injection systems include needle retraction systems such as those described in U.S. patent application Ser. Nos. 14/696,342, 14/543,787, 14/321,706, 15/801,239, 15/801,259, 15/801,281, 15/801,304, 16/908, 531, 17/031,108, and 63/094,313, the contents of which have been previously Incorporated by reference herein. Retracting the needle assembly moves the sharp needle distal end inside of the needle hub or the injection system body/syringe body to prevent accidental needle sticks.

Some existing injection and/or needle retraction systems include needle assemblies with openings that may become occluded when other portions of the needle assemblies are crushed during assembly and/or use. Some existing injection and/or needle retraction systems include needle assemblies that may structurally fail during assembly and/or use. Some existing injection and/or needle retraction systems include needle assemblies that may allow injectables and/or components of injectables to be inadvertently ejected from an interior of an injection system body to an exterior of the injection system body through a distal opening of the injection system body.

There is a need for needle retraction systems and components thereof that address the shortcomings of currently-available configurations. In particular, there is a need for needle assemblies with openings that resist occlusion as those other portions are crushed during assembly and/or use by other portions of the needle assemblies. There is also a need for needle assemblies that resist structural failure during assembly and/or use. There is a further need for needle assemblies that prevent inadvertent ejection of injectables through the distal opening of the injection system body. Addressing these and other limitations of needle retraction systems allows cost-effective and easy to manufacture injection and/or needle retraction systems.

SUMMARY

Some embodiments are directed to injection systems. In particular, the embodiments are directed to multiple chamber serial injection systems and multiple chamber safe injection systems that move the needle into a protected configuration to minimize accidental user injury and contamination with used needles.

In one embodiment, a system for serially injecting liquids includes a syringe body defining a syringe proximal opening and a distal needle interface at a distal end thereof. The system also includes proximal and distal stopper members disposed in the syringe body, forming a proximal chamber between the proximal and distal stopper members and a distal chamber between the distal stopper member and the distal end of the syringe body. The system further includes a first liquid in the distal chamber and a second liquid in the proximal chamber. Moreover, the system includes a plunger configured to be manually manipulated to insert the proximal stopper member distally relative to the syringe body. In addition, the system includes a needle hub assembly coupled to the distal needle interface of the syringe body, the needle assembly including a needle. The needle defines a needle interior, a distal end opening, a middle opening, and a proximal opening. The distal end opening, the middle opening, and the proximal opening are fluidly coupled through the needle interior. Manipulating the plunger member to insert the proximal stopper member distally relative to the syringe body initially expels the first liquid from the distal chamber through the needle, then serially expels the second liquid from the proximal chamber through the needle.

In one or more embodiments, the needle includes a tubular member and a solid proximal end feature coupled thereto. The needle interior, the distal end opening, the middle opening, and the proximal opening may be formed in the tubular member. The solid proximal end feature may be coupled to the tubular member with a weld. The weld may be a fillet weld configured to reducing cutting of the proximal stopper member when the needle penetrates the proximal stopper member compared to a needle without a fillet weld. The weld may taper in a proximal direction. The proximal opening may be adjacent to the weld. The solid proximal end feature may be cold formed. A distal end of the solid proximal end feature may be disposed in a proximal end of the tubular member. The distal end of the solid proximal end feature and the proximal end of the tubular member may define an annular lumen fluidly coupling the proximal opening to the needle interior, the middle opening, and the distal end opening.

In one or more embodiments, the proximal opening has a rounded edge configured to reducing cutting of the proximal stopper member when the needle penetrates the proximal stopper member compared to a needle without a rounded edge. The proximal opening may be an elongated slot. A length of the elongated slot may provide a tolerance for a variability relating to the proximal and/or distal stopper members. The variability relating to the proximal and/or distal stopper members may be selected from a group consisting of distortion of a proximal surface of the distal stopper member, a position of the proximal stopper member relative to the elongated slot, and a position of the distal stopper member relative to the elongated slot. The length of the elongated slot may be between about $\frac{1}{32}$ inch to about $\frac{1}{16}$ inch. A distance between the elongated slot and the solid proximal end may minimize retrograde leaking of the first and second liquids into the plunger. The elongated slot may be formed using a grinding wheel. First and second sizes of the respective distal and proximal chambers may be modified by movement of the proximal and distal stopper members relative to the syringe body.

In one or more embodiments, the plunger member includes a needle retention feature disposed in the plunger interior, an energy-storage member disposed in the plunger interior, and an energy-storage member latching member disposed in the plunger interior. The needle hub assembly may include a hub, and a needle holding member configured to couple the needle to the hub. The needle may be at least partially retractable into plunger interior upon manipulation of the plunger member relative to the syringe body to transform the energy-storage member latching member from a latched state to an unlatched state. The needle may be configured to pierce entirely through at least the distal stopper member to be retracted at least partially into the plunger interior. The energy-storage member latching member may be configured to transform from the latched state to the unlatched state at least partially retracting the needle into plunger interior after the second liquid has been expelled from the proximal chamber through the needle. The needle retention feature may be configured to actuate transformation of the energy-storage member latching member from the latched state to the unlatched state upon manipulation of the plunger member to insert the proximal stopper member to the distal end of the syringe body.

In one or more embodiments, a distance between the proximal opening and the distal end of the syringe body is substantially equal to a length of the distal stopper member, such that when the distal stopper member is inserted to the distal end of the syringe body, the proximal stopper member is inserted distally relative to the needle to position the proximal opening in the proximal chamber. The proximal and distal stopper members and the syringe body may be configured such that distally directed force applied to the proximal stopper member is transmitted through the second liquid to the distal stopper member until the proximal stopper member is inserted distally relative to the needle to position the proximal opening in the proximal chamber.

In one or more embodiments, the system has a first injection configuration where the proximal opening is disposed in the distal chamber or in the distal stopper member, and a second injection configuration where the proximal opening is disposed in the proximal chamber, thereby allowing transfer of the second liquid from the proximal chamber, through the proximal opening and the needle interior, and out the distal end opening. The proximal and distal stopper members may include respective first and second polymer coatings on respective distal and proximal surfaces thereof, such that the proximal chamber is defined by the syringe body and the first and second polymer coatings. The distal stopper member may have a funnel that tapers in a proximal direction, and a space disposed at a tapered proximal end of the funnel. The middle opening may be adjacent the distal end of the syringe body.

In another embodiment a method for serially injecting first and second liquids into a patient includes providing a system including a syringe body defining a syringe proximal opening and a distal needle interface at a distal end thereof. The system also includes proximal and distal stopper members disposed in the syringe body, forming a proximal chamber between the proximal and distal stopper members and a distal chamber between the distal stopper member and the distal end of the syringe body. The system further includes a first liquid in the distal chamber and a second liquid in the proximal chamber. Moreover, the system includes a plunger configured to be manually manipulated to insert the proximal stopper member distally relative to the syringe body. In addition, the system includes a needle having a needle interior, a distal end opening, a middle opening, and a proximal opening, where the distal end opening, the middle opening, and the proximal opening are fluidly coupled through the needle interior. The method also includes advancing the plunger member to expel a first portion of the first liquid from the distal chamber through the needle interior and the distal end opening. The method further includes further advancing the plunger member to expel the second liquid from the proximal chamber through the proximal opening, the needle interior and the distal end opening. Moreover, the method includes further advancing the plunger member to expel a second portion of the first liquid from the proximal chamber through the needle interior and the distal end opening.

In one or more embodiments, the method also includes automatically retracting the distal needle tip into a needle hub or the syringe body when the second portion of the first liquid been expelled through the distal end opening. The method may also include the needle piercing entirely through at least the distal stopper member, and retracting the needle at least partially into the plunger interior. The method may also include inserting a distal end of the needle into the patient before advancing the plunger member to expel the first portion of the first liquid from the distal chamber, thereby positioning the distal end opening of the needle in the patient before expelling the first portion of the first liquid. The method may also include removing air from the distal chamber before inserting a distal end of the needle into the patient. Removing air from the distal chamber may include holding the syringe body in a substantially vertical position, and manipulating the plunger member to insert the proximal stopper member distally relative to the syringe body. Advancing the plunger member may insert the proximal stopper member distally relative to the syringe body, thereby exerting a distally-directed force through the second liquid to insert the distal stopper member distally relative to the syringe body to expel the first portion of the first liquid from the distal chamber through the needle interior and the distal end opening.

In one or more embodiments, the system has a first injection configuration where the proximal opening is disposed in the distal chamber or in the distal stopper member, a second injection configuration where the proximal opening is disposed in the proximal chamber, thereby allowing transfer of the second liquid from the proximal chamber, through the proximal opening and the needle interior, and out the distal end opening, and a third injection configuration where the proximal and distal stopper members are in contact with each other, and where the proximal opening is occluded by the proximal and/or distal stopper members, The system may be in the first injection configuration when the plunger member is advanced to expel the first portion of the first liquid from the distal chamber through the needle interior and the distal end opening. The system may be in the second injection configuration when the plunger member is further advanced to expel the second liquid from the proximal chamber through the proximal opening, the needle interior and the distal end opening. The system may be in the third injection configuration when the plunger member is advanced to expel the second portion of the first liquid from the distal chamber through the needle interior and the distal end opening.

In one or more embodiments, the needle includes a tubular member and a solid proximal end feature coupled thereto, where the needle interior, the distal end opening, the middle opening, and the proximal opening are formed in the tubular member. The solid proximal end feature may be coupled to the tubular member with a weld. The weld may be a fillet weld configured to reducing cutting of the proximal stopper member when the needle penetrates the proximal stopper member compared to a needle without a fillet weld. A distal end of the solid proximal end feature may be disposed in a proximal end of the tubular member. The distal end of the solid proximal end feature and the proximal end of the tubular member may define an annular lumen fluidly coupling the proximal opening to the needle interior, the middle opening, and the distal end opening.

In one or more embodiments, the proximal opening has a rounded edge configured to reducing cutting of the proximal stopper member when the needle penetrates the proximal stopper member compared to a needle without a rounded edge. The proximal opening may be an elongated slot. A length of the elongated slot may provide a tolerance for a variability relating to the proximal and/or distal stopper members. The variability relating to the proximal and/or distal stopper members may be selected from a group consisting of distortion of a proximal surface of the distal stopper member, a position of the proximal stopper member relative to the elongated slot, and a position of the distal stopper member relative to the elongated slot. A length of the elongated slot may be between about $\frac{1}{32}$ inch to about $\frac{1}{16}$ inch. A length of the elongated slot may minimize retrograde leaking of the first and second liquids into the plunger.

In one or more embodiments, the distal stopper member has a funnel that tapers in a proximal direction, and a space disposed at a tapered proximal end of the funnel. The method may also include the funnel guiding the needle into the space at the tapered proximal end of the funnel, to thereby align the needle proximal end feature with the needle retention feature in the plunger interior. The middle opening may be adjacent the distal end of the syringe body.

In still another embodiment, a system for serially injecting liquids, includes a syringe body defining a syringe proximal opening and a distal needle interface at a distal end thereof. The system also includes proximal, middle, and distal stopper members disposed in the syringe body, forming a proximal chamber between the proximal and middle stopper members, a middle chamber between the middle and distal stopper members, and a distal chamber between the distal stopper member and the distal end of the syringe body. The system further includes a first liquid in the distal chamber, a second liquid in the middle chamber, and a third liquid in the proximal chamber. Moreover, the system includes a plunger configured to be manually manipulated to insert the proximal stopper member distally relative to the syringe body. In addition, the system includes a needle hub assembly coupled to the distal needle interface of the syringe body, the needle assembly including a needle. The needle may define a needle interior, a distal end opening, a middle opening, and a proximal opening. The distal end opening, the middle opening, and the proximal opening may be fluidly coupled through the needle interior. Manipulating the plunger member to insert the proximal stopper member distally relative to the syringe body may serially expel the first, second, and third liquid through the needle.

In one or more embodiments, manipulating the plunger member to insert the proximal stopper member distally relative to the syringe body serially expels the first, second, and third liquid through the needle in the following order a first portion of the first liquid from the distal chamber, the second liquid from the middle chamber, a second portion of the first liquid from the distal chamber, and the third liquid from the proximal chamber.

In one or more embodiments, manipulating the plunger member to insert the proximal stopper member distally relative to the syringe body serially expels the first, second, and third liquid through the needle in the following order the first liquid from the distal chamber, the second liquid from the middle chamber, and the third liquid from the proximal chamber. The needle may include a tubular member and a solid proximal end feature coupled thereto, where the needle interior, the distal end opening, the middle opening, and the proximal opening may be formed in the tubular member. The solid proximal end feature may be coupled to the tubular member with a weld. The weld may be a fillet weld configured to reducing cutting of the proximal and middle stopper members when the needle penetrates the proximal and middle stopper members compared to a needle without a fillet weld. The weld may taper in a proximal direction. The solid proximal end feature may be cold formed. A distal end of the solid proximal end feature may be disposed in a proximal end of the tubular member. The distal end of the solid proximal end feature and the proximal end of the tubular member may define an annular lumen fluidly coupling the proximal opening to the needle interior, the middle opening, and the distal end opening.

In one or more embodiments, the proximal opening has a rounded edge configured to reducing cutting of the proximal and middle stopper members when the needle penetrates the proximal and middle stopper members compared to a needle without a rounded edge. The proximal opening may be an elongated slot. A length of the elongated slot may provide a tolerance for a variability relating to the proximal, middle, and/or distal stopper members. The variability relating to the proximal and/or distal stopper members may be selected from a group consisting of distortion of a proximal surface of the distal stopper member, a distortion of a proximal surface of the middle stopper member, a position of the proximal stopper member relative to the elongated slot, a position of the middle stopper member relative to the elongated slot, and a position of the distal stopper member relative to the elongated slot. The length of the elongated slot may be between about $\frac{1}{16}$ inch to about $\frac{1}{8}$ inch. A distance between the elongated slot and the solid proximal end may minimize retrograde leaking of the first, second, and third liquids into the plunger. The elongated slot may be formed using a grinding wheel.

In one or more embodiments, first, second, and third sizes of the respective distal, middle, and proximal chambers can be modified by movement of the proximal, middle, and distal stopper members relative to the syringe body. The plunger member may include a needle retention feature disposed in the plunger interior, an energy-storage member disposed in the plunger interior, and an energy-storage member latching member disposed in the plunger interior. The needle hub assembly may include a hub, and a needle holding member configured to couple the needle to the hub. The needle may be at least partially retractable into plunger interior upon manipulation of the plunger member relative to the syringe body to transform the energy-storage member latching member from a latched state to an unlatched state. The needle may be configured to pierce entirely through at least the distal and middle stopper members to be retracted at least partially into the plunger interior. The energy-storage member latching member may be configured to transform from the latched state to the unlatched state at least partially retracting the needle into plunger interior after the third liquid has been expelled from the proximal chamber through the needle. The needle retention feature may be configured to actuate transformation of the energy-storage member latching member from the latched state to the unlatched state upon manipulation of the plunger member to insert the proximal stopper member to the distal end of the syringe body.

In one or more embodiments, the proximal, middle, and distal stopper members and the syringe body may be configured such that distally directed force applied to the proximal stopper member is transmitted through the third liquid to the middle stopper member and through the second liquid to the distal stopper member until the proximal stopper member is inserted distally relative to the needle to position the proximal opening in the middle chamber. The system may have a first injection configuration where the proximal opening is disposed in the distal chamber or in the distal stopper member, a second injection configuration where the proximal opening is disposed in the middle chamber, thereby allowing transfer of the second liquid from the middle chamber, through the proximal opening and the needle interior, and out the distal end opening, and a third injection configuration where the proximal opening is disposed in the proximal chamber, thereby allowing transfer of the third liquid from the proximal chamber, through the proximal opening and the needle interior, and out the distal end opening. The proximal and middle stopper members may include respective first and second polymer coatings on respective distal and proximal surfaces thereof, such that the proximal chamber is defined by the syringe body and the first and second polymer coatings. The distal stopper member may have a funnel that tapers in a proximal direction, and a space disposed at a tapered proximal end of the funnel. The middle opening may be adjacent the distal end of the syringe body.

In yet another embodiment, a method for serially injecting first and second liquids into a patient include providing a system including a syringe body defining a syringe proximal opening and a distal needle interface at a distal end thereof. The system also includes proximal, middle, and distal stopper members disposed in the syringe body, forming a proximal chamber between the proximal and middle stopper members, a middle chamber between the middle and distal stopper members, and a distal chamber between the distal stopper member and the distal end of the syringe body. The system further includes a first liquid in the distal chamber, a second liquid in the middle chamber, and a third liquid in the proximal chamber. Moreover the system includes a plunger configured to be manually manipulated to insert the proximal stopper member distally relative to the syringe body. In addition, the system includes a needle having a needle interior, a distal end opening, a middle opening, and a proximal opening, where the distal end opening, the middle opening, and the proximal opening are fluidly coupled through the needle interior. The method also includes advancing the plunger member to expel a first portion of the first liquid from the distal chamber through the needle interior and the distal end opening. The method further includes further advancing the plunger member to expel the second liquid from the middle chamber through the proximal opening, the needle interior and the distal end opening. Moreover, the method includes further advancing the plunger member to expel a second portion of the first liquid from the proximal chamber through the needle interior and the distal end opening. In addition, the method includes further advancing the plunger member to expel the third liquid from the proximal chamber through the proximal opening, the needle interior and the distal end opening.

In one or more embodiments, the method also includes automatically retracting the distal needle tip into a needle hub or the syringe body when the second portion of the first liquid been expelled through the distal end opening.

In another embodiment, a method for serially injecting first and second liquids into a patient includes providing a system including a syringe body defining a syringe proximal opening and a distal needle interface at a distal end thereof. The system also includes proximal, middle, and distal stopper members disposed in the syringe body, forming a proximal chamber between the proximal and middle stopper members, a middle chamber between the middle and distal stopper members, and a distal chamber between the distal stopper member and the distal end of the syringe body. The system further includes a first liquid in the distal chamber and a second liquid in the middle chamber. Moreover, the system includes a third liquid in the proximal chamber. In addition, the system includes a plunger configured to be manually manipulated to insert the proximal stopper member distally relative to the syringe body, and a needle having a needle interior, a distal end opening, a middle opening, and a proximal opening, where the distal end opening, the middle opening, and the proximal opening are fluidly coupled through the needle interior. The method also includes advancing the plunger member to expel the first liquid from the distal chamber through the needle interior and the distal end opening. The method further includes further advancing the plunger member to expel the second liquid from the middle chamber through the proximal opening, the needle interior and the distal end opening. Moreover, the system includes further advancing the plunger member to expel the third liquid from the proximal chamber through the proximal opening, the needle interior and the distal end opening.

In one or more embodiments, the method also includes automatically retracting the distal needle tip into a needle hub or the syringe body when the third liquid been expelled through the distal end opening.

Some embodiments are directed to injection systems. In particular, some embodiments are directed to safe injection systems with needle assemblies having channels therein that resist crushing and structural failure. Other embodiments are directed to safe injection systems with a needle assemblies having a distal valve to prevent inadvertent ejection of injectables through the distal opening of the injection system body.

In one embodiment, a syringe assembly includes a syringe body having a syringe interior, proximal and distal ends, and a needle attachment interface disposed at the distal end thereof. The assembly also includes a needle assembly having a proximal portion, a middle connector, and a distal portion. The assembly further includes a needle latch assembly configured to prevent the needle assembly from moving proximally in a closed state and to release the needle assembly to allow the needle assembly to move proximally in an open state. The proximal portion has a crescent or dumbbell shaped cross-section. The needle assembly is configured to be retracted into the syringe body after injection using the syringe assembly.

In one or more embodiments, the proximal portion includes a plurality of leaves, and two of the plurality of leaves form an approximately 90° angle. The proximal portion may include a section having a taper of approximately 12° to 15°. The proximal portion may include a reduced diameter section, and a proximal tip having a distally facing overhang relative to the reduced diameter section of approximately 0.0075". The distal portion may include a sharp distal end.

In one or more embodiments, the assembly includes proximal and distal stopper members. The proximal and distal stopper members and the syringe body define a proximal chamber, and the distal stopper member and the syringe body define a distal chamber. The needle assembly may include a radially extending annular flange adjacent a proximal end of the middle connector. The distal portion may include a radially enlarged portion defining a longitudinal tube having a squircle cross-sectional shape. The distal portion may include a radially smaller portion having a rounded-triangle cross-sectional shape.

In one or more embodiments, the distal stopper member includes a stopper insert including a pair of tabs. The syringe assembly may be configured to transfer a fluid from the proximal chamber to the distal chamber to mix with a component in the distal chamber before ejecting the mixed fluid and component from the distal chamber. The syringe assembly may be configured to eject a fluid from the distal chamber before ejecting a fluid from the proximal chamber.

The proximal portion may have two separate sections that each has a crescent or dumbbell shaped cross-section.

In another embodiment, a syringe assembly includes a syringe body having a syringe interior and proximal and distal ends, and a needle assembly, including a flow regulator disposed adjacent a distal end of the syringe body.

In one or more embodiments, the flow regulator includes a housing, where the housing defines a liquid port and a compliant pin. The flow regulator may include an elastomeric seal configured to form a fluid tight seal between the housing and the distal end of the syringe body. The elastomeric seal may be configured to close the liquid port where there is low pressure in an interior chamber of the syringe body. The elastomeric seal may be configured to open the liquid port where there is high pressure in an interior chamber of the syringe body. The assembly may include a stopper member having a stopper insert. The stopper insert may have an internal shape complementary to an external shape of the flow regulator.

Some embodiments are directed to injection systems. In particular, some embodiments are directed to safe injection systems with needle assemblies having channels therein that resist crushing and structural failure. Some embodiments are directed to multiple chamber serial injection systems and multiple chamber safe injection systems that move the needle into a protected configuration to minimize accidental user injury and contamination with used needles.

In one embodiment, a system for serially injecting liquids includes a syringe body defining a syringe proximal opening and a distal needle interface at a distal end thereof. The system also includes proximal and distal stopper members disposed in the syringe body, forming a proximal chamber between the proximal and distal stopper members and a distal chamber between the distal stopper member and the distal end of the syringe body. The system further includes first liquid in the distal chamber and a second liquid in the proximal chamber. Moreover, the system includes a plunger configured to be manually manipulated to insert the proximal stopper member distally relative to the syringe body. In addition, the system includes a needle assembly having a proximal portion, a middle connector, and a distal portion. The proximal portion has a crescent or dumbbell shaped cross-section. Manipulating the plunger member to insert the proximal stopper member distally relative to the syringe body initially expels the first liquid from the distal chamber through the needle, and then serially expels the second liquid from the proximal chamber through the needle.

In one or more embodiments, the distal portion includes a sharp distal end. The proximal portion and the middle connection may have respective diameters that are substantially equal to each other. The proximal portion may include a solid proximal end feature, and the middle connector may include a tubular member. The solid proximal end feature may be cold formed. A distal end of the solid proximal end feature may be disposed in a proximal end of the tubular member.

In one or more embodiments, the proximal portion defines a longitudinal channel on a surface thereof. A length of the longitudinal channel may be substantially equal to a length of the distal stopper member, such that when the distal stopper member is inserted to the distal end of the syringe body, the proximal stopper member is inserted distally relative to the needle to position the proximal end of the longitudinal channel in the proximal chamber. The proximal and distal stopper members and the syringe body may be configured such that distally directed force applied to the proximal stopper member is transmitted through the second liquid to the distal stopper member until the proximal stopper member is inserted distally relative to the needle to position the proximal opening in the proximal chamber. A length of the longitudinal channel may provide a tolerance for a variability relating to the proximal and/or distal stopper members. The variability relating to the proximal and/or distal stopper members may be selected from a group consisting of distortion of a proximal surface of the distal stopper member, a position of the proximal stopper member relative to the longitudinal channel, and a position of the distal stopper member relative to the longitudinal channel.

In one or more embodiments, a distance between the longitudinal channel and the solid proximal end minimizes retrograde leaking of the first and second liquids into the plunger. The longitudinal channel may be formed via stamping or injection molding.

In one or more embodiments, the system has a first injection configuration where a proximal end of the longitudinal channel is disposed in the distal chamber or in the distal stopper member, and a second injection configuration where the proximal end of the longitudinal channel is disposed in the proximal chamber, thereby allowing transfer of the second liquid from the proximal chamber, through the longitudinal channel, and out the a distal end opening of the distal portion of the needle assembly. First and second sizes of the respective distal and proximal chambers may be modified by movement of the proximal and distal stopper members relative to the syringe body.

In one or more embodiments, the system also includes a needle hub assembly having a hub and a needle holding member configured to removably couple the needle to the hub. The plunger member may include a needle retention feature disposed in the plunger interior, an energy-storage member disposed in the plunger interior, and an energy-storage member latching member disposed in the plunger interior. The needle may be at least partially retractable into plunger interior upon manipulation of the plunger member relative to the syringe body to transform the energy-storage member latching member from a latched state to an unlatched state. The needle may be configured to pierce entirely through at least the distal stopper member to be retracted at least partially into the plunger interior. The energy-storage member latching member may be configured to transform from the latched state to the unlatched state at least partially retracting the needle into plunger interior after the second liquid has been expelled from the proximal chamber through the needle. The needle retention feature may be configured to actuate transformation of the energy-storage member latching member from the latched state to the unlatched state upon manipulation of the plunger member to insert the proximal stopper member to the distal end of the syringe body. The proximal and distal stopper members may include respective first and second polymer coatings on respective distal and proximal surfaces thereof, such that the proximal chamber is defined by the syringe body and the first and second polymer coatings.

In another embodiment, a system for serially injecting liquids includes a syringe body defining a syringe proximal opening and a distal needle interface at a distal end thereof. The system also includes proximal and distal stopper members disposed in the syringe body, forming a proximal chamber between the proximal and distal stopper members and a distal chamber between the distal stopper member and the distal end of the syringe body. The system further includes a first liquid in the distal chamber and a second liquid in the proximal chamber. Moreover, the system includes a plunger configured to be manually manipulated to insert the proximal stopper member distally relative to the syringe body. In addition, the system includes a fluid transfer assembly having a proximal portion, and a middle connector. The proximal portion has a longitudinal channel formed on a surface thereof. The middle connector has a distal anchor member. Manipulating the plunger member to insert the proximal stopper member distally relative to the syringe body initially expels the first liquid from the distal chamber through the needle, and then serially expels the second liquid from the proximal chamber through the needle.

In one or more embodiments, the proximal portion is a solid metal elongate body, and the middle connector is a polymeric body having a recess configured to receive a distal end of the proximal portion. The fluid transfer assembly may be molded from a polymer as one piece. The fluid transfer assembly may be formed from a metal as one piece.

In one or more embodiments, the distal anchor member has a rectangular cross-sectional shape. The distal anchor member may include a slot having a biasing member disposed therein, and the biasing member may be configured to exert a radially outward directed force against an interior wall of the distal needle interface. The distal anchor member may include a wavy wire-like member configured to exert a radially outward directed force against an interior wall of the distal needle interface. The distal anchor member may include a pair of flexible arms configured to exert a radially outward directed force against an interior wall of the distal needle interface. The distal anchor member may include a rubber sleeve configured to increase friction between the distal anchor member and an interior wall of the distal needle interface. The distal anchor member may also include proximal and distal openings configured to bypass the rubber sleeve.

In yet another embodiment, a system for serially injecting liquids includes a syringe body defining a syringe proximal opening and a distal needle interface at a distal end thereof. The system also includes proximal and distal stopper members disposed in the syringe body, forming a proximal chamber between the proximal and distal stopper members and a distal chamber between the distal stopper member and the distal end of the syringe body. The system further includes a first liquid in the distal chamber and a second liquid in the proximal chamber. Moreover the system includes a plunger configured to be manually manipulated to insert the proximal stopper member distally relative to the syringe body. In addition, the system includes, a fluid transfer assembly having a proximal portion and a middle connector. The middle connector has a distal anchor member. Manipulating the plunger member to insert the proximal stopper member distally relative to the syringe body initially expels the first liquid from the distal chamber through the needle, then serially expels the second liquid from the proximal chamber through the needle.

In one or more embodiments, the proximal portion defines a plurality of arms as a distal end thereof, and the middle connector is a polymeric body having an opening configured to receive the arms of the proximal portion. The plurality of arms tapers may radially outward to couple the proximal portion to the middle connector. The plurality of arms may taper radially outward to exert a radially outward directed force against an interior wall of the distal needle interface.

In one or more embodiments, the distal anchor member includes a slot having a biasing member disposed therein. The distal anchor member may define a pair of bumps in the slot. The biasing member may define a pair of notches configures to receive the pair of bumps. The biasing member may be configured to exert a radially outward directed force against an interior wall of the distal needle interface, The proximal portion may have a longitudinal channel formed on a surface thereof.

In still another embodiment, the system for serially injecting liquids, includes a syringe body defining a syringe proximal opening and a distal needle interface at a distal end thereof. The system also includes proximal and distal stopper members disposed in the syringe body, forming a proximal chamber between the proximal and distal stopper members and a distal chamber between the distal stopper member and the distal end of the syringe body. The system further includes a powder drug component in the distal chamber and a liquid drug component in the proximal chamber. Moreover, the system includes a plunger configured to be manually manipulated to insert the proximal stopper member distally relative to the syringe body. In addition, the system includes a needle assembly having a proximal portion, a middle connector, and a distal portion. The system also includes a one-way valve disposed partially in the distal needle interface and configured to minimize migration of the powder drug component from the distal chamber into the needle assembly.

In one or more embodiments, manipulating the plunger member to insert the proximal stopper member a first distance distally relative to the syringe body transfers the liquid drug component from the proximal chamber to the distal chamber to form a mixed liquid drug with the powder drug component. Manipulating the plunger member to insert the proximal stopper member a second distance distally relative to the syringe body may expel the mixed liquid drug from the distal chamber, pass the one-way valve, and through the needle assembly.

In one or more embodiments, the distal portion includes a sharp distal end. The system may also include a needle retraction system disposed in the plunger member and configured to retract the needle assembly at least partially into the plunger member after injection. The one-way valve may include proximal and distal valve portions, and the proximal valve portion may include a sleeve extending distally from a center thereof.

In one or more embodiments, the sleeve is configured to have a tight tolerance with the distal valve portion of the needle assembly passing therethrough such that a powder drug component cannot pass between the sleeve and the distal valve portion of the needle assembly. The tight tolerance may allow a liquid drug under pressure to pass between the sleeve and the distal valve portion of the needle assembly. The sleeve may define a plurality of longitudinal channels on a surface thereof.

In one or more embodiments, the proximal valve portion of the one-way valve defines an opening therethrough, and when a liquid drug is under pressure in the distal chamber, a liquid flow path is formed from the distal chamber through the opening, between the proximal and distal valve portions of the one-way valve, along the longitudinal channels, through the needle assembly to an exterior of the system. The proximal and distal valve portions of the one-way valve may be configured to have a tight tolerance with each other such that a powder drug component cannot pass between the proximal and distal valve portions of the one-way valve. The tight tolerance may allow a liquid drug under pressure to pass between the proximal and distal valve portions of the one-way valve. The proximal valve portion may be rigid and the distal valve portion may be compliant. When a liquid drug is under pressure in the distal chamber, at least a portion of the distal valve portion may bend away from the proximal valve portion.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein:

FIGS. 1A to 5C illustrate various aspects of conventional injection syringe configurations.

FIGS. 6A-18 illustrate a safe sequential injection method using a prefilled dual chamber serial safe injection system according to some embodiments.

FIGS. 19A-22 illustrate a safe sequential injection method using a prefilled dual chamber serial safe injection system according to some embodiments.

FIGS. 23A-24 illustrate a safe sequential injection method using a prefilled dual chamber serial safe injection system according to some embodiments.

FIGS. 25A-36 illustrate a sequential injection method using a prefilled triple chamber serial injection system according to some embodiments.

FIGS. 48A-B, 49A-B, and 50A-B are perspective, detailed perspective, and axial cross-sectional views of proximal portions of needle assemblies according to two embodiments.

FIG. 51 schematically depicts a theoretical pipe according to some embodiments.

FIGS. 52A and 52B are detailed perspective views of proximal portions and middle connectors of needle assemblies according to two embodiments.

FIGS. 53, 54A-B, 55, 56, and 57 are side, detailed perspective (front and back), perspective, axial, and perspective views of proximal portions of needle assemblies according to some embodiments showing the proximal tip thereof.

FIGS. 58 to 61 are longitudinal cross-sectional views of various steps in injection and needle capture using a safe injection system according to some embodiments.

FIGS. 69A, 69B, and 70 are perspective and side views of a proximal portion of a fluid transfer assembly according to some embodiments.

FIGS. 71A, 71C, and 71D are detailed perspective views of a proximal portion of a fluid transfer assembly according to some embodiments.

FIG. 71B is an axial view of a proximal portion of a fluid transfer assembly according to some embodiments.

FIGS. 76A, 76B, and 76C are detailed perspective views of a stopper member with a stopper insert according to some embodiments.

FIGS. 121A to 121C are longitudinal cross-sectional and axial cross-sectional views of a fluid transfer proximal according to some embodiments.

FIGS. 148A to 148C are perspective, side, exploded the use of a one-way valve for use in a dual chamber safe injection system according to some embodiments.

Figure 1A:
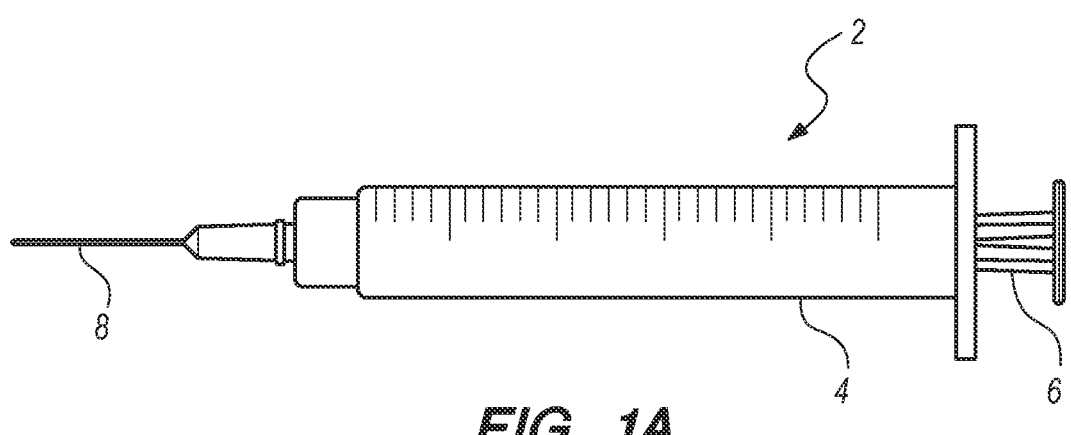
Figure 1B:
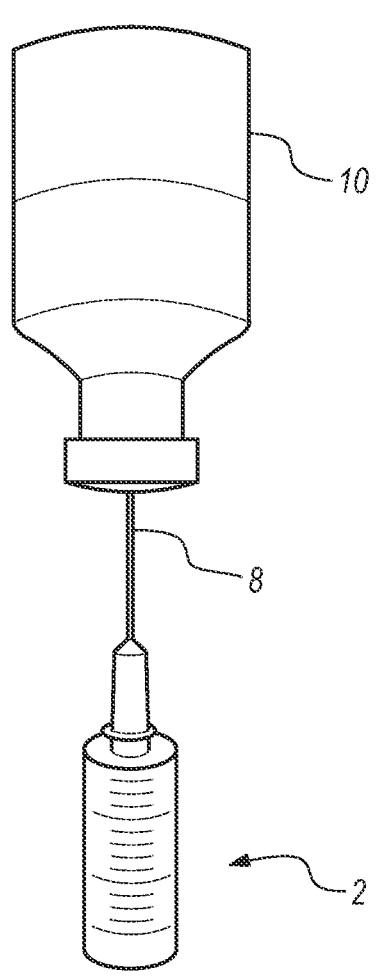
Figure 2A:
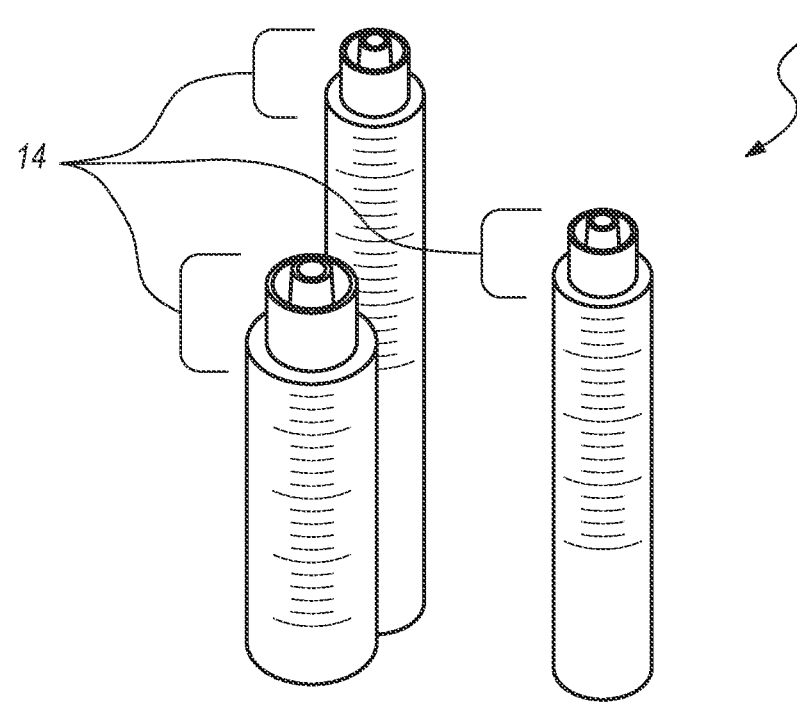
Figure 2B:
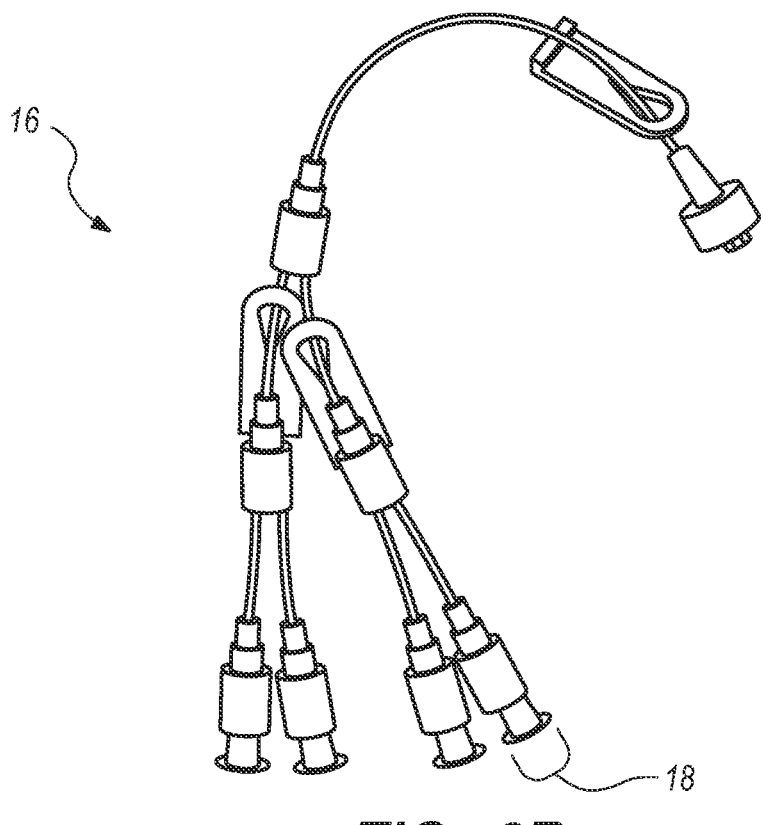
Figure 5A:
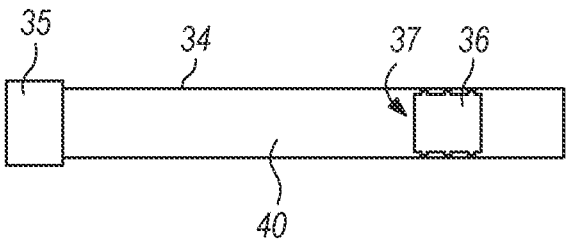
Figure 5B:
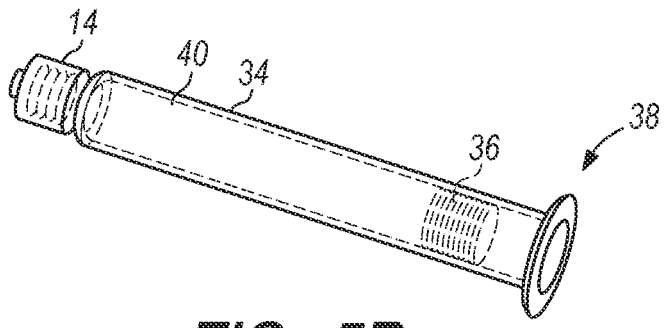
Figure 5C:
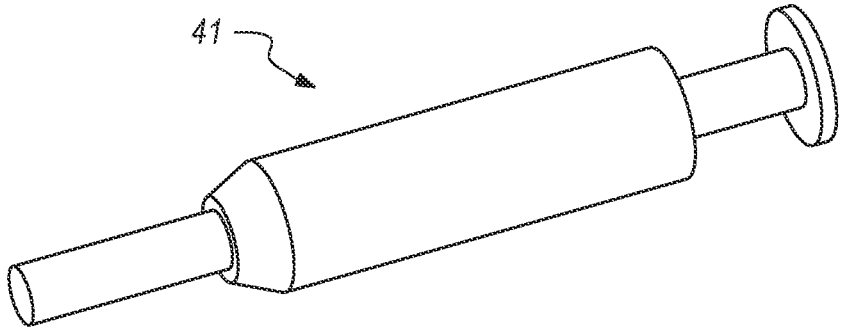

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Prefilled Multi-Chamber Sequential Injection Systems and Method

I. Dual Chamber Safe Injection System and Method

Figures 6A, 6B:
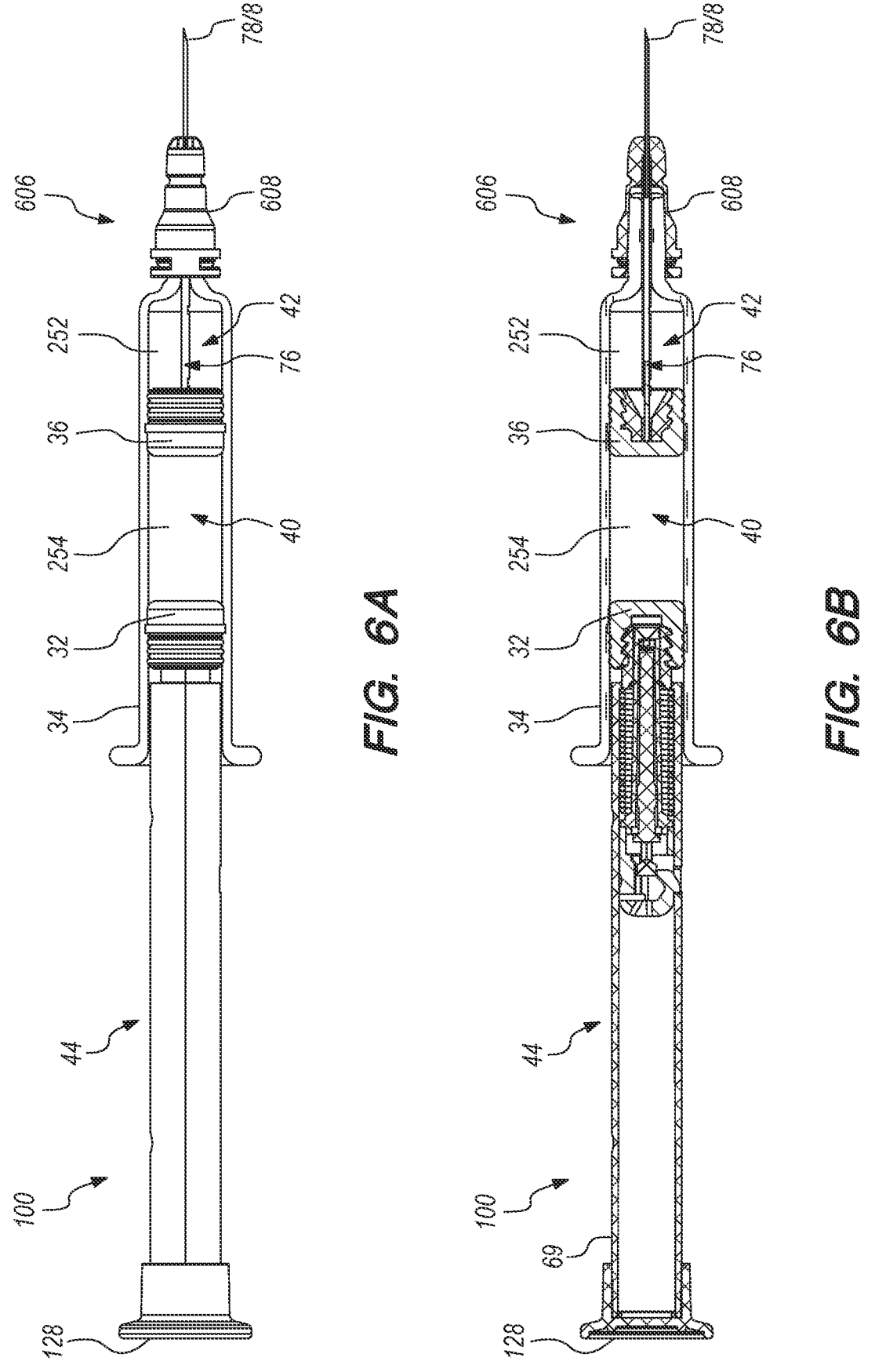
Figure 7:
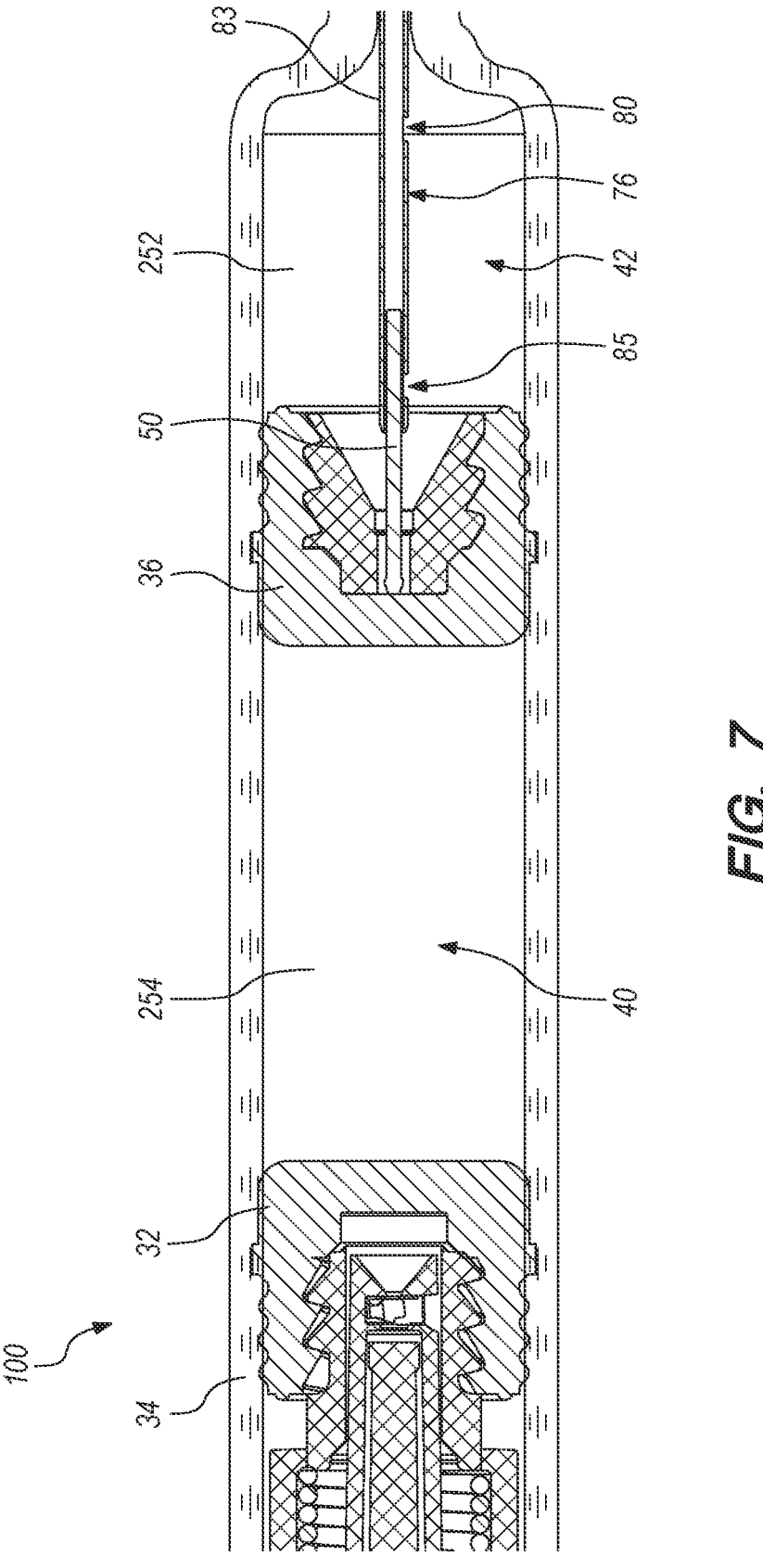

FIGS. 6A, 6B, and 7 are a longitudinal side view, a longitudinal cross-section view, and a detailed longitudinal cross-section view depicting a prefilled dual chamber serial safe injection system (100) according to some embodiments. The prefilled dual chamber serial safe injection system (100) includes a conventional off-the-shelf prefilled syringe body (34) with conventional off-the-shelf proximal and distal stopper members (32, 36) disposed therein. The proximal and distal stopper members (32, 36) together with the syringe body (34) define proximal and distal chambers (40, 42). First and second liquids (252, 254) are contained in the distal and proximal chambers (42, 40) respectively. The proximal and distal stopper members (32, 36) occlude the proximal and distal ends of the proximal chamber (40). The distal stopper member (36) occludes a proximal end of the distal chamber (42). In some embodiments, the distal surface of the proximal stopper member (32) and the proximal surface of the distal stopper member (36) are each coated with a lubricious polymer coating (e.g., PTFE or ETFE), the first and second polymer coatings of the proximal and distal stopper members (32, 36), together with the syringe body (34) define the proximal chamber (40). The lubricious polymer coating also serves to isolate the rubber of the proximal and distal stopper members (32, 36) from the second liquid (254). The proximal and distal stopper members (32, 36) may be oriented as shown in FIGS. 6A and 6B or the distal stopper (36) may be flipped so the lubricious coating faces the distal chamber (42) such that the first liquid (252) in the distal chamber (42) contacts the lubricious coating for storage.

A needle hub assembly (606) is disposed at the distal end of the distal chamber (42). The needle hub assembly (606) includes a needle hub (608) and a needle spine assembly ("needle") (76) removably coupled thereto. In some embodiments, a needle cover member (not shown) may be installed on the needle hub assembly (606) for storage. The dual chamber serial safe injection system (100) facilitates sequential injection of the first liquid (252) from the distal chamber (42) followed by injection of the second liquid (254) from the proximal chamber (40) subject to sequential insertion of a plunger assembly (44) relative to the syringe body (34) to various degrees by a user. The plunger assembly (44) includes a plunger housing member (69) coupled to the proximal stopper member (32) and a plunger manipulation interface (128). The first and second liquids (252, 254) located in the distal and proximal chambers (42, 40) respectively may be any liquid or gel, such as aqueous or oil based medicine solutions.

The dual chamber serial safe injection system (100) has a staked needle configuration wherein upon presentation to the user, a needle hub assembly (606) is mounted in position ready for injection after removal of a needle cover member (not shown) which may comprise an elastomeric sealing material on its internal surface to interface with a needle distal end (78) and/or the distal hub (608) during storage. While the staked needle is depicted as mounted in position, the staked needle may be removably coupled to the syringe body (34) using a Luer slip or a Luer lock interface (not shown), with the proximal end (50; see FIG. 7) of the needle (76) extending through the Luer interface and into the distal chamber (42). Alternatively, the needle may be fixedly or removably mounted to the flange on a cartridge body instead of a syringe. Such cartridge injection systems are disclosed in U.S. Utility patent application Ser. No. 15/801,281, which was previously incorporated by reference herein.

The needle (76) includes a needle proximal end (50; see FIG. 7) and a needle distal end (78; see FIGS. 6A and 6B) coupled to opposite (i.e., respective proximal and distal) ends of a needle joining member (83; see FIG. 7). The needle joining member (83) is a tubular member coupled to the sharp needle distal end (78), which also defines a distal opening (81). The needle joining member (83) also defines proximal and middle openings (85, 80). The middle opening (80) is disposed adjacent a distal end of the syringe body (34). The proximal opening (85) is disposed adjacent a proximal end of the needle joining member (83). The needle proximal end (50) is a solid proximal end feature.

Figure 12:
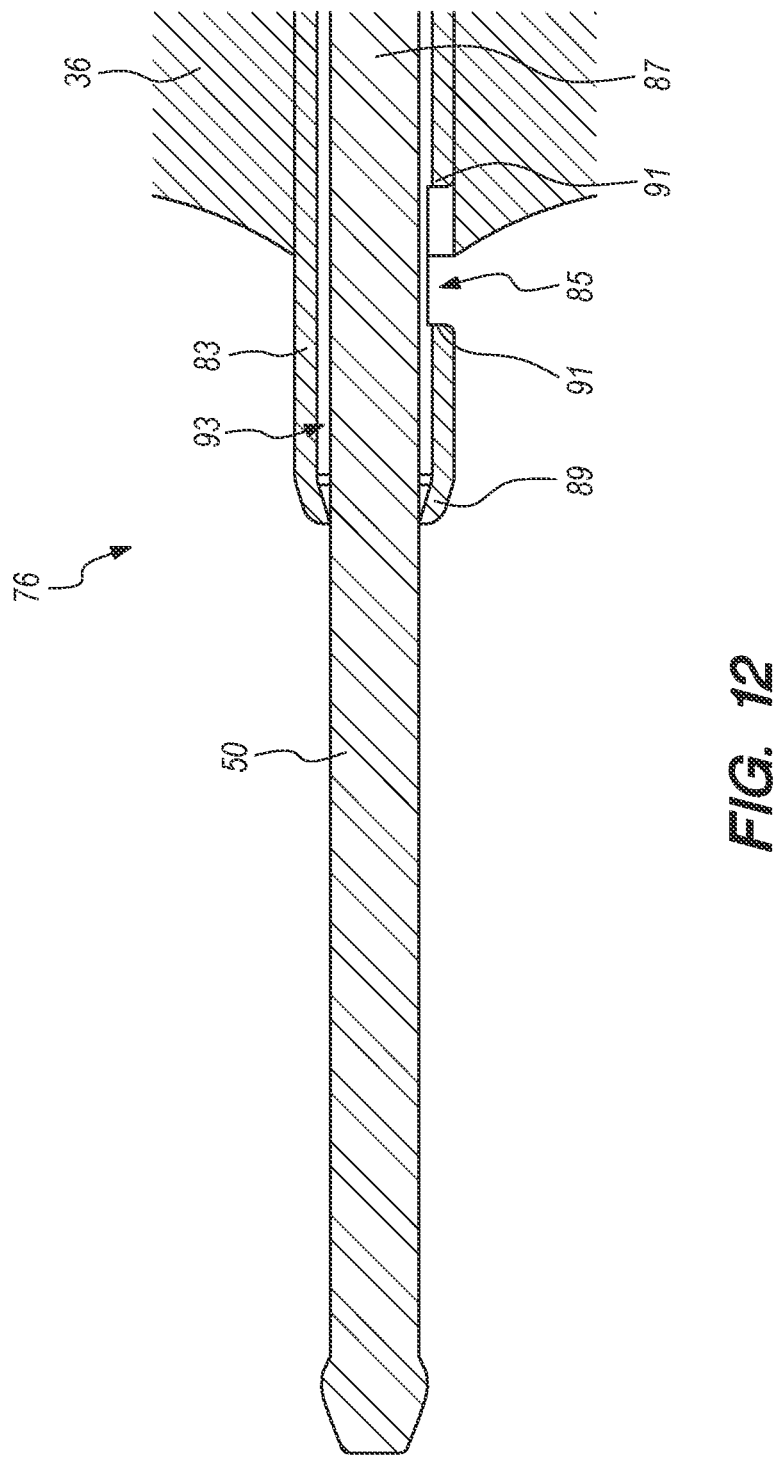

As shown in FIG. 12, a distal end (87) of the solid needle proximal end (50) is disposed in an interior of the tubular needle joining member (83). A proximal end (89) of the tubular needle joining member (83) is welded to the solid needle proximal end (50) with a fillet weld. The proximal end (89) of the tubular needle joining member (83) is tapered in a proximal direction to facilitate the needle (76) penetrating a rubber stopper, such as the distal stopper member (36), while reducing or eliminating cutting/shredding of the rubber stopper (described herein). Cutting/shredding of rubber stoppers can otherwise generate unwanted rubber particles that may interfere with the injection system and/or be injected into a patient. The proximal and distal edges (91) of the proximal opening (85) may also be rounded (e.g., by tumbling or grinding) to reduce or eliminate cutting/shredding of rubber stoppers during penetration thereof.

As also shown in FIG. 12, the distal end (87) of the solid needle proximal end (50) and the tubular needle joining member (83) defines an annular lumen (93). The annular lumen (93) fluidly couples the proximal opening (85) to an interior of the needle (76), the middle opening (80; see FIG. 7), and the distal opening (81). Fluidly coupling the proximal opening (85) to the interior of the needle though the annular lumen (93) allows the proximal opening (85) to be disposed in close proximity to the proximal end (89) of the tubular needle joining member (83), thereby allowing for a more compact system design. Fluidly coupling the proximal opening (85) to the interior of the needle though the annular lumen (93) also allows more of the distal end (87) of the solid needle proximal end (50) to be disposed in the interior of the tubular needle joining member (83), thereby facilitating manufacture of the prefilled dual chamber serial safe injection system (100).

As also shown in FIG. 12, the proximal opening (85) is an elongated slot, which can be formed in the tubular needle joining member (83) using a grinding wheel. Using a grinding wheel facilitates bulk manufacturing of tubular needle joining members (83). The length of the proximal opening (85) is configured to provide a tolerance for a variability relating to the proximal and/or distal stopper members (32, 36). The variability relating to the proximal and/or distal stopper members (32, 36) may be distortion of a proximal surface of the distal stopper member, a position of the proximal stopper member relative to the elongated slot, and/or a position of the distal stopper member relative to the elongated slot (described herein). The length of the proximal opening (85) also minimizes or eliminates retrograde leaking of the first and second liquids (252, 254) into the plunger. In some embodiments, the length of the proximal opening (85) is between about $\frac{1}{32}$ inch to about $\frac{1}{16}$ inch. The proximal and distal edges (91) of the proximal opening (85) may also be rounded (e.g., by tumbling or grinding) to reduce or eliminate cutting/shredding of rubber stoppers during penetration thereof as described herein.

Other details regarding the dual chamber serial safe injection system (100) are disclosed in U.S. Utility patent application Ser. No. 16/435,429, which was previously incorporated by reference herein. In brief, additional components of the dual chamber serial safe injection system (100) include a retraction system in the interior of the plunger member (44): a needle retention feature; an energy-storage member (e.g., spring); and an energy-storage member latch. In the embodiments depicted in FIGS. 6A to 24, a significant portion of the safe needle retraction hardware resides within the plunger housing (69). Additional components also include a needle holder member (e.g., O-ring, needle latches, and/or detents) in the interior of the needle hub (608). Additional components further include a funnel in the distal stopper member (36) to guide the needle proximal end (50) into the center of the distal stopper member (36).

FIGS. 6A-18 illustrate a safe sequential injection method using the prefilled dual chamber serial safe injection system (100) described herein according to some embodiments. FIGS. 6A, 6B, and 7 depict the prefilled dual chamber serial safe injection system (100) in a first/ready to use configuration. The only difference between the first/ready to use configuration and a shipping configuration (not shown) is that a needle cover member (not shown) present in the shipping configuration has been removed in the first/ready to use configuration. In the first/ready to use configuration, the proximal opening (85) is disposed in the distal chamber (42), along with the middle opening (80). As such, there is no flow path between the proximal chamber (40), and the distal opening (81). Therefore, any distally directed force applied to the plunger manipulation interface (128) is transferred through the plunger member (44), the proximal stopper member (32), and the incompressible second liquid (254) in the proximal chamber (40) to move the distal stopper member (36) distally relative to the syringe body (34).

Moving the distal stopper member (36) distally relative to the syringe body (34) increases a pressure in the distal chamber (42), which drives the first liquid (252) from the distal chamber (42) through the middle and proximal openings (80, 85) and out the distal opening (81).

Figures 8A, 8B:
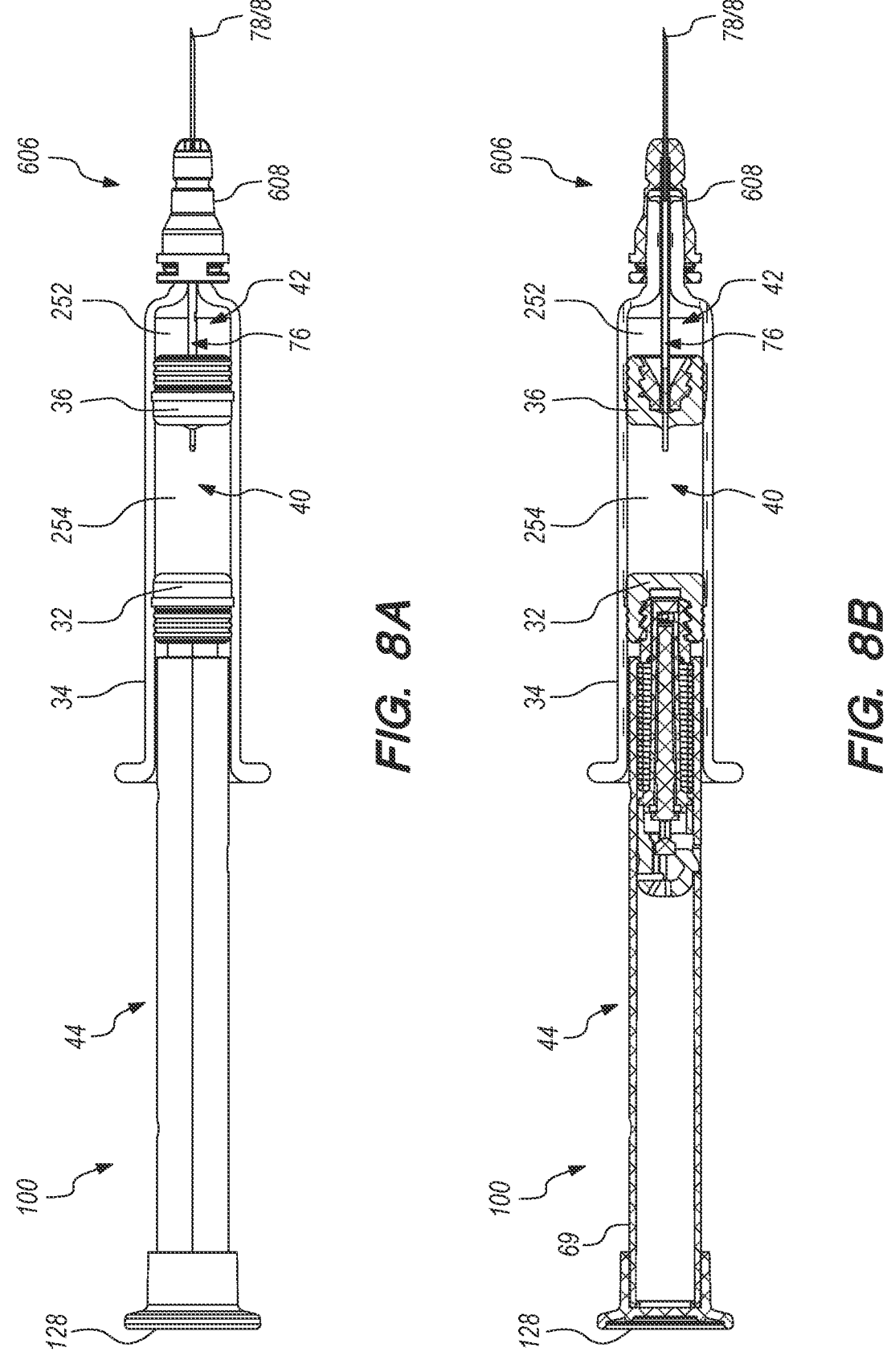
Figure 9:
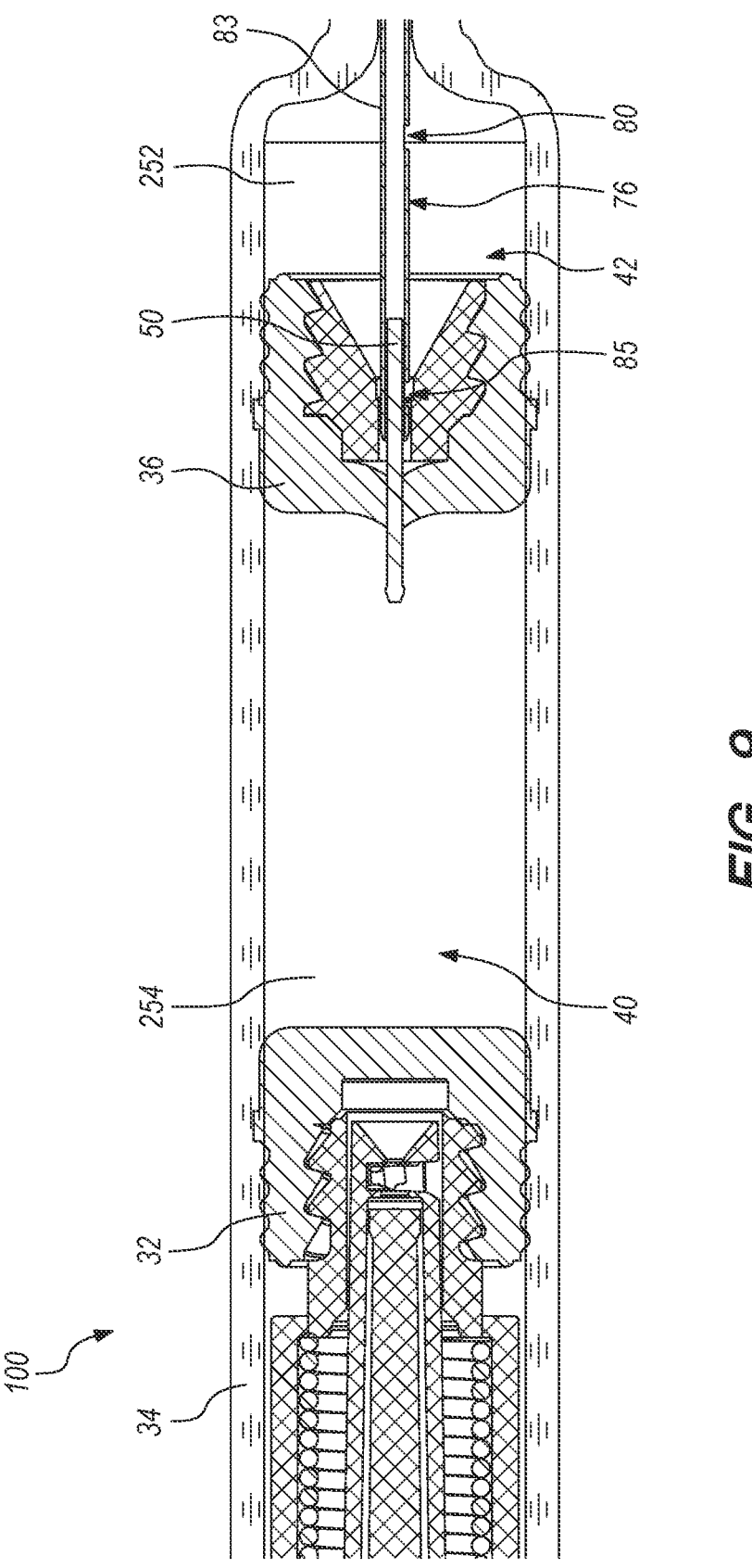
Figures 10A, 10B:
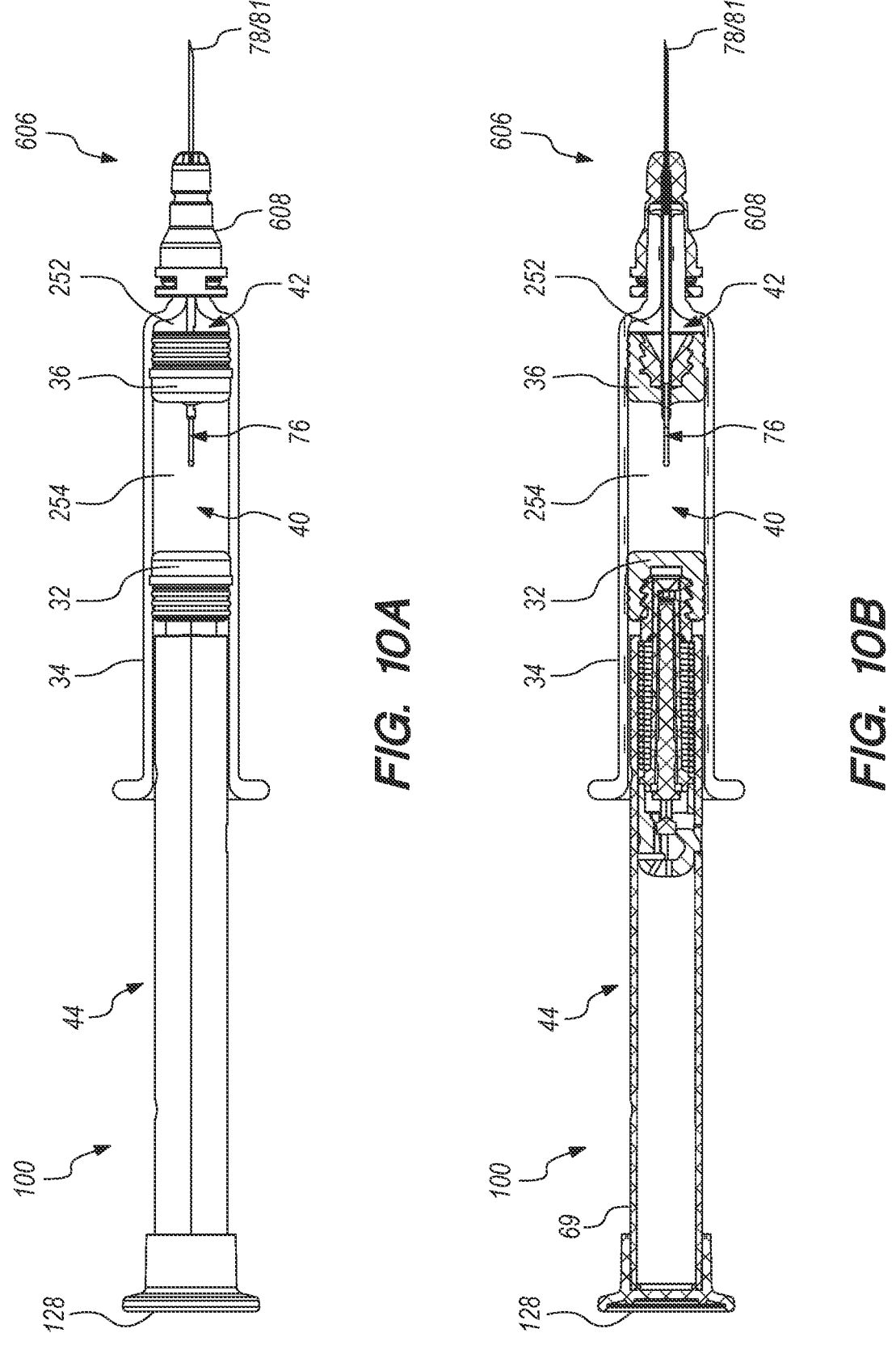

FIGS. 8A, 8B, and 9 depict the prefilled dual chamber serial safe injection system (100) after the distal stopper member (36) has been moved a first distance distally relative to the syringe body (34). The distal chamber (42) has partially collapsed/been reduced in size, and some of the first liquid (252) has been ejected from the prefilled dual chamber serial safe injection system (100) through the distal opening (81). Moving the distal stopper member (36) distally relative to the syringe body (34) has also caused the proximal end (50) of the needle (76) to penetrate the distal stopper member (36). As shown in FIG. 9, the rubber material from which the distal stopper member (36) is made deforms/tents in a proximal direction as the proximal end (50) of the needle (76) penetrates the distal stopper member (36) in a proximal direction due to friction between the distal stopper member (36) and the proximal end (50). This friction may be reduced by applying a lubricant to the various components of the prefilled dual chamber serial safe injection system (100). The proximal opening (85) is still in the distal chamber (42) or is occluded by the distal stopper member (36). Accordingly, there is no flow path between the proximal chamber (40) and the distal opening (81), and distally directed force applied to the plunger manipulation interface (128) is still transmitted to the distal stopper member (36) as described above.

Figure 11:
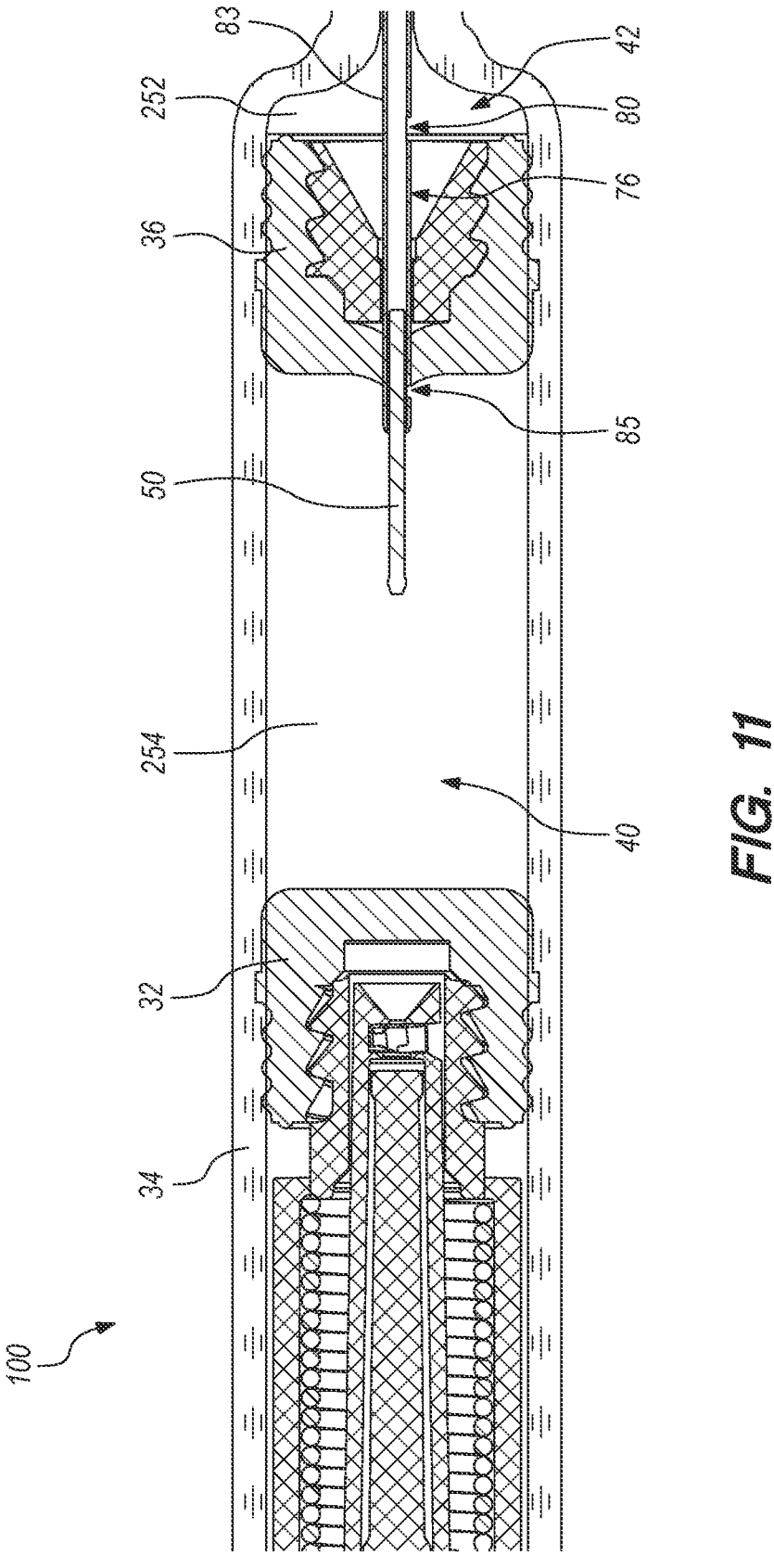

FIGS. 10A, 10B, 11, and 12 depict the prefilled dual chamber serial safe injection system (100) after the distal stopper member (36) has been moved a second distance (further than the first distance) distally relative to the syringe body (34). The distal chamber (42) has almost fully collapsed/been almost completely eliminated, and most of the first liquid (252) has been ejected from the prefilled dual chamber serial safe injection system (100) through the distal opening (81). Further moving the distal stopper member (36) distally relative to the syringe body (34) has also caused the proximal end (50) of the needle (76) to further penetrate the distal stopper member (36). As shown in FIGS. 11 and 12, the rubber material from which the distal stopper member (36) is made deforms/tents in a proximal direction as the proximal end (50) of the needle (76) penetrates the distal stopper member (36) in a proximal direction due to friction between the distal stopper member (36) and the proximal end (50). As also shown in FIGS. 11 and 12, with further penetration of the proximal end (50) of the needle (76), the proximal opening (85) is now disposed in the proximal chamber (40). Accordingly, there is now a flow path between the proximal chamber (40) and the distal opening (81), and distally directed force applied to the plunger manipulation interface (128) now moves the proximal stopper member (32) distally relative to the syringe body (34) to eject the second liquid (254) from the proximal chamber (40). Opening of the flow path between the proximal chamber (40) and the distal opening (81) places the prefilled dual chamber serial safe injection system (100) in a second configuration in which the second liquid (254) may be ejected from the proximal chamber (40).

As shown in FIG. 12, the length of the proximal opening (85) provides tolerance for variability in the degree of deformation/tenting of the distal stopper member (36) as the proximal end (50) of the needle (76) penetrates the distal stopper member (36) in a proximal direction. In particular, even if the distal stopper member (36) is made deforms/tents more than expected, the proximal opening (85) will still fluidly couple the proximal chamber (40) at the distal opening (81). FIG. 12 also shows that the proximal end (89) of the tubular needle joining member (83) is welded to the solid needle proximal end (50) with a fillet weld, which tapers in a proximal direction to facilitate the needle (76) penetrating the distal stopper member (36), while reducing or eliminating cutting/shredding of the distal stopper member (36). Cutting/shredding of rubber stoppers can otherwise generate unwanted rubber particles that may interfere with the injection system and/or be injected into a patient. The proximal and distal edges (91) of the proximal opening (85) are also rounded (e.g., by tumbling or grinding) to reduce or eliminate cutting/shredding of distal stopper member (36) during penetration thereof.

Figures 13A, 13B:
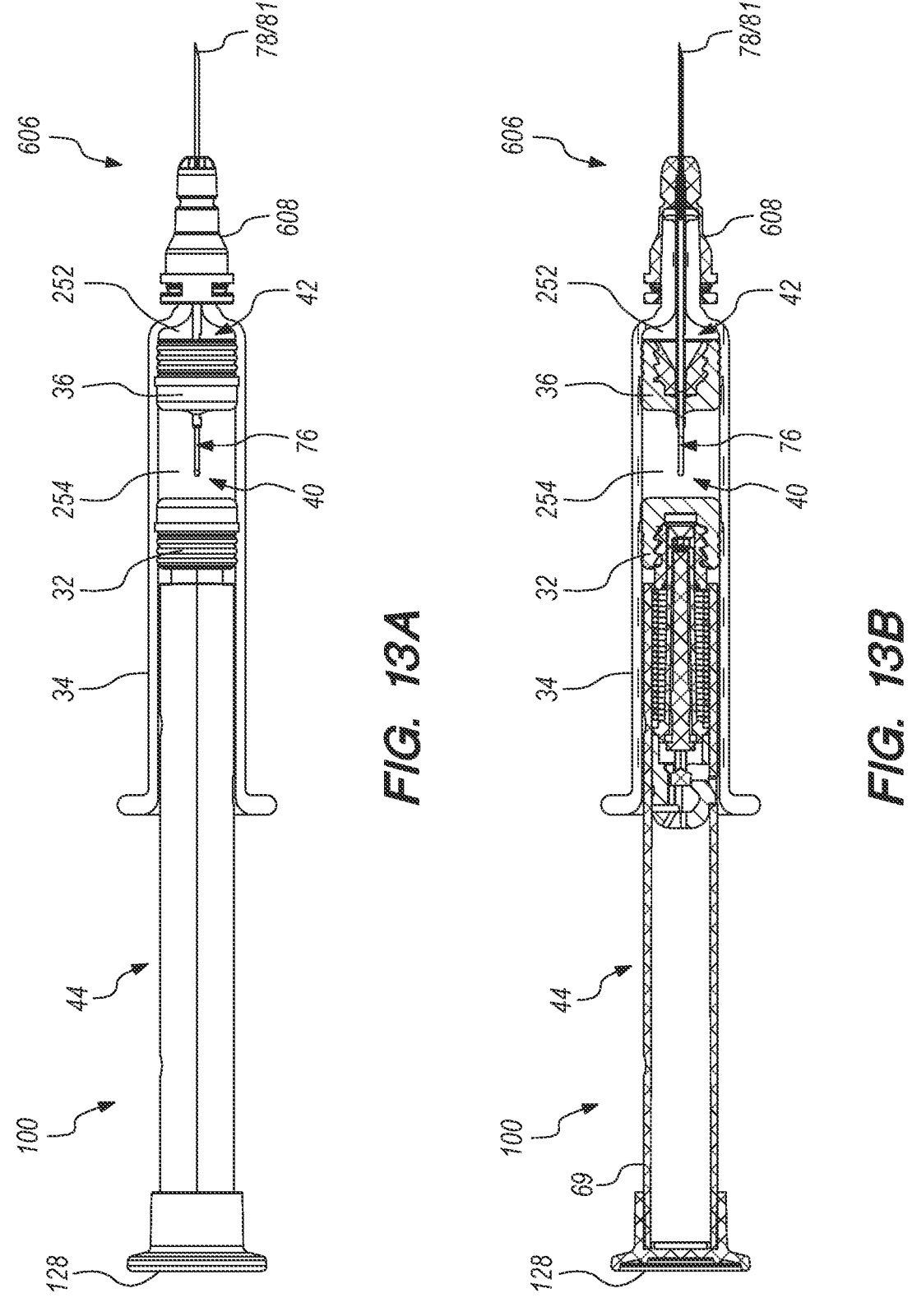
Figure 14:
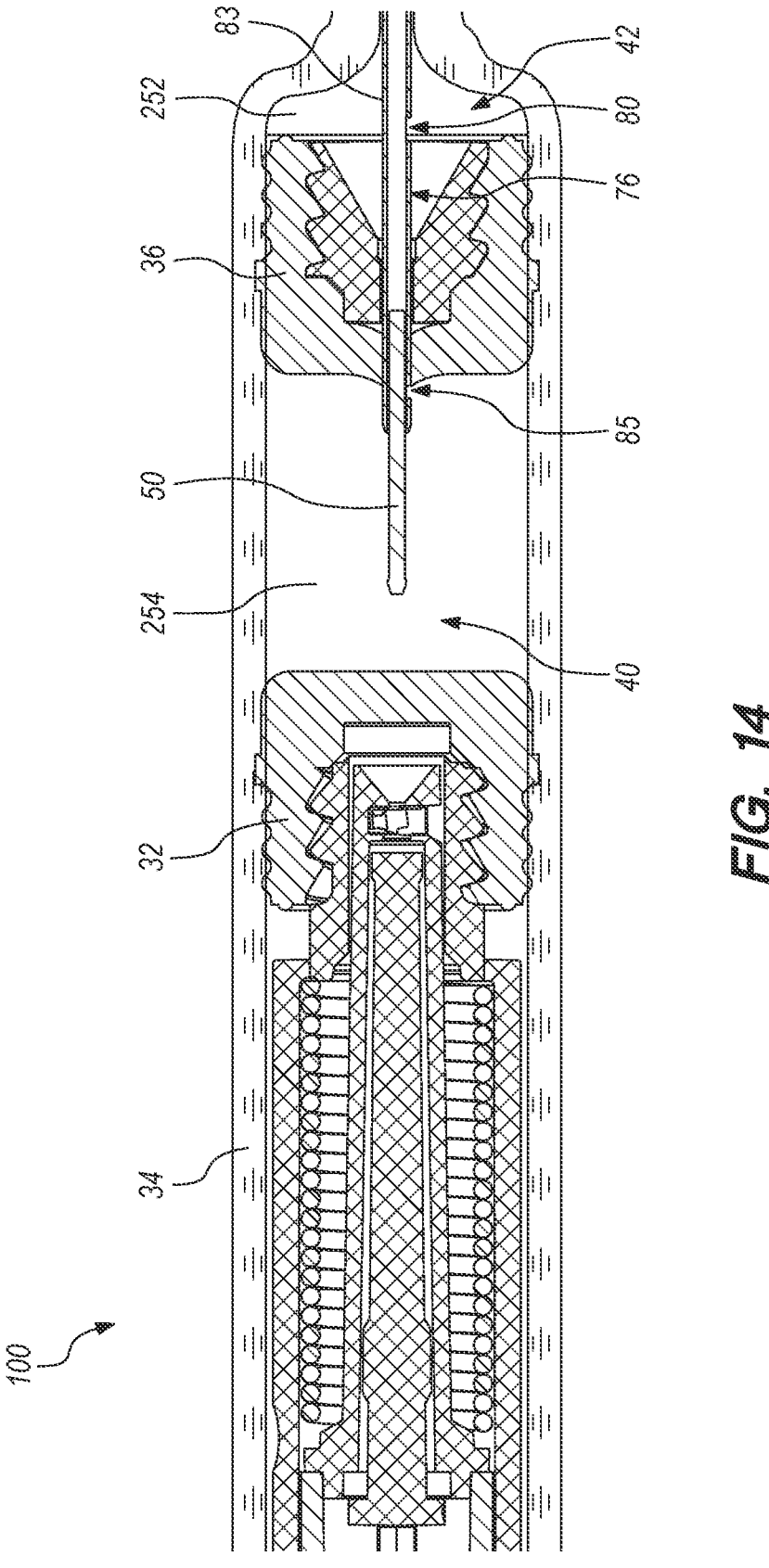

FIGS. 13A, 13B, and 14 depict the prefilled dual chamber serial safe injection system (100) after the proximal stopper member (32) has been moved a first distance distally relative to the syringe body (34). The proximal chamber (40) has partially collapsed/been reduced in size, and some of the second liquid (254) has been ejected from the prefilled dual chamber serial safe injection system (100) through the distal opening (81). As shown in FIG. 14, because the proximal opening (85) is in the proximal chamber (40), there is now a flow path between the proximal chamber (40) and the distal opening (81). The flow path between the proximal chamber (40 and the distal opening (81) allows the proximal stopper member (32) to move distally toward the distal stopper member (36) by ejecting some of the second liquid (254) through the proximal opening (85). Because distally directed force applied to the plunger manipulation interface (128) is transmitted to move the proximal stopper member (32), the distal stopper member (36) has substantially stopped moving at this point.

Figures 15A, 15B:
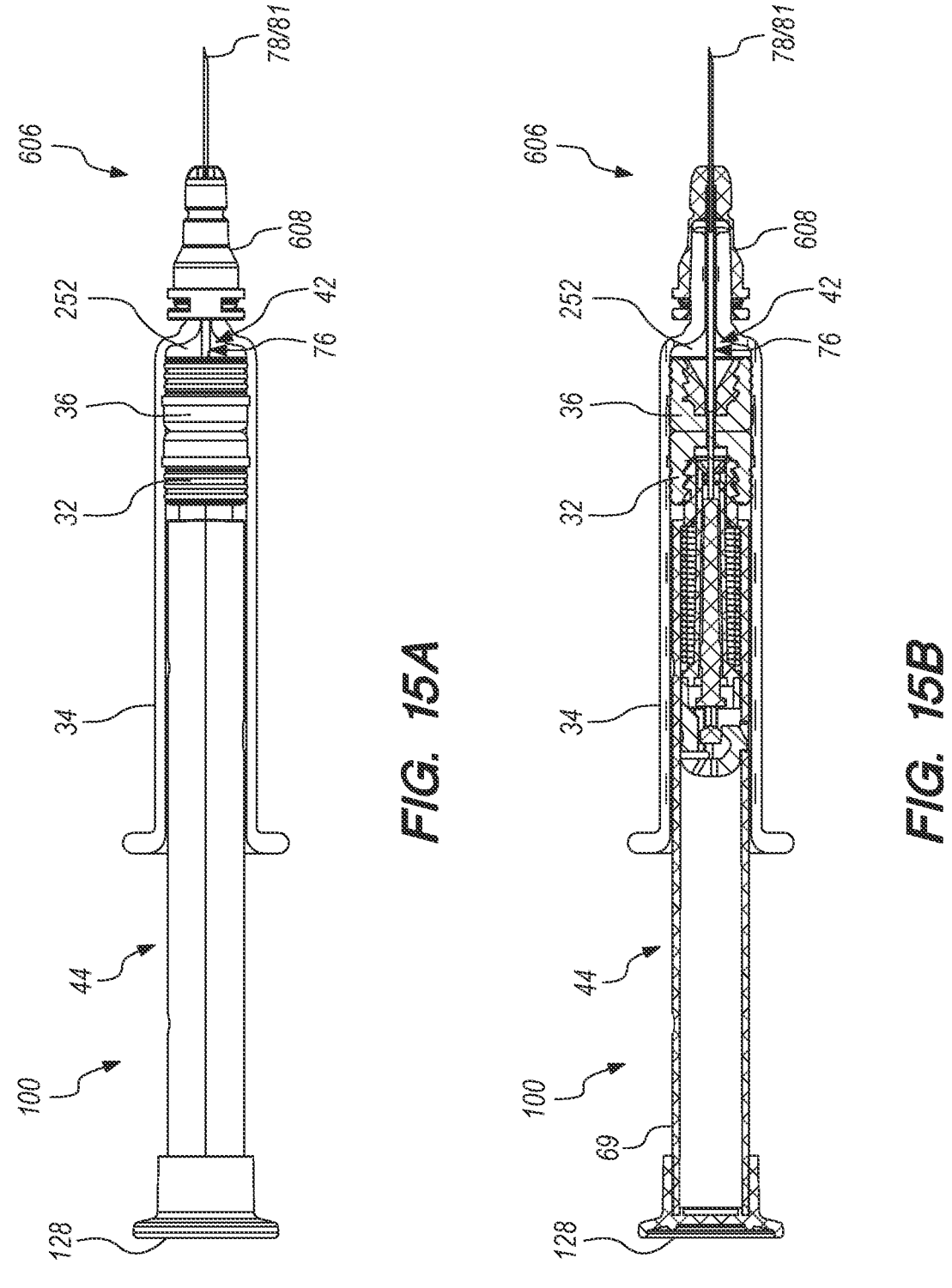
Figure 16:
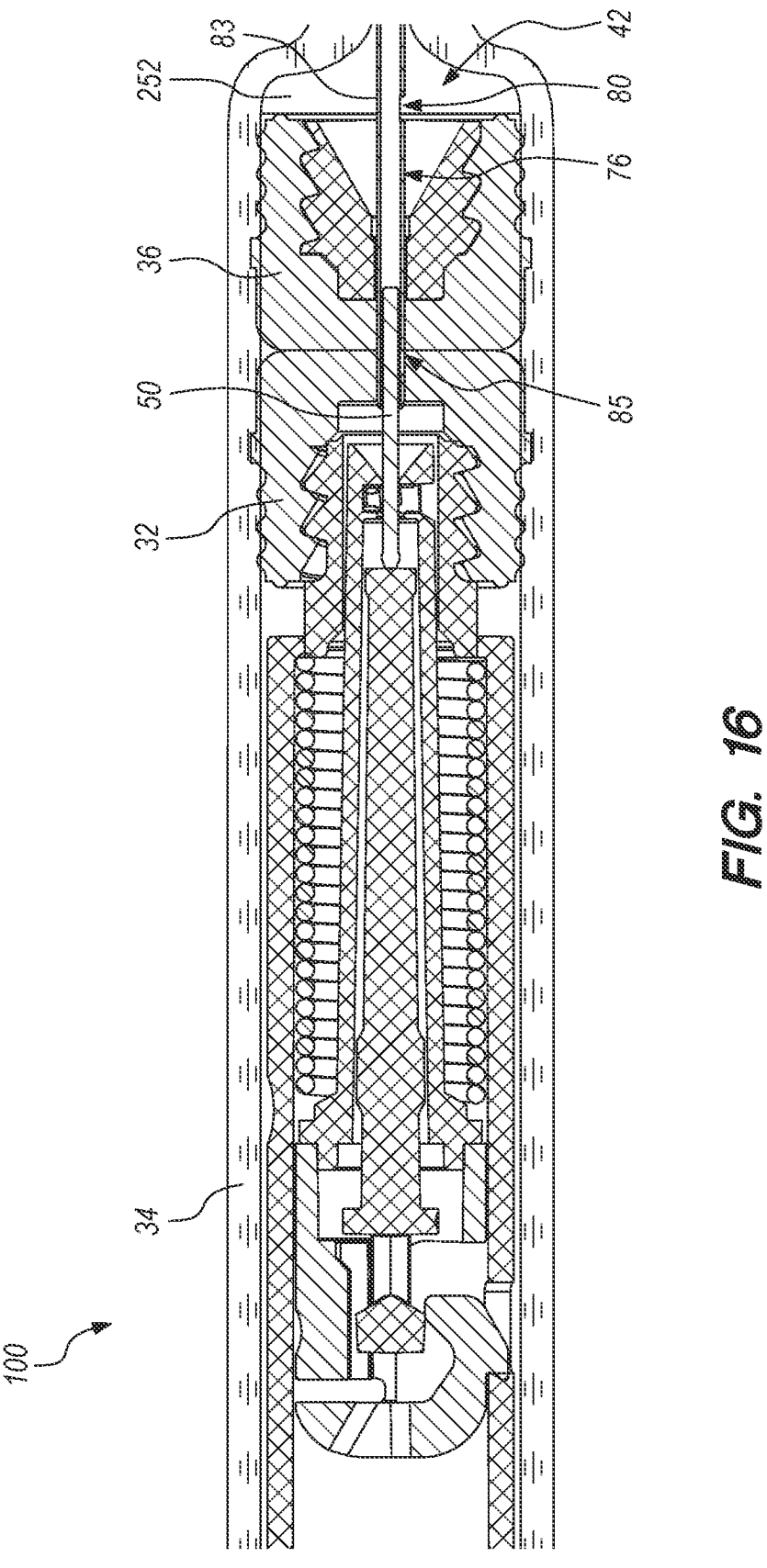

FIGS. 15A, 15B, and 16 depict the prefilled dual chamber serial safe injection system (100) after the proximal stopper member (32) has been moved a second distance (further than the first distance) distally relative to the syringe body (34). The proximal chamber (40) has completely collapsed/been eliminated, and substantially all of the second liquid (254) has been ejected from the prefilled dual chamber serial safe injection system (100) through the distal opening (81). Further moving the proximal stopper member (32) distally relative to the syringe body (34) has also caused the proximal end (50) of the needle (76) to penetrate the proximal stopper member (32) and enter the plunger assembly (44). With penetration of the proximal stopper member (32), the proximal end (50) of the needle (76) is captured by a needle retention feature as described in U.S. Utility patent application Ser. No. 16/435,429, which was previously incorporated by reference herein.

As shown in FIG. 16, the length of the proximal opening (85) provides tolerance for variability in the positions of the proximal and distal stopper members (32, 36) as the proximal chamber (40) is collapsed. In particular, even if the proximal end distal stopper members (32, 36) are disposed in slightly different positions as the proximal chamber (40) is collapsed, the proximal opening (85) will still fluidly couple the proximal chamber (40) at the distal opening (81). The length of the proximal opening (85) is also configured to avoid retrograde leaking of the first and second liquids (252, 254) into the plunger assembly (44), by limiting the distance between the proximal opening (85) and the solid needle proximal end (50) such that the proximal opening (85) will never enter the plunger assembly (44).

Figures 17A, 17B:
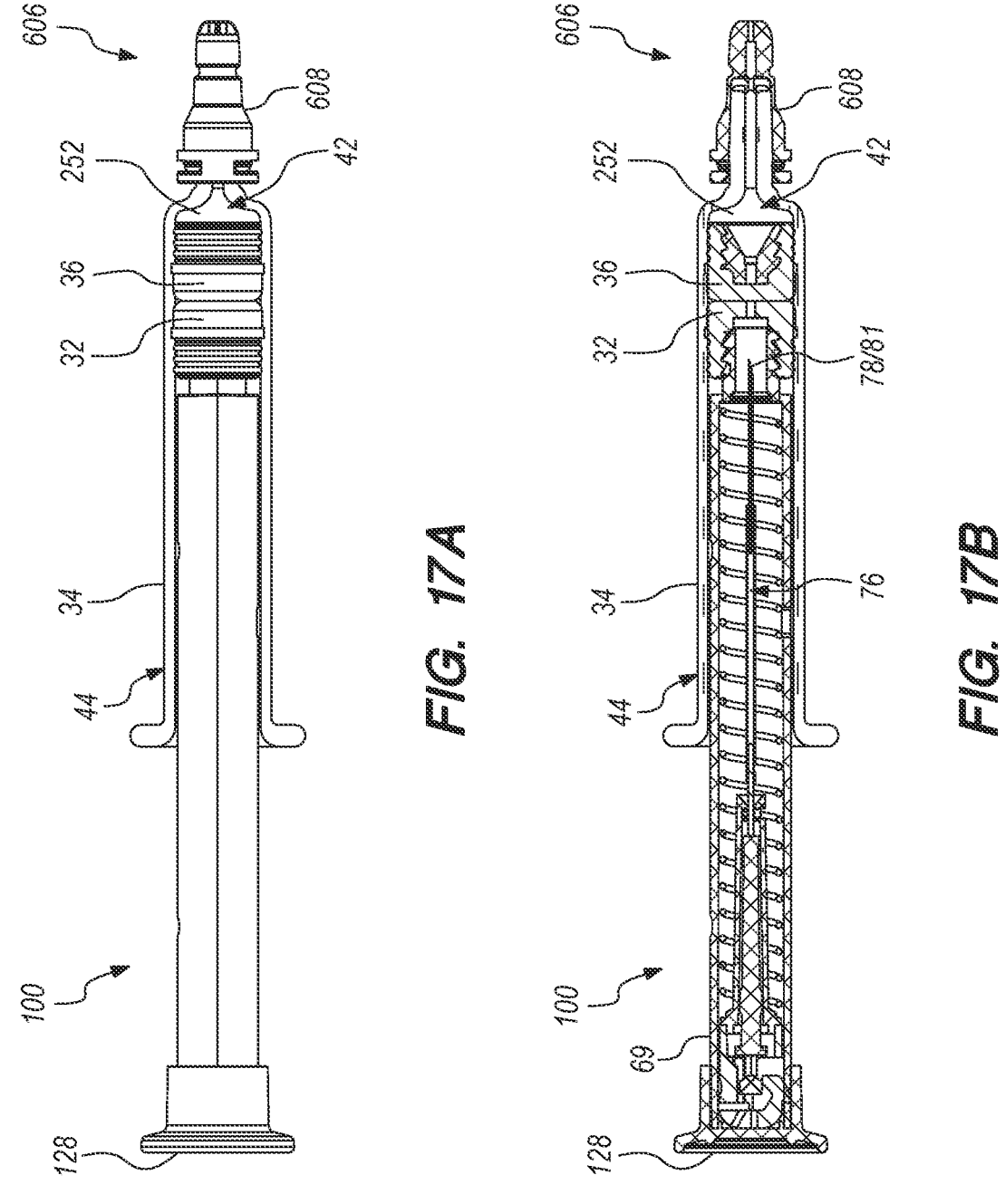
Figure 18:
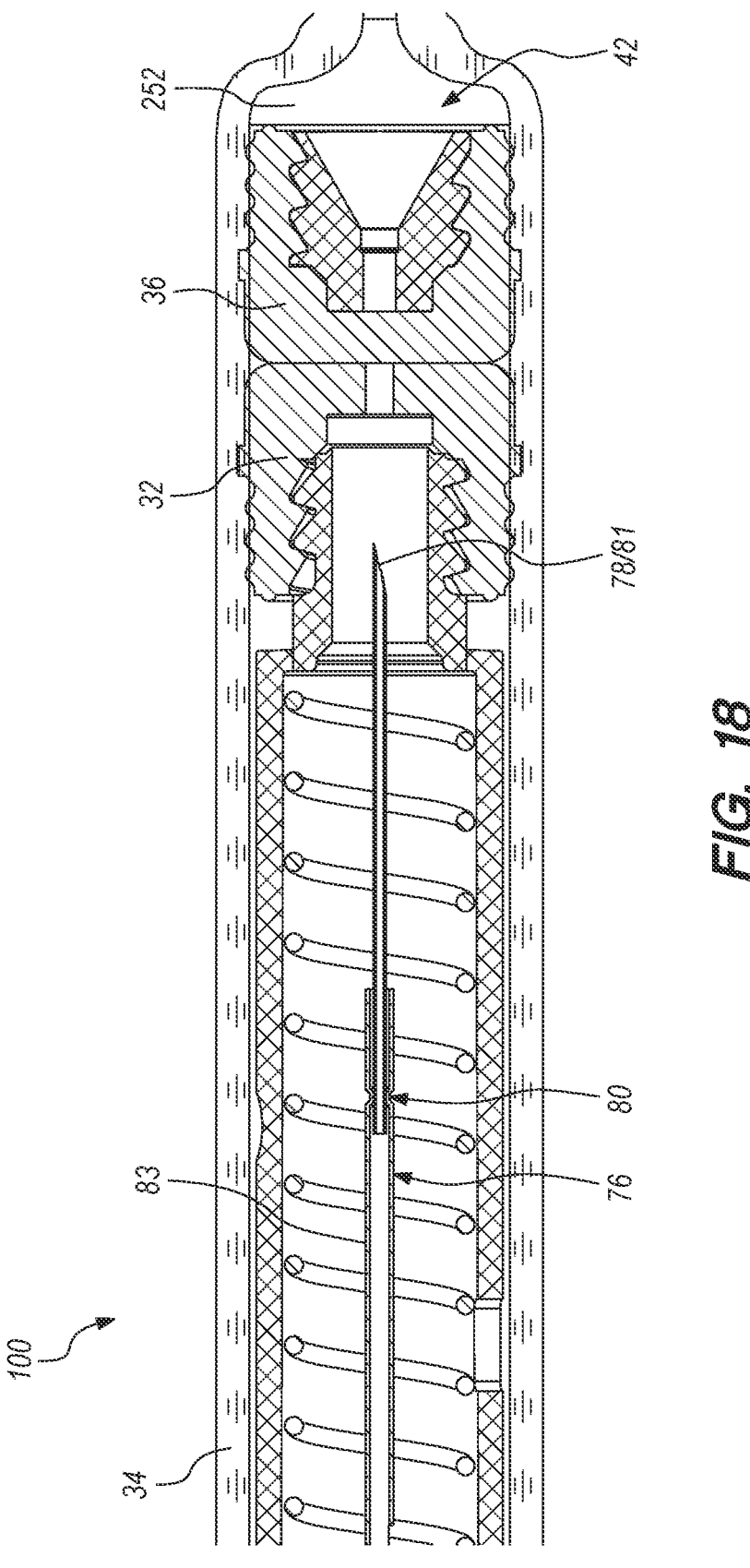

FIGS. 17A, 17B, and 18 depict the prefilled dual chamber serial safe injection system (100) after the proximal stopper member (32) has been moved a third distance (further than the first and second distances) distally relative to the syringe body (34). With movement of the proximal end (50) of the needle (76) further proximally into the plunger assembly (44), an energy-storage member latch is actuated releasing an energy-storage member (spring), which pulls/retracts the needle (76) at least partially into the plunger assembly (44) to position the sharp distal end (78) of the needle (76) inside of the syringe body (34). Retraction of the needle (76) places the prefilled dual chamber serial safe injection system (100) in a safe configuration for disposal after injection.

Figures 19A, 19B:
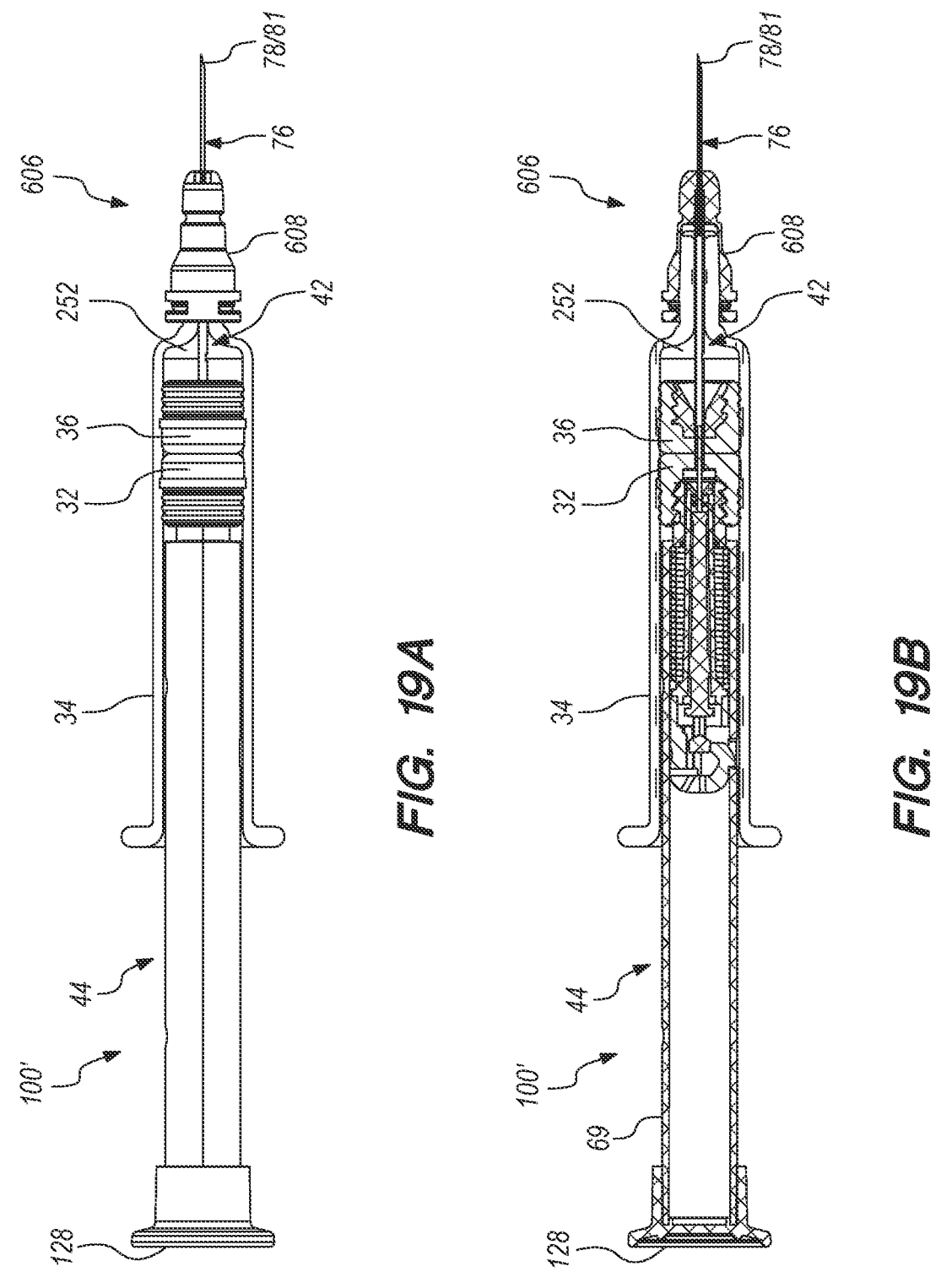
Figure 20:
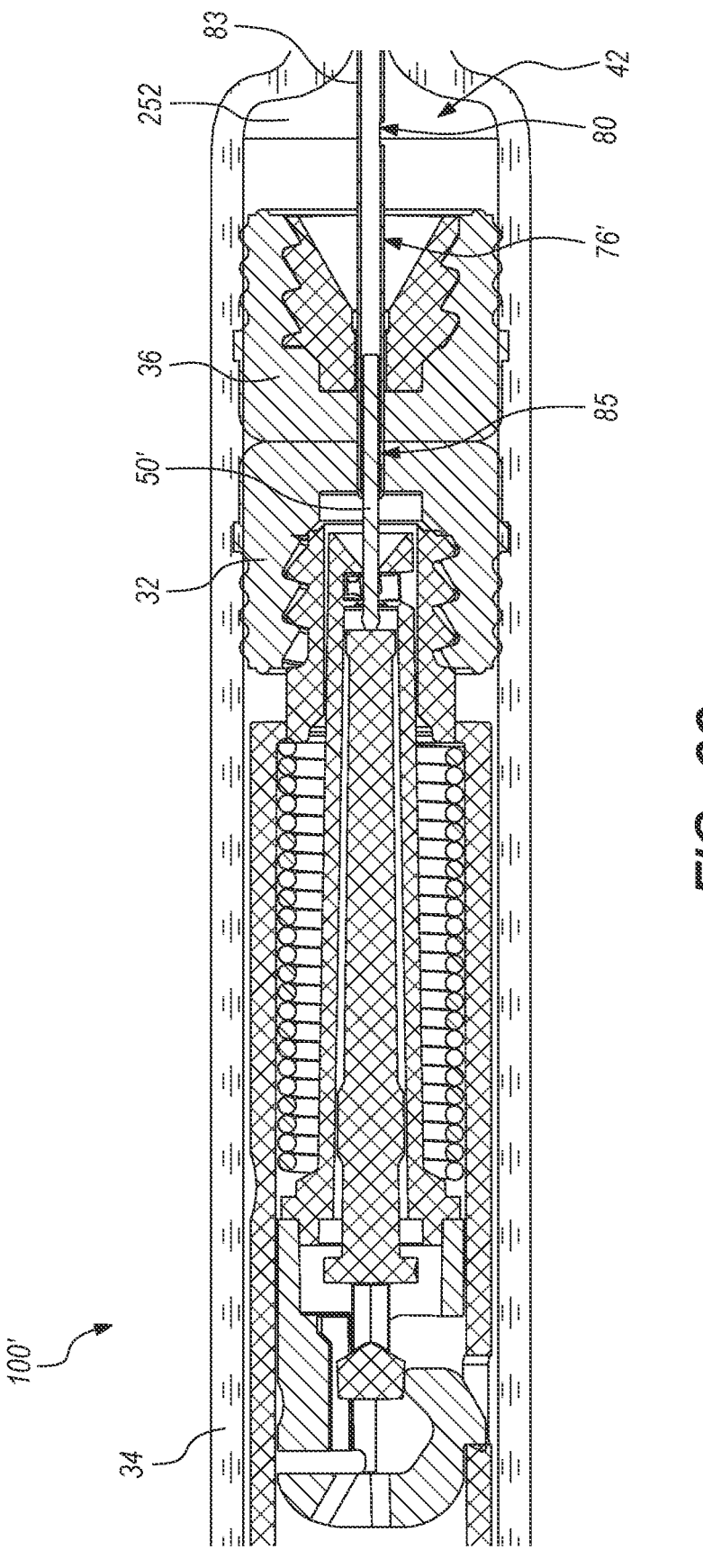

FIGS. 19A-22 depict a late portion of a safe sequential injection method using a prefilled dual chamber serial safe injection system (100') described herein according to some embodiments. FIGS. 19A, 19B, and 20 depicts the prefilled dual chamber serial safe injection system (100') in the middle of a safe sequential injection method in a step similar to the step in the method depicted in FIGS. 15A, 15B, and 16, which uses system (100). One difference between the prefilled dual chamber serial safe injection systems (100, 100') is that the proximal end (50') and needle (76') of system (100') is longer than the corresponding proximal end (50) and needle (76) of system (100). As such, the proximal opening (85) of system (100') enters the proximal chamber (not shown, but see (40) in FIG. 7) before the distal chamber (42) has substantially collapsed. Accordingly, during steps corresponding to those in FIGS. 6A-14, only a first portion of the first liquid (252) is ejected from the distal chamber (42). As shown in FIG. 20, when the proximal chamber (40) has completely collapsed/been eliminated, and substantially all of the second liquid (254) has been ejected from the prefilled dual chamber serial safe injection system (100) through the distal opening (81), a second portion of the first liquid (252) remains in the distal chamber (42).

Figures 21A, 21B:
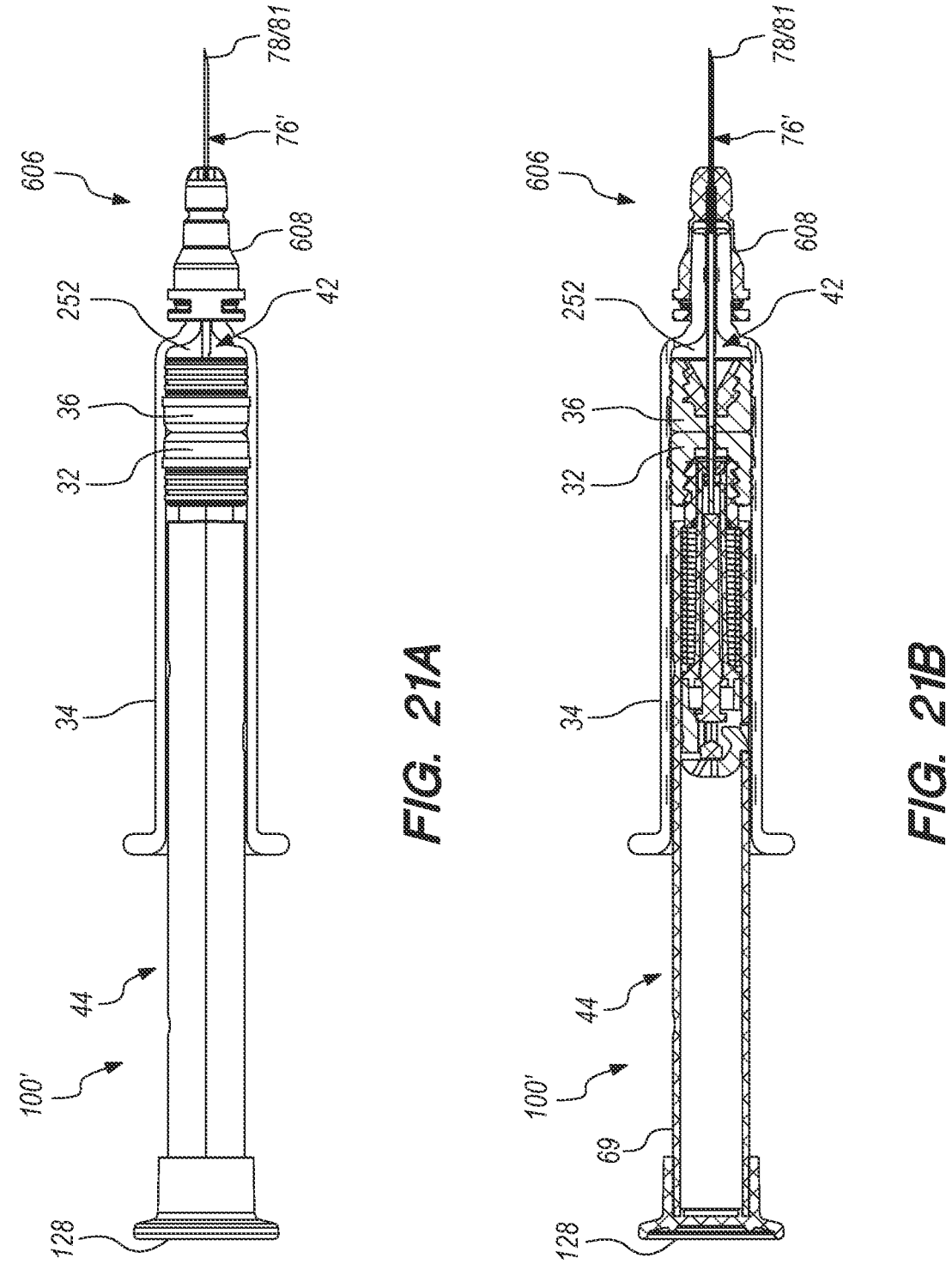
Figure 22:
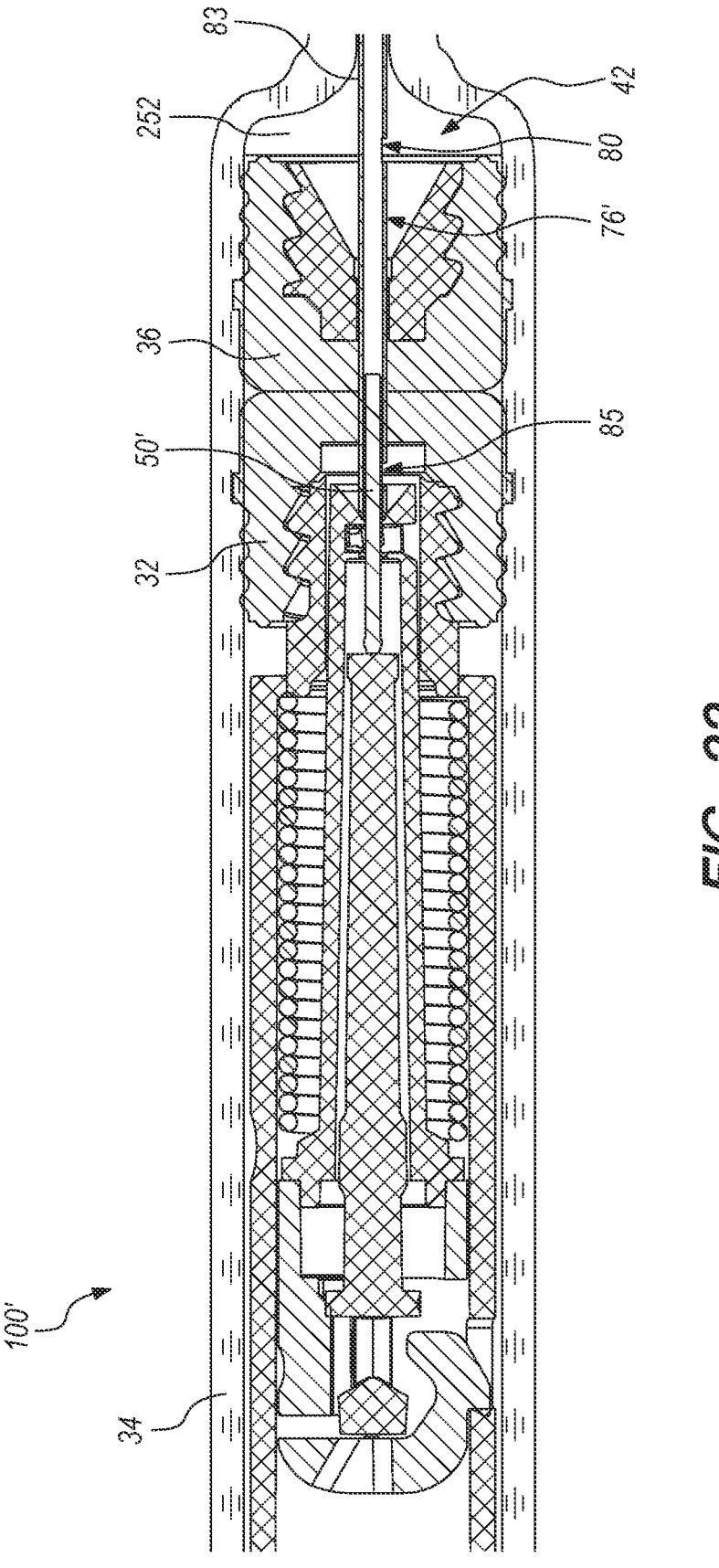

FIGS. 21A, 21B, and 22 depict the prefilled dual chamber serial safe injection system (100') after the proximal and distal stopper members (32, 36) has been moved a distance distally relative to the syringe body (34). Moving the proximal and distal stopper members (32, 36) distally relative to the syringe body (34) ejects the second portion of the first liquid (252) from the distal chamber (42) through the middle opening (80). The ejections/injection pattern of the embodiment depicted in FIGS. 19A-22 is a first portion of the first liquid (252) in the distal chamber (42), followed by substantially all of the second liquid (254) in the proximal chamber (40), and lastly a second portion of the first liquid (252) in the distal chamber (42). After the second portion of the first liquid (252) has been ejected, the needle (76') is retracted at least partially into the plunger assembly 44 as shown in FIGS. 17A, 17B, and 18 and described above. While specific portions of the first liquid (252) were depicted in FIGS. 19A-22, the dimensions of various portions of the needle (76') can be modified to adjust the portions of the first liquid (252).

Figures 23A, 23B:
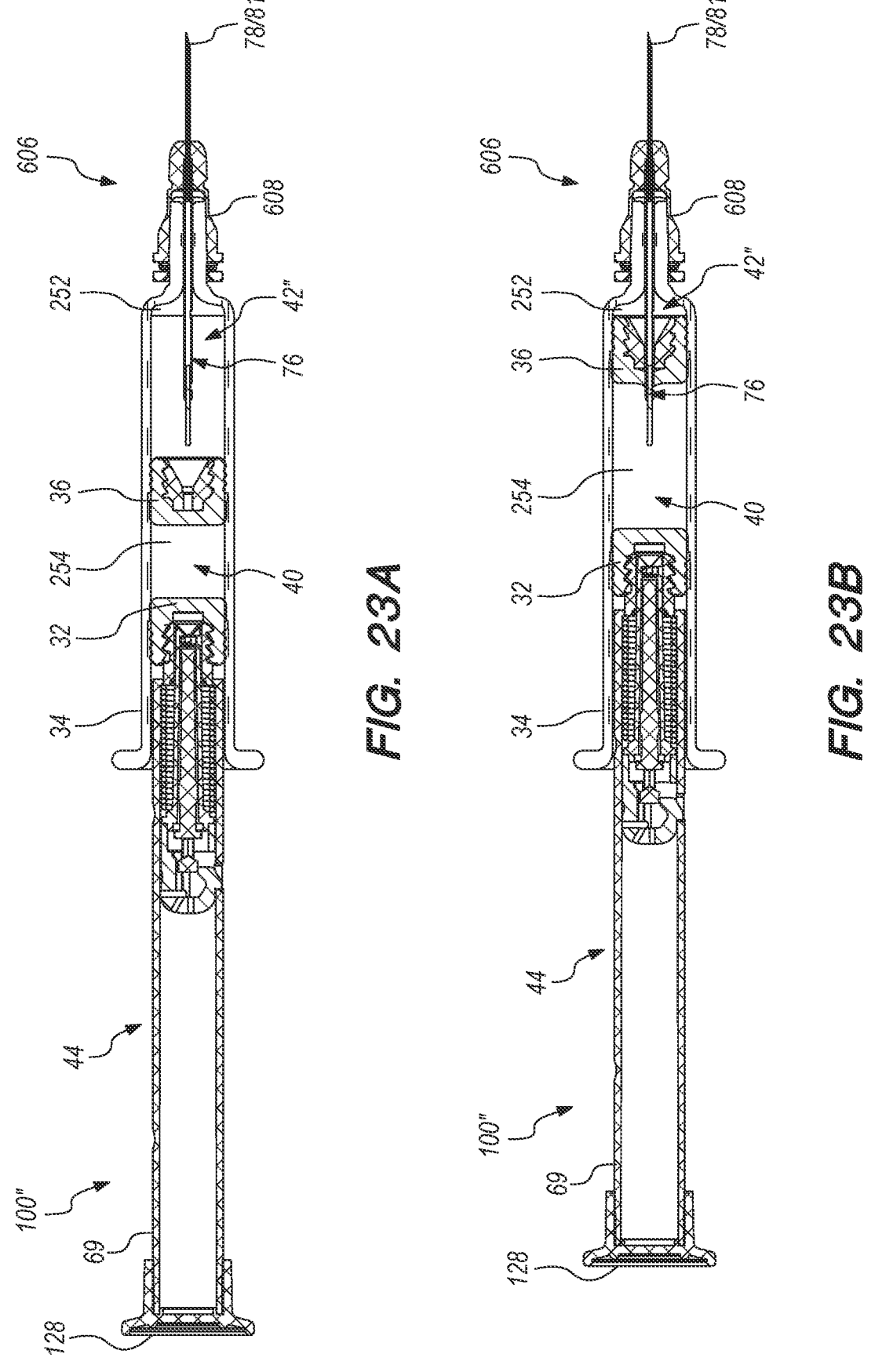
Figure 24:
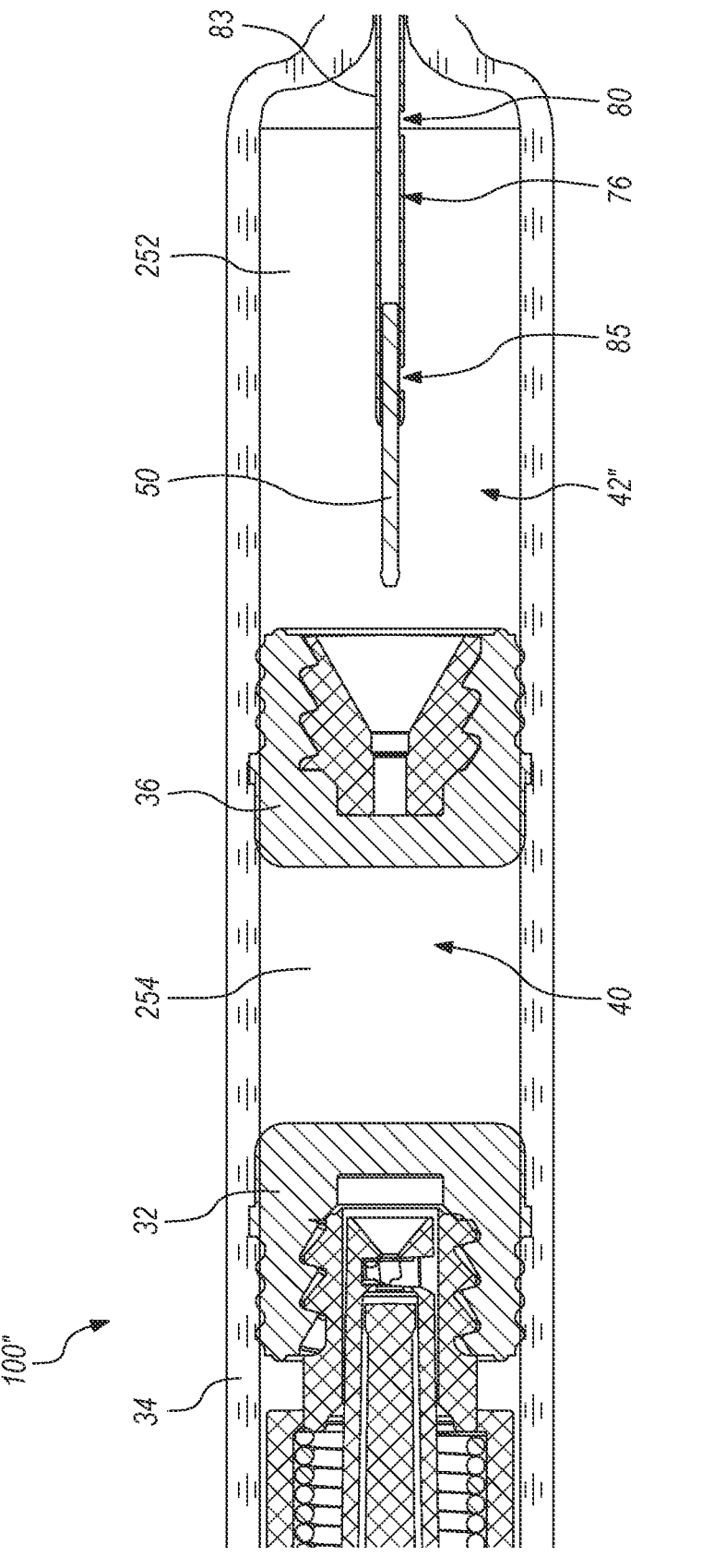

FIGS. 23A, 23B, and 24 depict a prefilled dual chamber serial safe injection system (100") in a first/ready to use configuration according to some embodiments. The various components of the prefilled dual chamber serial safe injection system (100") may be identical to the corresponding components of the prefilled dual chamber serial safe injection system (100) depicted in FIGS. 6A-18. One difference between the prefilled dual chamber serial safe injection systems (100, 100") is that the system (100") depicted in FIGS. 23A, 23B, and 24 has a larger distal chamber (42") compared to the distal chamber (42) of the system (100) depicted in FIGS. 6A-18. As such, the system (100") is configured to inject more of the first liquid (252) from the larger distal chamber (42"). In fact, the distal chamber (42") is larger because more first liquid (252) was added during manufacture of the system (100"). The system (100") can be used to serially inject first and second liquids (252, 254) in a method similar to the method depicted in FIGS. 6A-18 and described herein.

As shown in the prefilled dual chamber serial safe injection systems (100, 100', 100"), various components of the systems (100, 100', 100") and their positions can be modified to tailor the amounts of first and second liquids (252, 254) to be injected, including portions of the first liquid (252) that may be injected before and after the second liquid (254).

II. Triple Chamber Injection System and Method

Figures 25A, 25B:
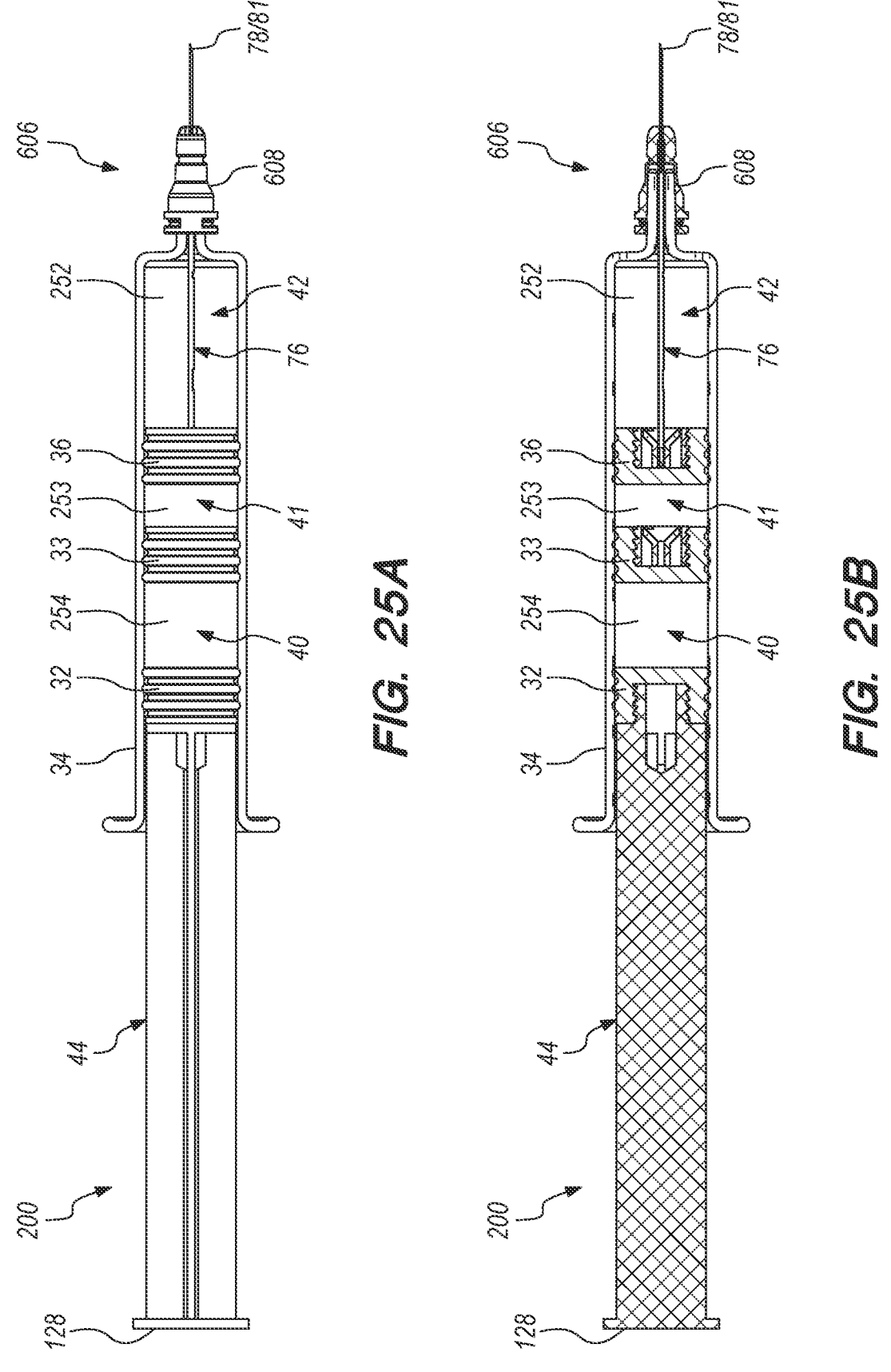
Figure 26:
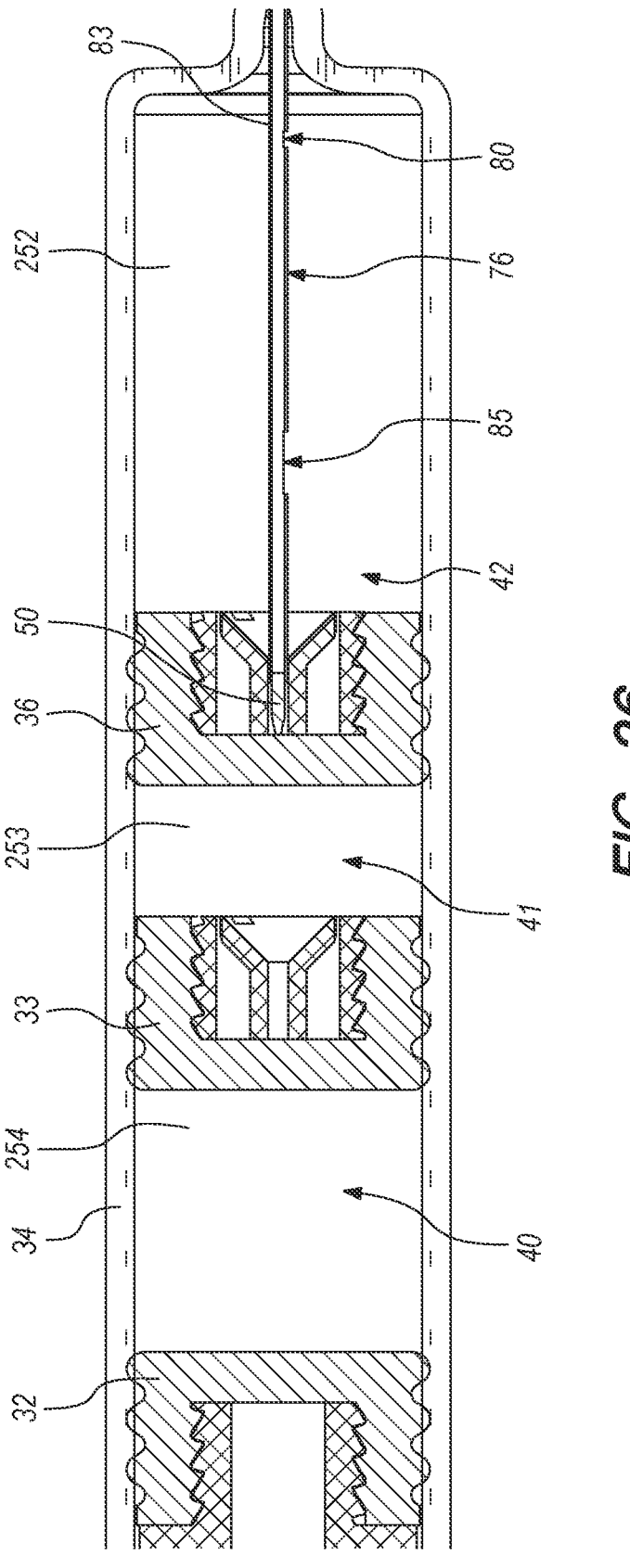

FIGS. 25A, 25B, and 26 are a longitudinal side view, a longitudinal cross-section view, and a detailed longitudinal cross-section view depicting a prefilled triple chamber serial injection system (200) according to some embodiments. The prefilled triple chamber serial injection system (200) includes a conventional off-the-shelf prefilled syringe body (34) with conventional off-the-shelf proximal, middle, and distal stopper members (32, 33, 36) disposed therein. The proximal, middle, and distal stopper members (32, 33, 36) together with the syringe body (34) define proximal, middle, and distal chambers (40, 41, 42). First, second, and third liquids (252, 253, 254) are contained in the distal, middle, and proximal chambers (42, 41, 40) respectively. The proximal and middle stopper members (32, 33) occlude the proximal and distal ends of the proximal chamber (40). The middle and distal stopper members (33, 36) occlude the proximal and distal ends of the middle chamber (41). The distal stopper member (36) occludes a proximal end of the distal chamber (42). In some embodiments, various surfaces of the proximal, middle, and distal stopper members (32, 33, 36) are each coated with a lubricious polymer coating (e.g., PTFE or ETFE), such that the coatings together with the syringe body (34) define the distal, middle, and proximal chambers (42, 41, 40). The lubricious polymer coating also serves to isolate the rubber of the proximal, middle, and distal stopper members (32, 33, 36) from the first, second, and third liquids (252, 253, 254), respectively. The proximal, middle, and distal stopper members (32, 33, 36) may be oriented as shown in FIGS. 6A and 6B or the distal stopper (36) may be flipped.

A needle hub assembly (606) is disposed at the distal end of the distal chamber (42). The needle hub assembly (606) includes a needle hub (608) and a needle spine assembly ("needle") (76) coupled thereto. In some embodiments, a needle cover member (not shown) may be installed on the needle hub assembly (606) for storage. The prefilled triple chamber serial injection system (200) facilitates sequential injection of a first portion of the first liquid (252) from the distal chamber (42) followed by injection of the second liquid (253) from the middle chamber (41) followed by injection of the remaining portion of the first liquid (252) from the distal chamber (42) followed by injection of the third liquid (254) from the proximal chamber (40) subject to sequential insertion of a plunger assembly (44) relative to the syringe body (34) to various degrees by a user. The plunger assembly (44) is coupled to the proximal stopper member (32) and includes a plunger manipulation interface (128). The first, second, and third liquids (252, 253, 254) located in the distal, middle, and proximal chambers (42, 41, 40) respectively may be any liquid or gel, such as aqueous or oil based medicine solutions.

The prefilled triple chamber serial injection system (200) has a staked needle configuration wherein upon presentation to the user, a needle hub assembly (606) is mounted in position ready for injection after removal of a needle cover member (not shown) which may comprise an elastomeric sealing material on its internal surface to interface with a needle distal end (78) and/or the distal hub (608) during storage. While the staked needle is depicted as mounted in position, the staked needle may be removably coupled to the syringe body (34) using a Luer slip or a Luer lock interface (not shown), with the proximal end (50; see FIG. 26) of the needle (76) extending through the Luer interface and into the distal chamber (42). Alternatively, the needle may be fixedly or removably mounted to the flange on a cartridge body instead of a syringe. Such cartridge injection systems are disclosed in U.S. Utility patent application Ser. No. 15/801, 281, which was previously incorporated by reference herein.

The needle (76) includes a needle proximal end (50; see FIG. 26) and a needle distal end (78; see FIGS. 6A and 6B) coupled to opposite (i.e., respective proximal and distal) ends of a needle joining member (83; see FIG. 7). The needle joining member (83) is a tubular member coupled to the sharp needle distal end (78), which also defines a distal opening (81). The needle joining member (83) also defines proximal and middle openings (85, 80). The middle opening (80) is disposed adjacent a distal end of the syringe body (34). The proximal opening (85) is disposed adjacent a proximal end of the needle joining member (83). The needle proximal end (50) is a solid proximal end feature.

The prefilled triple chamber serial injection system (200) includes many of the same components and is assembled in a similar manner to the prefilled dual chamber serial safe injection system (100) depicted in FIGS. 6A-18. For instance the tubular needle joining member (83) is welded to the solid needle proximal end (50) with a fillet weld configured to facilitate the needle (76) penetrating a rubber stopper, such as the distal stopper member (36), while reducing or eliminating cutting/shredding of the rubber stopper (described herein). The proximal and distal edges of the proximal opening (85) may also be rounded (e.g., by tumbling or grinding) to reduce or eliminate cutting/shredding of rubber stoppers during penetration thereof.

The elongated slot, which can be formed in the tubular needle joining member (83) using a grinding wheel. Using a grinding wheel facilitates bulk manufacturing of tubular needle joining members (83). The length of the proximal opening (85) is configured to provide a tolerance for a variability relating to the proximal, middle, and/or distal stopper members (32, 33, 36). The variability relating to the proximal, middle, and/or distal stopper members (32, 33, 36) may be distortion of a proximal surface of the distal stopper member, distortion of a proximal surface of the middle stopper member, a position of the proximal stopper member relative to the elongated slot, a position of the middle stopper member relative to the elongated slot, and/or a position of the distal stopper member relative to the elongated slot (described herein). In some embodiments, the length of the proximal opening (85) is between about 1/16 inch to about 1/8 inch. The proximal and distal edges of the proximal opening (85) may also be rounded (e.g., by tumbling or grinding) to reduce or eliminate cutting/shredding of rubber stoppers during penetration thereof as described herein.

Other details regarding the prefilled triple chamber serial injection system (200) are disclosed in U.S. Utility patent application Ser. No. 16/435,429, which was previously incorporated by reference herein. Additional components further include a funnel in the distal stopper member (36) to guide the needle proximal end (50) into the center of the distal stopper member (36).

FIGS. 25A-36 illustrate a sequential injection method using the prefilled triple chamber serial injection system (200) described herein according to some embodiments. FIGS. 25A, 25B, and 26 depict the prefilled triple chamber serial injection system (200) in a first/ready to use configuration. The only difference between the first/ready to use configuration and a shipping configuration (not shown) is that a needle cover member (not shown) present in the shipping configuration has been removed in the first/ready to use configuration. In the first/ready to use configuration, the proximal opening (85) is disposed in the distal chamber (42), along with the middle opening (80). As such, there is no flow path between the middle and proximal chambers (41, 40), and the distal opening (81). Therefore, any distally directed force applied to the plunger manipulation interface (128) is transferred through the plunger member (44), the proximal stopper member (32), the incompressible third liquid (254) in the proximal chamber (40), the middle stopper member (33), and the incompressible second liquid (253) in the middle chamber (41) to move the distal stopper member (36) distally relative to the syringe body (34). Moving the distal stopper member (36) distally relative to the syringe body (34) increases a pressure in the distal chamber (42), which drives the first liquid (252) from the distal chamber (42) through the middle and proximal openings (80, 85) and out the distal opening (81).

Figures 27A, 27B:
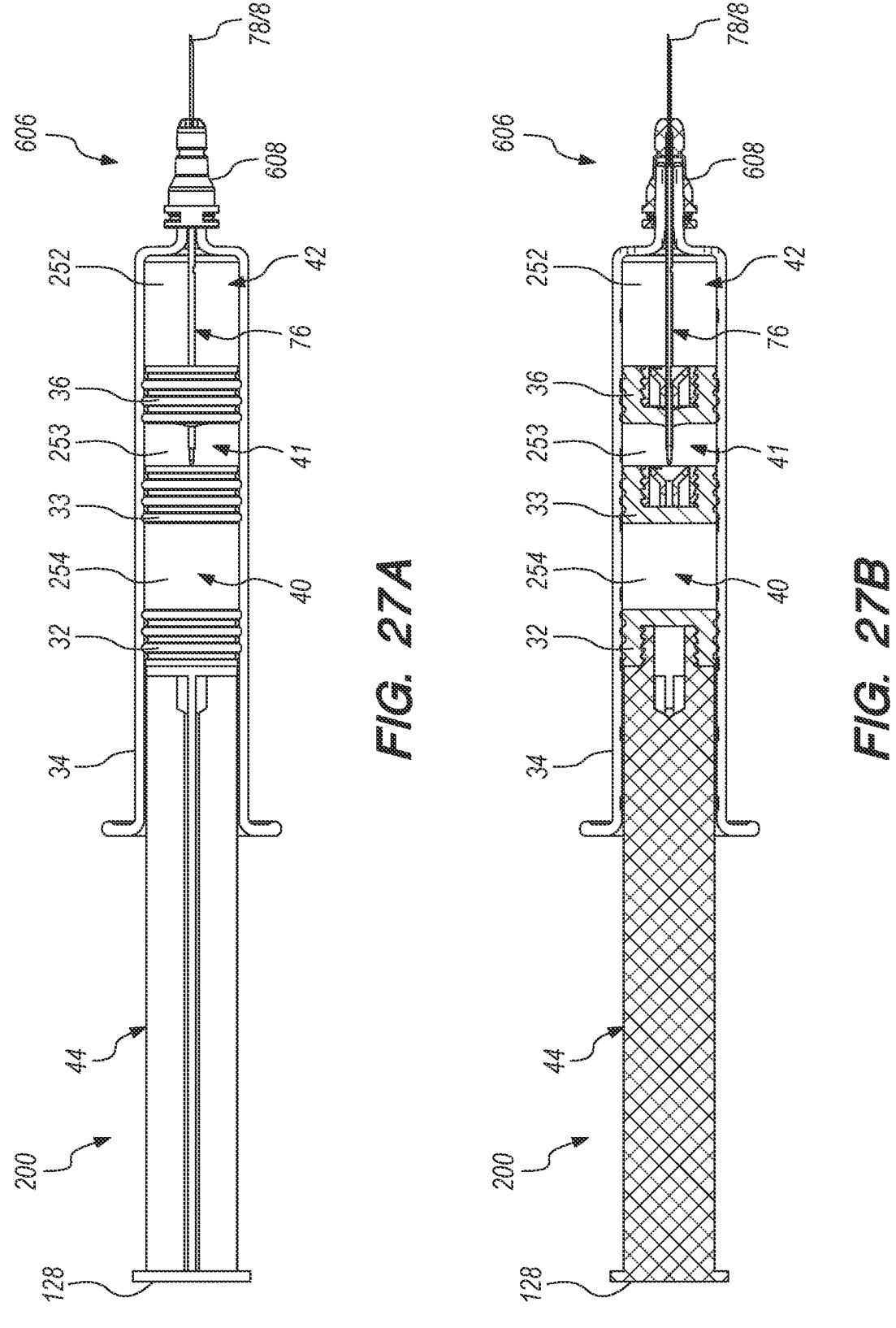
Figure 28:
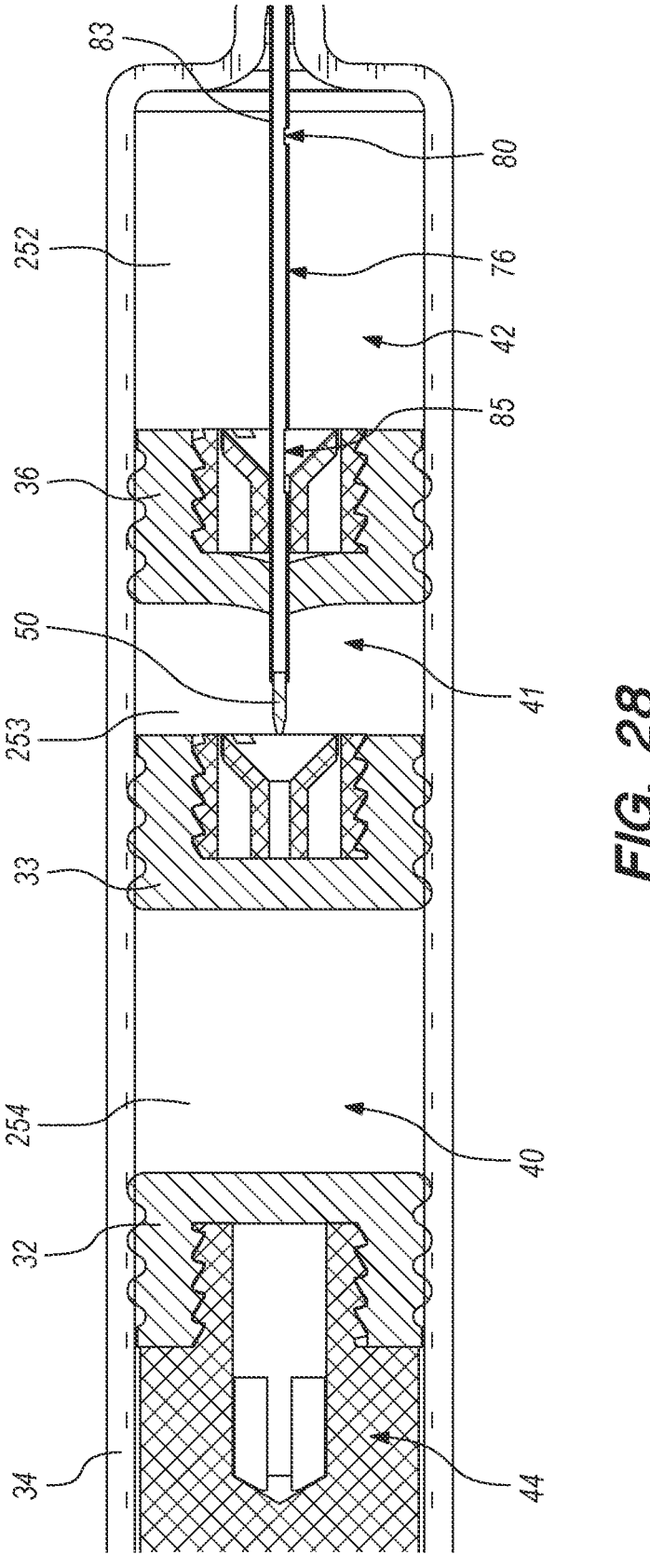

FIGS. 27A, 27B, and 28 depict the prefilled triple chamber serial injection system (200) after the distal stopper member (36) has been moved a first distance distally relative to the syringe body (34). The distal chamber (42) has partially collapsed/been reduced in size, and some of the first liquid (252) has been ejected from the prefilled triple chamber serial injection system (200) through the distal opening (81). Moving the distal stopper member (36) distally relative to the syringe body (34) has also caused the proximal end (50) of the needle (76) to penetrate the distal stopper member (36). As shown in FIG. 28, the rubber material from which the distal stopper member (36) is made deforms/tents in a proximal direction as the proximal end (50) of the needle (76) penetrates the distal stopper member (36) in a proximal direction due to friction between the distal stopper member (36) and the proximal end (50). This friction may be reduced by applying a lubricant to the various components of the prefilled triple chamber serial injection system (200). The proximal opening (85) is still in the distal chamber (42) or is occluded by the distal stopper member (36). Accordingly, there is no flow path between the middle chamber (41) and the distal opening (81), and distally directed force applied to the plunger manipulation interface (128) is still transmitted to the distal stopper member (36) as described above.

Figures 29A, 29B:
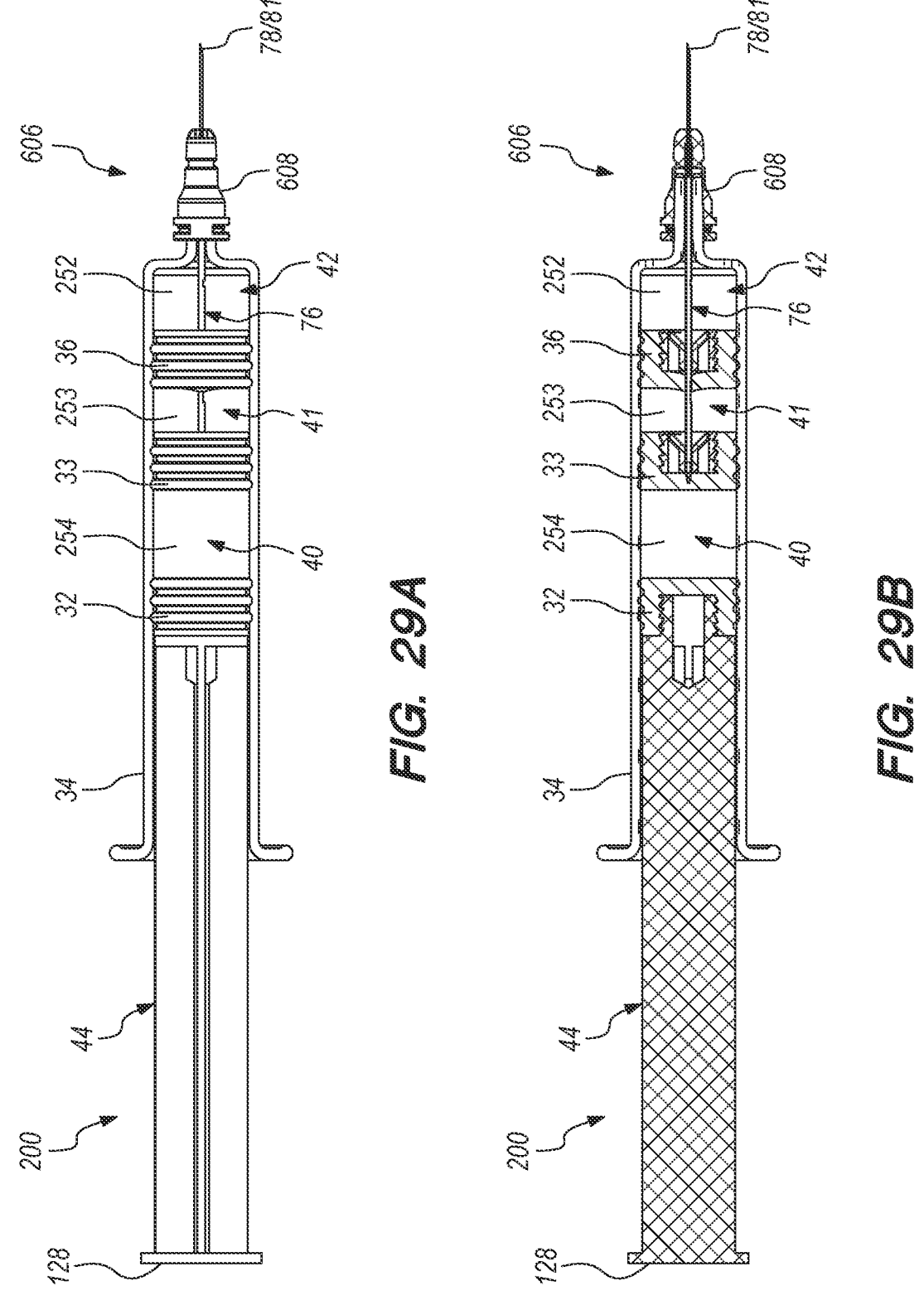
Figure 30:
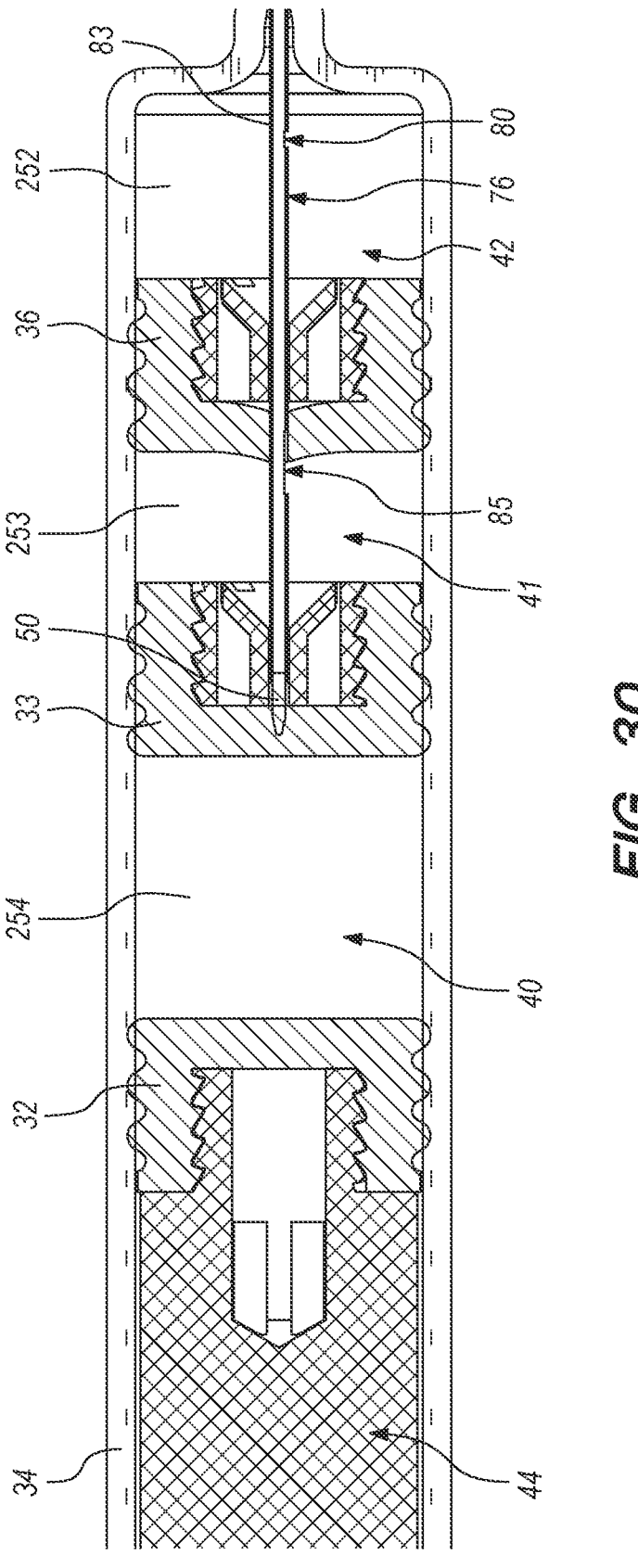

FIGS. 29A, 29B, and 30 depict the prefilled triple chamber serial injection system (200) after the distal stopper member (36) has been moved a second distance (further than the first distance) distally relative to the syringe body (34). The distal chamber (42) has further collapsed, and a first portion of the first liquid (252) has been ejected from the prefilled triple chamber serial injection system (200) through the distal opening (81). Further moving the distal stopper member (36) distally relative to the syringe body (34) has also caused the proximal end (50) of the needle (76) to further penetrate the distal stopper member (36). As shown in FIG. 30, the rubber material from which the distal stopper member (36) is made deforms/tents in a proximal direction as the proximal end (50) of the needle (76) penetrates the middle stopper member (33) in a proximal direction due to friction between the distal stopper member (36) and the proximal end (50). As also shown in FIG. 30, with penetration of the proximal end (50) of the needle (76) through the distal stopper member (36), the proximal opening (85) is now disposed in the middle chamber (41). Accordingly, there is now a flow path between the middle chamber (41) and the distal opening (81), and distally directed force applied to the plunger manipulation interface (128) now moves the middle stopper member (33) distally relative to the syringe body (34) to eject the second liquid (253) from the middle chamber (41). Opening of the flow path between the middle chamber (41) and the distal opening (81) places the prefilled triple chamber serial injection system (200) in a second configuration in which the second liquid (253) may be ejected from the middle chamber (41).

Figures 31A, 31B:
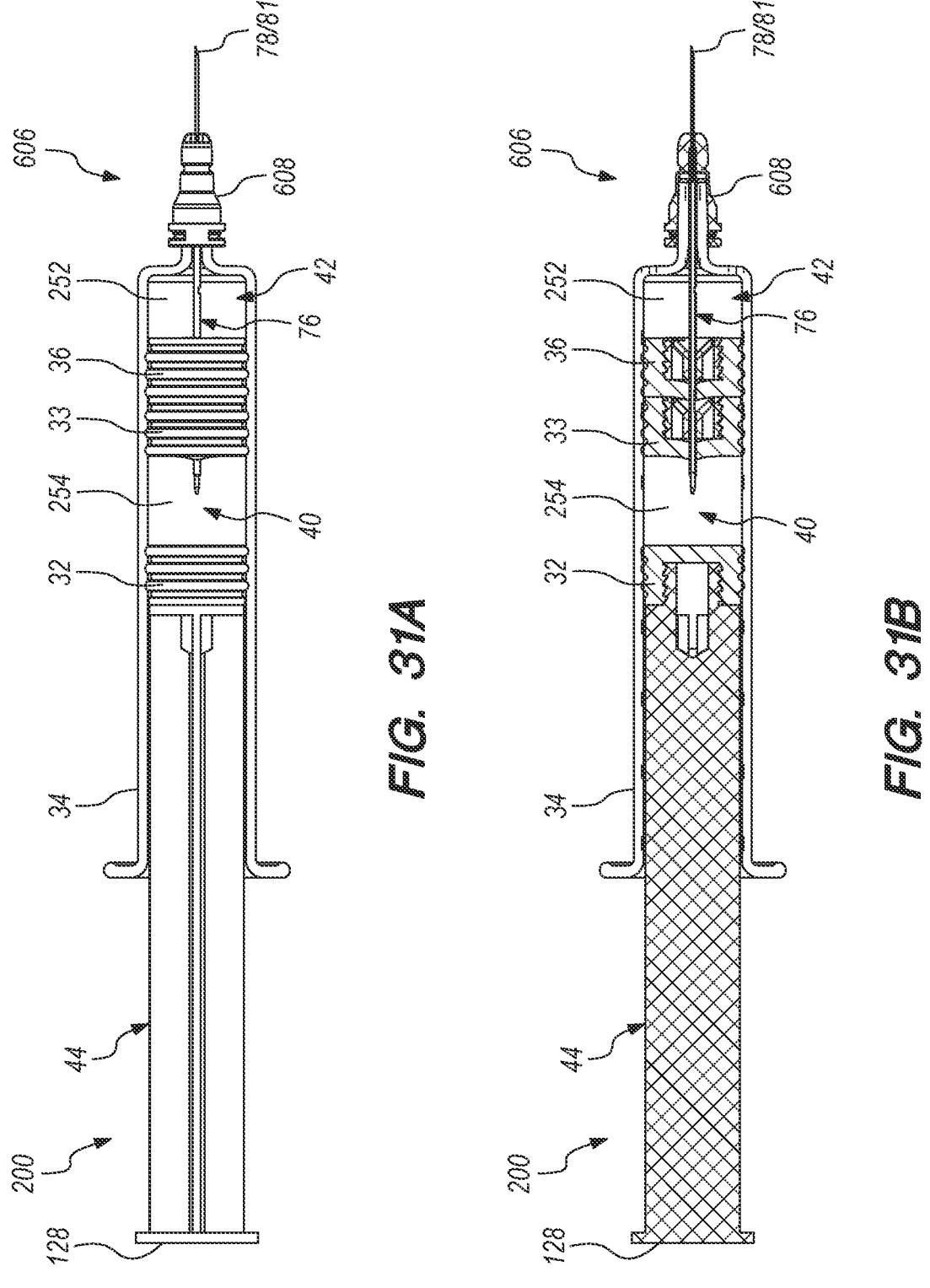
Figure 32:
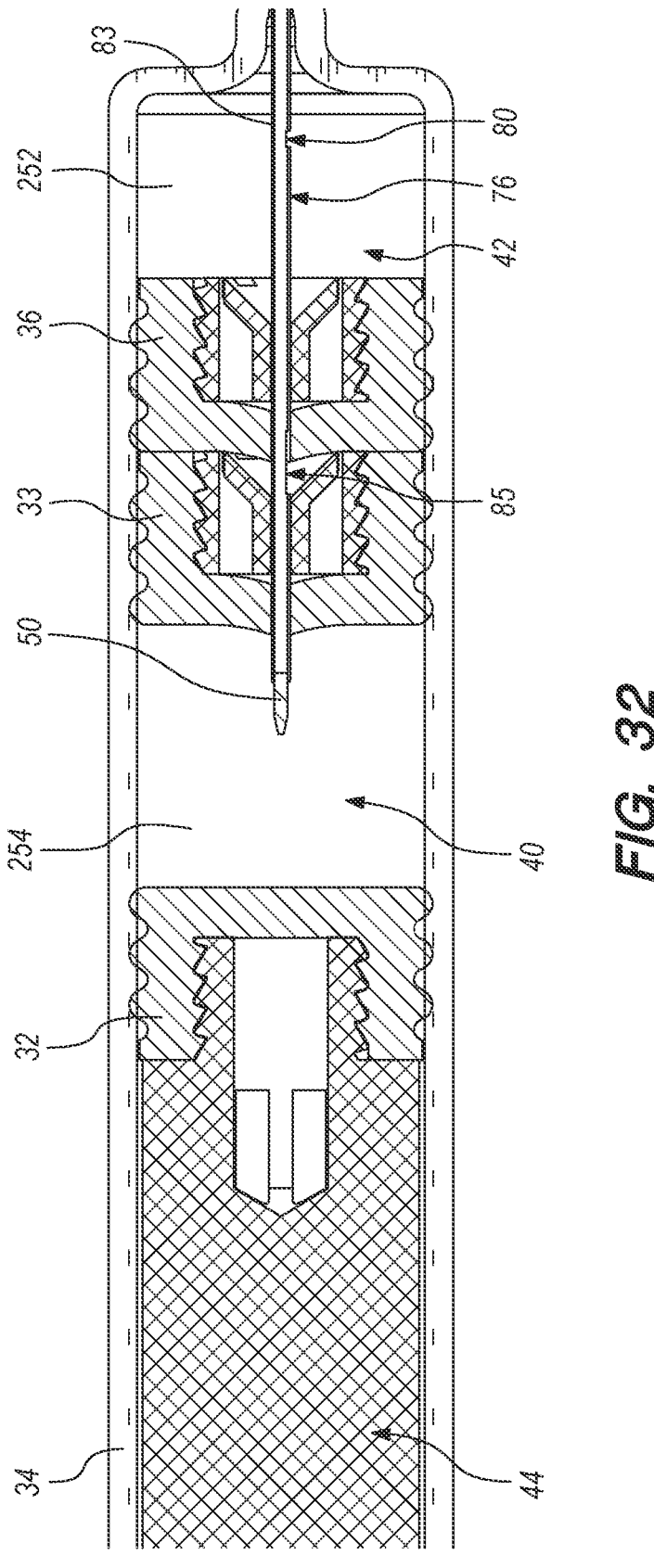

FIGS. 31A, 31B, and 32 depict the prefilled triple chamber serial injection system (200) after the middle stopper member (33) has been moved distally relative to the syringe body (34) until it contacts the distal stopper member (36). The middle chamber (41; see FIG. 26) has collapsed, and substantially all of the second liquid (253) has been ejected from the prefilled triple chamber serial injection system (200) through the distal opening (81). Further moving the middle stopper member (33) distally relative to the syringe body (34) has also caused the proximal end (50) of the needle (76) to penetrate the middle stopper member (33). As shown in FIG. 32, the rubber material from which the middle stopper member (33) is made deforms/tents in a proximal direction as the proximal end (50) of the needle (76) penetrates the distal stopper member (36) in a proximal direction due to friction between the middle stopper member (33) and the proximal end (50). As also shown in FIG. 32, with penetration of the proximal end (50) of the needle (76) through the middle stopper member (33), the proximal opening (85) is now occluded by the middle and distal stopper members (33, 36). Accordingly, the only open flow path in the system (200) is from the distal chamber (42) through the distal opening (80) to the distal opening, and distally directed force applied to the plunger manipulation interface (128) now moves the middle and distal stopper members (33, 36) distally relative to the syringe body (34) to eject a second portion of the first liquid (252) from the distal chamber (42). Re-opening of the flow path between the distal chamber (42) and the distal opening (81) places the prefilled dual chamber serial safe injection system (100) in a third configuration in which a second portion of the first liquid (252) may be ejected from the distal chamber (42).

Figures 33A, 33B:
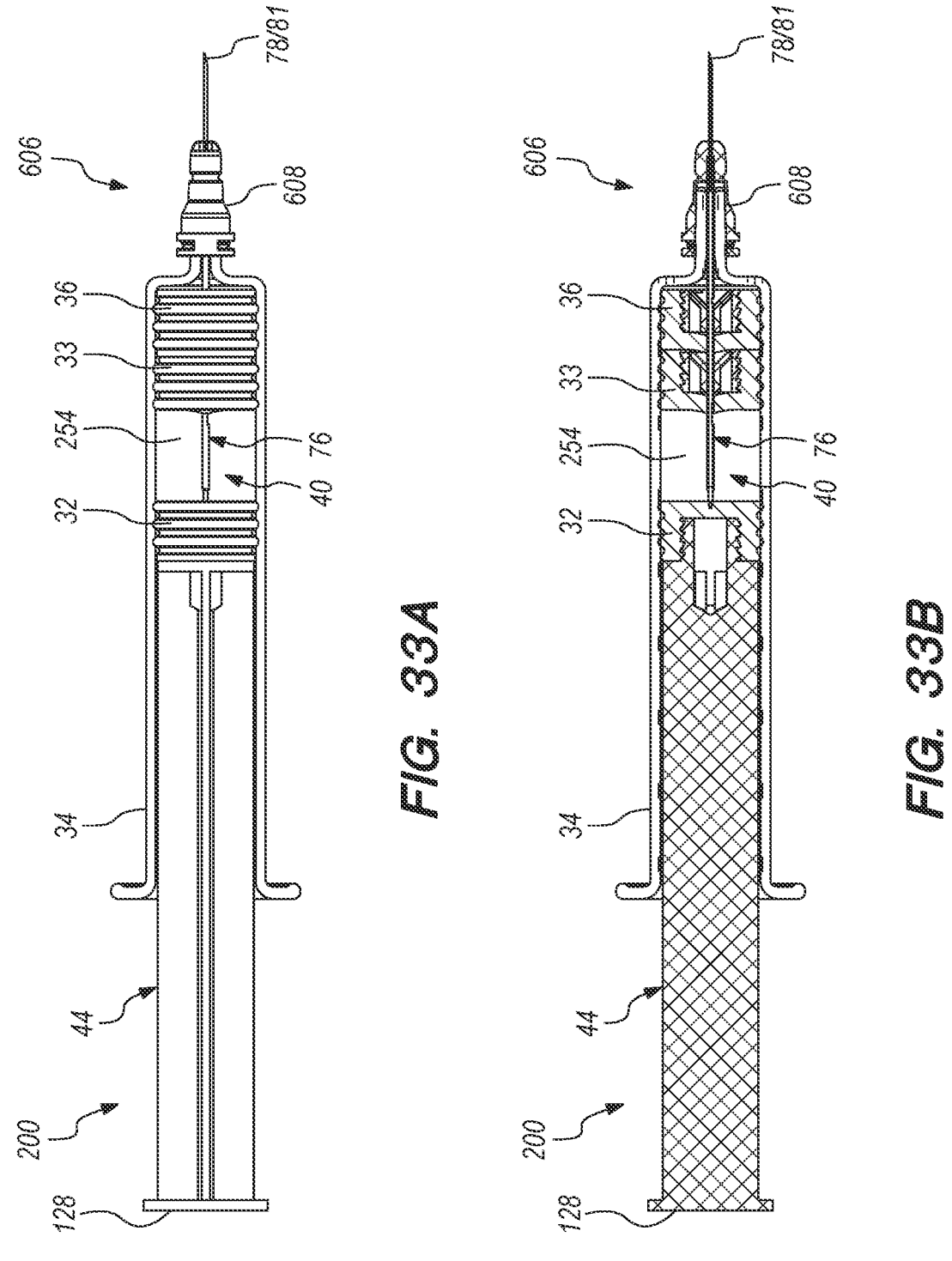
Figure 34:
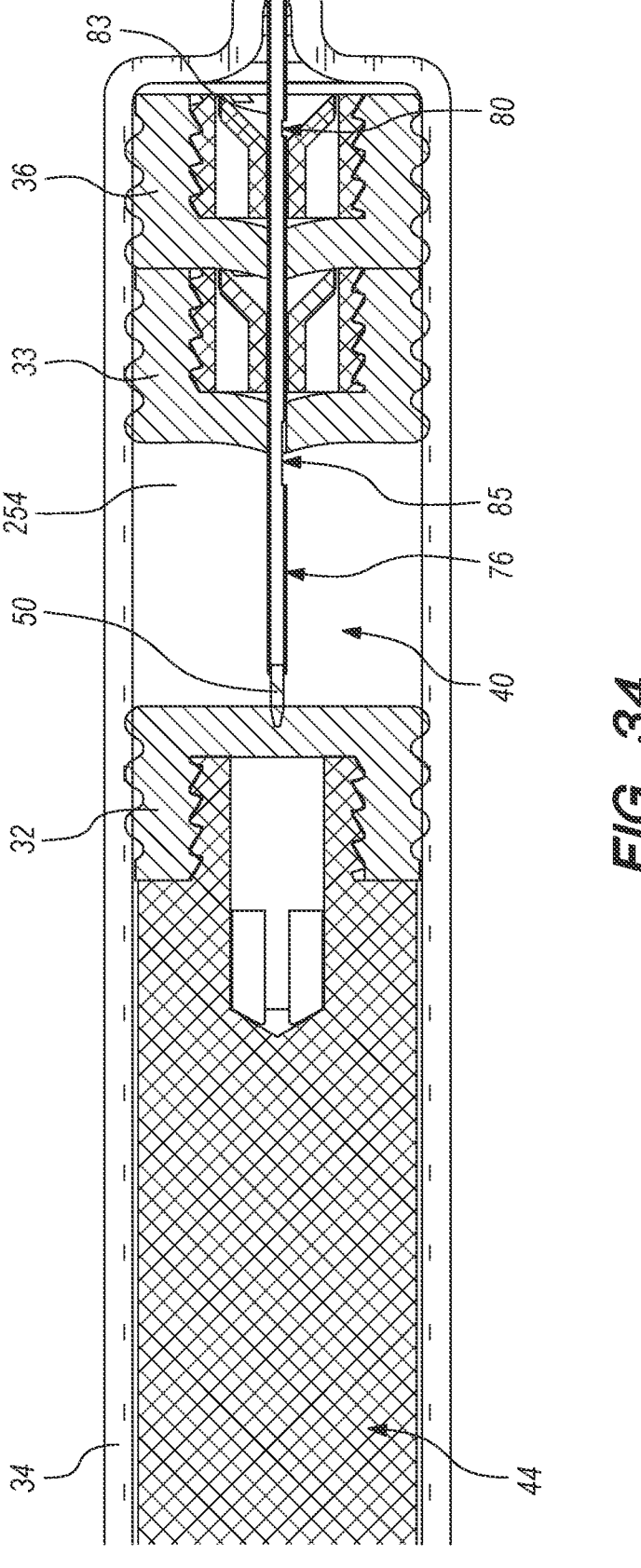

FIGS. 33A, 33B, and 34 depict the prefilled triple chamber serial injection system (200) after the middle and distal stopper members (33, 36) have been moved distally relative to the syringe body (34) until the distal stopper member (36) contacts the distal end of the syringe body (34). The distal chamber (42; see FIG. 26) has collapsed, and substantially all of the first liquid (252) has been ejected from the prefilled triple chamber serial injection system (200) through the distal opening (81). Further moving the middle stopper member (33) distally relative to the syringe body (34) has also caused the proximal end (50) of the needle (76) to penetrate the middle stopper member (33). As also shown in FIG. 34, with penetration of the proximal end (50) of the needle (76) through the middle stopper member (33), the proximal opening (85) is now disposed in the proximal chamber (40). Accordingly, there is now a flow path between the proximal chamber (40) and the distal opening (81), and distally directed force applied to the plunger manipulation interface (128) now moves the proximal stopper member (32) distally relative to the syringe body (34) to eject the third liquid (254) from the proximal chamber (40). Opening of the flow path between the proximal chamber (40) and the distal opening (81) places the prefilled dual chamber serial safe injection system (100) in a fourth configuration in which the third liquid (254) may be ejected from the proximal chamber (40).

Figures 35A, 35B:
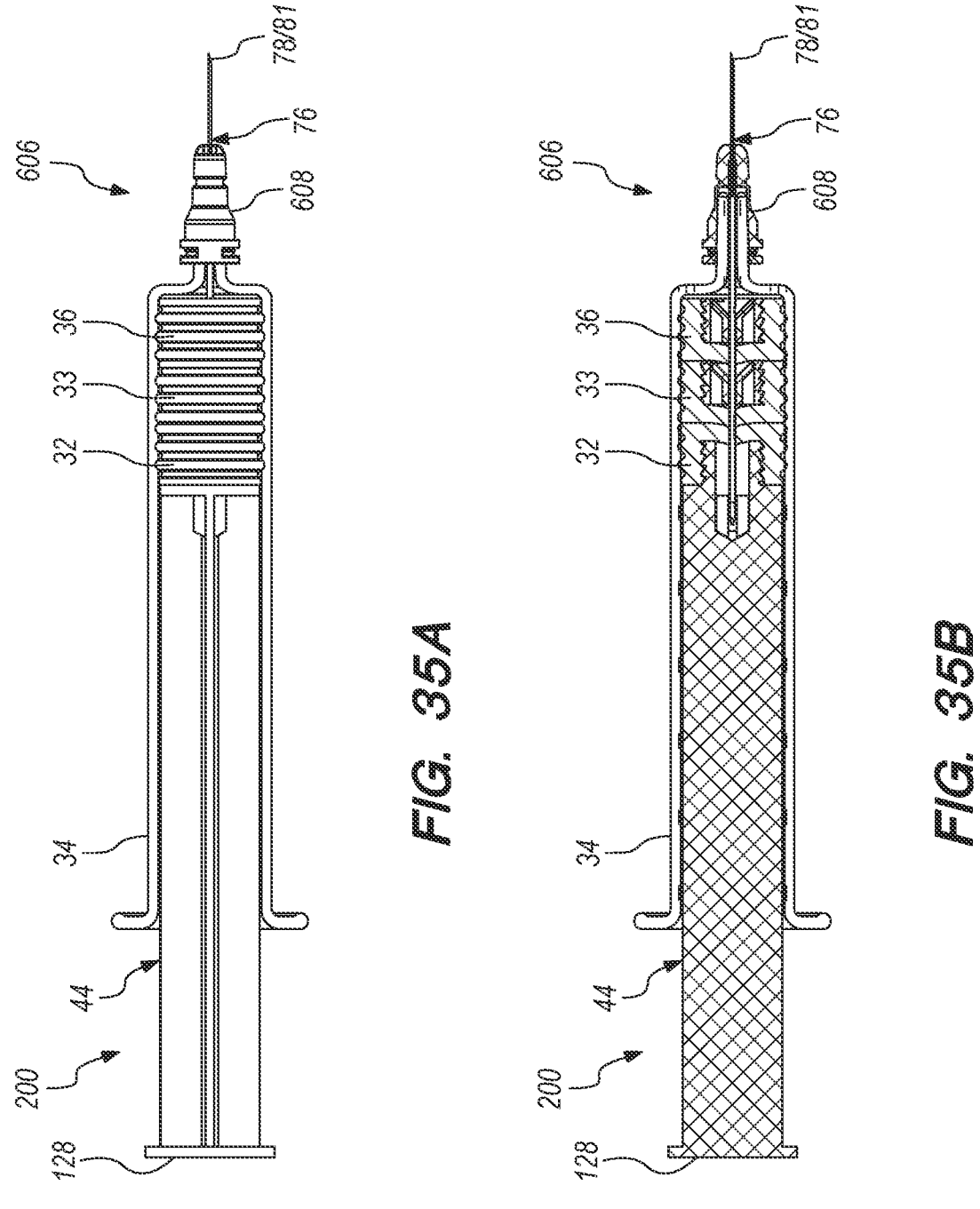
Figure 36:
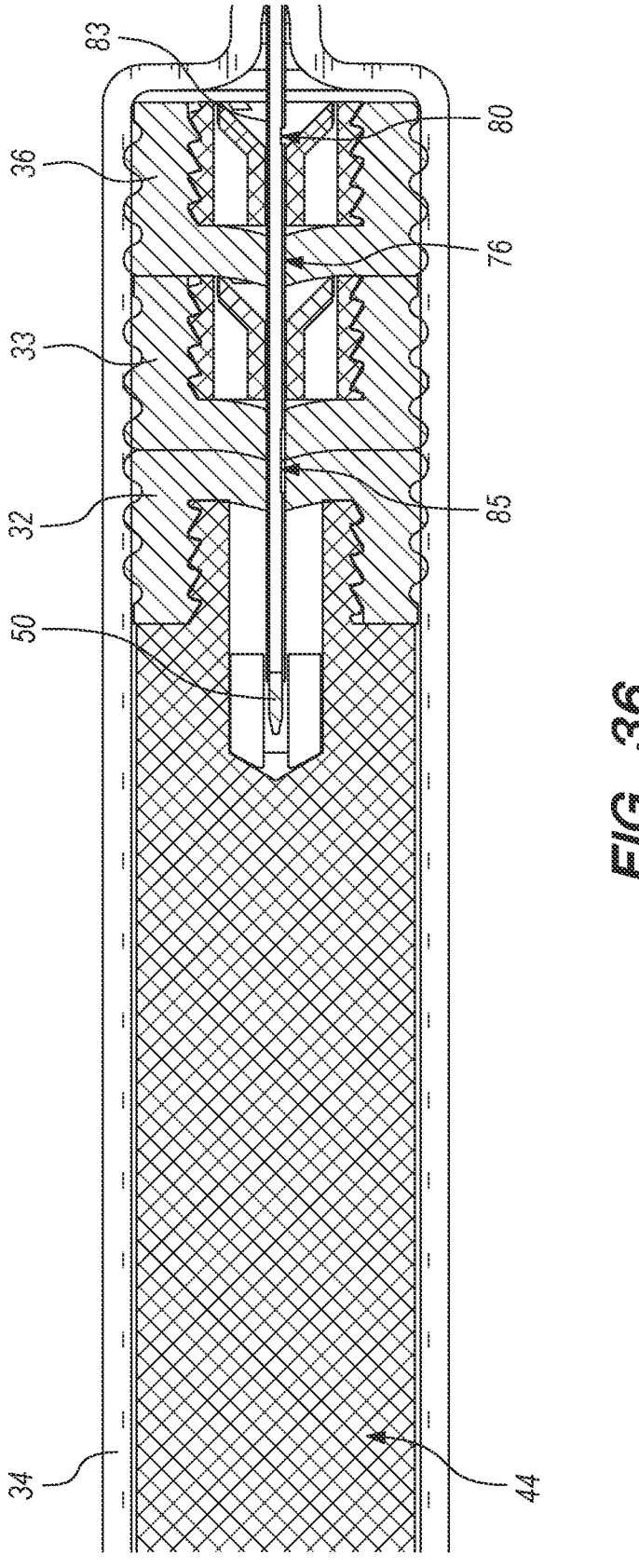

FIGS. 35A, 35B, and 36 depict the prefilled triple chamber serial injection system (200) after the proximal stopper member (32) has been moved distally relative to the syringe body (34) until it contacts the middle stopper member (33). The proximal chamber (40; see FIG. 26) has collapsed, and substantially all of the third liquid (254) has been ejected from the prefilled triple chamber serial injection system (200) through the distal opening (81). FIGS. 35A, 35B, and 36 depicts a completion state of the sequential injection method using the prefilled triple chamber serial injection system (200).

The ejections/injection pattern of the embodiment depicted in FIGS. 25A-36 is a first portion of the first liquid (252) in the distal chamber (42), followed by substantially all of the second liquid (253) in the middle chamber (41), followed by a second portion of the first liquid (252) in the distal chamber (42), and lastly substantially all of the third liquid (254) in the proximal chamber (40). While specific portions of the first liquid (252) were depicted in FIGS. 25A-36, the dimensions of various portions of the needle (76) can be modified to adjust the portions of the first liquid (252). Various components of the system (200) and their positions can be modified to tailor the amounts of first, second, and third liquids (252, 253, 254) to be injected, including portions of the first liquid (252) that may be injected. While the system (200) depicted in FIGS. 25A-36 did not include a safe injection needle retraction system, a triple chamber serial injection system can be modified to include a safe injection needle retraction system. While the system (200) depicted in FIGS. 25A-36 includes three chambers, injection systems according to some embodiments can include more than three chambers.

Exemplary Distal Tube Connector/Retainer

Figure 37:
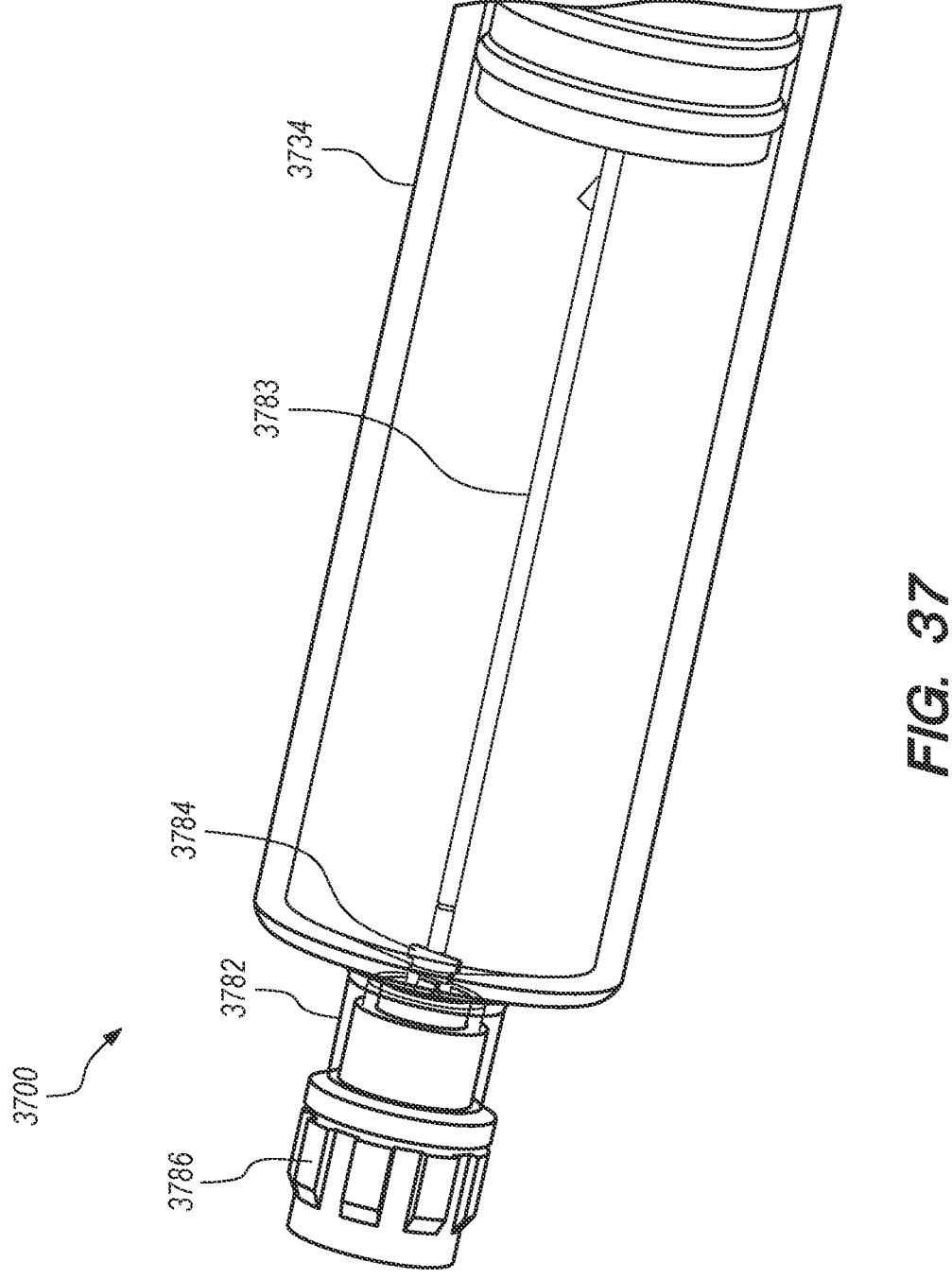
FIGS. 37 to 42 illustrate a multiple chamber injection system including a distal tubular member coupled to a distal end of a syringe body by a connector/retainer according to some embodiments.
Figure 38:
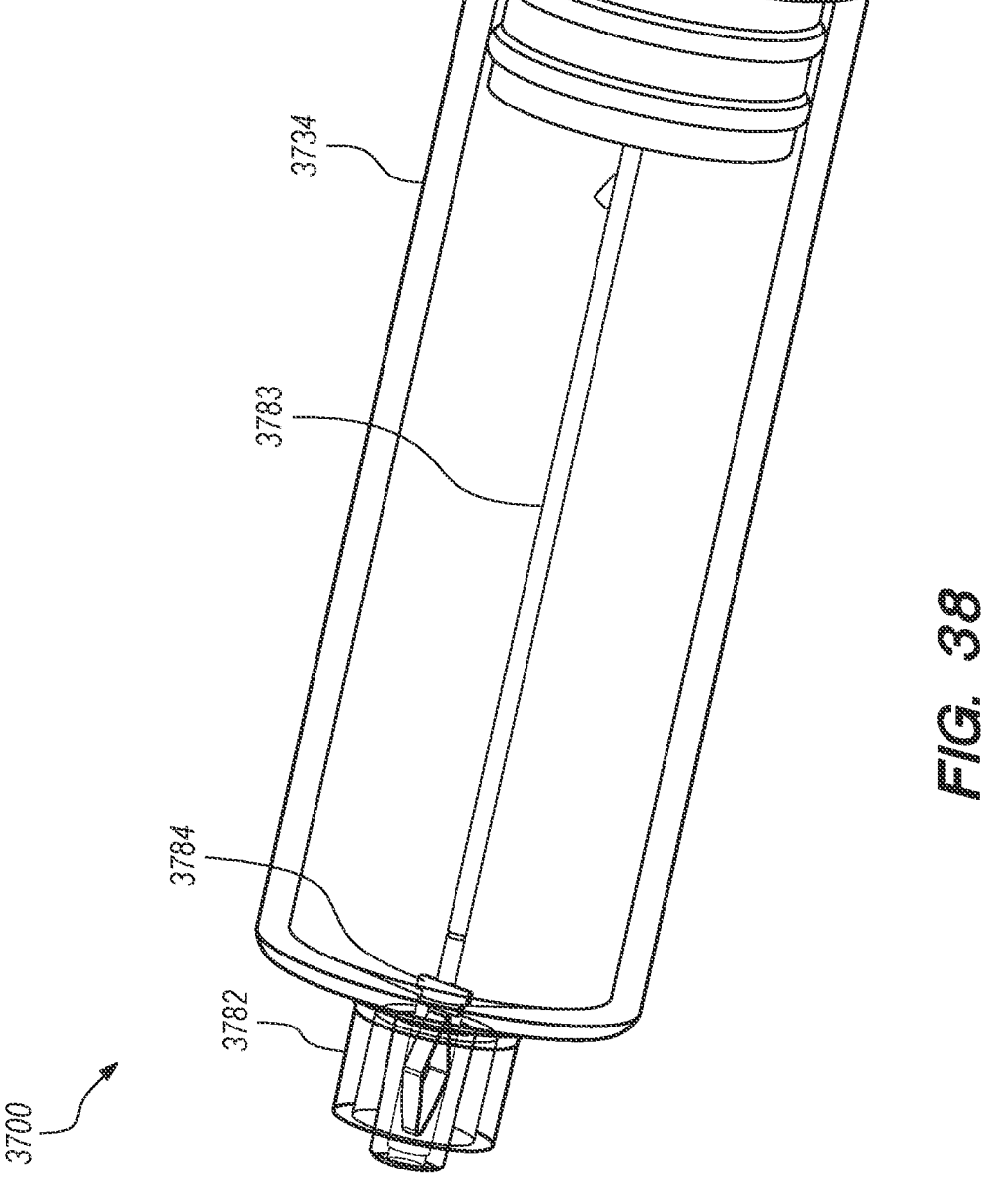

FIGS. 37 to 42 depict a multiple chamber injection system (3700) including a distal tubular member (3783) coupled to a distal end (3782) of a syringe body (3734) by a connector/retainer (3784). The distal end (3782) of the syringe body (3734) may be a Luer lock connector for coupling to a needle (not shown). FIG. 37 shows the distal end (3782) of the syringe body (3734) with a cap (3786) coupled thereto. FIG. 38 shows the distal end (3782) of the syringe body (3734) without a cap (3786).

Figure 39:
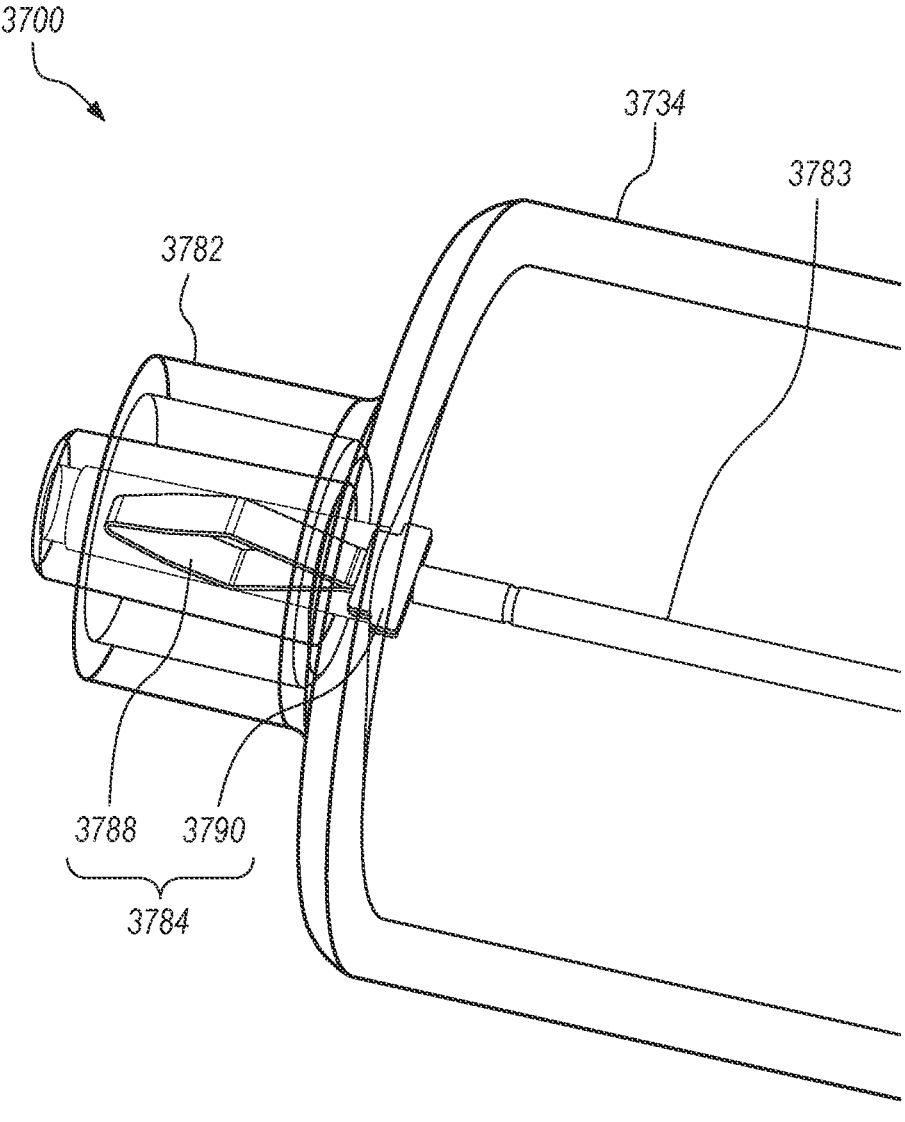
Figure 41:
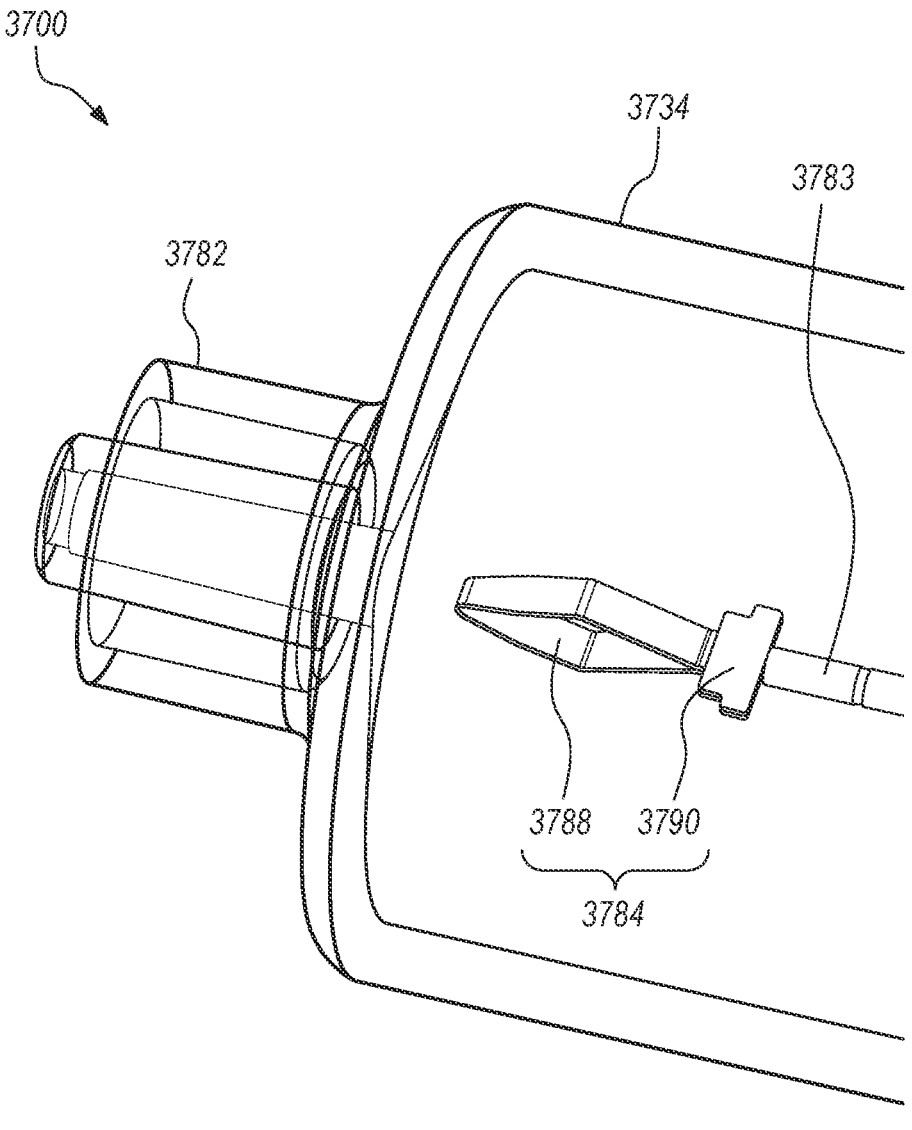
Figure 42:
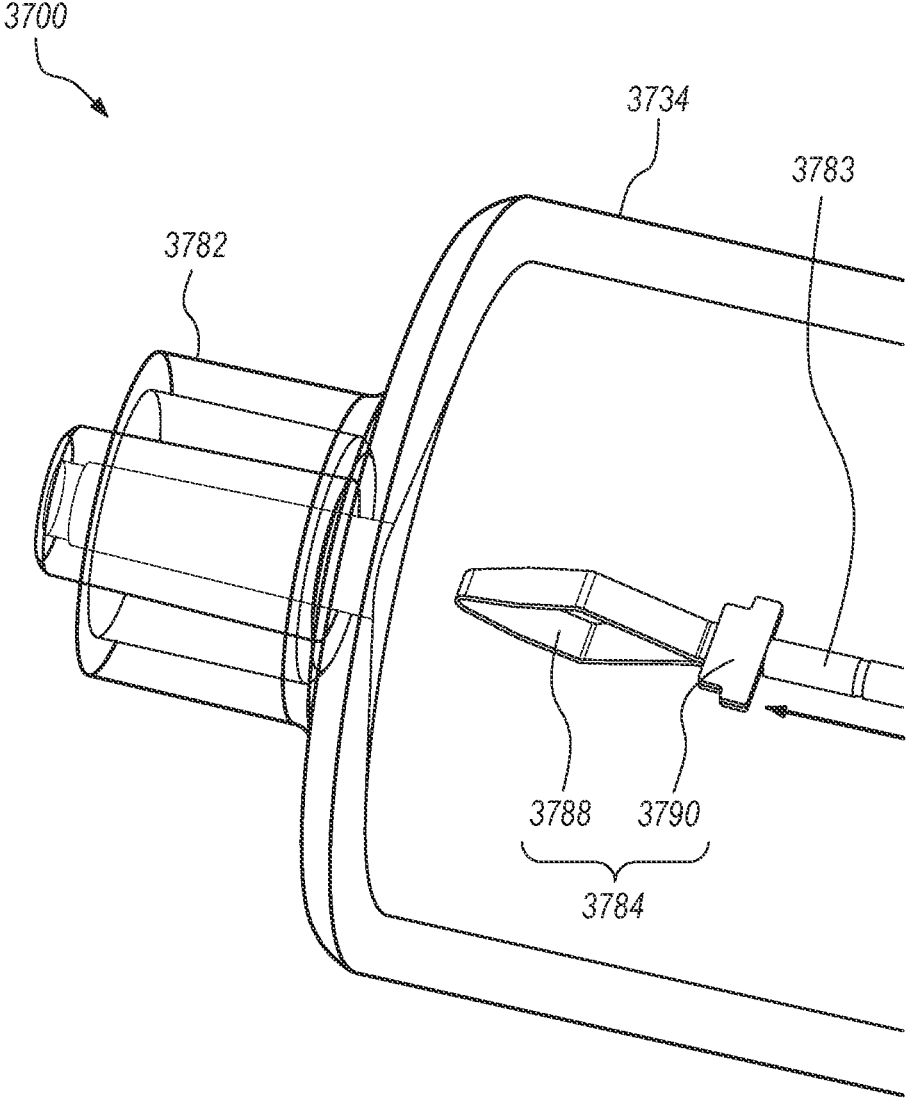

FIG. 39 shows the connector/retainer (3784) in more detail. The connector/retainer (3784) includes a diamond shaped portion (3788) and a flat portion (3790). The diamond shaped portion (3788) is elastically compressible to fit inside of the distal end (3782) of the syringe body (3734) from a proximal direction. FIGS. 41 and 42 depict insertion of the connector/retainer (3784) with a distal tubular member (3783) coupled thereto into a distal end (3782) of the syringe body (3734) during assembly. Once installed inside of the distal end (3782) of the syringe body (3734) the diamond shaped portion (3788) is biased to expand to increase friction between an inner surface of the distal end (3782) of the syringe body (3734) and the diamond shaped portion (3788) to resist longitudinal (e.g., proximal) movement of the connector/retainer (3784) and the distal tubular member (3783) coupled thereto relative to the syringe body (3734).

The flat portion (3790) of the connector/retainer (3784) is larger in at least one dimension compared to an opening the distal end (3782) of the syringe body (3734). As such, the flat portion (3790) of the connector/retainer (3784) interferes with the distal end (3782) of the syringe body (3734) to limit distal movement of the connector/retainer (3784) and the distal tubular member (3783) coupled thereto relative to the syringe body (3734).

Figure 40:
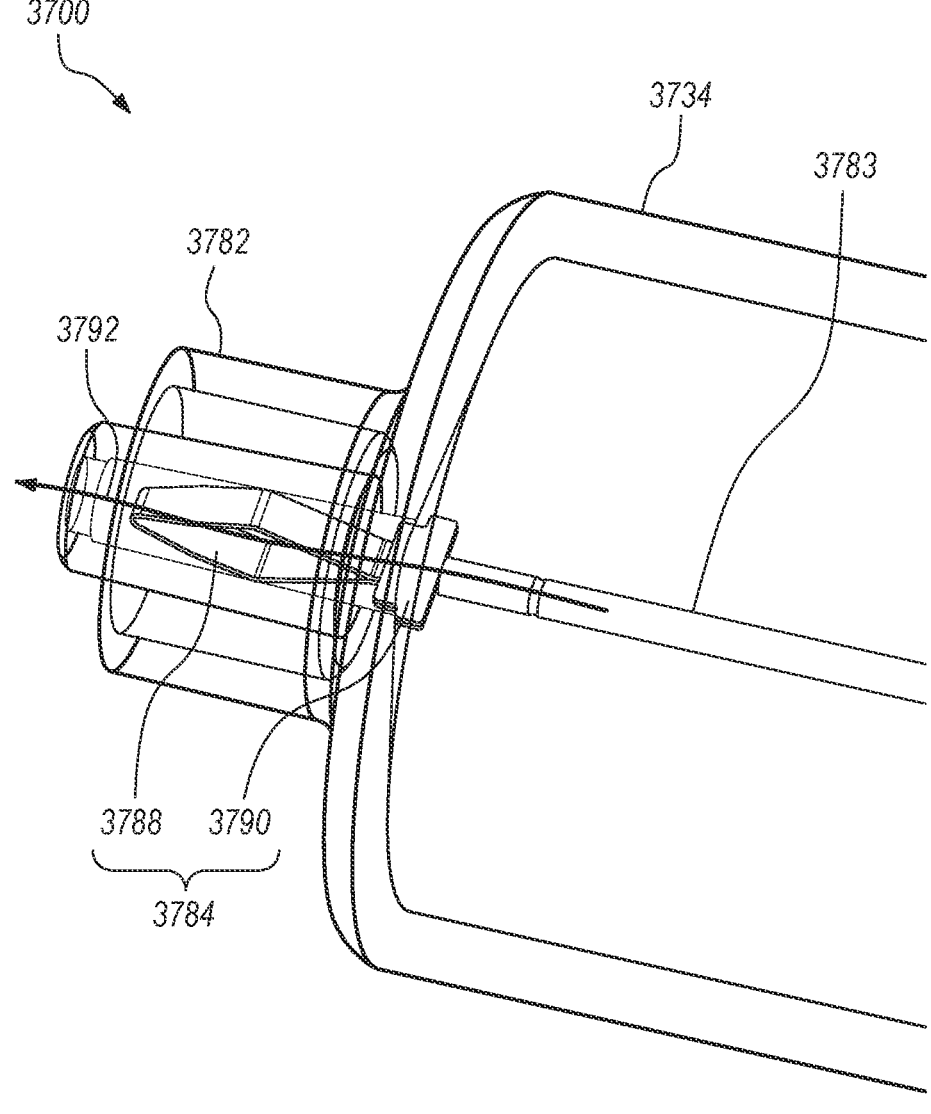

As shown in FIG. 40, after assembly, a flow path (3792) is open between an interior of the syringe body (3734) and an exterior thereof past the connector/retainer (3784).

The connector/retainer (3784) may be cut or stamped as one piece from a flat sheet of metal (e.g., stainless steel), with the distal end of the diamond shaped portion (3788) in the middle of the cut/stamped piece. The cut/stamped piece can then be bent to form the diamond shaped portion (3788). The material from which the cut/stamped piece is cut/stamped gives the diamond shaped portion (3788) it elastic quality. The two pieces forming the flat portion (3790) can be laid on top of each other. The free ends of the flat portion (3790) may include one or more tangs configured to fit into a distal opening at the distal end of the distal tubular member (3783) to facilitate coupling of the connector/retainer (3784) to the distal tubular member (3783) (e.g., by welding).

III. Exemplary Safe Injection Systems

Figures 43A, 43B:
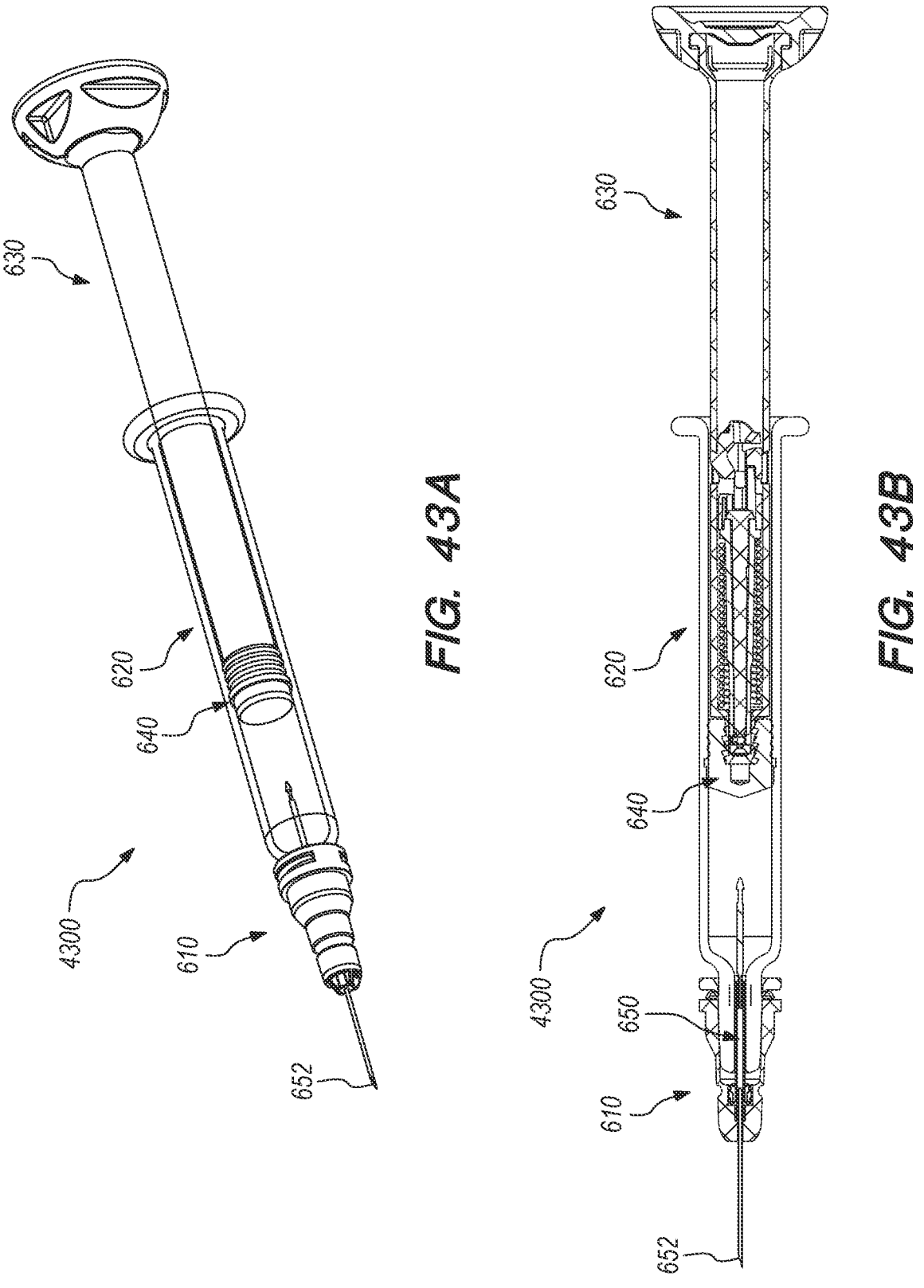
FIGS. 43A and 43B are perspective and side views of a safe injection system according to some embodiments.

FIGS. 43A and 43B depict a single chamber, staked needle safe injection system (600) according to some embodiments. The safe injection system (600) includes a needle hub assembly (610) coupled to a syringe body (620), and a plunger member (630) coupled to a stopper member (640) disposed in an interior of the syringe body (620). The needle hub assembly (610) includes a needle assembly (650) such as those described below. The safe injection system (600) includes a needle retraction system such as those described in U.S. patent application Ser. Nos. 14/696,342, 14/543,787, 14/321,706, 15/801,239, 15/801,259, 15/801, 281, 15/801,304, 16/908,531, 17/031,108, and 63/094,313, the contents of which have been previously Incorporated by reference herein. The needle retraction system is mostly disposed in an interior of the plunger member (630). The needle retraction system exerts a proximally directed force on the needle assembly (650) after injection is completed to pull the needle assembly (650) at least partially inside of the needle hub assembly (610) and/or the syringe body (620) such that the sharp distal tip (652) of the needle assembly (650) is disposed in the needle hub assembly (610) and/or the syringe body (620) to prevent accidental needle sticks. In some embodiments, the proximally directed force is from about 2 lbs. to about 3 lbs.

Exemplary Needle Assemblies

FIGS. 44A to 58 depict various needle assemblies and features thereof according to various embodiments.

Figure 44A:
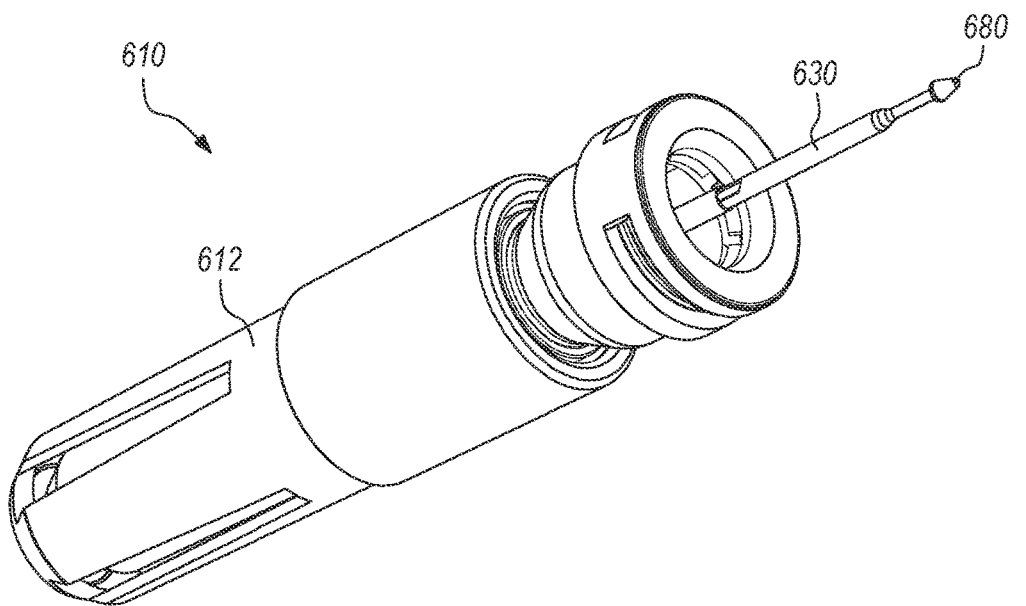
FIG. 44A is a perspective view of a needle hub assembly according to some embodiments.
Figure 44B:
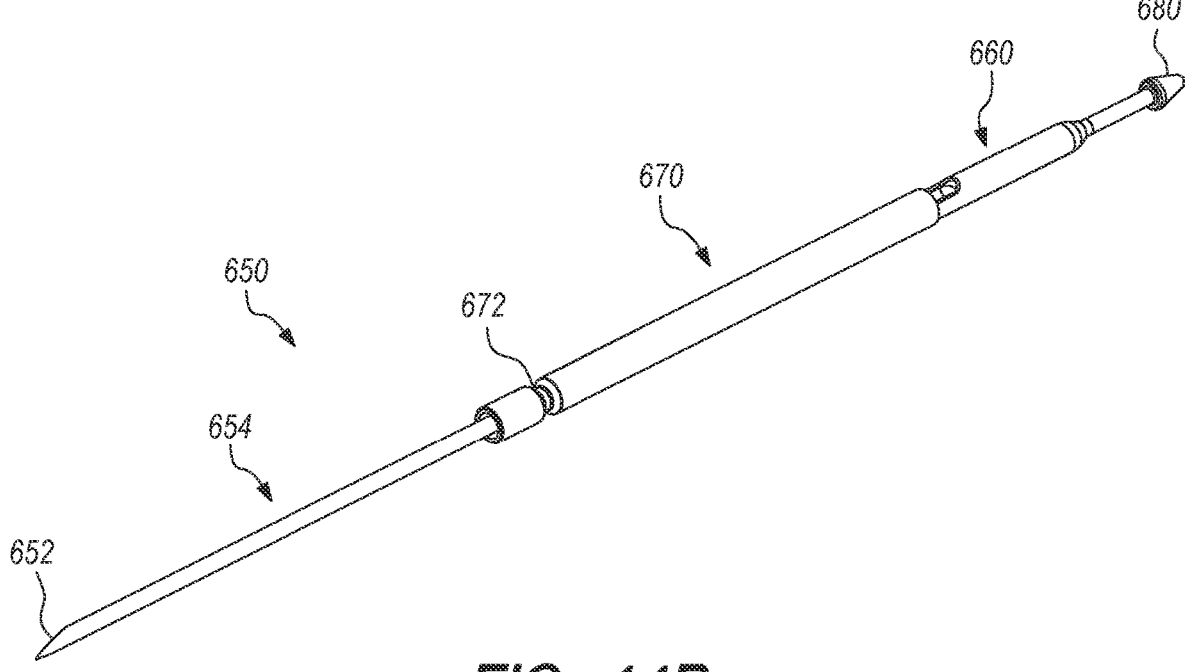
FIGS. 44B, 45A, 45B, and 46 are perspective, exploded, detailed longitudinal cross-sectional, and detailed perspective views of needle assemblies according to some embodiments.

FIG. 44A depicts a needle hub assembly (610) with a rigid needle shield (612) attached thereto according to some embodiments. FIG. 44A also shows the proximal end of the needle assembly (650). FIG. 44B depicts a needle assembly (650) according to some embodiments.

Figure 45A:
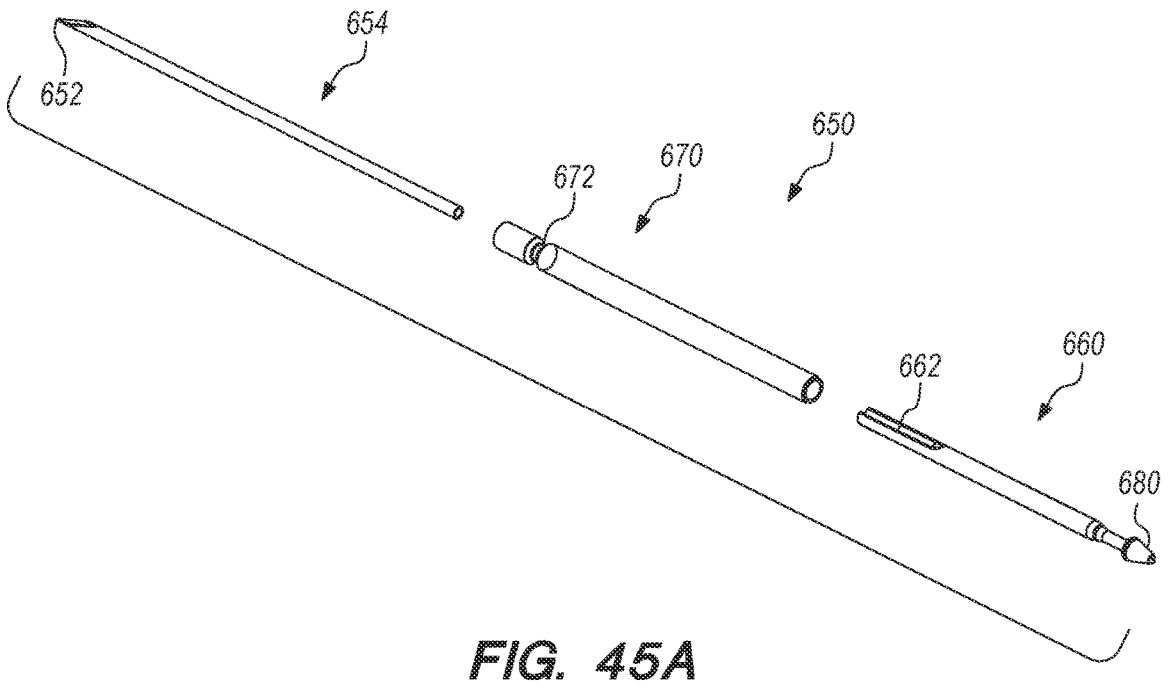

FIG. 45A is an exploded view of the needle assembly (650) depicted in FIG. 44B. The needle assembly (650) includes a proximal portion (660) and a distal portion (654) each configured to be partially disposed in respective proximal and distal ends of a middle connector (670). The distal end of the distal portion (654) includes a sharp distal tip (652) configured to pierce target tissue for injections. The middle connector (670) includes an annular recess (672)

configured to interfere with a needle latch as described in U.S. patent application Ser. Nos. 14/696,342, 14/543,787, 14/321,706, 15/801,239, 15/801,259, 15/801,281, 15/801, 304, 16/908,531, 17/031,108, and 63/094,313, the contents of which have been previously Incorporated by reference herein, to prevent proximal retraction of the needle assembly (650) before the end of injection.

Figure 45B:
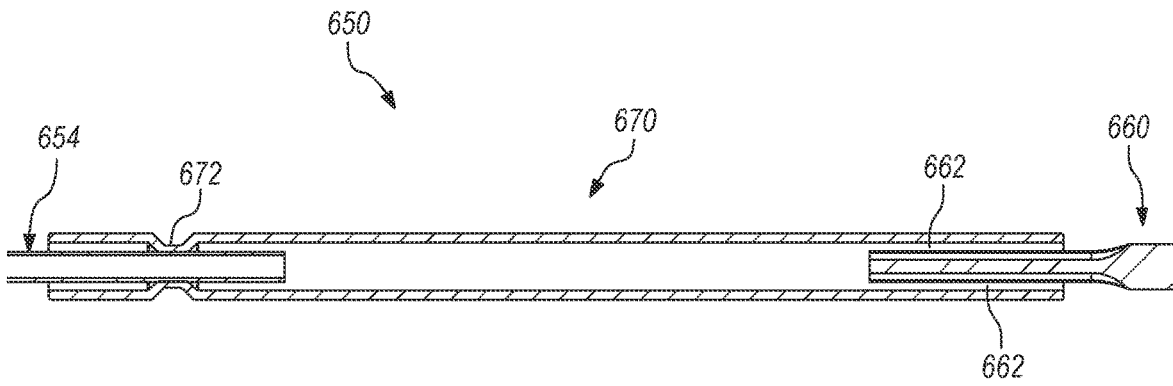

The proximal portion (660) includes a proximal tip (680) at a proximal end thereof and one or more longitudinal channels (662) extending from a distal end thereof. FIG. 45B is a longitudinal cross-sectional view of a middle connector (670) with proximal and distal portions (660, 654) partially disposed therein according to some embodiments. FIG. 45B shows that the proximal portion (660) includes two longitudinal channels (662) formed in approximately opposite surfaces of the proximal portion (660). The longitudinal channels (662) form two flow paths from outside of the needle assembly (650) into the middle connector (670), then into the distal portion (654) through a proximal opening (656) in the distal portion (654), and out of the sharp distal tip (652) of the distal portion (654).

Figure 46:
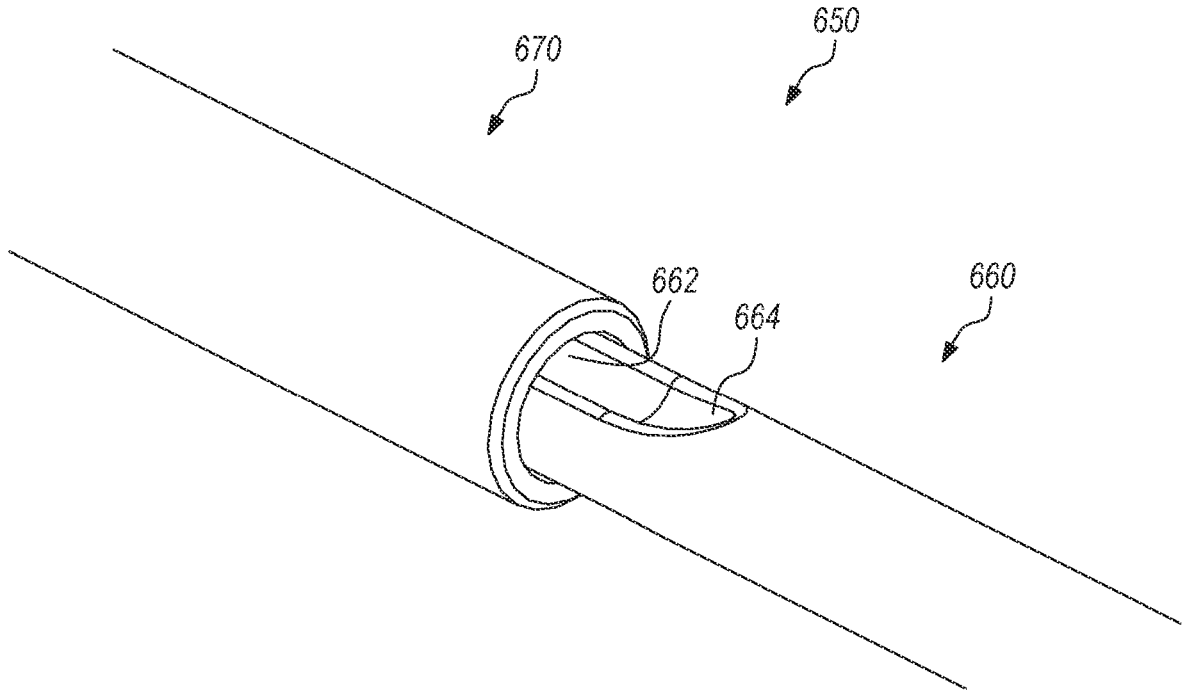

FIG. 46 depicts the proximal end of the middle connector (670) with the distal end of the proximal portion (660) inserted therein until only a proximal end of the longitudinal channel (662) remains outside of the middle connector (670). This proximal end of the longitudinal channel (662) forms an opening (664) fluidly coupling the interior and exterior of the needle assembly (650).

Figure 47A:
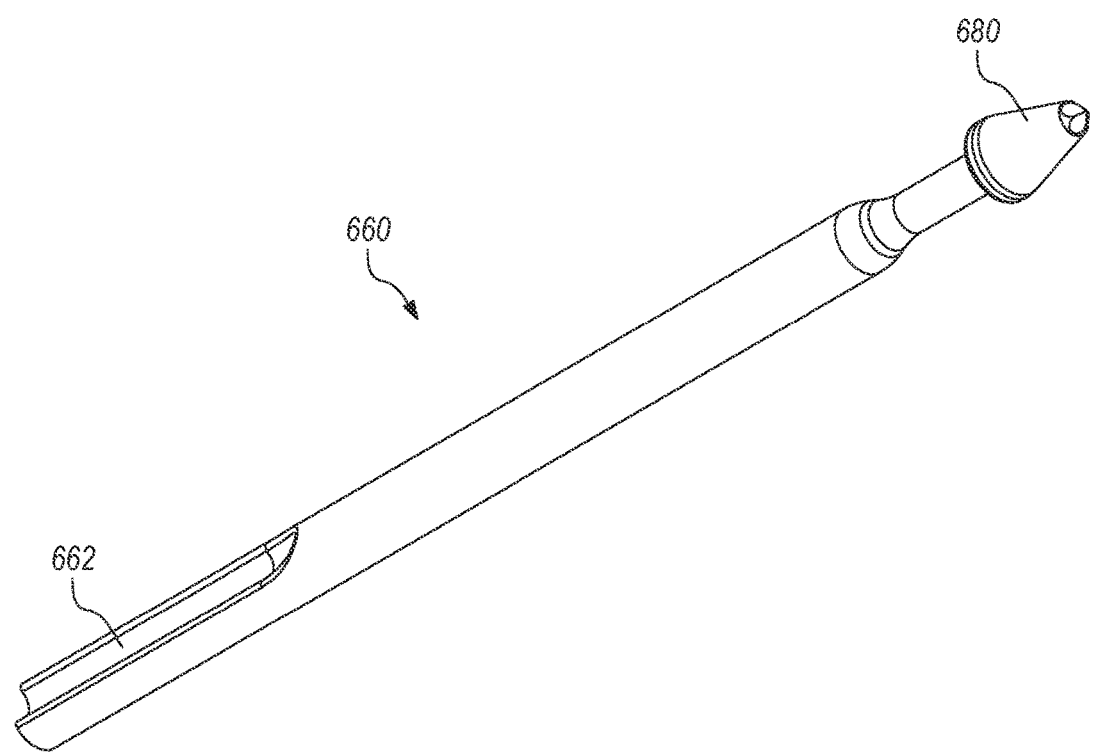
FIGS. 47A and 47B are perspective and side views of a proximal portion of a needle assembly according to some embodiments.
Figure 47B:
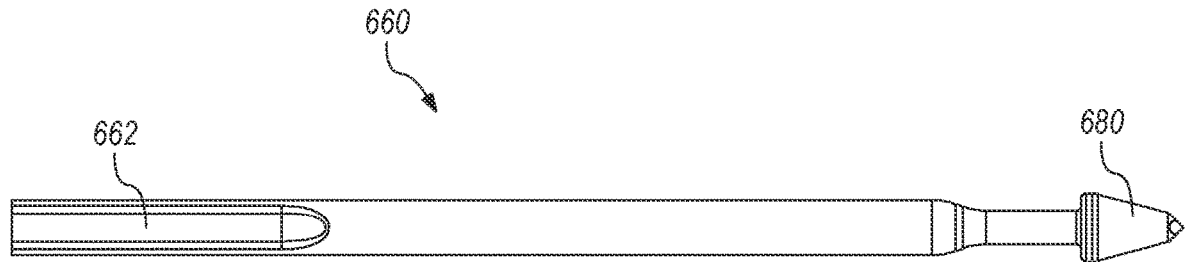

FIGS. 47A and 47B are perspective and side views of a proximal portion (660) of a needle assembly (650) according to some embodiments. The proximal portion (660) may be formed by stamping a piece of flat sheet metal, or a metal wire to form the various features of the proximal portion (660) described herein. Forming a proximal portion (660) by stamping reduces manufacturing complexity and costs.

Figures 48A, 48B:
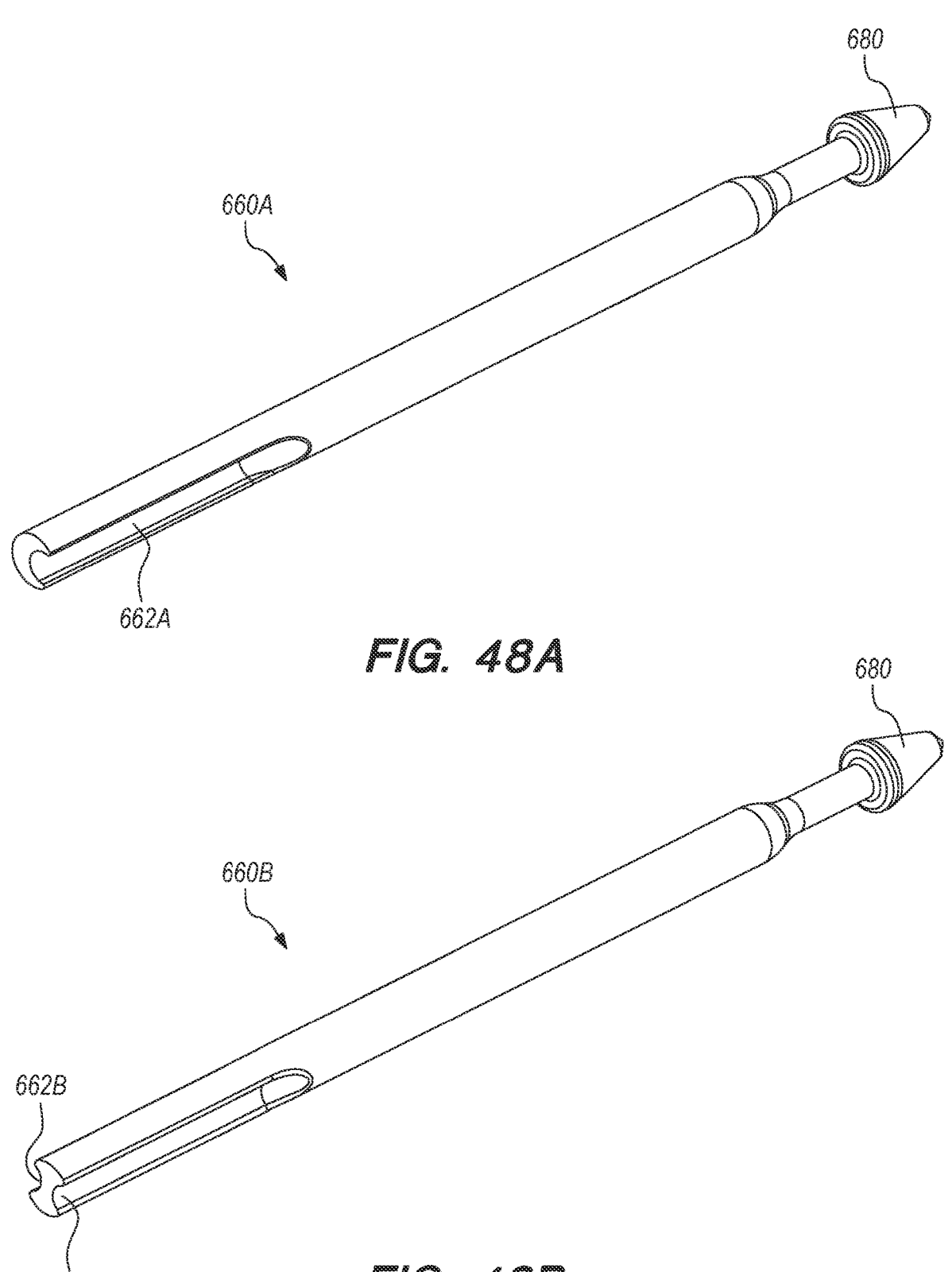
Figure 55:
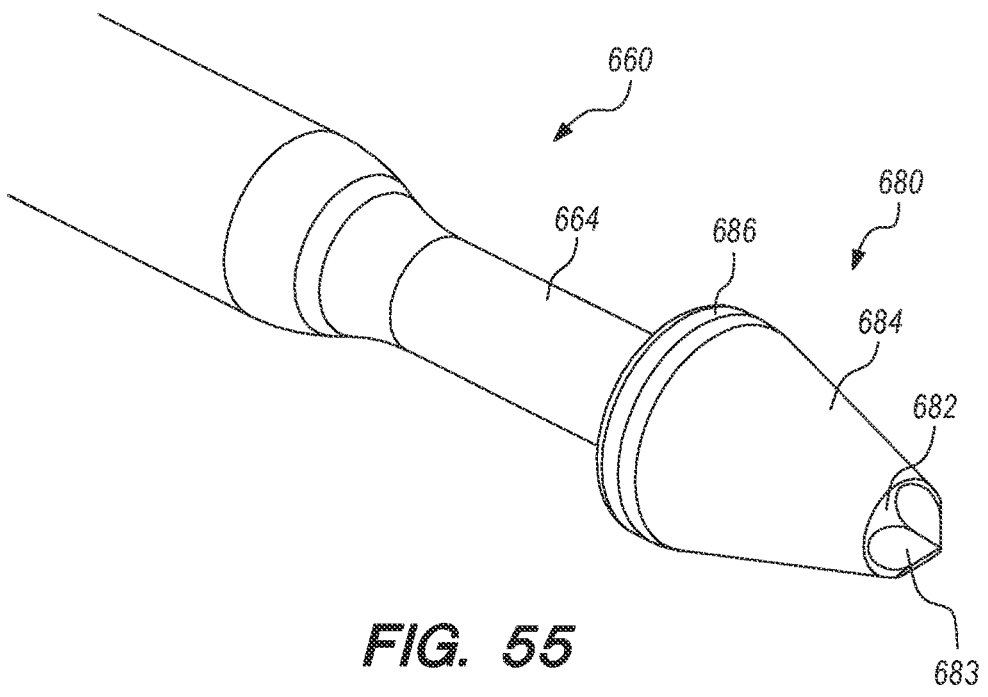

FIGS. 48A and 48B are perspective views of two proximal portions (660A, 660B) according to two embodiments. FIGS. 49A and 49B are detailed perspective views of respective distal ends of the proximal portions (660A, 660B). FIGS. 50A and 50B are axial cross-sectional views of respective distal ends of the proximal portions (660A, 660B).

As best shown in FIGS. 50A and 50B, the axial cross-sections of respective distal ends of the proximal portions (660A, 660B) form a crescent and dumbbell shape respectively. The crescent and dumbbell shapes define one and two longitudinal channels (662A, 662B) respectively. The longitudinal channels (662A, 662B) have a rounded/circular cross-section, which minimizes fluid flow restriction through the longitudinal channels (662A, 662B). A circular cross-section is a highly efficient cross-section for fluid flow due to its minimization of fluid interaction with the wall of the channel, which would otherwise impart a zero velocity boundary condition on the flowing fluid. Minimizing wall exposure thus minimizes the amount of shear resistance the fluid experiences during flow. A single round channel (662A) (see FIG. 50A), may have a lower fluid flow resistance compared to a double channel (662B) (see FIG. 50B), even when cross-sectional area is preserved, because the resistance of a theoretical pipe 1400 (see FIG. 51) is inversely proportional to $r^4$, according to the Hagen-Poiseuille formula:

$$\Delta P = \frac{8\mu L Q}{\pi R^4}.$$

Even with the longitudinal channels (662A, 662B) formed therein, the proximal portions (660A, 660B) have sufficient bending moments of inertia for improved rigidity and resistance to bending. In fact, the proximal portions (660A, 660B) resemble steel I-beams and have similar rigidity characteristics. Resistance to bending is particularly important as the proximal portions (660A, 660B) puncture through the stopper member (640). Minimizing bending of the proximal portions (660A, 660B) as they puncture through the stopper member (640), improves the probability of capture of the proximal tip (680) of the proximal portion (664) to enable retraction of the needle assembly (650) (see FIGS. 58 to 62 and 63 to 66).

The diameter of the proximal portions (660A) and (660B) are also relatively large (e.g., about 0.026" compared to cold-formed proximal portions, which have a diameter of about 0.020). The larger diameter of the proximal portion (660) results in a higher overall bending moment of inertia, and more resistance to bending, which also improves the probability of capture. The proximal portions (660A) and (660B) are also quite close in diameter to the middle portion (670), which may have a diameter of about 0.036". The similarity in diameters renders the needle assembly (650) easier to retract through stopper members during retraction, as compared to a needle assembly made with a cold formed proximal portion, because the proximal opening of the middle portion (670) is less likely to snag the stopper member during retraction due to the diameter difference between the middle portion (670) and the proximal portion (660) being relatively small.

FIGS. 52A and 52B are detailed perspective views of respective distal ends of the proximal portions (660A, 660B) showing a cut away section of the middle connector (670) with the respective distal ends partially disposed therein. As shown in FIGS. 52A and 52B, the crescent and dumbbell cross-sectional shapes of the proximal portions (660A, 660B) provide the substantial amount of contact between the outer diameter of the proximal portions (660A, 660B) and the inner diameter of the tubular middle connector (670). The substantial amount of contact reduces the amount of welding power required to join the proximal portions (660A, 660B) and the tubular middle connector (670). Reducing the amount of required welding power in turn minimizes the probability of occlusion of the channels (662A, 662B) resulting from the collapsed, welded metal of the proximal portions (660A, 660B) and the tubular middle connector (670).

Figure 56:
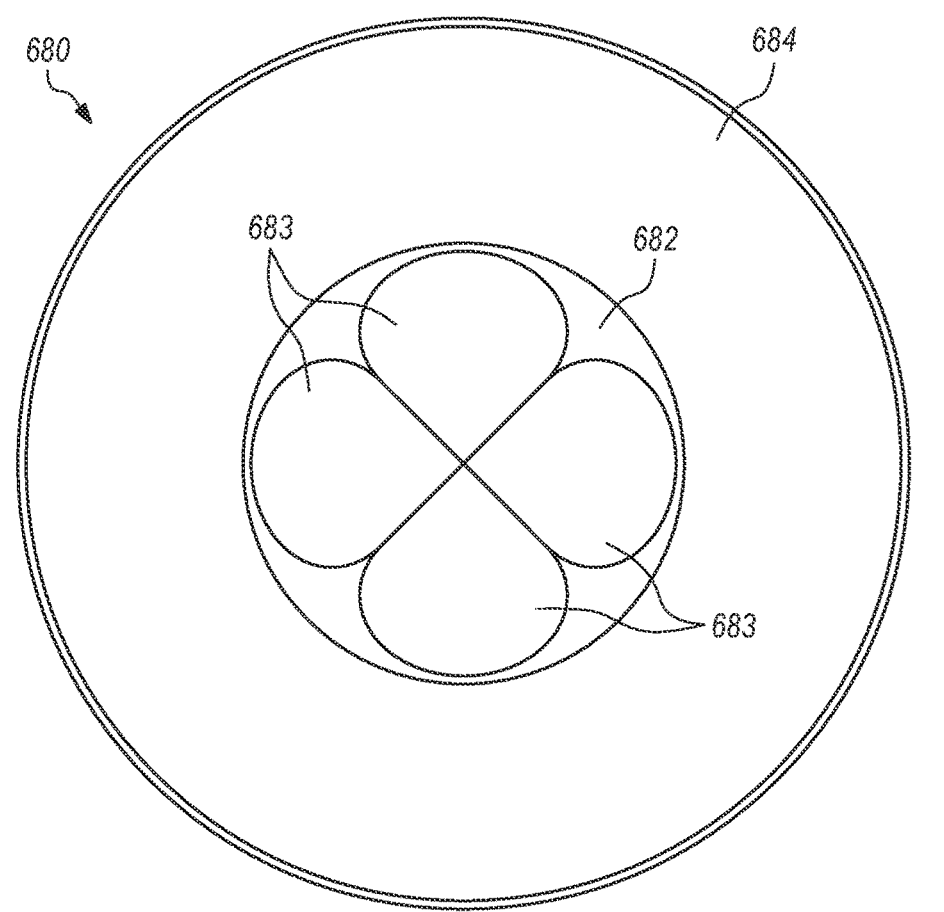

FIGS. 53 to 57 depict the proximal tip (680) of the proximal portion (664) in greater detail. The proximal tip (680) includes a pyramidal proximal piercing tip (682), a mildly-tapered middle portion (684), and a toroid-shaped distal flange (686). As shown in FIG. 56, the pyramidal proximal piercing tip (682) includes four faces/leaves 683. As shown in FIG. 53, edges defining the leaves 683 of the pyramidal proximal piercing tip (682) form an approximately 90° tip when viewed from the side. Compared to the more blunt 90° angled tip, the middle portion (684) has a sharper taper at approximately 12° to 15°. The sharper taper in the middle portion (684) reduces the force required to pierce stopper members.

The pyramidal proximal piercing tip (682) and the mildly-tapered middle portion (684) form a composite tip shape of the proximal tip (680). The 90° pyramidal proximal piercing tip (682) is configured to snag/grab the distal surface of the stopper member (640), which may be convex in shape and which may be coated with a slippery, hard coating in some embodiments, without slipping off the distal surface of the stopper member (640). The 12° to 15° middle portion (684) is configured to require lower piercing force as the proximal tip (680) penetrates through the stopper member (640). The transition between the pyramidal proximal piercing tip (682) and the middle portion (684) is smoothed, and therefore configured to minimize snagging or seizing of the funnel component during capture of the proximal tip (680) of the proximal portion (664) to enable retraction of the needle assembly (650) (see FIGS. 58 to 62 and 63 to 66).

The proximal portion (660) of the needle assembly (650) also includes a reduced diameter portion (664) immediately distal of the proximal tip (680). In embodiments where the proximal portion (660) of the needle assembly (650) is formed by stamping, the radial overhang between the outer diameter of the toroid-shaped distal flange (686) and the reduced diameter portion (664) can be up to about 0.0075". This relatively large overhang (e.g., compared to cold-formed proximal tips) increases the probability and security of capture of the proximal tip (680) of the proximal portion (664) to enable retraction of the needle assembly (650) (see FIGS. 58 to 62 and 63 to 66).

IV. Exemplary Safe Injection Systems

Figures 57, 58:
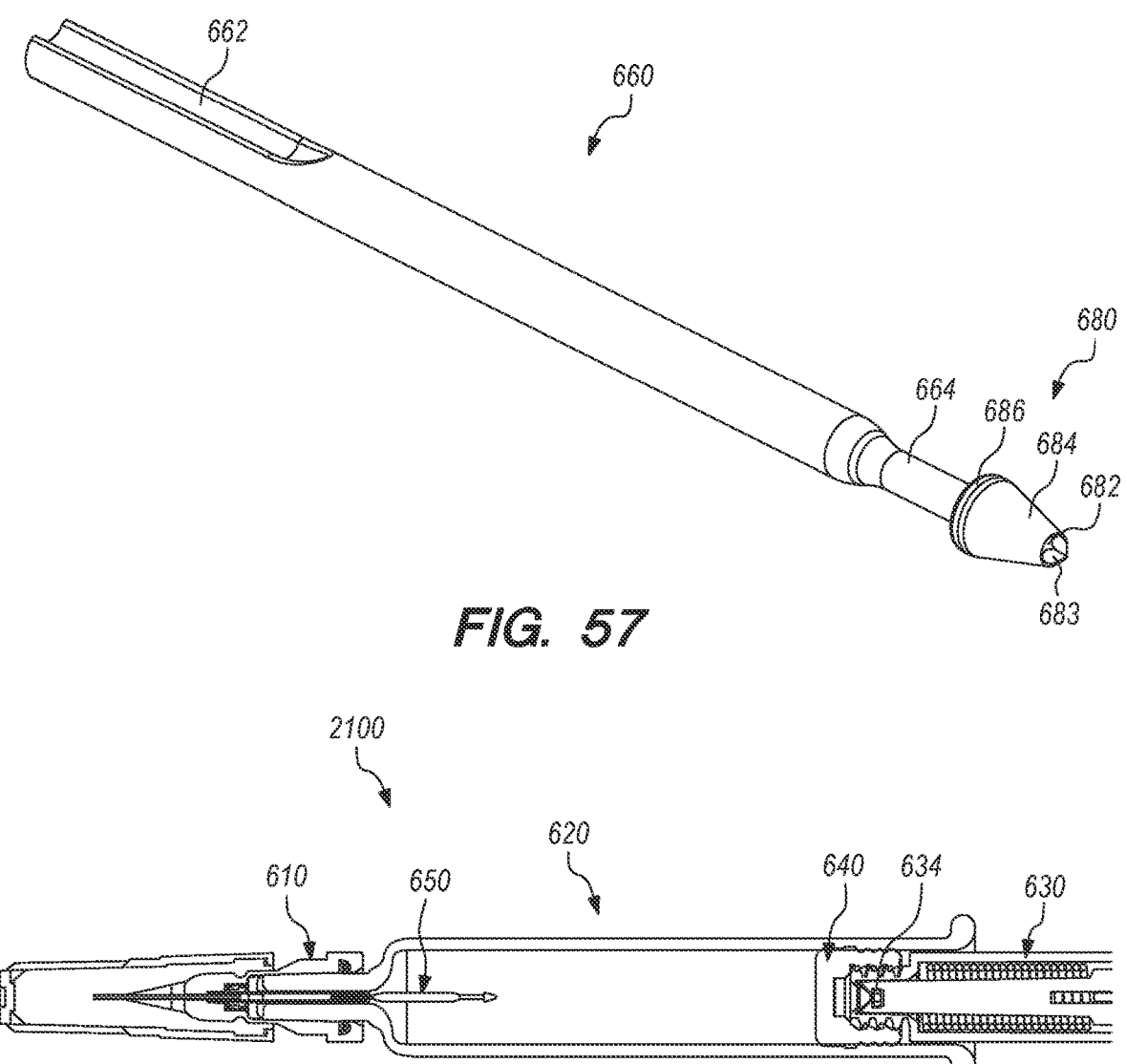

FIGS. 58 to 62 depict injection and needle capture using a safe injection system (2100) according to some embodiments. FIG. 58 depicts a safe injection system (2100) including a needle assembly (650) having a proximal portion (660) similar to the embodiments depicted in FIGS. 53 to 57 in a pre-injection configuration. The safe injection system (2100) includes a needle retraction system (e.g., the needle retraction systems described in U.S. patent application Ser. Nos. 14/696,342, 14/543,787, 14/321,706, 15/801,239, 15/801,259, 15/801,281, 15/801,304, 16/908,531, 17/031, 108, and 63/094,313, the contents of which have been previously Incorporated by reference herein).

Figure 59:
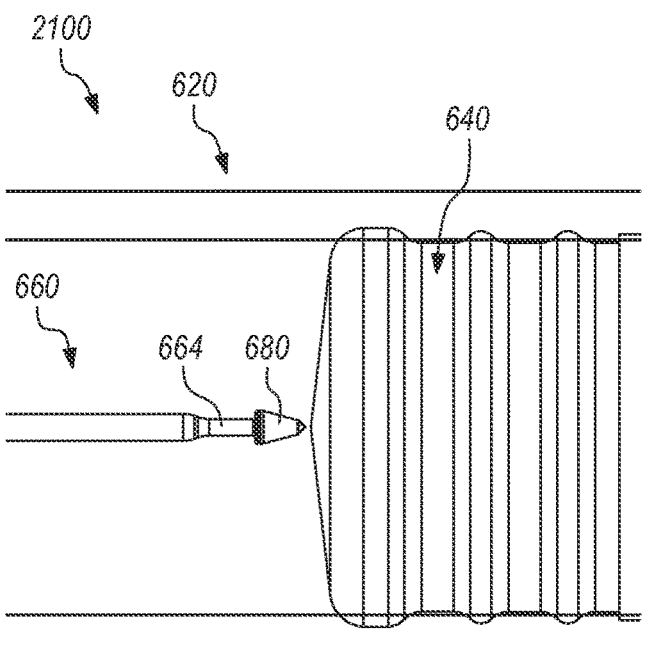

In FIG. 59, the proximal tip (680) of the proximal portion (660) is about to puncture the stopper member (640), which is shown to have a convex distal surface. The 90° pyramidal proximal piercing tip (682) of the proximal tip (680) is configured to snag/grab the distal surface (642) of the stopper member (640) without slipping off thereof. As described above, the distal surface (642) of the stopper member (640) may also be coated with a slippery, hard coating.

Figure 60:
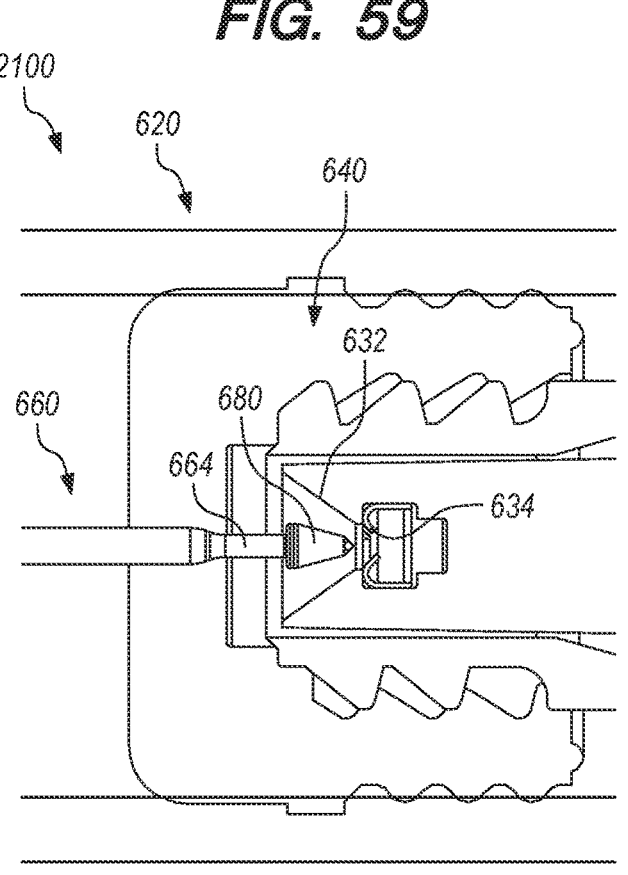

FIG. 60 depicts continued distal movement of the stopper member (640) relative to the needle assembly (650). As described in U.S. patent application Ser. Nos. 14/696,342, 14/543,787, 14/321,706, 15/801,239, 15/801,259, 15/801, 281, 15/801,304, 16/908,531, 17/031,108, and 63/094,313, the contents of which have been previously Incorporated by reference herein, needle retraction systems according to some embodiments include a funnel (632) configured to guide the proximal tip (680) into a needle catch cup (634). The smoothed transition between the pyramidal proximal piercing tip (682) and the middle portion (684) is configured to minimize snagging or seizing of the funnel (632) during capture of the proximal tip (680) of the proximal portion (664) by the needle catch cup (634).

Figure 61:
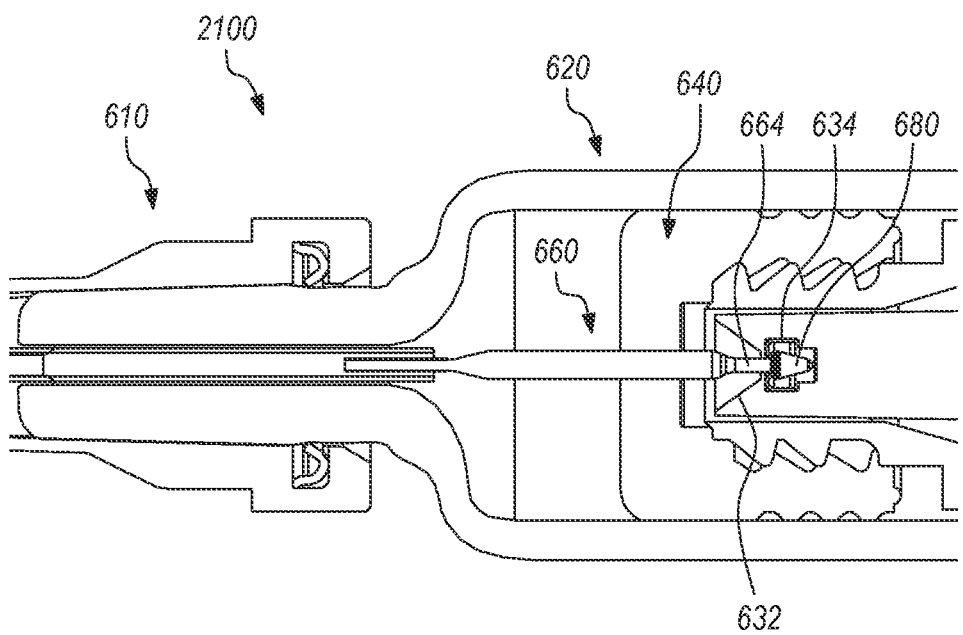
Figure 62:
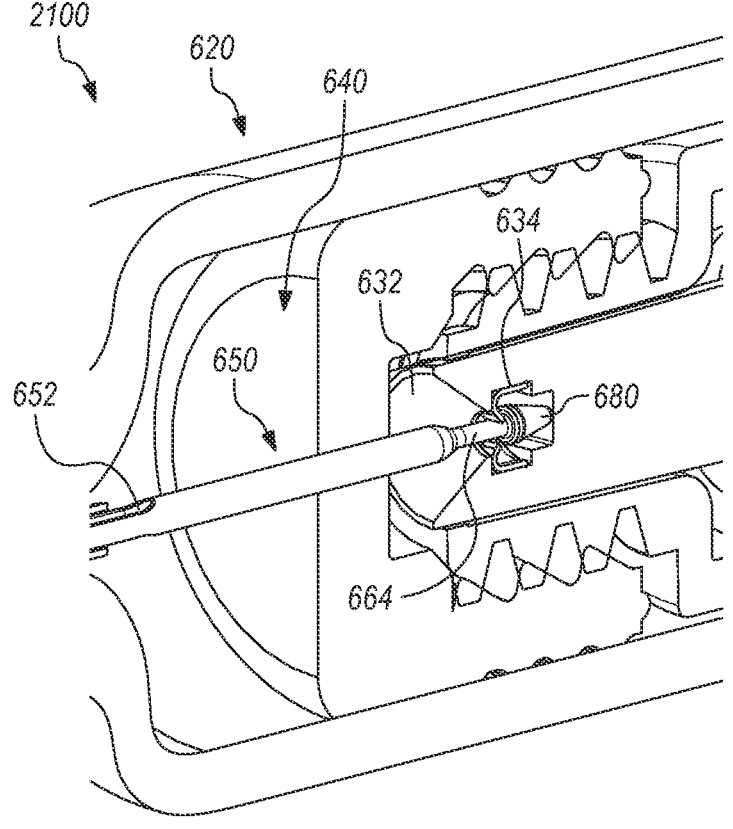
FIGS. 62 to 66 are longitudinal cross-sectional views of various steps in injection and needle capture using a safe injection system according to some other embodiments.

FIGS. 61 and 62 shows continued distal movement of the stopper member (640) relative to the needle assembly (650). The interaction between the proximal tip (680) and the funnel (632) has guided the proximal tip (680) into the needle catch cup (634). The relatively large radial overhang (about 0.0075") between the outer diameter of the toroid-shaped distal flange (686) of the proximal tip (680) and the reduced diameter portion (664) increases the probability and security of capture of the proximal tip (680) by the needle catch cup (634). The relatively large radial overhang also allows for a wider opening in the needle catch cup (634) without compromising retention of the proximal tip (680) after capture. The wider opening and the mildly-tapered middle portion (684) allows insertion of the proximal tip (680) into the needle catch cup (634) without triggering the needle retraction mechanism (e.g., a spring release latch).

Figures 63, 64:
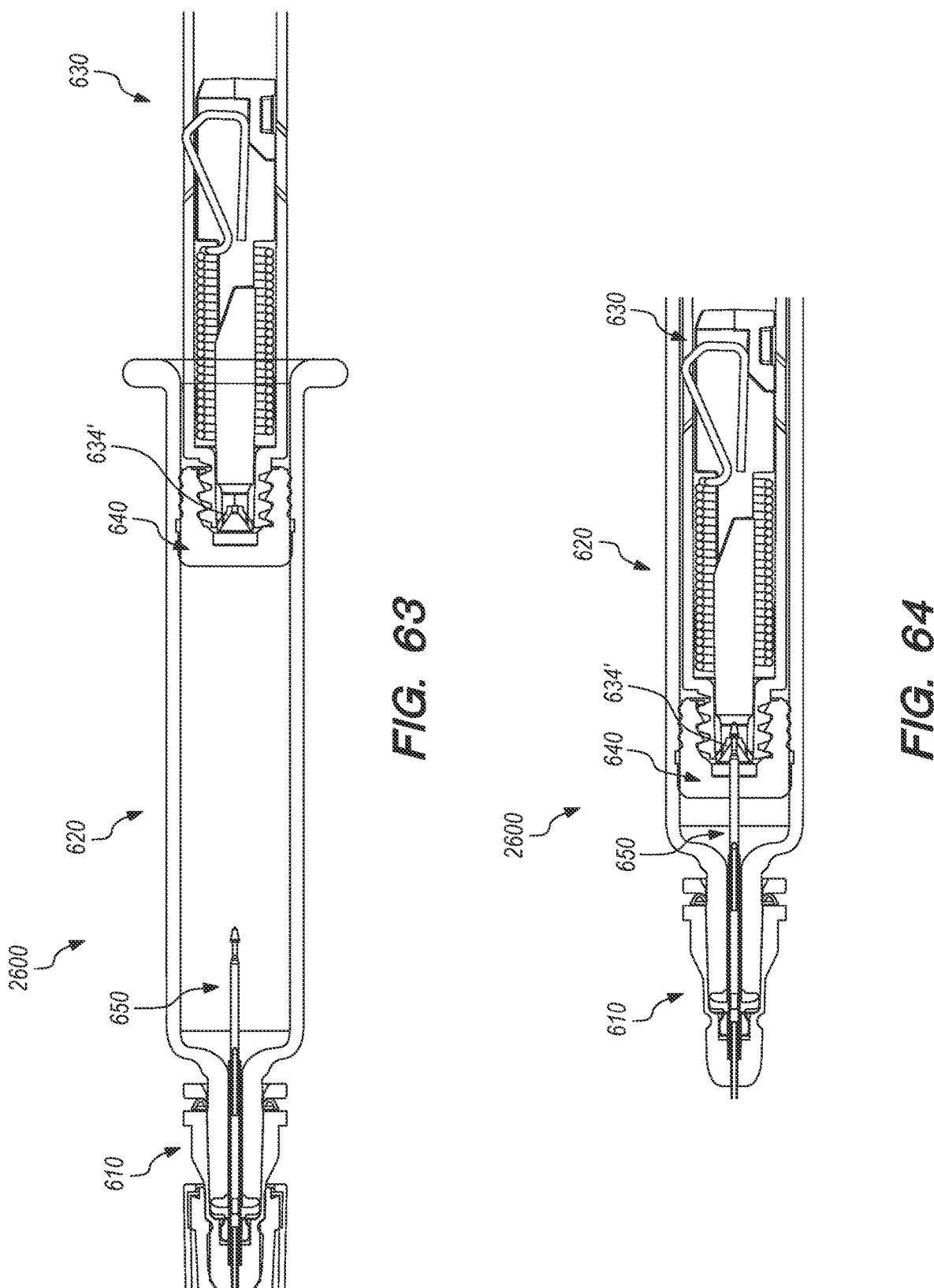

FIGS. 63 to 66 depict injection and needle capture using a safe injection system (2600) according to some embodiments. FIG. 63 depicts a safe injection system (2600) including a needle assembly (650) having a proximal portion (660) similar to the embodiments depicted in FIGS. 53 to 57. The safe injection system (2600) includes a needle retraction system (e.g., the needle retraction systems described in U.S. patent application Ser. Nos. 14/696,342, 14/543,787, 14/321,706, 15/801,239, 15/801,259, 15/801, 304, 16/908,531, 17/031,108, and 63/094,313, the contents of which have been previously Incorporated by reference herein). The difference between the safe injection system (2100) depicted in FIGS. 58 to 62 and the safe injection system (2600) depicted in FIGS. 63 to 66 is that instead of a needle catch cup (634) is shown in safe injection system (2100), the safe injection system (2600) includes a pair of self-energizing tabs (634') that form a funnel (632'). Also, the pair of self-energizing tabs (634') are molded into the trigger component to reduce the number of components (e.g., for assembly).

FIG. 63 depicts a safe injection system (2600) including a needle assembly (650) having a proximal portion (660) similar to the embodiments depicted in FIGS. 53 to 57 in a pre-injection configuration. The safe injection system (2600) includes a needle retraction system (e.g., the needle retraction systems described in U.S. patent application Ser. Nos. 14/696,342, 14/543,787, 14/321,706, 15/801,239, 15/801, 259, 15/801,281, 15/801,304, 16/908,531, 17/031,108, and 63/094,313, the contents of which have been previously Incorporated by reference herein).

Figure 65:
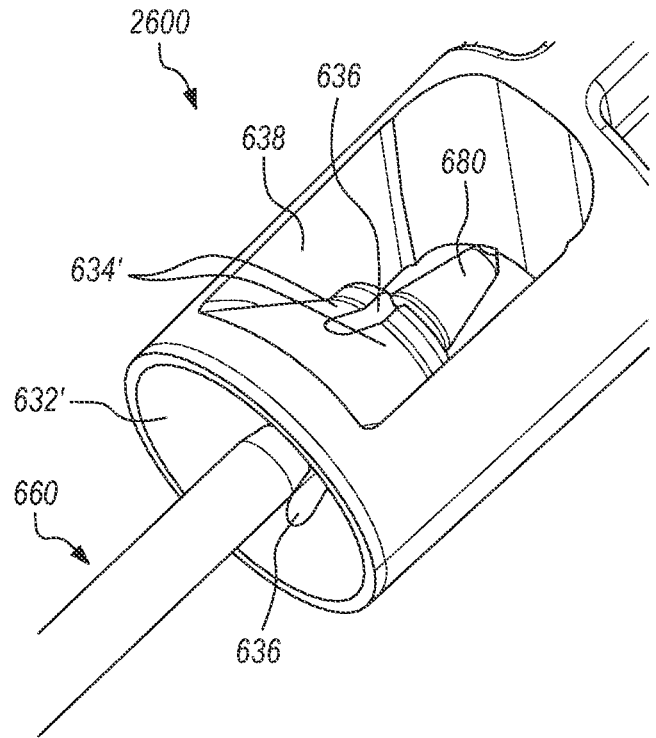
Figure 66:
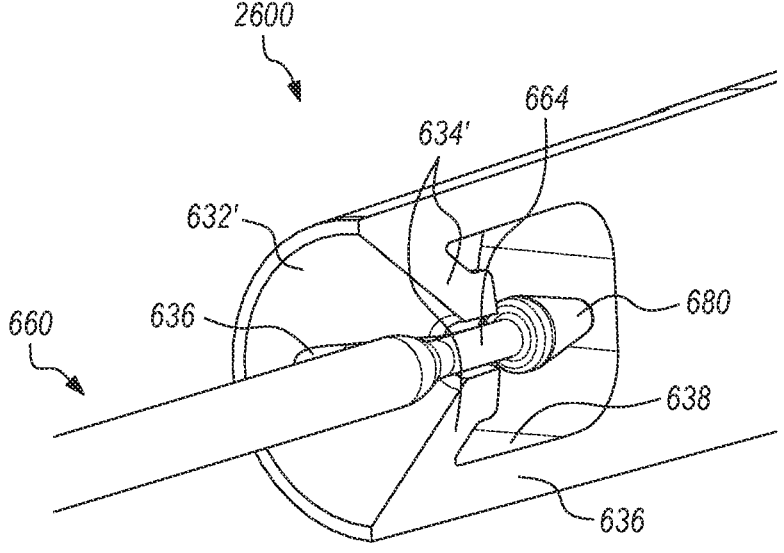
Figure 67A:
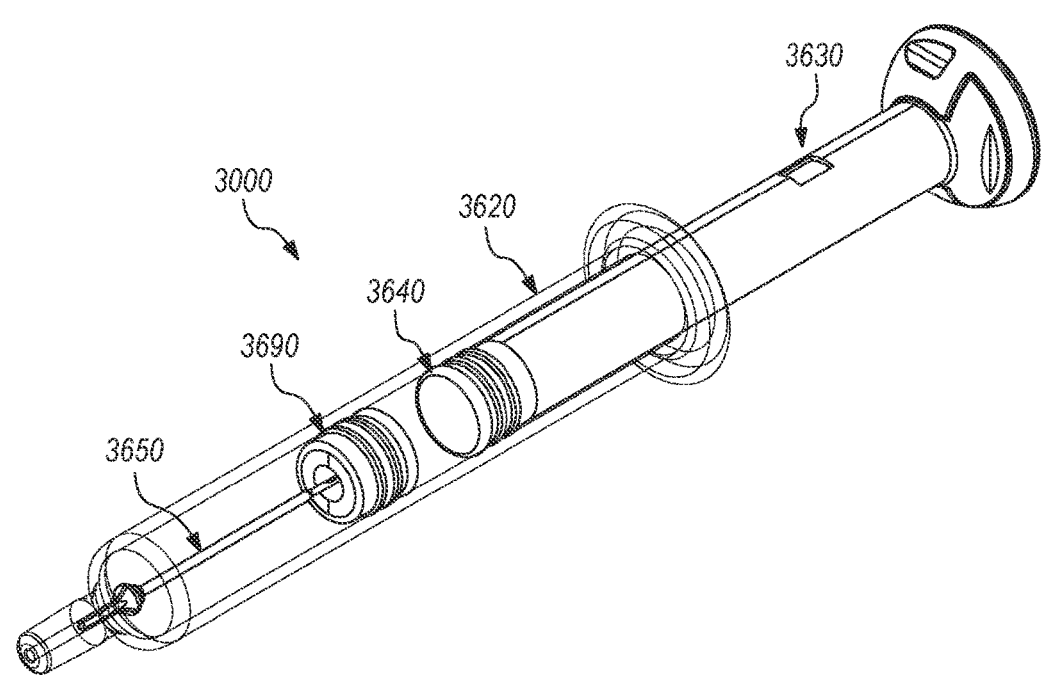
FIGS. 67A and 67B are perspective and side views of a dual chamber safe injection system according to some embodiments.
Figure 67B:
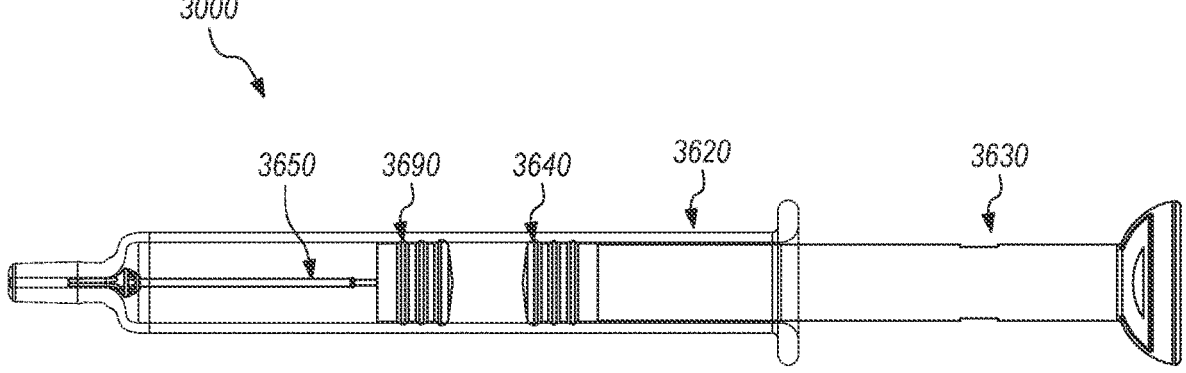

FIGS. 64 to 66 depict injection and needle capture upon distal movement of the stopper member (640) relative to the needle assembly (650). The interaction between the proximal tip (680) and the funnel (632') has guided the proximal tip (680) proximal of the pair of self-energizing tabs (634'). The relatively large radial overhang (about 0.0075") between the outer diameter of the toroid-shaped distal flange (686) of the proximal tip (680) and the reduced diameter portion (664) increases the probability and security of capture of the proximal tip (680) by the self-energizing tabs (634'). The self-energizing tabs (634') are separated by two slots (636) (see FIG. 65), which are parallel to the sidewalls of the needle catch member and the longitudinal axis. Due to the parallel configuration of the slots (636) relative to the sidewalls of the needle catch member, the tabs (634') are self-energizing in that the tabs (634') tighten around the reduced diameter portion (664) of the needle assembly (650) when the proximal tip (680) is pulled distally relative to the tabs (634'). The rotation of the tabs (634') and the portion of the funnel (632') distal of the slots (636) contribute to this self-energizing feature. The needle catch also includes a pair of windows 638, which facilitate rotation of the tabs (634').

The relatively large radial overhang also allows for a wider opening between the self-energizing tabs (634') without compromising retention of the proximal tip (680) after capture. In an embodiment with a relatively large radial overhang (e.g., 0.0075"), the self-energizing tabs (634') are configured to capture the proximal tip (680) with as much as 12 lbf of pull off force. The wider opening and the mildly-tapered middle portion (684) allows insertion of the proximal tip (680) between the self-energizing tabs (634') without triggering the needle retraction mechanism (e.g., a spring release latch).

V. Exemplary Dual Chamber Injection System

FIGS. 67A to 77 depict a dual chamber injection system (3600) having a fluid transfer assembly (3650) according to some embodiments. The fluid transfer assembly (3650) is similar to the needle assembly (650) described herein in that it has one or more channels (3662) and a proximal tip (3680) similar to corresponding channels (662) and proximal tip (680) in the needle assembly (650) described herein. The dual chamber injection system (3600) includes a needle connector (3610) formed at a distal end of a syringe body (3620), and a plunger member (3630) coupled to a proximal stopper member (3640) disposed in an interior of the syringe body (3620). A distal stopper member (3690) is also disposed in the interior of the syringe body (3620). While not depicted herein, the dual chamber injection system (3600) may include a needle retraction system such as those described in U.S. patent application Ser. Nos. 14/696,342, 14/543,787, 14/321,706, 15/801,239, 15/801,259, 15/801, 281, 15/801,304, 16/908,531, 17/031,108, and 63/094,313, the contents of which have been previously Incorporated by reference herein. The needle retraction system is mostly disposed in an interior of the plunger member (3630).

Figure 68A:
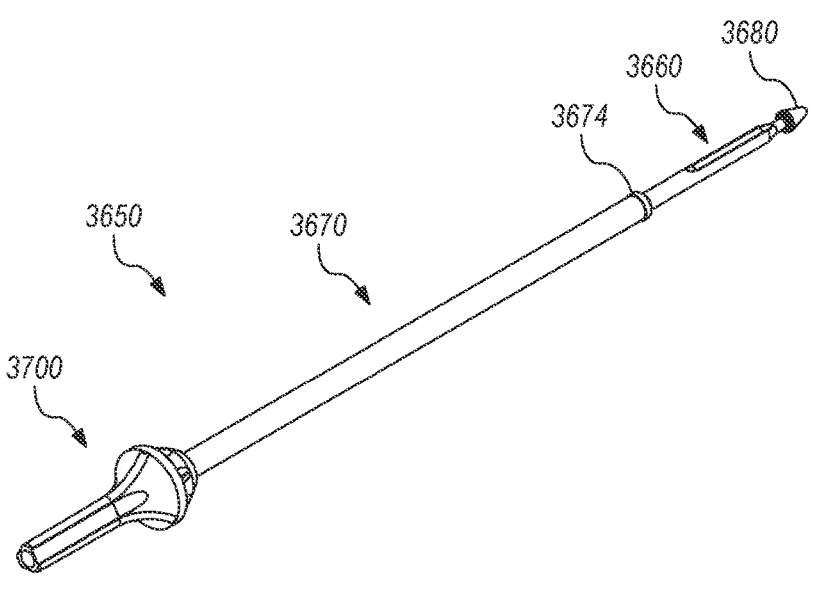
FIGS. 68A and 68B are perspective and exploded views of a fluid transfer assembly according to some embodiments.
Figure 68B:
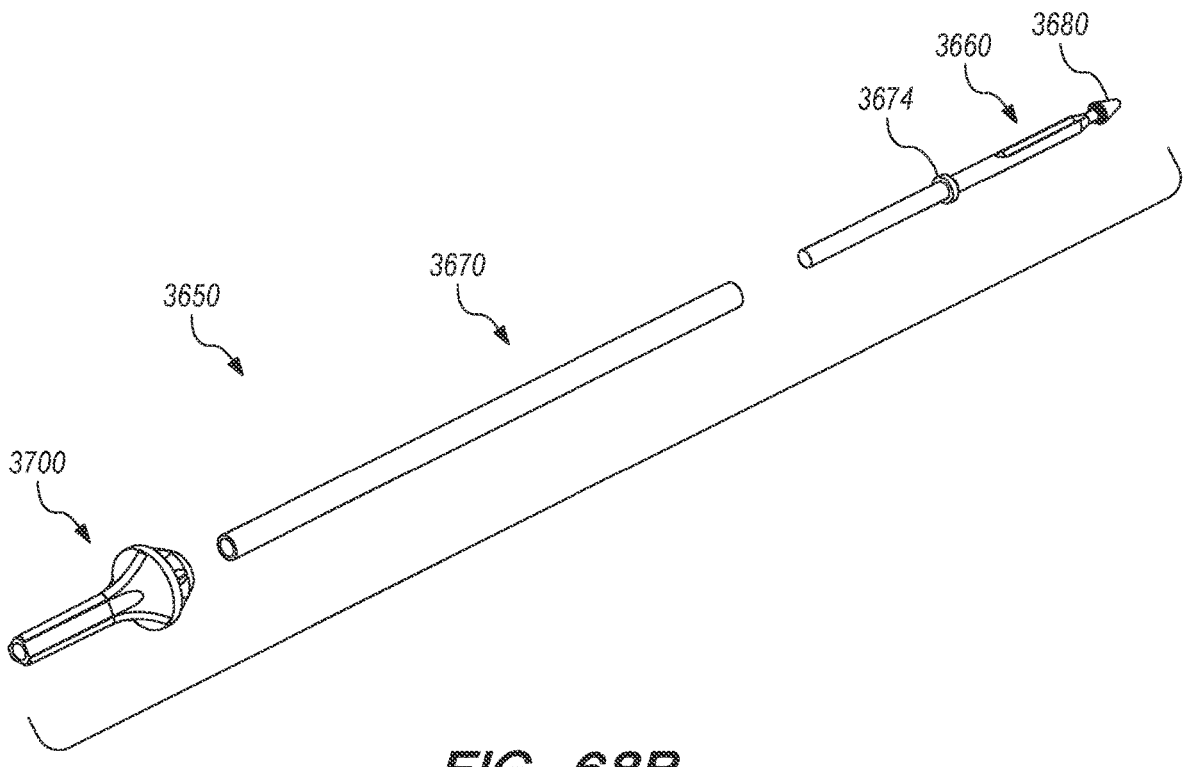
Figure 69A:
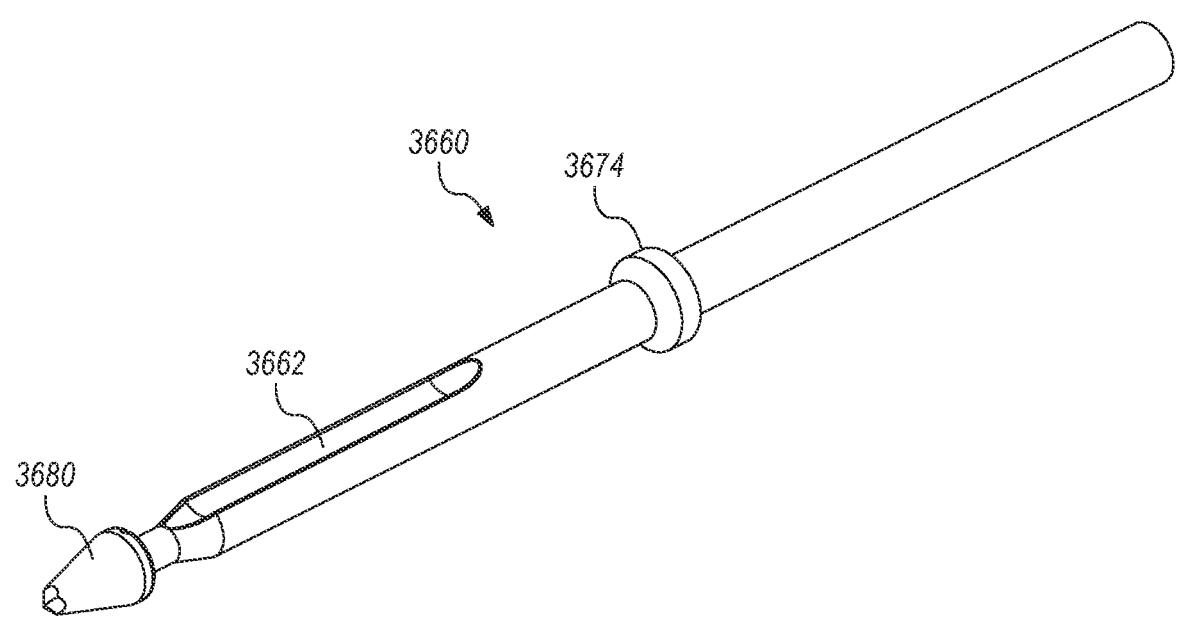
Figure 69B:
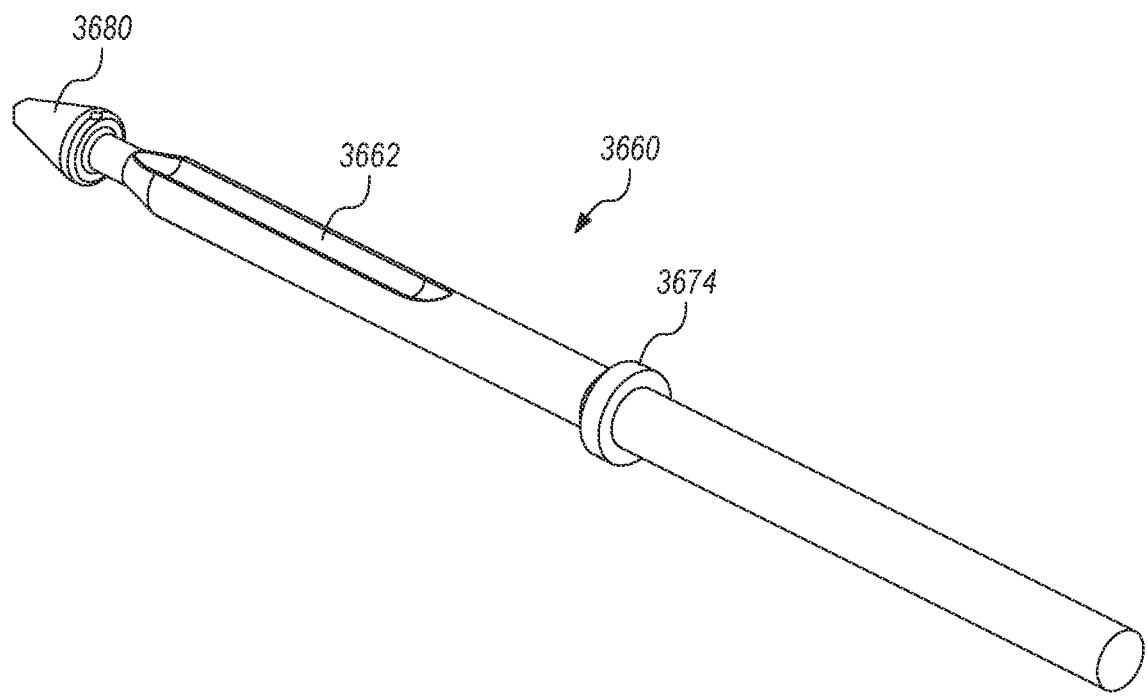
Figure 72A:
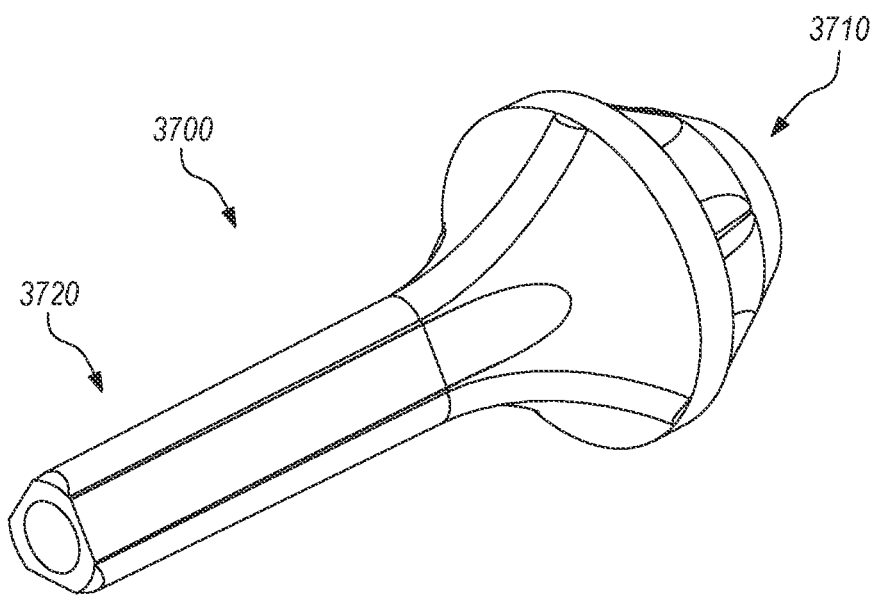
FIGS. 72A, 72B, 73A, 73B, and 73C are perspective, side, and axial cross-sectional views of a distal connector of a fluid transfer assembly according to some embodiments.
Figure 72B:
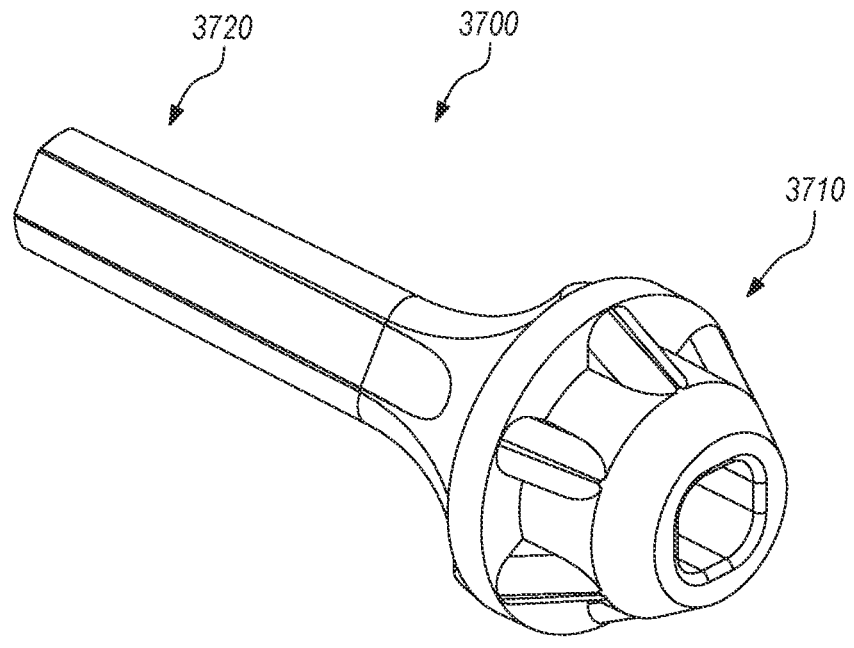

FIGS. 68A and 68B depicts a fluid transfer assembly (3650) according to some embodiments. FIG. 68B is an exploded view of the fluid transfer assembly (3650) depicted in FIG. 68A. The fluid transfer assembly (3650) includes a proximal portion (3660) configured to be partially disposed in the proximal end of a middle connector (3670). The fluid transfer assembly (3650) also includes a distal connector (3700) configured to receive a distal end of the middle connector which is in turn configured to be to be partially disposed in the proximal end of the distal connector (3700). The middle connector (3670) includes a radially extending annular flange (3674) configured to interfere with a distal stopper member (3690) as described in U.S. patent application Ser. Nos. 15/801,259, 16/435,429, 16/798,188, 16/908, 531, and 63/046,517, the contents of which are fully incorporated herein by reference as though set forth in full.

FIGS. 69A to 71D depicts a proximal portion (3660) of a fluid transfer assembly (3650) and various components thereof according to some embodiments. The proximal portion (3660) of the fluid transfer assembly (3650) includes a proximal tip (3680), a longitudinal channel (3662), and a radially extending annular flange (3674). The proximal tip (3680) in the fluid transfer assembly (3650) is similar to the proximal tip (680) in the needle assembly (650) described herein. In particular, the proximal tip (3680) includes a pyramidal proximal piercing tip (3682), a mildly-tapered middle portion (3684), a toroid-shaped distal flange (3686) (see FIG. 71A), which are structurally and functionally similar to respective pyramidal proximal piercing tip (682), mildly-tapered middle portion (684), toroid-shaped distal flange (686) of proximal tip (680). Like in the proximal tip (680), the transition between the pyramidal proximal piercing tip (3682) and the middle portion (3684) in proximal tip (3680) is smoothed. Accordingly, the proximal tip (3680) is configured to minimize snagging or seizing of a funnel (3696) during penetration of the proximal tip (3680) through the distal stopper member (3690) (see FIGS. 75A to 77).

As shown in FIG. 71B, the longitudinal channel (3662) in the proximal portion (3660) of the fluid transfer assembly (3650) has a rounded/circular cross-section, which minimizes fluid flow restriction through the longitudinal channel (3662).

As shown in FIGS. 71C and 71D, the radially extending annular flange (3674) is configured to temporarily interfere with a pair of tabs (3698) in stopper insert (3694) to hold the distal stopper member (3690) and the fluid transfer assembly (3650) in a transfer configuration relative to each other (see FIGS. 75A to 77) when a sufficient amount of force is applied to the plunger member (3630) to transfer fluid through the longitudinal channel (3662) in the fluid transfer assembly (3650). The a pair of tabs (3698) are also configured to allow the radially extending annular flange (3674) to pass therethrough when additional force is applied to the plunger member (3630) after transfer of fluid across the longitudinal channel (3662) is complete. The longitudinal channel (3662) is configured so that fluid flow is stopped after the annular flange (3674) has moved proximal of the tabs (3698). Further details regarding fluid transfer in dual chamber injection systems are described in U.S. patent application Ser. Nos. 15/801,259, 16/435,429, 16/798,188, 16/908,531, and 63/046,517, the contents of which have been previously Incorporated by reference herein.

FIGS. 72A to 74B depict the distal connector (3700) according to various embodiments. The distal connector (3700) includes a radially enlarged proximal portion (3710) and a distal portion (3720). The radially enlarged proximal portion (3710) is configured to receive a distal end of the middle connector (3670) of the fluid transfer assembly (3650). As shown in FIG. 73C, the opening (3712) in the proximal portion (3710) has a squircle cross-sectional shape. Accordingly, when the middle connector (3670), which is tubular with a circular cross-sectional shape, is inserted into the opening (3712) in the proximal portion (3710) (see FIG. 74A), a mechanical fit is formed between the distal end of the middle connector (3670) and the proximal portion (3710) of the distal connector (3700).

Figure 73A:
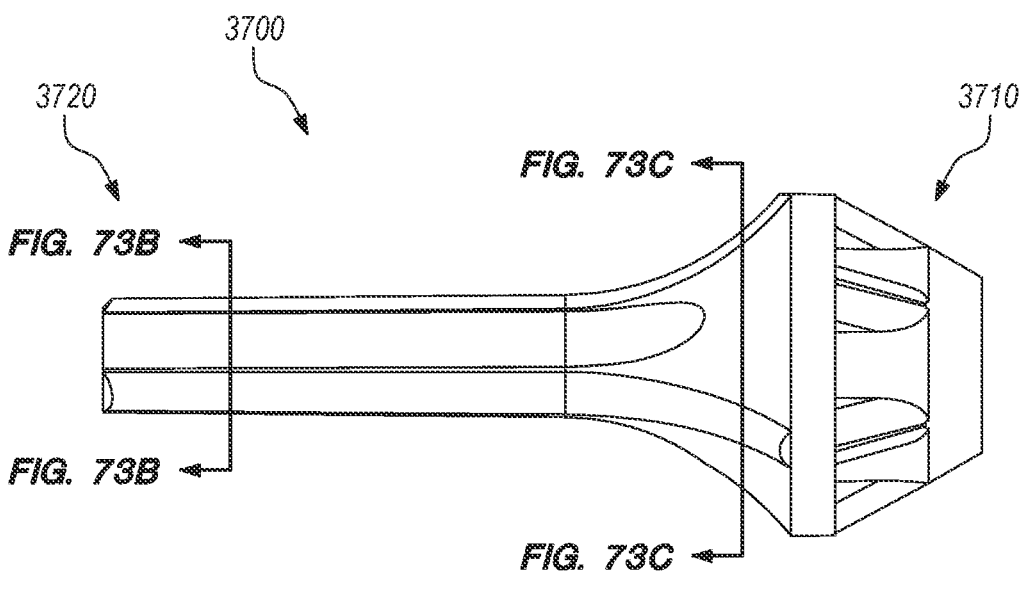
Figure 73B:
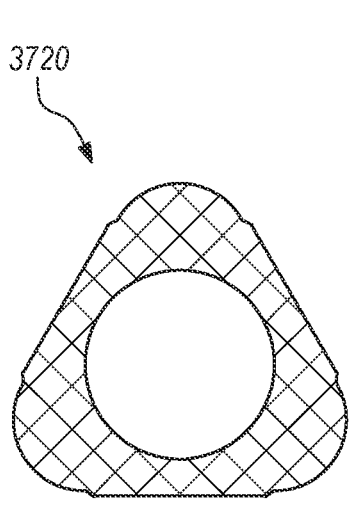
Figure 73C:
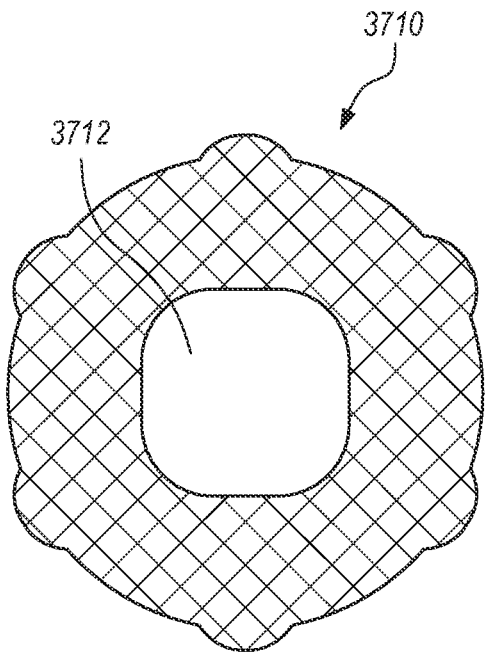
Figure 74A:
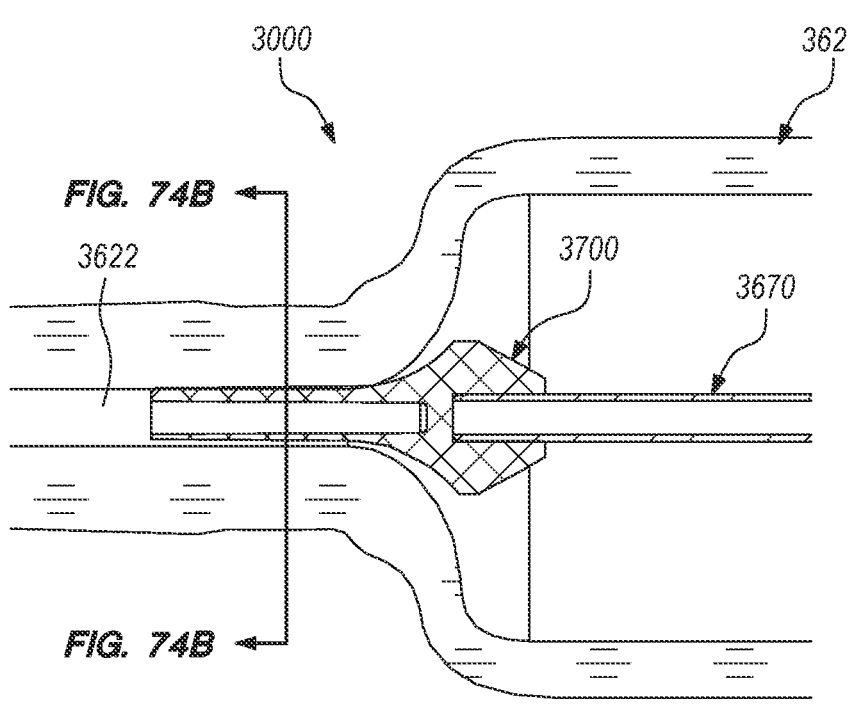
FIGS. 74A and 74B are detailed longitudinal and axial cross-section views of a distal connector of a fluid transfer inserted into a distal end of a syringe body according to some embodiments.
Figure 74B:
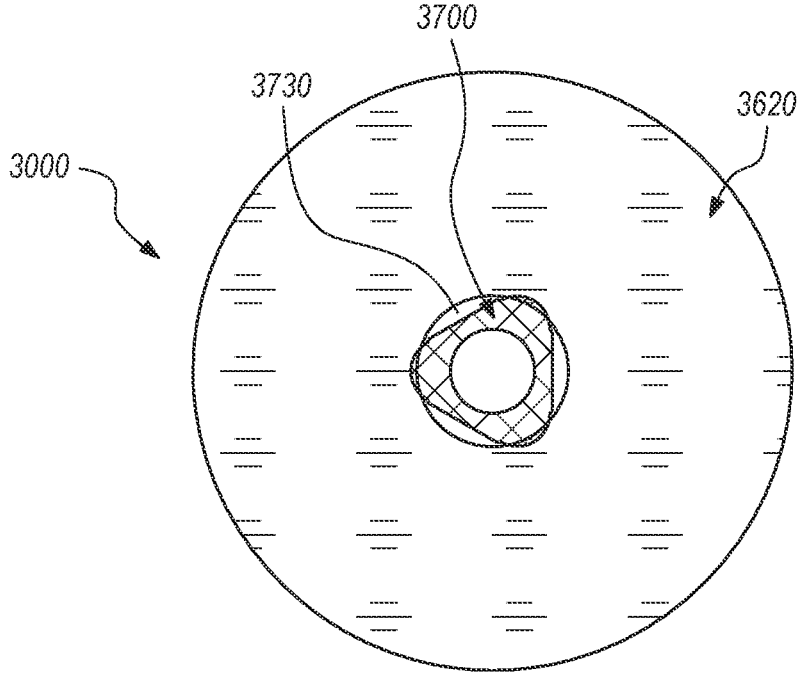
Figure 75A:
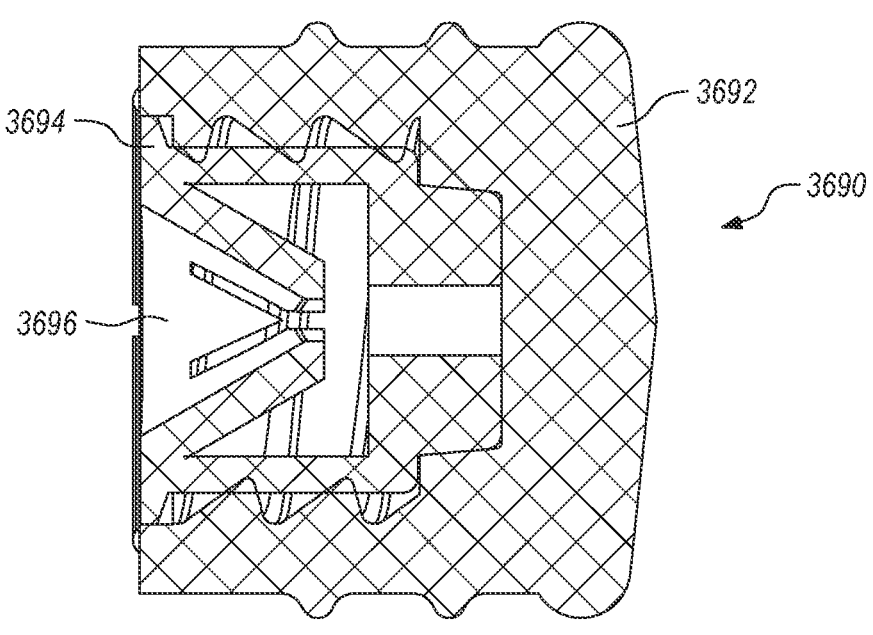
FIGS. 75A and 75B are longitudinal cross-sectional and exploded views of a distal connector of a stopper member with a stopper insert according to some embodiments.
Figure 75B:
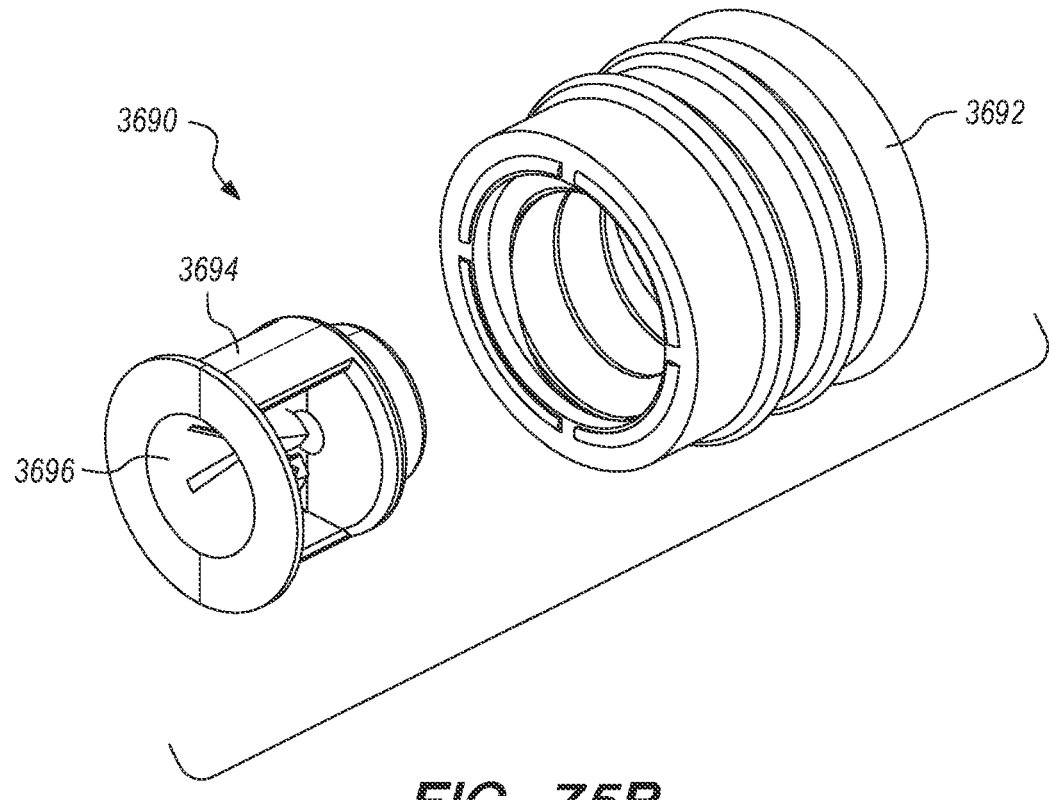

As shown in FIGS. 73B and 74B, the distal portion (3720) is configured to fit into a distal opening of a syringe body (3620) couple the fluid transfer assembly (3650) thereto. The outside of the distal portion (3720) has a rounded triangle cross-section. Accordingly, when the distal connector (3700) is inserted into the opening (3622) in the distal end of the syringe body (3620) (see FIG. 74A), a mechanical fit is formed between the distal portion (3720) of the distal connector (3700) and the distal end of the syringe body (3620). FIG. 74B also shows that three channels (3730) are formed between the exterior of the distal portion (3720) of the distal connector (3700) and the distal end of the syringe body (3620). These channels (3730) allow fluid to exit from the interior of the syringe body (3620) to the exterior of the syringe body (3620).

FIGS. 75A to 76C depict a distal stopper member (3690) for use with dual chamber injection systems according to some embodiments. The distal stopper member (3690) includes an off-the-shelf rubber stopper (3692) and a stopper insert (3694) disposed therein. The stopper insert (3694) includes a pair of elastically deformable tabs (3698) (see FIGS. 76A to 76B), which form part of a distally facing funnel (3696). As described herein, the tabs (3698) are configured to temporarily interfere with the radially extending annular flange (3674) of the fluid transfer assembly (3650) to hold the distal stopper member (3690) and the fluid transfer assembly (3650) in a transfer configuration relative to each other (see FIG. 77) when a sufficient amount of force is applied to the plunger member (3630) to transfer fluid through the longitudinal channel (3662) in the fluid transfer assembly (3650). The tabs (3698) are also configured to allow the radially extending annular flange (3674) to pass therethrough when additional force is applied to the plunger member (3630) after transfer of fluid across the longitudinal channel (3662) is complete.

Figure 77:
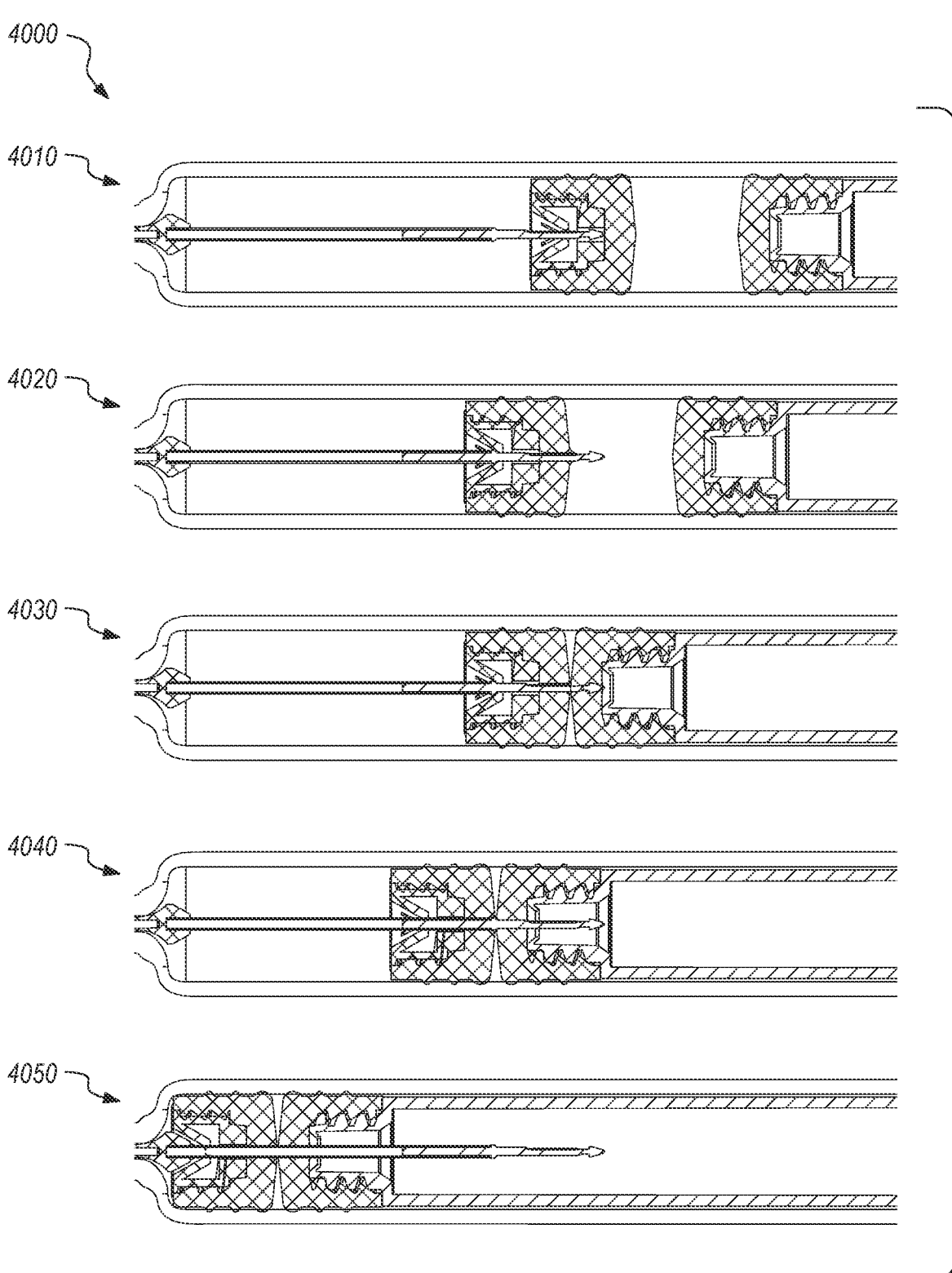
FIG. 77 schematically depicts various steps in fluid transfer and injection using a dual chamber injection system according to some embodiments.
Figure 78A:
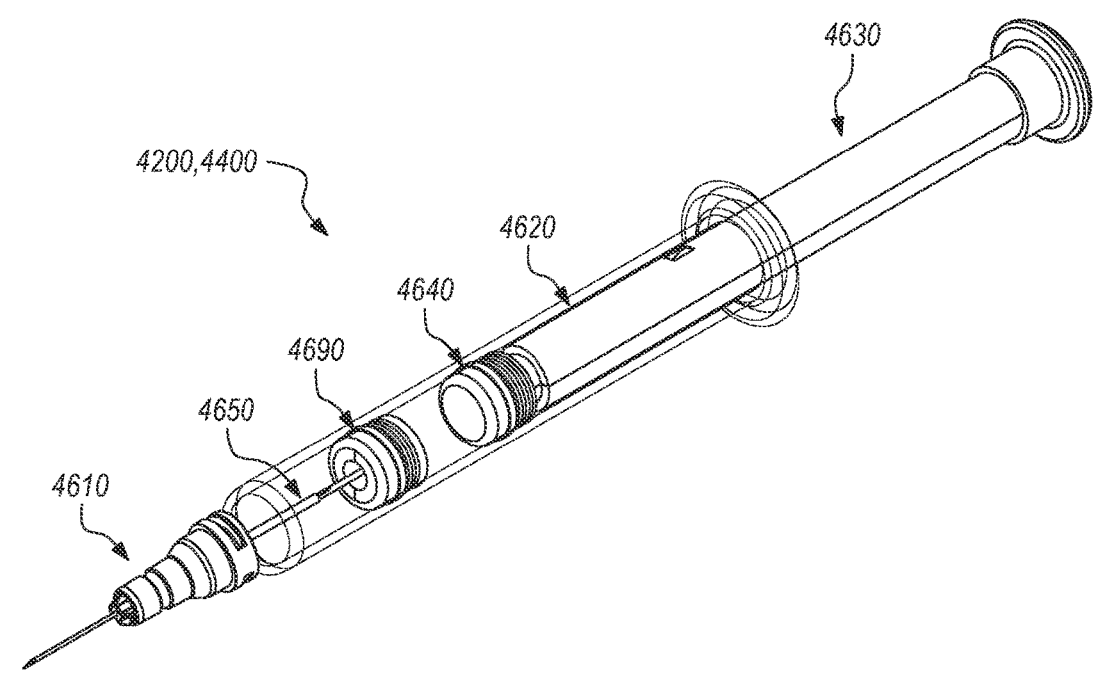
FIGS. 78A and 78B are perspective and side views of a dual chamber safe sequential injection system according to some embodiments.
Figure 78B:
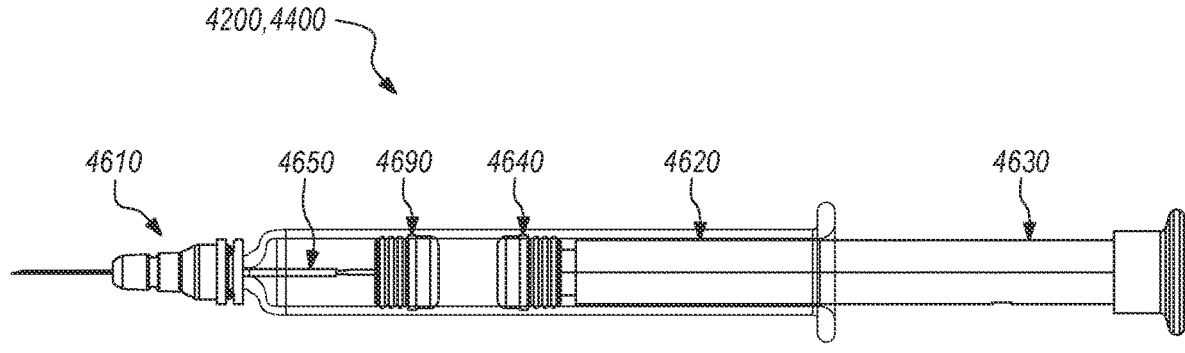

FIG. 77 depicts various steps in fluid transfer and injection (4000) using a dual chamber injection system such as the system (3600) described herein. At step (4010), the system is in a transport configuration, where the proximal tip (3680) is disposed against a distal surface of the rubber stopper (3692).

At step (4020), sufficient force has been applied to the plunger assembly (3630) to drive the distal stopper member (3690) distally against the proximal tip (3680), which pierces the rubber stopper (3692). With the transfer tube assembly (3650) and the distal stopper member (3690) in the position depicted in step (4020), the system is in a fluid transfer configuration where proximal and distal chambers are fluidly coupled via the longitudinal channel (3662) in the needle assembly (3650). As described herein, interference between the tabs (3698) of the stopper insert (3694) and the radially extending annular flange (3674) of the needle assembly (3650) holds the in the fluid transfer configuration while continued application of force to the plunger member (3630) transfers fluid from the proximal chamber to the distal chamber.

At step (4030), the proximal stopper member (3640) has moved distally until it is in contact with the distal stopper member (3690), thereby completing fluid transfer. At this point, increased force can be applied to the distal stopper member (3690) because fluid transfer has ceased.

At step (4040), the increased force applied to the distal stopper member (3690) overcomes the interference between the tabs (3698) of the stopper insert (3694) and the radially extending annular flange (3674) of the needle assembly (3650) to move the distal stopper member (3690) distally relative to the fluid transfer member (3650) to eject fluid from the distal chamber to the exterior of the syringe body (3620).

At step (4050), the ejection of fluid from the distal chamber to the exterior of the syringe body (3620) is completed. The distal stopper member (3690) has moved to the distal end of the syringe body (4020). Further details regarding fluid transfer and injection using dual chamber injection systems are described in U.S. patent application Ser. Nos. 15/801,259, 16/435,429, 16/798,188, 16/908,531, and 63/046,517, the contents of which have been previously Incorporated by reference herein.

VI. Exemplary Sequential Safe Injection System

FIGS. 78A to 85 depict sequential safe injection systems (4200, 4400) having a needle assembly (4650, 4750) according to some embodiments. The needle assemblies (4650, 4750) are similar to the needle assembly (650) described herein in that it has one or more channels (4662) and a proximal tip (4680) similar to corresponding channels (662) and proximal tip (680) in the needle assembly (650) described herein. The sequential safe injection systems (4200, 4400) include a needle hub assembly (4610) coupled to a syringe body (4620), and a plunger member (4630) coupled to a proximal stopper member (4640) disposed in an interior of the syringe body (4620). A distal stopper member (4690) is also disposed in the interior of the syringe body (4620). The sequential safe injection system (4600) also includes a needle retraction system such as those described in U.S. patent application Ser. Nos. 14/696,342, 14/543,787, 14/321,706, 15/801,239, 15/801,259, 15/801,281, 15/801,304, 16/908,531, 17/031,108, and 63/094,313, the contents of which have been previously Incorporated by reference herein. The needle retraction system is mostly disposed in an interior of the plunger member (4630).

Figure 79:
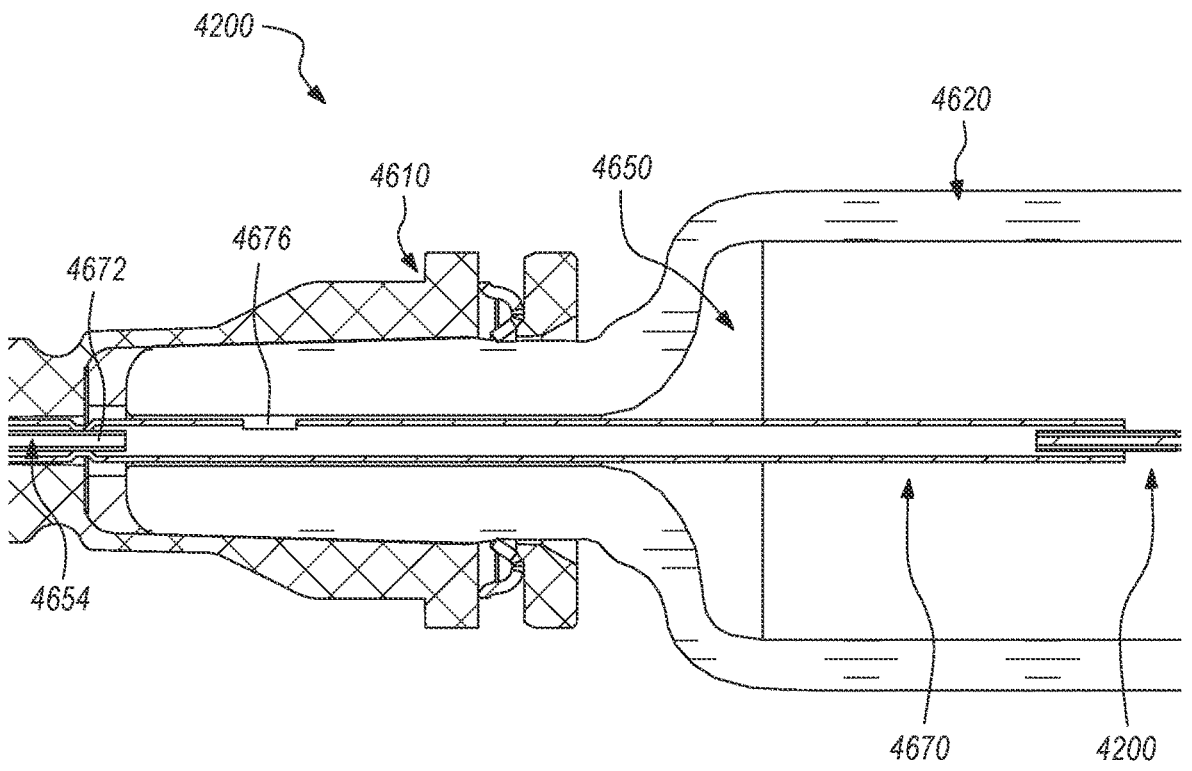
FIG. 79 is a detailed longitudinal cross-sectional view of a dual chamber safe sequential injection system according to some embodiments.

FIG. 79 depicts a sequential safe injection system (4200) according to some embodiments. The sequential safe injection system (4200) includes a needle assembly (4650) having a proximal portion (4660) and a distal portion 4654 each configured to be partially disposed in respective proximal and distal ends of a middle connector (4670). The needle assembly (4650) is similar to the needle assembly (650) described herein in that it has one or more channels and a proximal tip similar to corresponding channels (662) and proximal tip (680) in the needle assembly (650) described herein. The middle connector (4670) includes an annular recess (4672) configured to interfere with a needle latch as described in U.S. patent application Ser. Nos. 14/696,342, 14/543,787, 14/321,706, 15/801,239, 15/801,259, 15/801, 281, 15/801,304, 16/908,531, 17/031,108, and 63/094,313, the contents of which have been previously Incorporated by reference herein, to prevent proximal retraction of the needle assembly (4650) before the end of injection. The middle connector (4670) also includes a vent opening (4676) two release pressure buildup during injection.

Figure 80:
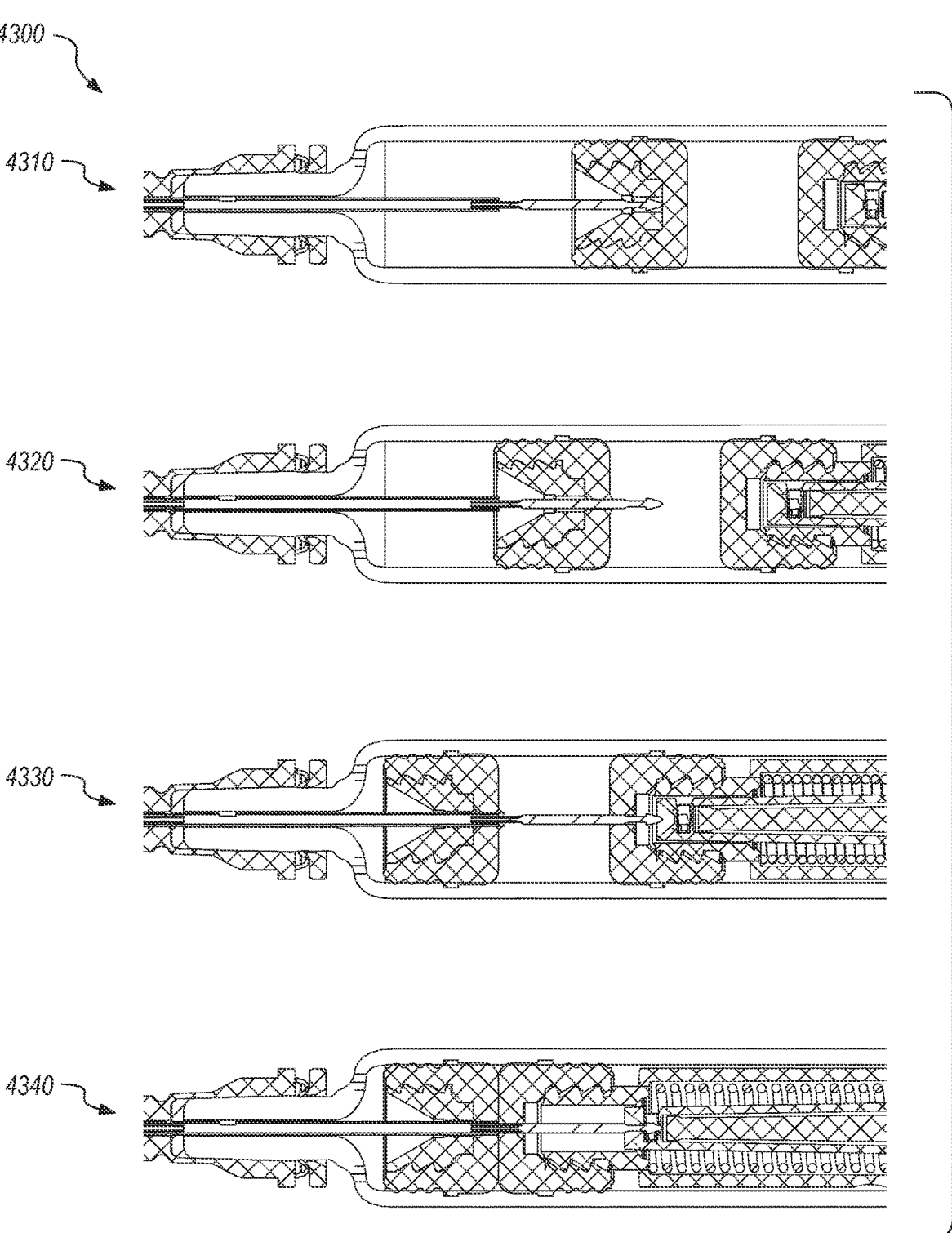
FIG. 80 schematically depicts various steps in sequential injection using a dual chamber injection system according to some embodiments.

FIG. 80 depicts various steps in sequential injection (4300) using a dual chamber injection system such as the system (4200) described herein. At step (4310), the system is in a transport configuration, where the proximal tip of the needle assembly is disposed against a distal surface of a rubber stopper of the distal stopper member (4290).

At step (4320), sufficient force has been applied to the plunger assembly to drive the distal stopper member (4290) distally against the proximal tip, which pierces the rubber stopper. Distal movement of the distal stopper member (4290) ejects fluid from the distal chamber through the longitudinal channel in the needle assembly (4650).

At step (4030), the distal stopper member (4290) has moved distally until it is at a distal end of the syringe body (4620), thereby completing fluid transfer from the distal chamber. Fluid transfer from the distal chamber also ceases because the longitudinal channel is no longer fluidly connected to the distal chamber. Instead, movement of the distal stopper member (4290) has brought the longitudinal channel into fluid communication with the proximal chamber.

At step (4040), the proximal stopper member (4240) has moved distally until it is until it is in contact with the distal stopper member (4290), thereby completing fluid transfer from the proximal chamber. As such, the system (4200) has been used to serially inject fluid first from the distal chamber, then from the proximal chamber. After injection of fluid from both the distally proximal chambers, a needle retraction system may exerts a proximally directed force on the needle assembly (4650) to pull the needle assembly (4650) at least partially inside of the needle hub assembly (4610) and/or the syringe body (4620) such that the sharp distal tip of the needle assembly (4650) is disposed in the needle hub assembly (4610) and/or the syringe body (4620) to prevent accidental needle sticks as described in U.S. patent application Ser. Nos. 14/696,342, 14/543,787, 14/321,706, 15/801,239, 15/801,259, 15/801,281, 15/801,304, 16/908, 531, 17/031,108, and 63/094,313, the contents of which have been previously Incorporated by reference herein. Further details regarding sequential injection systems are described in U.S. Patent Application Ser. No. 63/046,517, the contents of which have been previously Incorporated by reference herein.

Figure 81:
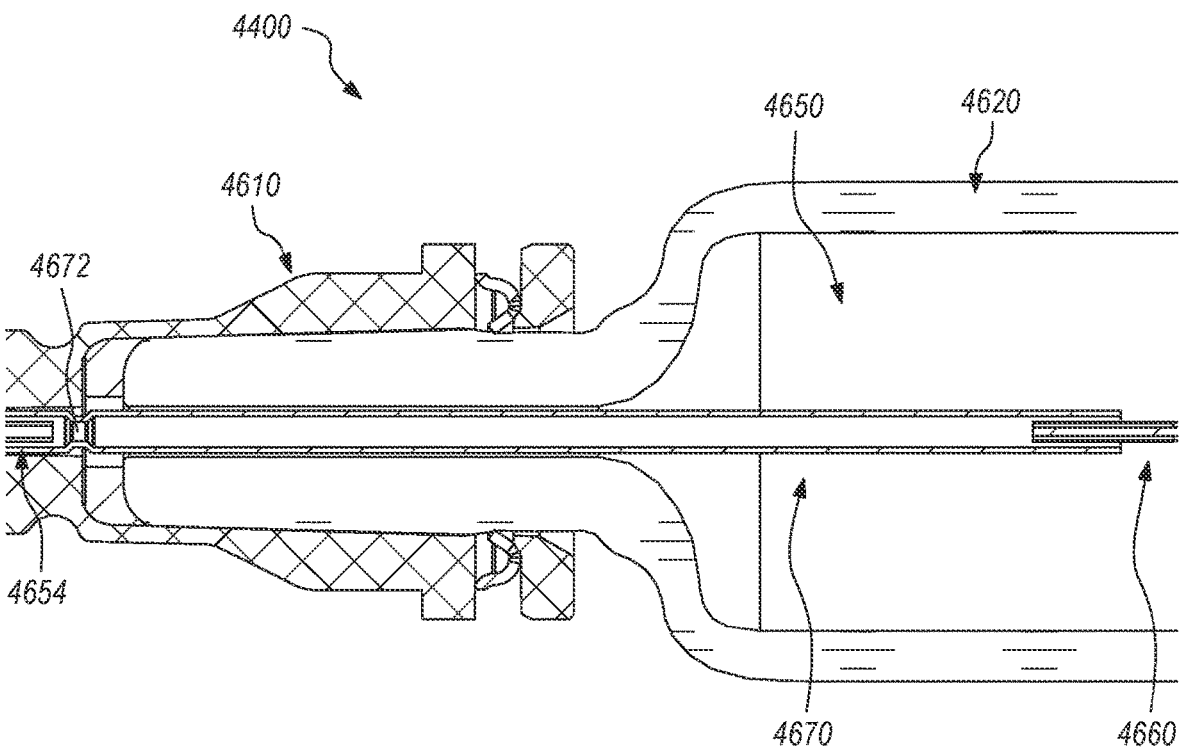
FIG. 81 is a detailed longitudinal cross-sectional view of a dual chamber safe sequential injection system according to some embodiments.
Figure 82:
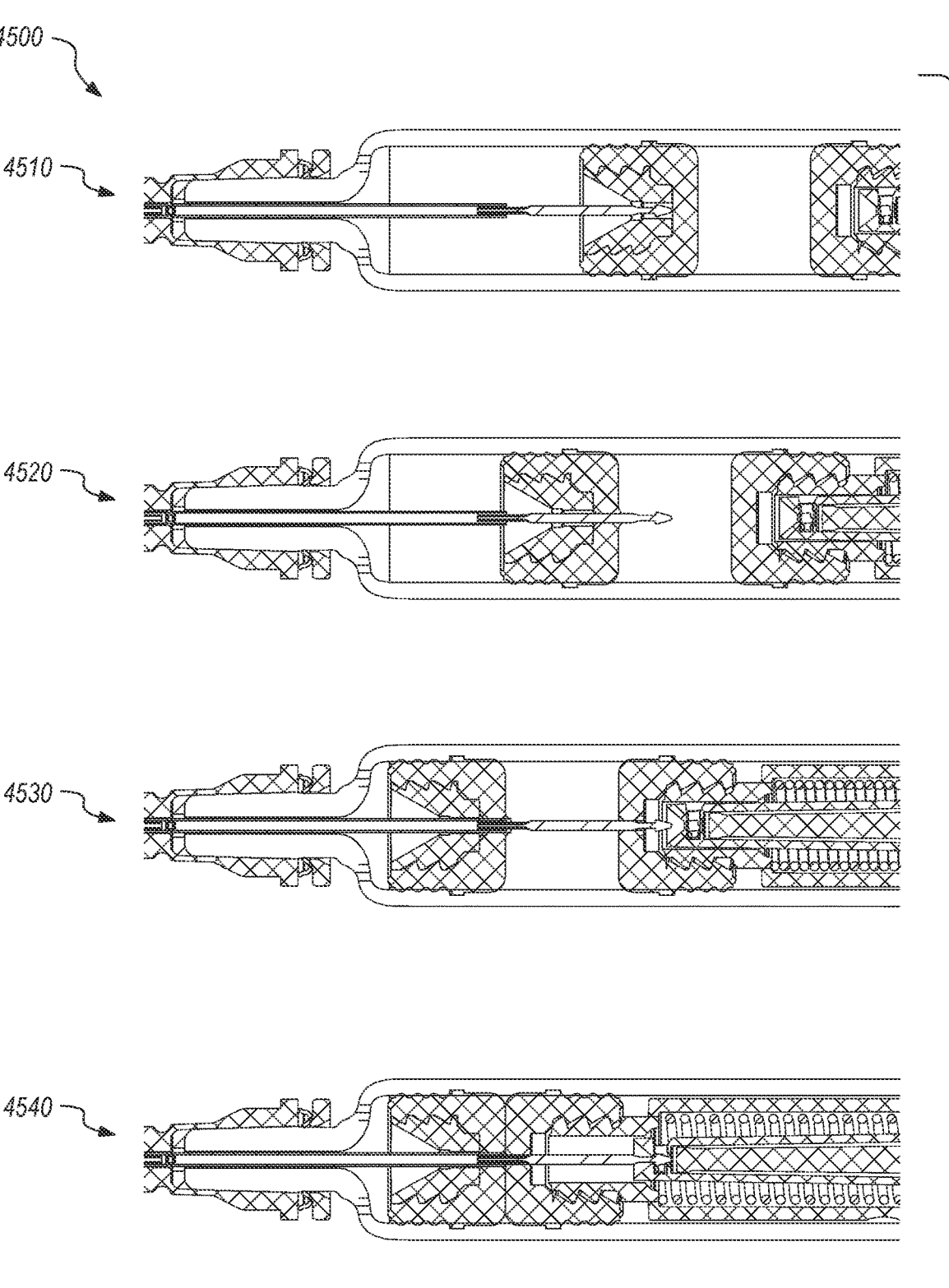
FIG. 82 schematically depicts various steps in injection using a dual chamber injection system according to some embodiments.

FIGS. 81 and 82 depict a dual chamber safe injection system (4400) according to some embodiments. The difference between the safe injection system (4400) depicted in FIGS. 81 and 82 and the sequential safe injection system (4200) depicted in FIGS. 79 and 80 is that the safe injection system (4200) includes a distal slot (4676) in the middle connector (4670), and the safe injection system (4400) does not include a distal slot in the middle connector (4670). There is no fluid drug/injectable stored in the distal chamber of the dual chamber safe injection system (4400). The sequence (4500) of steps (4510) to (4540) depicted in FIG. 82 is designed to minimize interaction between the stainless steel components of the needle assembly (4650) and the drug stored in the proximal chamber of the dual chamber safe injection system (4400) during long-term storage of the pre-filled dual chamber safe injection system (4400). The drug and stainless steel components only come into contact momentarily at time of injection. The dual chamber safe injection system (4400) may include only polymer latching mechanisms to further minimize interaction between injectables and metals. Steps (4510) to (4540) depicted in FIG. 82 are almost identical to steps (4310) to (4340) depicted in FIG. 80, except that there is no fluid drug/injectable stored in the distal chamber of the dual chamber safe injection system (4400). Accordingly, steps (4520) and (4530) only introduce the needle assembly (4650) into the proximal chamber for injection of fluid therein (immediately after introduction of the needle assembly (4650)).

FIGS. 83A to 85 depict a various components of a needle assembly (4550) for use with a sequential safe injection system (e.g., the systems (4200, 4400) described herein) according to some embodiments. The difference between the needle assembly (4550) depicted in FIGS. 83A to 85 and the needle assemblies (4650) depicted in FIGS. 78A to 82 is that the needle assembly (4550) includes two longitudinally separated longitudinal channels (4562A, 4562B) (see FIGS. 83B and 84) instead of a single longitudinal channel.

Figure 83A:
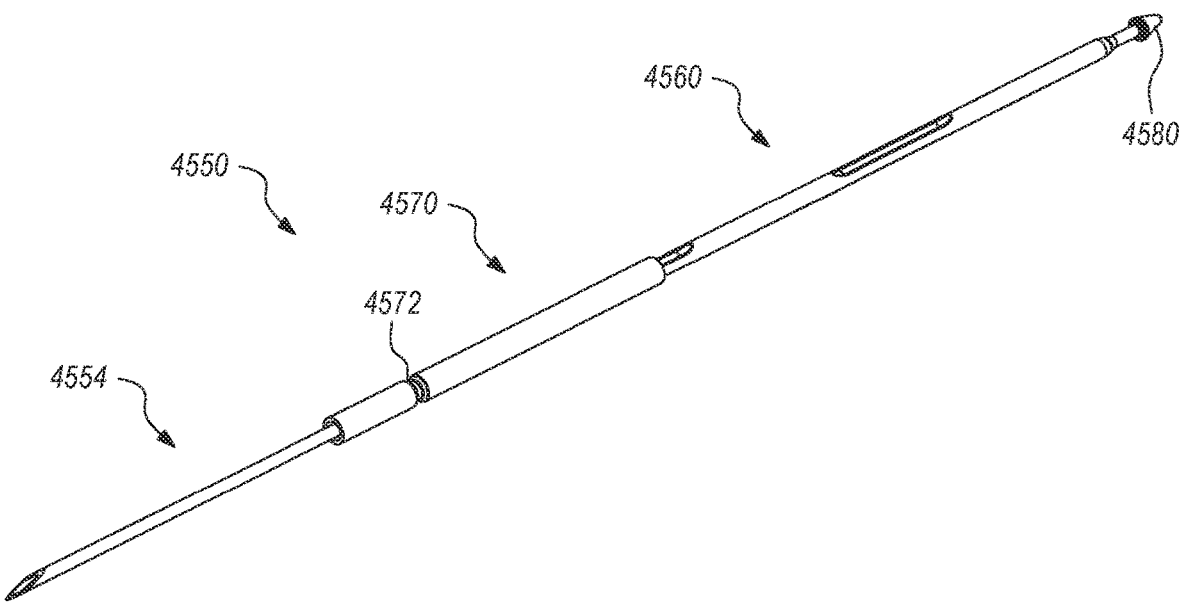
FIG. 83A is a detailed perspective view of a fluid transfer assembly according to some embodiments.

FIG. 83A depicts a needle assembly (4550) for use with a safe sequential injection system according to some embodiments. The needle assembly (4550) a proximal portion (4560) and a distal portion (4554) each configured to be partially disposed in respective proximal and distal ends of a middle connector (4570). The needle assembly (4550) is similar to the needle assembly (650) described herein in that it has one or more channels and a proximal tip similar to corresponding channels (662) and proximal tip (680) in the needle assembly (650) described herein. The middle connector (4570) includes an annular recess (4572) configured to interfere with a needle latch as described in U.S. patent application Ser. Nos. 14/696,342, 14/543,787, 14/321,706, 15/801,239, 15/801,259, 15/801,281, 15/801,304, 16/908, 531, 17/031,108, and 63/094,313, the contents of which have been previously Incorporated by reference herein, to prevent proximal retraction of the needle assembly (4550) before the end of injection.

Figure 83B:
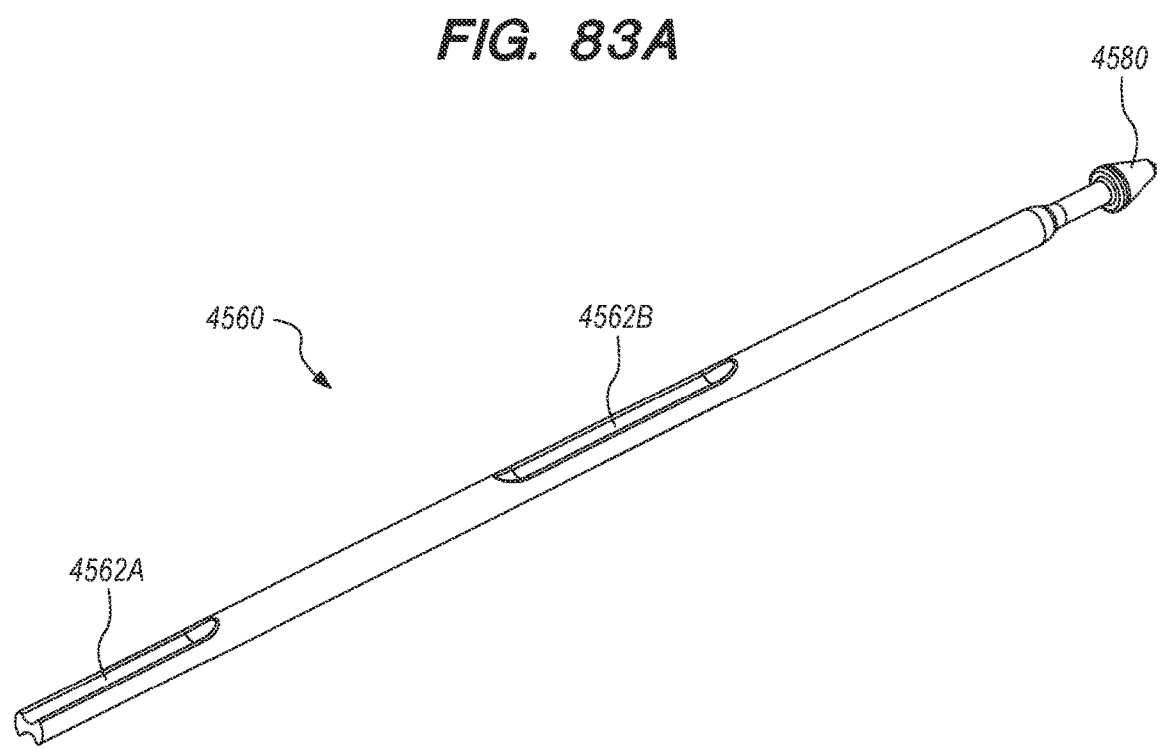
FIGS. 83B is and 84 are detailed perspective views of a proximal portion of a fluid transfer assembly according to some embodiments.
Figure 84:
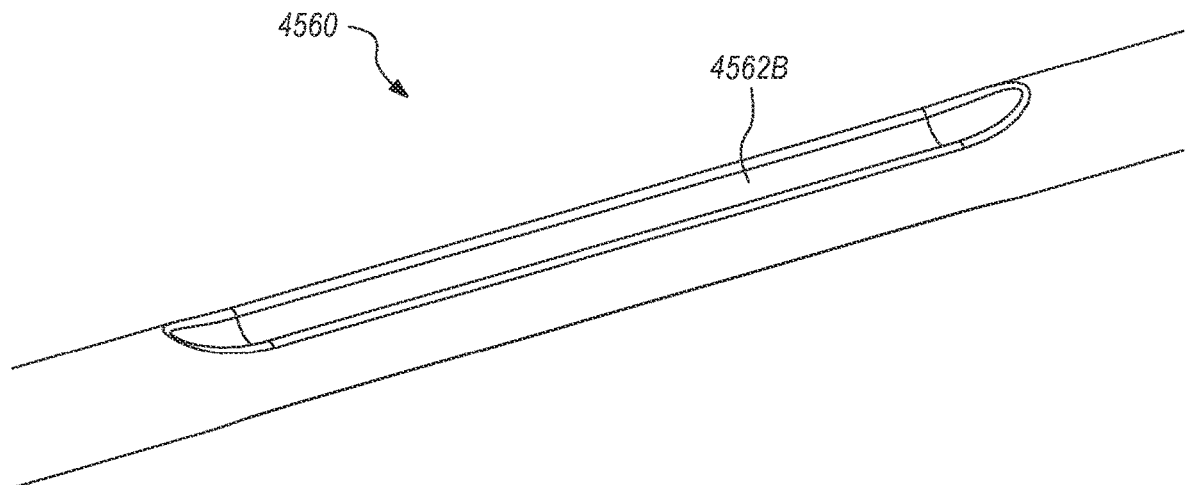

FIG. 83B depicts a proximal portion (4560) of the needle assembly (4550) according to some embodiments. The proximal portion (4560) has a distal longitudinal channel (4562A) and a proximal longitudinal channel (4562B). The proximal portion (4560) also has a proximal tip (4580) similar to the proximal tip (680) described herein. FIG. 84 depicts the proximal portion (4560) in greater detail showing the proximal longitudinal channel (4562B). The distal longitudinal channel (4562A) is configured to provide an exit from a distal chamber to an exterior of the syringe body (4520). The proximal longitudinal channel (4562B) is configured to provide an exit from a proximal chamber to an exterior of the syringe body (4520).

Figure 85:
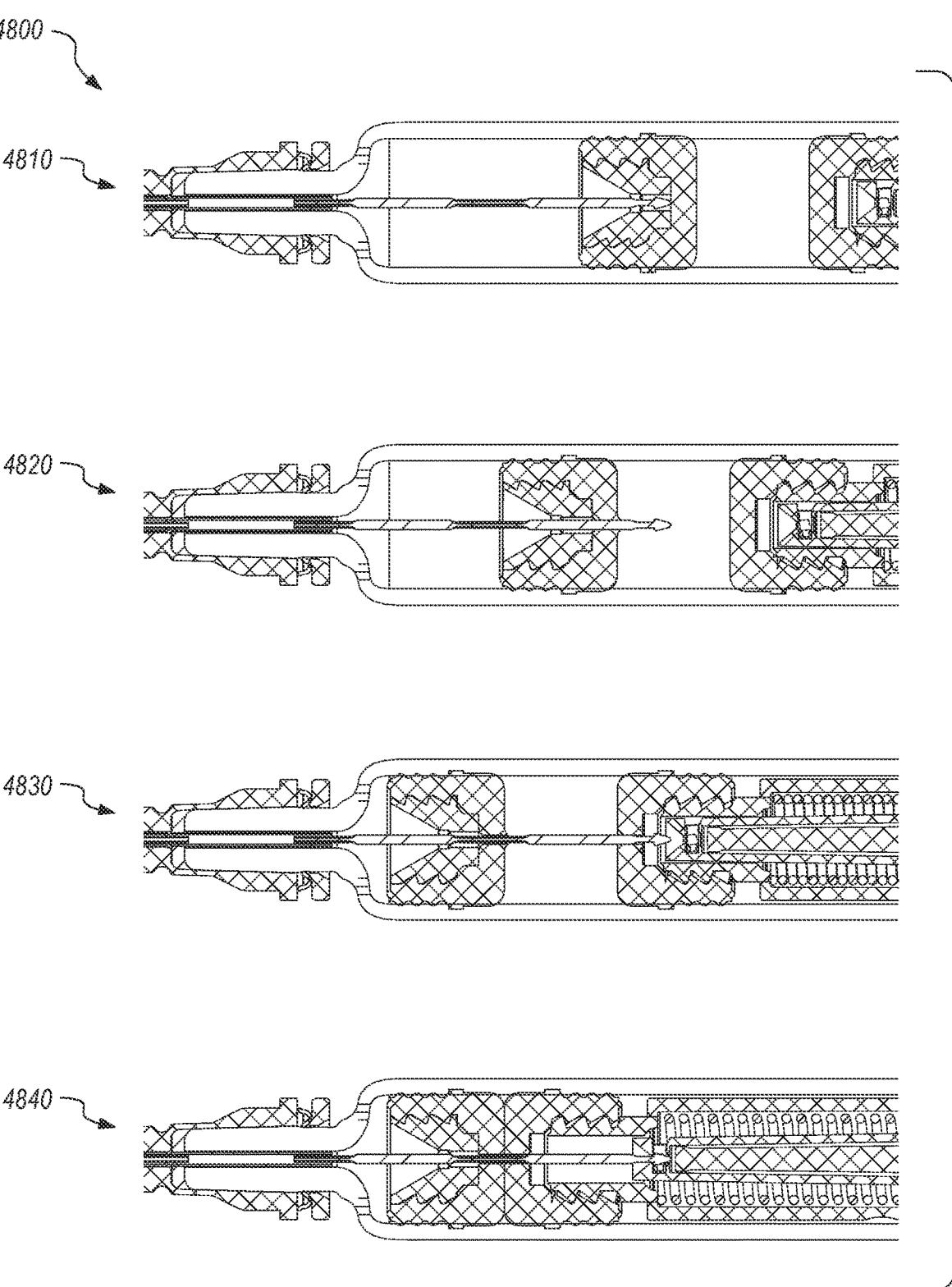
FIG. 85 schematically depicts various steps in sequential injection using a dual chamber injection system according to some embodiments.

FIG. 85 depicts various steps in sequential injection (4800) using a dual chamber injection system with the needle assembly (4550) described herein. At step (4810), the system is in a transport configuration, where the proximal tip (4580) of the needle assembly (4550) is disposed against a distal surface of a rubber stopper of the distal stopper member (4690).

At step (4820), sufficient force has been applied to the plunger assembly (4630) to drive the distal stopper member (4690) distally against the proximal tip (4580), which pierces the rubber stopper. Distal movement of the distal stopper member (4690) ejects fluid from the distal chamber through the distal longitudinal channel (4562A) in the needle assembly (4550).

At step (4830), the distal stopper member (4690) has moved distally until it is at a distal end of the syringe body (4620), thereby completing fluid transfer from the distal chamber. Fluid transfer from the distal chamber also ceases because the proximal longitudinal channel (4562B) is fluidly connected to the proximal chamber. At this point, the fluid transfer from the proximal chamber can begin via the proximal longitudinal channel (4562B).

At step (4040), the proximal stopper member (4840) has moved distally until it is until it is in contact with the distal stopper member (4690), thereby completing fluid transfer from the proximal chamber through the proximal longitudinal channel (4562B). As such, the system has been used to serially inject fluid first from the distal chamber, then from the proximal chamber. After injection of fluid from both the distally proximal chambers, a needle retraction system may exerts a proximally directed force on the needle assembly (4550) to pull the needle assembly (4550) at least partially inside of the needle hub assembly (4610) and/or the syringe body (4620) such that the sharp distal tip of the needle assembly (4550) is disposed in the needle hub assembly (4610) and/or the syringe body (4620) to prevent accidental needle sticks as described in U.S. patent application Ser. Nos. 14/696,342, 14/548,787, 14/321,706, 15/801,239, 15/801,259, 15/801,281, 15/801,304, 16/908,531, 17/031, 108, and 63/094,313, the contents of which have been previously Incorporated by reference herein. Further details regarding sequential injection systems are described in U.S. Patent Application Ser. No. 63/046,517, the contents of which have been previously Incorporated by reference herein.

VII. Exemplary Injection System with Valve

Figure 86:
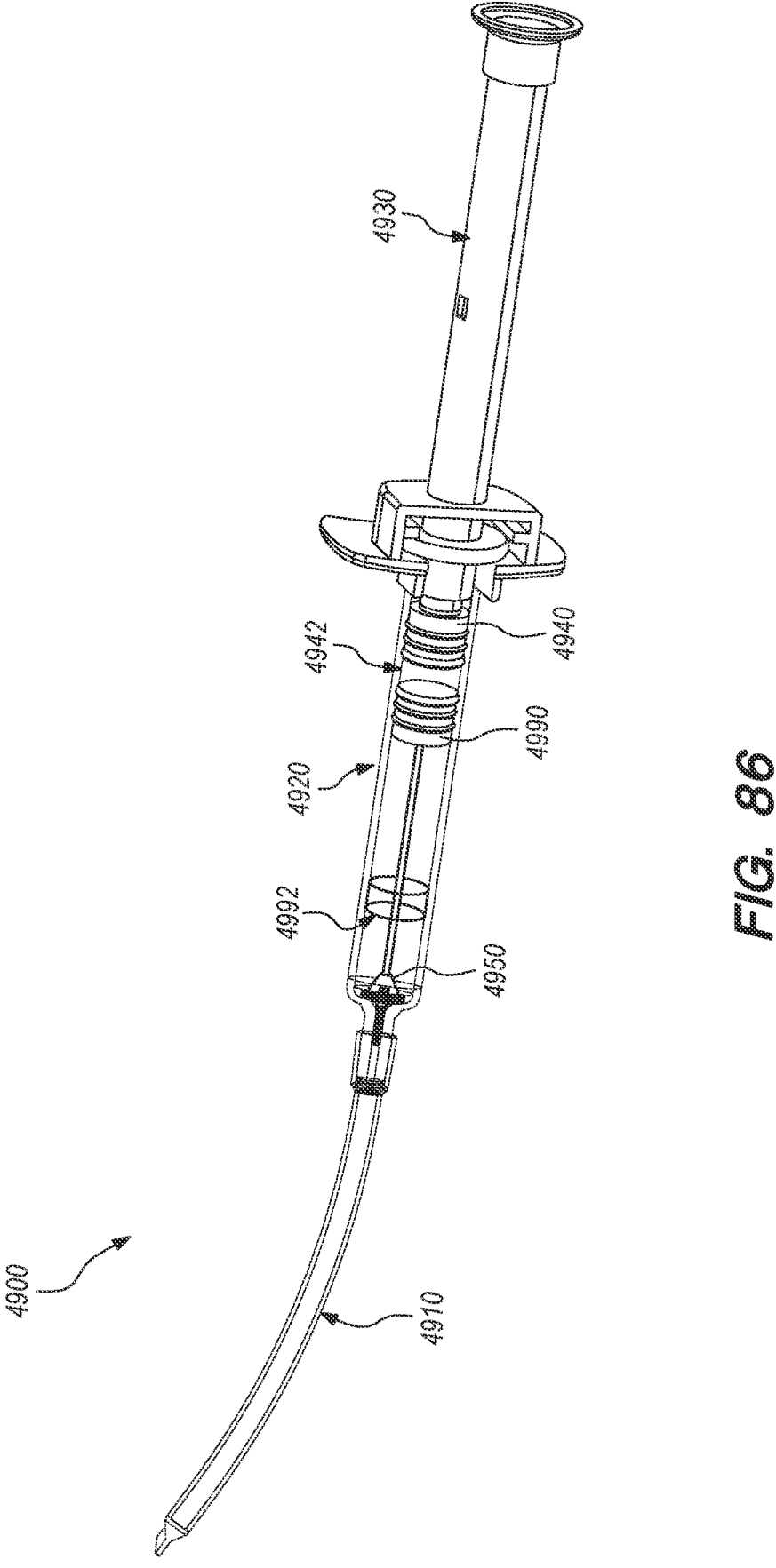
FIG. 86 is a perspective view of a dual chamber injection system having a flow regulator according to some embodiments.
Figure 87:
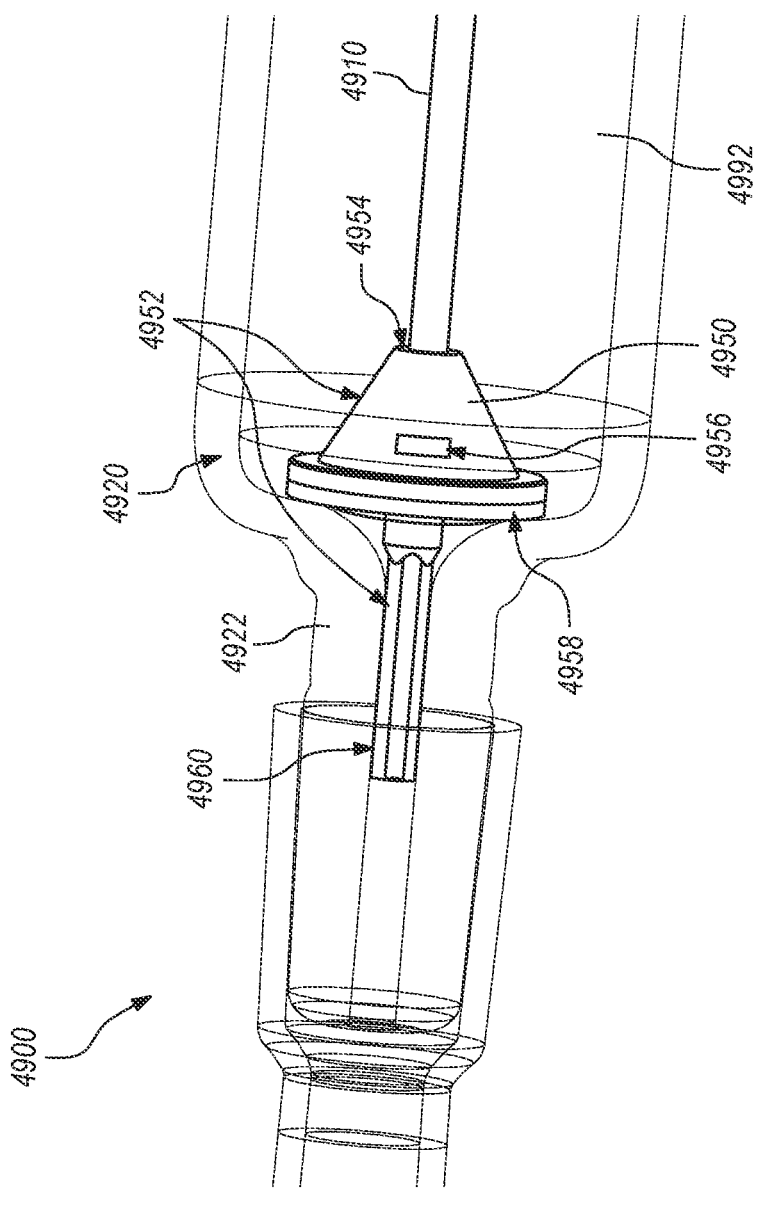
FIGS. 87 to 91 are detailed perspective views of a dual chamber injection system having a flow regulator according to some embodiments.

FIGS. 86 to 91 depict an injection system (4900) with a flow regulator (4950) according to some embodiments. FIG. 86 depicts the injection system (4900), which is a dual chamber injection system with a flow regulator (4950). The injection system (4900) includes a tubing (4910) coupled to a syringe body (4920), and a plunger member (4930) coupled to a proximal stopper member (4940) disposed in an interior of the syringe body (4920). The needle hub assembly (4910) also includes a distal stopper member (4990) disposed in the interior of the syringe body (4920). The proximal and distal stopper members (4940, 4990) define a proximal chamber (4942). The distal stopper member (4990) and the distal end of the syringe body (4920) define a distal chamber (4992). The proximal and distal chambers (4942, 4992) may contain liquids and/or lyophilized powders configured to be mixed before injection. Further details regarding fluid transfer in dual chamber injection systems are described in U.S. patent application Ser. Nos. 15/801,259, 16/435,429, 16/798,188, 16/908,531, and 63/046,517, the contents of which have been previously Incorporated by reference herein.

During use of dual chamber injection systems for mixing drug components, pressure can build up in the distal chamber, which may unintentionally/prematurely eject some of the drug component from the distal chamber in existing systems. The flow regulator (4950) in the injection system (4900) described herein minimizes and/or prevents unintentional/premature injection of drug component from the distal chamber (4992) during mixing and unintentional migration of the drug component out of the distal chamber through the distal opening during shipping.

Figure 88:
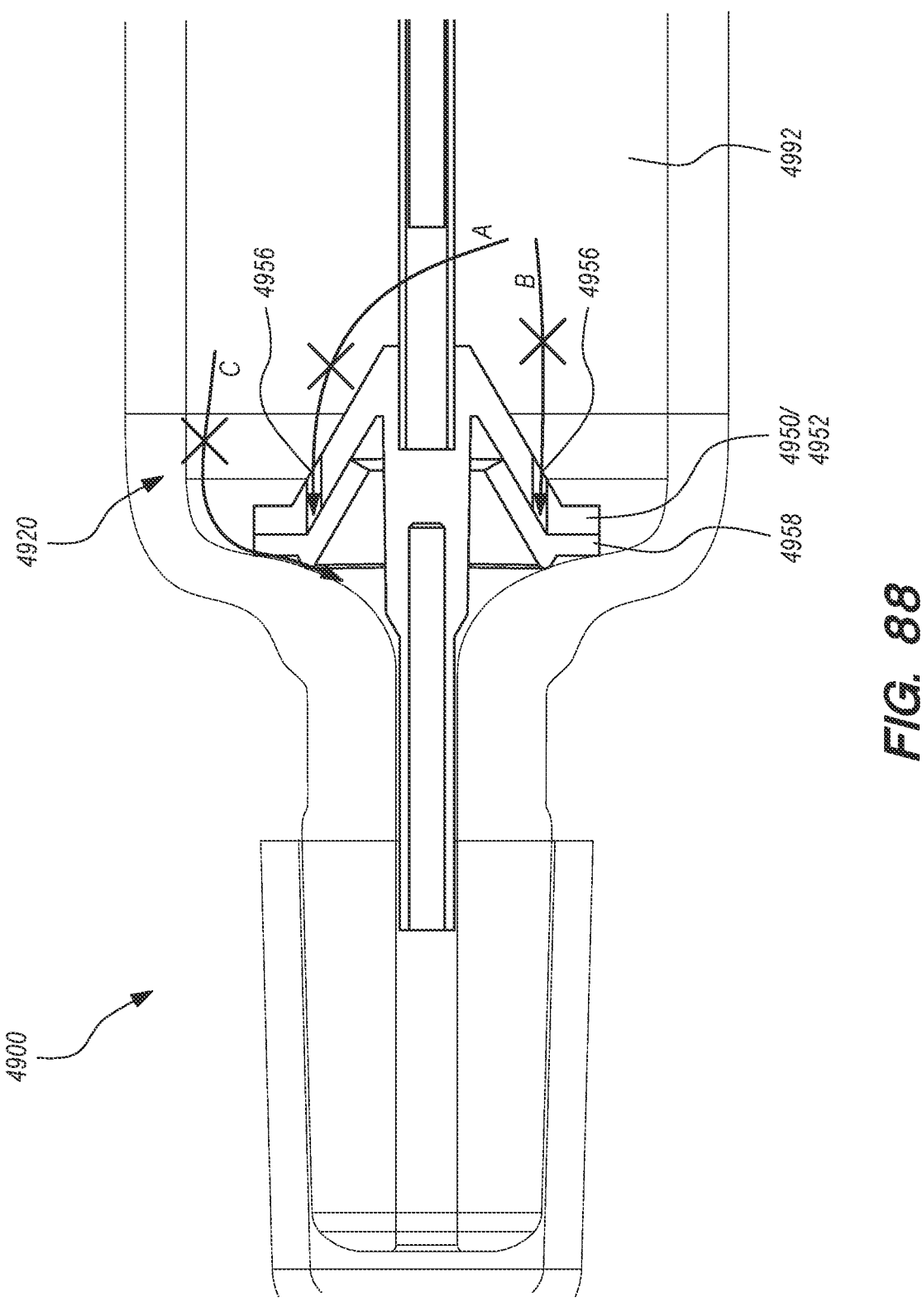

FIG. 88 depicts the flow regulator (4950) installed in the injection system (4900) greater detail according to some embodiments. The flow regulator (4950) includes a housing (4952), which defines a harpoon mount (4954) configured to couple (e.g., via a mechanical fit) to a distal end of a transfer tube (4910). The housing (4952) also defines a liquid port (4956) configured to provide an exit from the distal chamber (4992) to an exterior of the syringe body (4920). The flow regulator (4950) also includes an elastomeric seal (4958). The housing (4952) also defines a compliant pin (4960) configured to wedge into an inner diameter of a distal opening (4922) of the syringe body (4920). The compliant pin (4960) is hollow to provide a selectively open flow path between the liquid port (4956), through the compliant pin (4960), and out the distal opening (4920).

Figure 89:
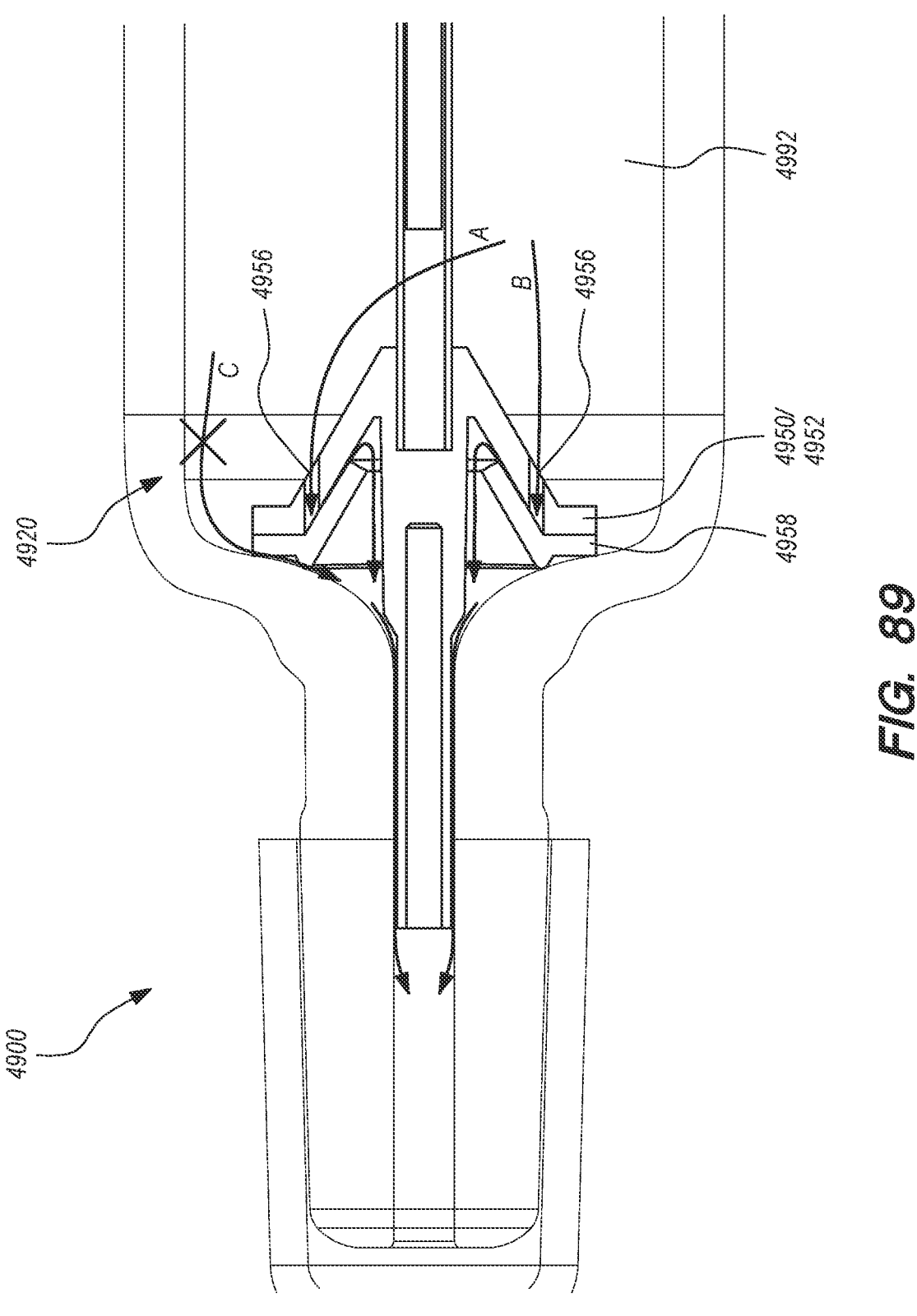

FIGS. 88 and 89 are detailed longitudinal cross-sectional views of the flow regulator (4950) installed in the injection system (4900) showing the components of the flow regulator (4950) in the closed (FIG. 88) and open (FIG. 89) configurations. The elastomeric seal (4958) in the flow regulator (4950) is configured and/or biased to stay closed at pressures lower than a predetermined pressure (e.g., 5 psi) in the distal chamber (4992). Pressures higher than the predetermined pressure in the distal chamber (4992) will push the elastomeric seal (4958) open.

FIG. 88 shows the flow regulator (4950) in the close configuration. With low pressure in the distal chamber (4992), the elastomeric seal (4958) is biased to close the liquid ports (4956) defined by the housing (4952) (see paths A and B). Further, the elastomeric seal (4958) provides a fluid tight seal between the housing (4952) and the distal end of the syringe body (4920) (see path C). Accordingly, with the flow regulator (4950) installed and low pressure in the distal chamber (4992), all potential flow paths (A, B, and C) are closed to prevent inadvertent/premature ejection of drug component from the distal chamber (4992).

FIG. 89 shows the flow regulator (4950) in the open configuration. With higher pressure in the distal chamber (4992) (e.g., during injection), the elastomeric seal (4958) is pushed away from the liquid ports (4956) defined by the housing (4952) to open paths A and B. However, the elastomeric seal (4958) continues to provide a fluid tight seal between the housing (4952) and the distal end of the syringe body (4920) (see path C). Accordingly, with the flow regulator (4950) installed and higher pressure in the distal chamber (4992), two of the three flow paths (A and B) are open to allowed ejection of mixed drug from the distal chamber (4992).

Figure 90:
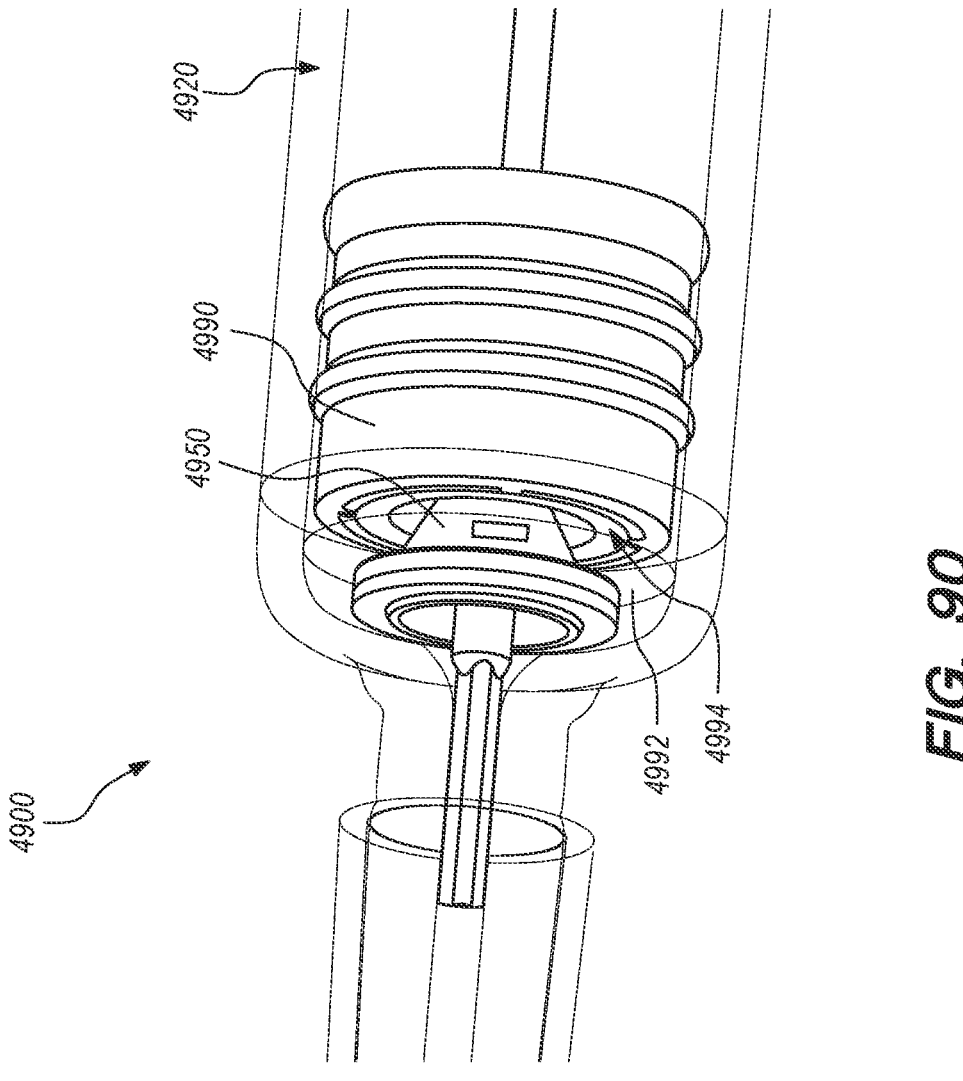
Figure 91:
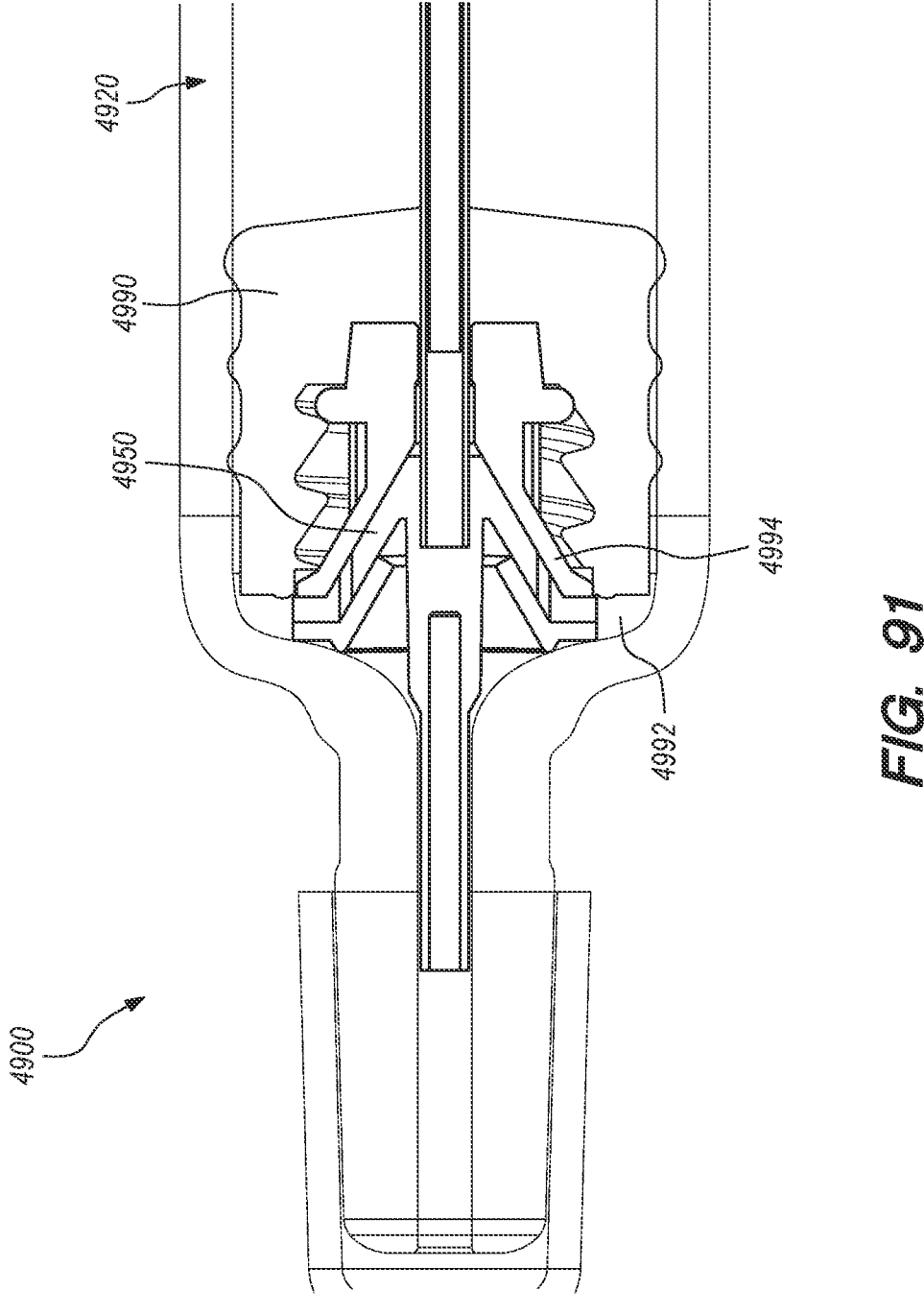

FIGS. 90 and 91 depict the end of injection using the dual chamber injection system (4900) described herein. At the end of injection of mixed drug from the distal chamber (4992), the distal stopper member (4990) is at a distal end of the syringe body (4920). The complementary conical shapes of the guide 4994 in the distal stopper member (4990) and the flow regulator (4950) minimize space lost when adding the flow regulator (4950) to the system (4900). The flow regulator (4950) described herein minimizes and/or prevents unintentional/premature injection of drug component from the distal chamber (4992).

Figure 92:
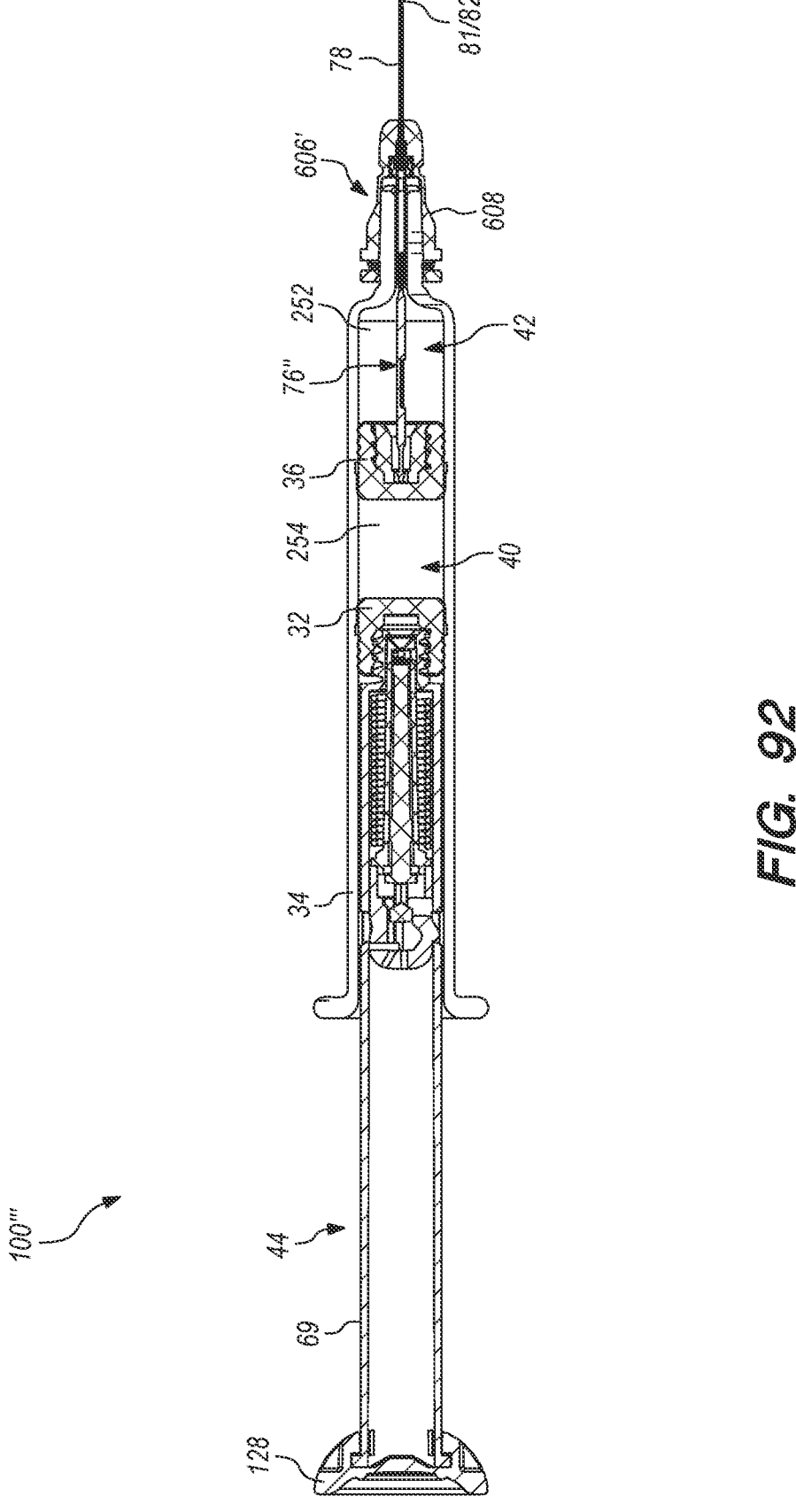
FIGS. 92 to 97 are longitudinal cross-sectional views of various degrees of detail illustrating a safe sequential injection method using a prefilled dual chamber serial safe injection system according to some embodiments.
Figure 93:
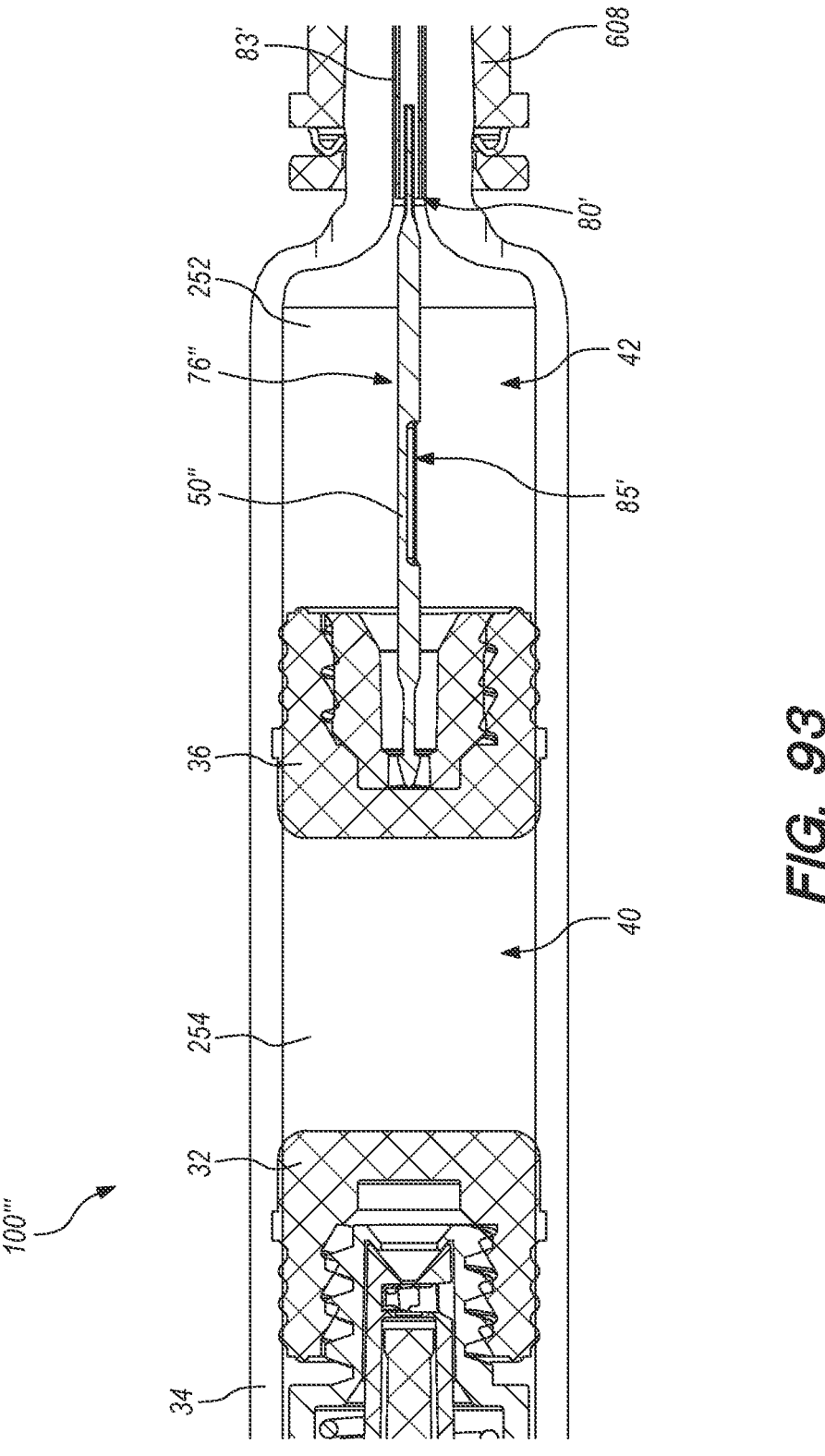
Figure 94:
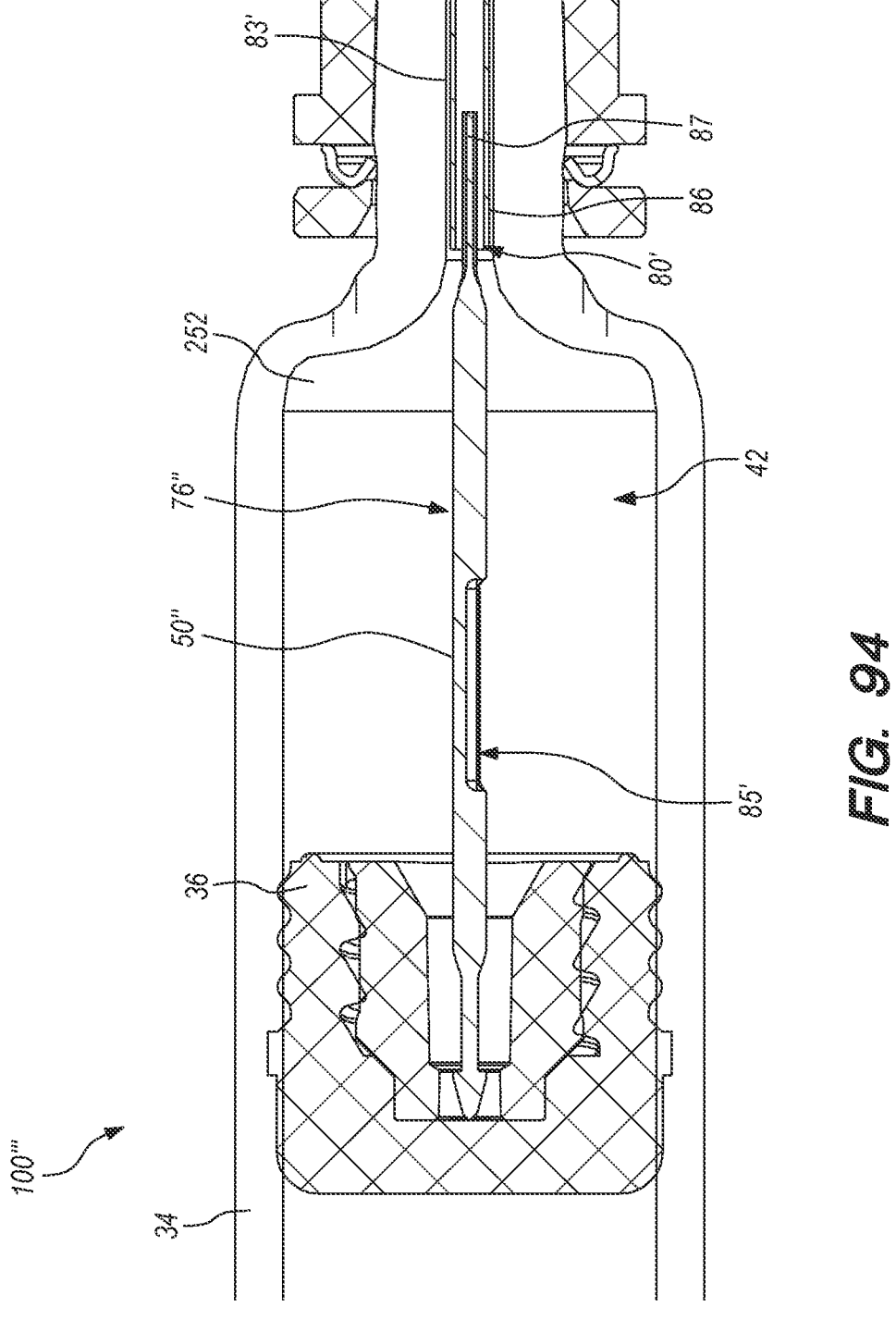

VIII. Exemplary Prefilled Dual Chamber Sequential Safe Injection System and Method FIGS. 92 to 94 are a longitudinal cross-sectional view and two increasingly detailed longitudinal cross-sectional views depicting a prefilled dual chamber serial safe injection system (100''') according to some embodiments. The pre-filled dual chamber serial safe injection system (100''') includes a conventional off-the-shelf prefilled syringe body (34) with conventional off-the-shelf proximal and distal stopper members (32, 36) disposed therein. The proximal and distal stopper members (32, 36) together with the syringe body (34) define proximal and distal chambers (40, 42). First and second liquids (252, 254) are contained in the distal and proximal chambers (42, 40) respectively. The proximal and distal stopper members (32, 36) occlude the proximal and distal ends of the proximal chamber (40). The distal stopper member (36) occludes a proximal end of the distal chamber (42). In some embodiments, the distal surface of the proximal stopper member (32) and the proximal surface of the distal stopper member (36) are each coated with a lubricious polymer coating (e.g., PTFE or ETFE), the first and second polymer coatings of the proximal and distal stopper members (32, 36), together with the syringe body (34) define the proximal chamber (40). The lubricious polymer coating also serves to isolate the rubber of the proximal and distal stopper members (32, 36) from the second liquid (254). The proximal and distal stopper members (32, 36) may be oriented as shown in FIGS. 92 to 94 or the distal stopper (36) may be flipped so the lubricious coating faces the distal chamber (42) such that the first liquid (252) in the distal chamber (42) contacts the lubricious coating for storage.

A needle hub assembly (606') is disposed at the distal end of the distal chamber (42). The needle hub assembly (606') includes a needle hub (608) and a needle assembly ("needle") (76") removably coupled thereto. In some embodiments, a needle cover member (not shown) may be installed on the needle hub assembly (606') for storage. The prefilled dual chamber serial safe injection system (100''') facilitates sequential injection of the first liquid (252) from the distal chamber (42) followed by injection of the second liquid (254) from the proximal chamber (40) subject to sequential insertion of a plunger assembly (44) relative to the syringe body (34) to various degrees by a user. The plunger assembly (44) includes a plunger housing member (69) coupled to the proximal stopper member (32) and a plunger manipulation interface (128). The first and second liquids (252, 254) located in the distal and proximal chambers (42, 40) respectively may be any liquid or gel, such as aqueous or oil based medicine solutions.

The prefilled dual chamber serial safe injection system (100''') has a staked needle configuration wherein upon presentation to the user, a needle hub assembly (606') is mounted in position ready for injection after removal of a needle cover member (not shown) which may comprise an elastomeric sealing material on its internal surface to inter-face with a needle distal member (78) and/or the distal hub (608) during storage. While the staked needle is depicted in a mounted in position, the staked needle may be removably coupled to the syringe body (34) (e.g., using a Luer slip or a Luer lock interface (not shown)), with the proximal member (50; see FIGS. 93 and 94) of the needle assembly (76") extending through the Luer interface and into the distal chamber (42). Alternatively, the needle may be fixedly or removably mounted to the flange on a cartridge body instead of a syringe. Such cartridge injection systems are described in U.S. Utility patent application Ser. No. 15/801,281, which was previously incorporated by reference herein.

The needle assembly (76") includes a needle proximal member (50; see FIGS. 93 and 94) and a needle distal member (78; omitted in FIGS. 93 and 94; see FIG. 92) coupled to opposite (i.e., respective proximal and distal) ends of a needle joining member (83; see FIGS. 93 and 94). The needle joining member (83') is a tubular member coupled to the needle distal member (78), which also defines a sharp distal end (81) with a distal opening (82). The needle assembly (76") defines proximal longitudinal channel (85') and middle opening (80'). The middle opening (80') is disposed adjacent a distal end of the syringe body (34). The proximal longitudinal channel (85') is defined by the proxi-mal needle member (50"). In some embodiments, the needle proximal member (50") is a solid proximal end feature.

As shown in FIG. 94, a proximal member distal anchor (87) of the needle proximal member (50") is disposed in an interior of a proximal end of (89) the tubular needle joining member (83'). In some embodiments, the needle proximal member (50") is coupled to proximal end (89) of the tubular needle joining member (83') by an interference fit between the proximal member distal anchor (87) and the proximal end (89) of the tubular needle joining member (83'). In other embodiments the proximal end (89) of the tubular needle joining member (83') is welded to the needle proximal member (50"). In some embodiments, the weld is a "lap joint" weld, through the needle joining member (83') and into the needle proximal member (50"). The cross-section of the needle proximal member (50") at the weld can be rectangular, crescent-shaped, or dumbbell-shaped such that the components are fastened together, but allow liquid to flow across the joint through the interior of the needle joining member (83'). Other details regarding the tubular needle joining member (83') and the needle proximal mem-ber (50") are described in U.S. Provisional Patent Applica-tion Ser. No. 63/156,264, which was previously incorpo-rated by reference herein.

In some embodiments, the needle proximal member (50") is formed by stamping a piece of flat sheet metal, or a metal wire to form the various features of the needle proximal member (50"). Forming a needle proximal member (50") by stamping reduces manufacturing complexity and costs. The outer diameters of the needle proximal member (50") and the needle joining member (83') are substantially similar, which facilitates retraction of the needle assembly (76") while minimizing snagging of the proximal and distal stop-per members (32, 36).

Other details regarding the prefilled dual chamber serial safe injection system (100''') are described in U.S. Utility patent application Ser. No. 16/435,429 and U.S. Provisional Patent Application Ser. No. 63/046,517, which were previ-ously incorporated by reference herein. In brief, additional components of the prefilled dual chamber serial safe injec-tion system (100''') include a retraction system in the interior of the plunger member (44): a needle retention feature; an energy-storage member (e.g., spring); and an energy-storage member latch. In the embodiments depicted in FIGS. 92 to 97, a significant portion of the safe needle retraction hard-ware resides within the plunger housing (69). Additional components also include a needle holder member (e.g., O-ring, needle latches, and/or detents) in the interior of the needle hub (608). Additional components further include a funnel in the distal stopper member (36) to guide the needle proximal member (50") into the center of the distal stopper member (36).

FIGS. 92 to 97 illustrate a safe sequential injection method using the prefilled dual chamber serial safe injection system (100''') described herein according to some embodiments.

FIGS. 92 to 94 depict the prefilled dual chamber serial safe injection system (100''') in a first/ready to use configuration. The only difference between the first/ready to use configuration and a shipping configuration (not shown) is that a needle cover member (not shown) present in the shipping configuration has been removed in the first/ready to use configuration. In the first/ready to use configuration, the proximal longitudinal channel (85') is disposed in the distal chamber (42), along with the middle opening (80'). As such, there is no flow path between the proximal chamber (40), and the distal opening (82). Therefore, any distally directed force applied to the plunger manipulation interface (128) is transferred through the plunger member (44), the proximal stopper member (32), and the incompressible second liquid (254) in the proximal chamber (40) to move the distal stopper member (36) distally relative to the syringe body (34). Moving the distal stopper member (36) distally relative to the syringe body (34) increases a pressure in the distal chamber (42), which drives the first liquid (252) from the distal chamber (42) through the middle opening (80'), the tubular needle joining member (83') and the distal needle member (78), and out the distal opening (82) of the distal needle member (78).

Figure 95:
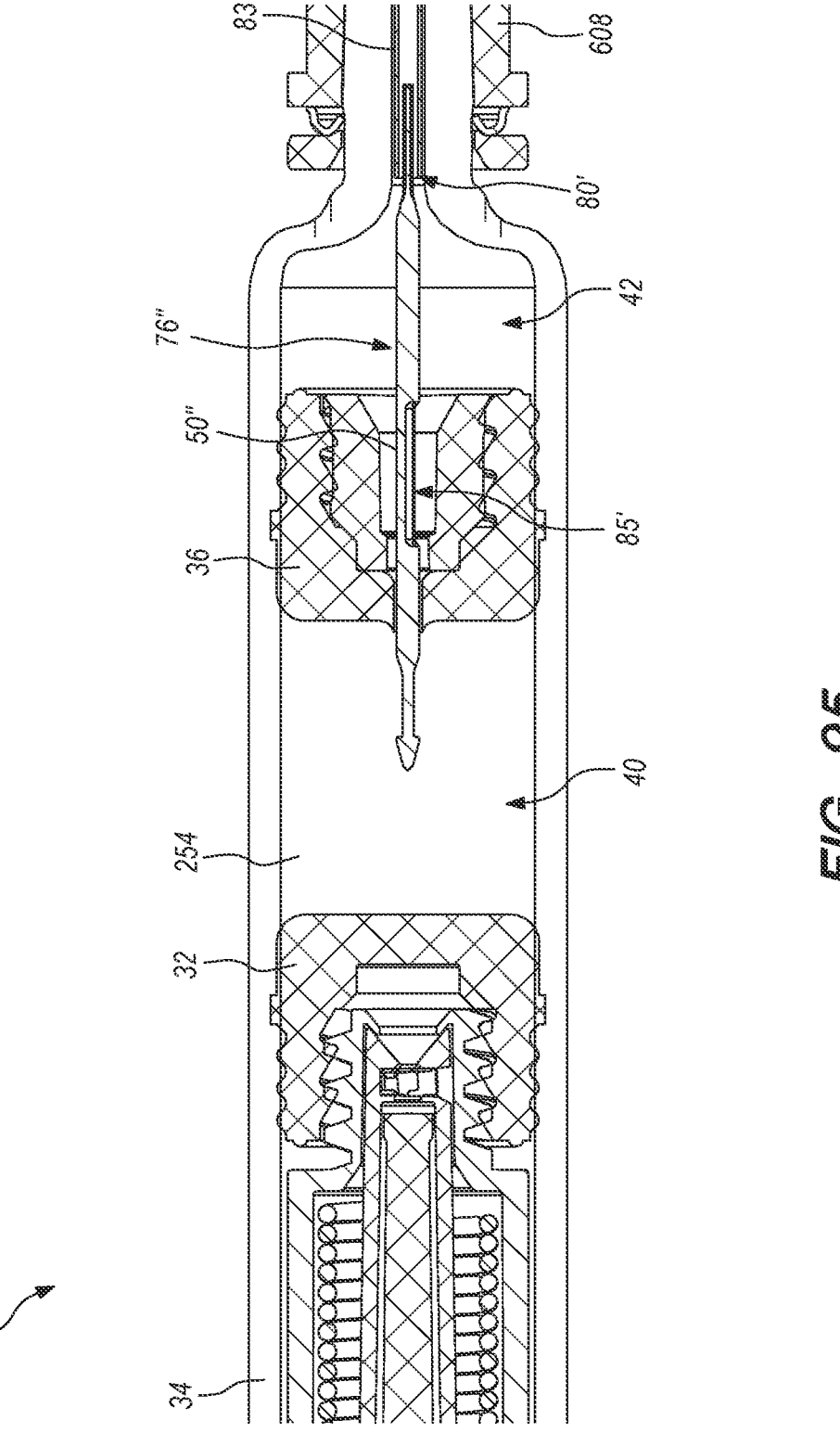

FIG. 95 depicts the prefilled dual chamber serial safe injection system (100''') after the distal stopper member (36) has been moved a first distance distally relative to the syringe body (34). The distal chamber (42) has partially collapsed/been reduced in size, and some of the first liquid (252) has been ejected from the prefilled dual chamber serial safe injection system (100''') through the distal opening (82). Moving the distal stopper member (36) distally relative to the syringe body (34) has also caused the needle proximal member (50") of the needle assembly (76") to penetrate the distal stopper member (36). The proximal longitudinal channel (85') is still in the distal chamber (42) or is occluded by the distal stopper member (36). Accordingly, there is no flow path between the proximal chamber (40) and the distal opening (82), and distally directed force applied to the plunger manipulation interface (128) is still transmitted to the distal stopper member (36) as described above.

Figure 96:
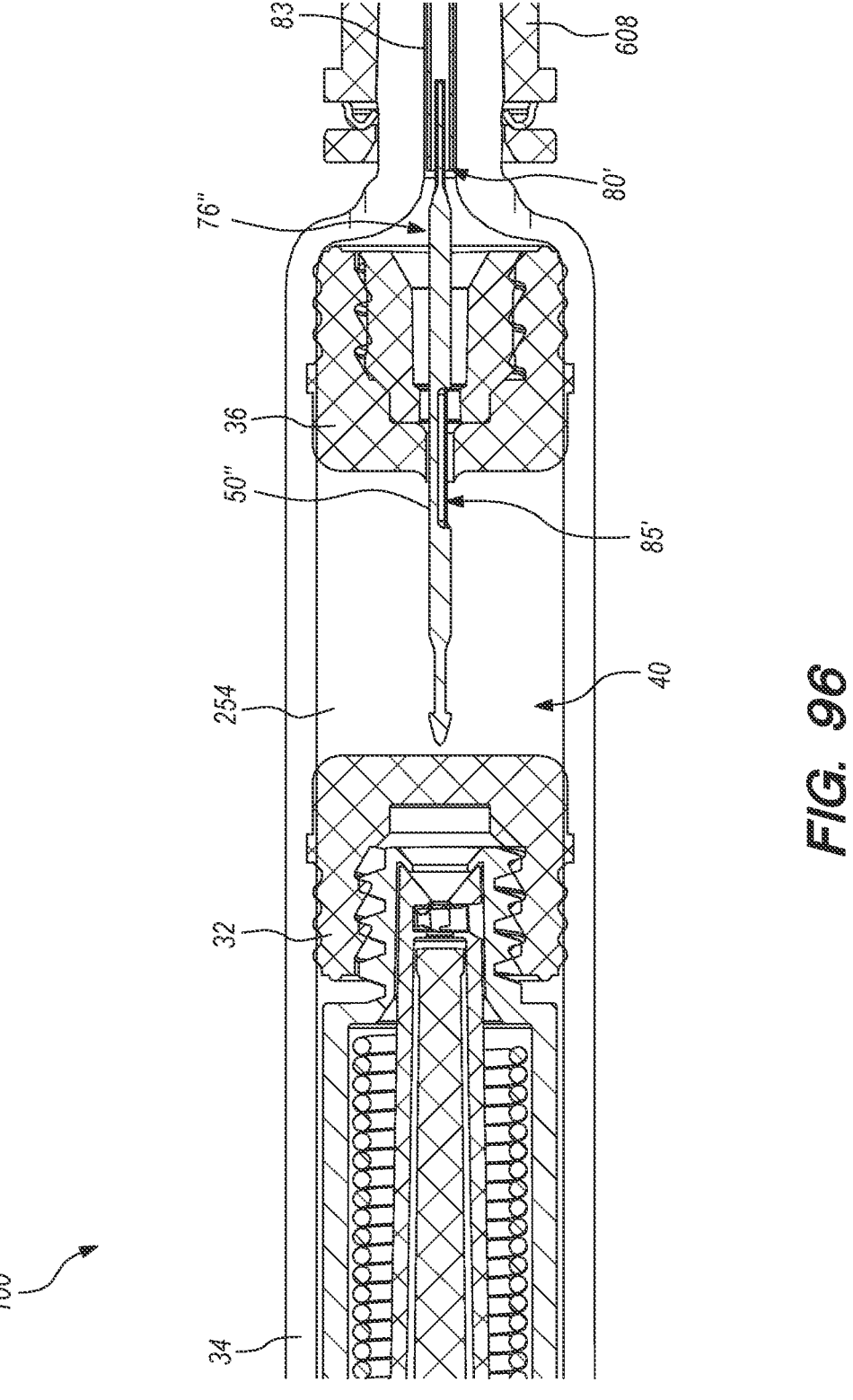

FIG. 96 depicts the prefilled dual chamber serial safe injection system (100''') after the distal stopper member (36) has been moved a second distance (further than the first distance depicted in FIG. 95) distally relative to the syringe body (34). The distal chamber (42, see FIG. 95) has almost fully collapsed/been almost completely eliminated, and most of the first liquid (252, see FIG. 95) has been ejected from the prefilled dual chamber serial safe injection system (100''') through the distal opening (82). Further moving the distal stopper member (36) distally relative to the syringe body (34) has also caused the needle proximal member (50") of the needle assembly (76") to further penetrate the distal stopper member (36). With further penetration of the needle proximal member (50") of the needle assembly (76"), the proximal longitudinal channel (85') is now disposed in the proximal chamber (40). Accordingly, there is now a flow path between the proximal chamber (40) and the distal opening (82), and distally directed force applied to the plunger manipulation interface (128) now moves the proximal stopper member (32) distally relative to the syringe body (34) and the distal stopper member (36) to eject the second liquid (254) from the proximal chamber (40). Opening of the flow path between the proximal chamber (40) and the distal opening (82) places the prefilled dual chamber serial safe injection system (100''') in a second configuration in which the second liquid (254) may be ejected from the proximal chamber (40) in sequence after the first liquid (252) is mostly ejected from the distal chamber (42).

Figure 100:
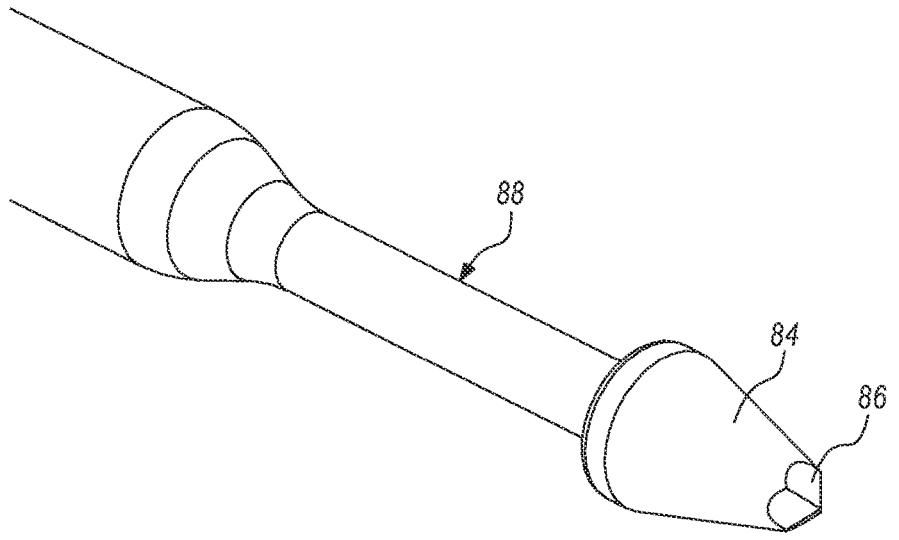
FIG. 100 is a detailed perspective view of a needle proximal member of a needle assembly according to some embodiments.

FIG. 96 also depicts the prefilled dual chamber serial safe injection system (100''') after the proximal stopper member (32) has been moved a first distance distally relative to the syringe body (34) with the prefilled dual chamber serial injection safe system (100''') in the second configuration. The proximal chamber (40) has partially collapsed/been reduced in size, and some of the second liquid (254) has been ejected from the prefilled dual chamber serial safe injection system (100''') through the distal opening (82). As shown in FIG. 100, because the proximal longitudinal channel (85') is in the proximal chamber (40), there is now a flow path between the proximal chamber (40) and the distal opening (82). The flow path between the proximal chamber (40 and the distal opening (82) allows the proximal stopper member (32) to move distally toward the distal stopper member (36) by ejecting some of the second liquid (254) through the proximal longitudinal channel (85'). Because distally directed force applied to the plunger manipulation interface (128) is transmitted to move the proximal stopper member (32), the distal stopper member (36) has substantially stopped moving at this point.

Figure 97:
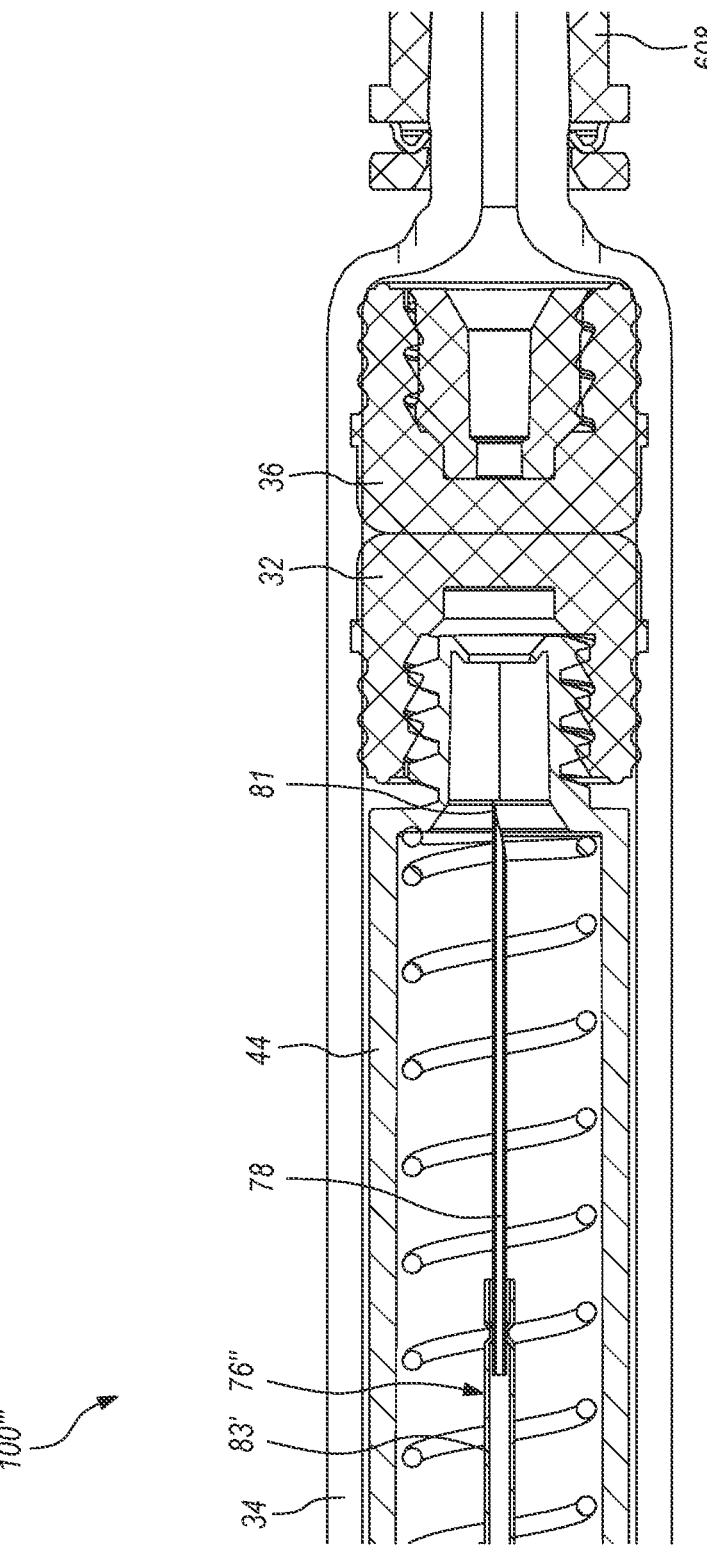

FIG. 97 depicts the prefilled dual chamber serial safe injection system (100''') after the second liquid (254, see FIG. 96) has been substantially ejected from the proximal chamber (40, see FIG. 96) with continued distal movement of the proximal stopper member (32) with the prefilled dual chamber serial injection safe system (100''') in the second configuration. With relative movement of the needle proximal member (50") of the needle assembly (76") further proximally into the plunger assembly (44), an energy-storage member latch is actuated releasing an energy-storage member (spring), which pulls/retracts the needle assembly (76") at least partially into the plunger assembly (44) to position the sharp distal end (81) of the needle distal member (78) of the needle assembly (76") inside of the syringe body (34). Retraction of the needle assembly (76") places the prefilled dual chamber serial safe injection system (100''') in a safe configuration for disposal after injection. Other details regarding safe sequential injection method are described in U.S. Provisional Patent Application Ser. No. 63/046,517, which was previously incorporated by reference herein.

Exemplary Needle Assembly

FIGS. 98 to 103B depict a needle assembly (76") for use with the prefilled dual chamber serial safe injection system (100''') according to some embodiments.

Figure 98:
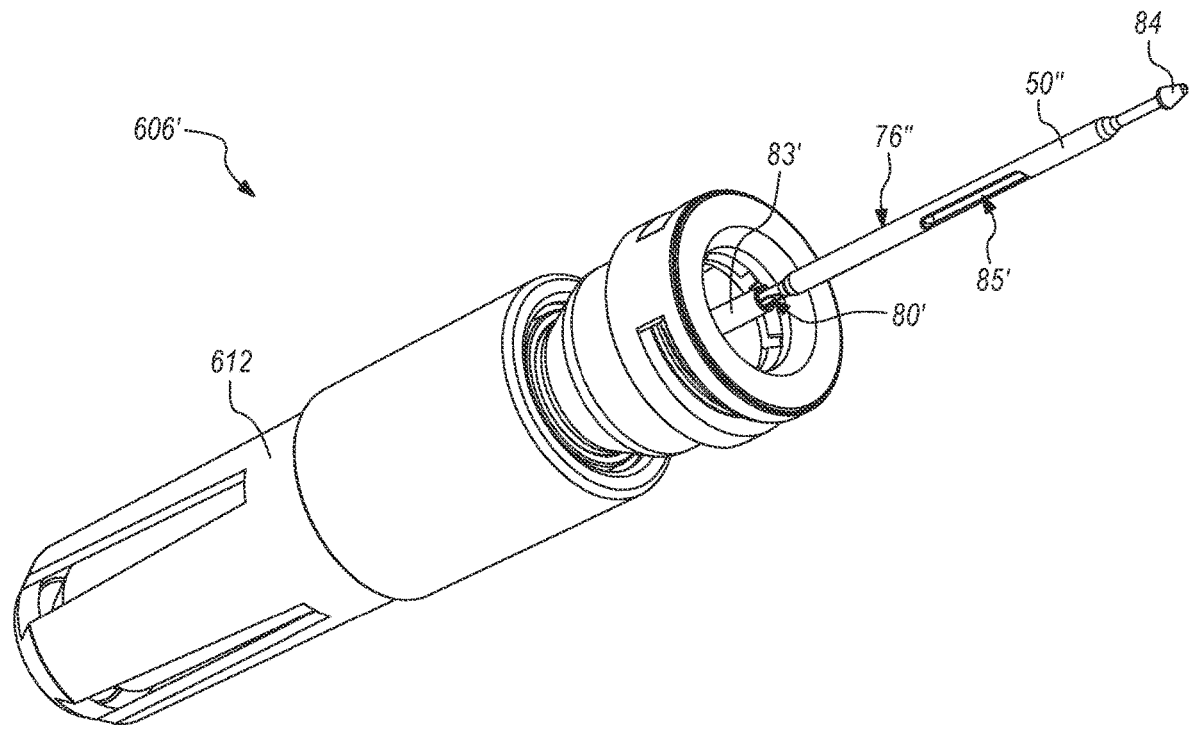
FIG. 98 is a perspective view of a needle hub assembly according to some embodiments.

FIG. 98 depicts a needle hub assembly (606') with a rigid needle shield (612) attached thereto according to some embodiments. FIG. 98 also shows the needle proximal member (50") and the needle joining member (83') of the needle assembly (76").

Figure 99:
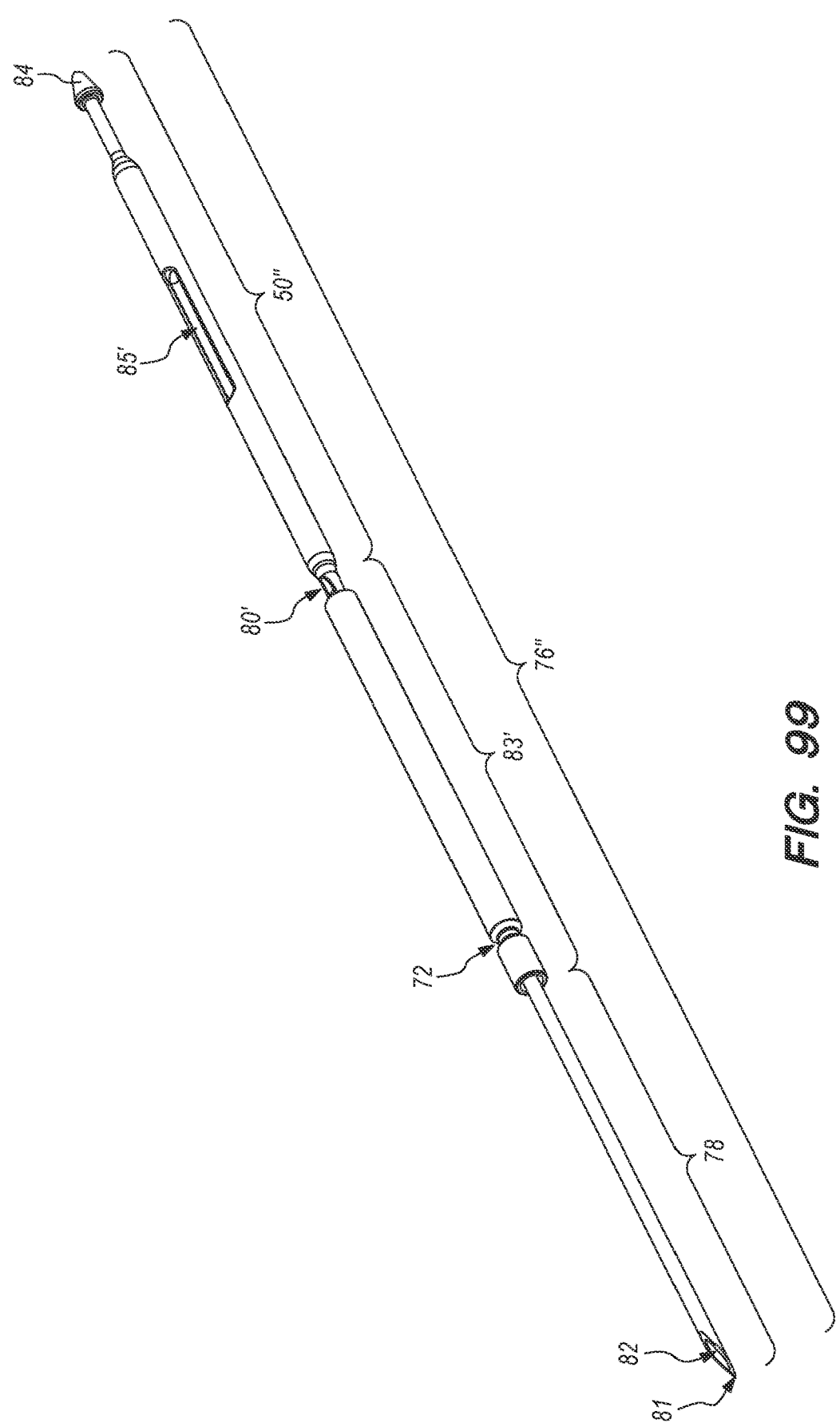
FIG. 99 is a perspective view of a needle assembly according to some embodiments.

FIG. 99 depicts a needle assembly (76") according to some embodiments. The needle assembly (76") includes a needle proximal member (50") and a needle distal member (78) each configured to be partially disposed in respective proximal and distal ends of a needle joining member (83'). The needle proximal member (50") includes a proximal tip (84) at a proximal end thereof configured to be captured for retraction of the needle assembly (76") after injection. The distal end of the needle distal member (78) includes a sharp distal end (81) configured to pierce target tissue for injections. The sharp distal end (81) defines a distal opening (82) for injections. The needle joining member (83') includes an annular recess (72) configured to interfere with a needle latch as described in U.S. patent application Ser. Nos. 14/696,342, 14/543,787, 14/321,706, 15/801,239, 15/801, 259, 15/801,281, 15/801,304, 16/908,531, 17/031,108, and 63/094,313, the contents of which have been previously incorporated by reference herein, to prevent proximal retraction of the needle assembly (76") before the end of injection.

FIG. 100 depicts the proximal tip (84) of the needle proximal member (50") in greater detail. The proximal tip (84) includes a faceted proximal piercing tip (86). The faceted proximal piercing tip (86) facilitates penetration of the proximal and distal stopper members (32, 36). The needle proximal member (50") of the needle assembly (76") also includes a reduced diameter portion (88) immediately distal of the proximal tip (84). The reduced diameter portion (88) increases the probability and security of capture of the proximal tip (84) of the needle proximal member (50") to enable retraction of the needle assembly (76").

Figure 101:
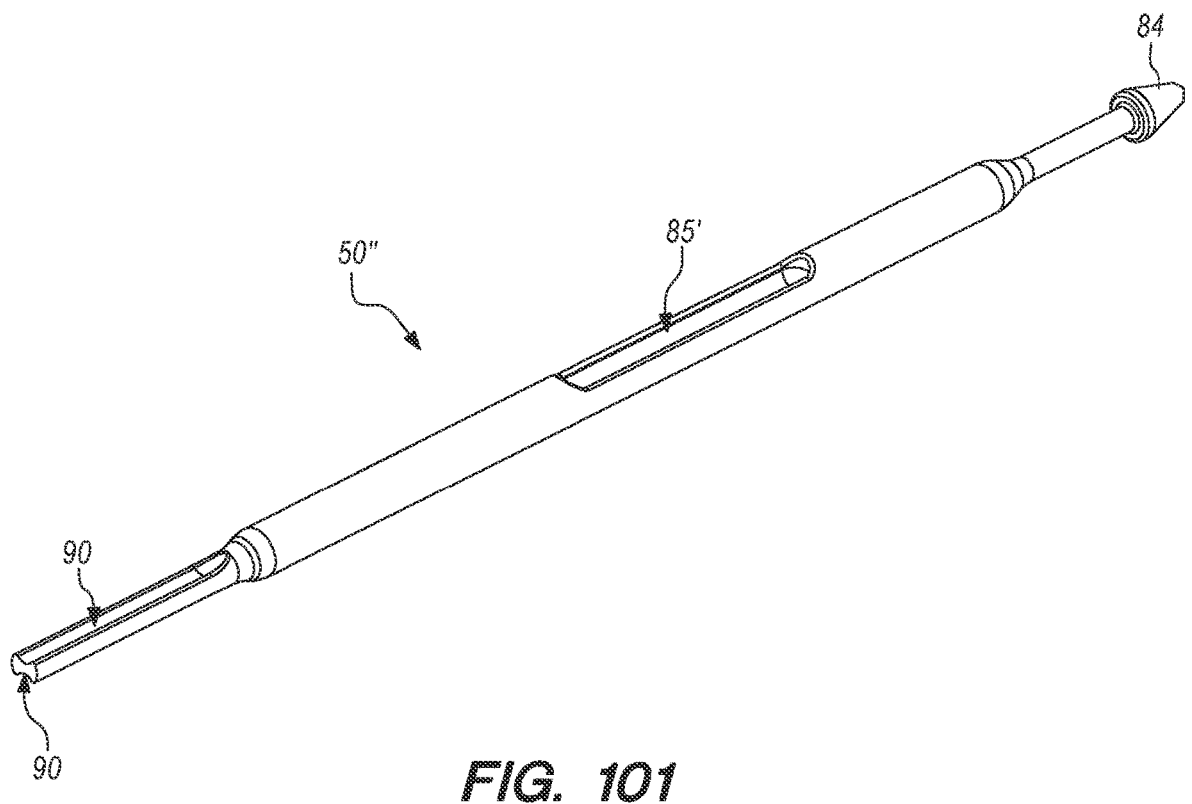
FIGS. 101 and 102 are perspective and longitudinal cross-sectional views of a needle proximal member according to some embodiments.

FIG. 101 depicts a needle proximal member (50") according to some embodiments. The needle proximal member (50") includes a proximal tip (84) at a proximal end thereof, a proximal longitudinal channel (85') between the proximal and distal ends thereof, and two distal longitudinal channels (90) extending from a distal end thereof.

Figures 102, 103A, 103B:
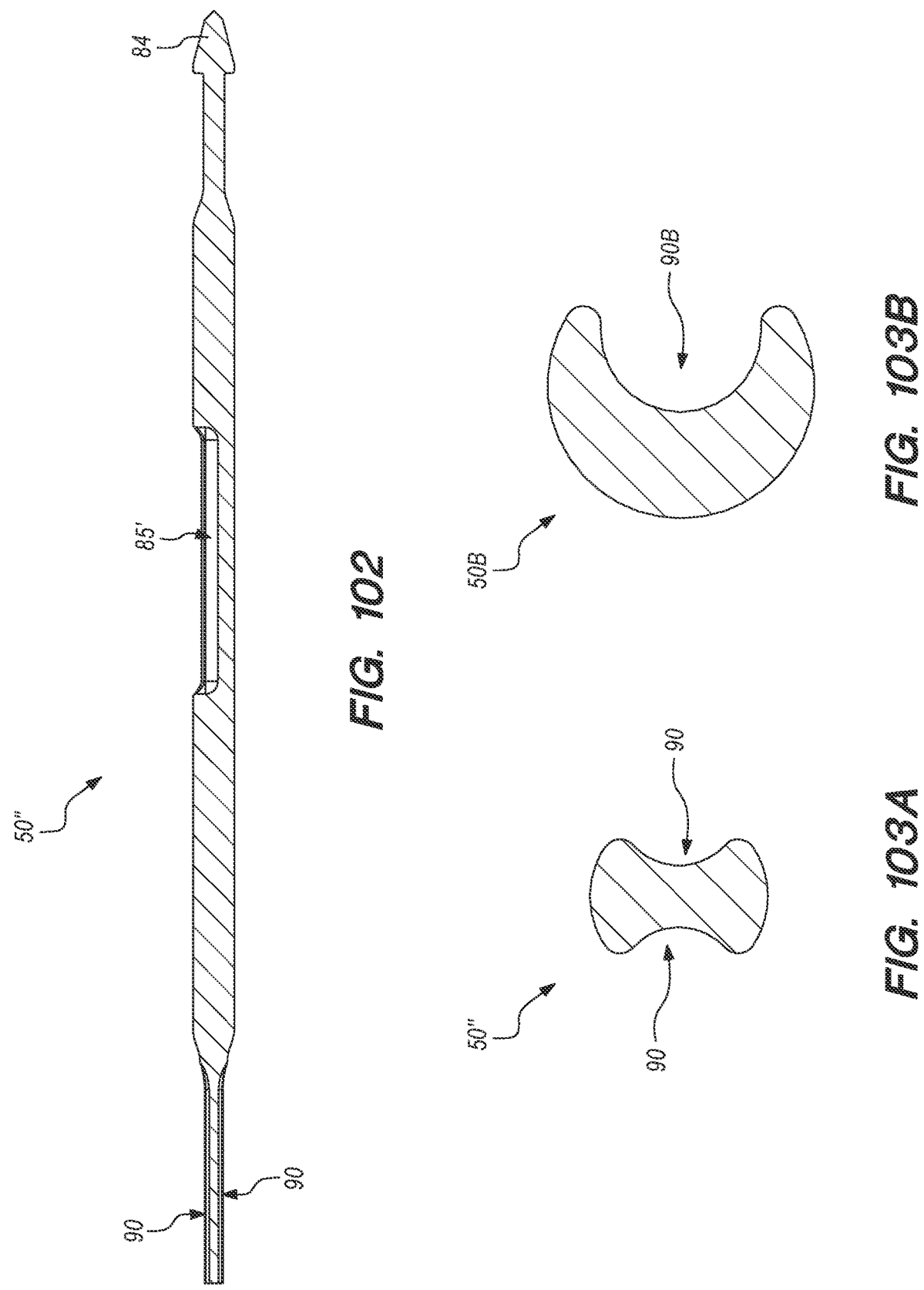
FIGS. 103A and 103B are axial cross-sectional views of respective distal ends of two needle proximal members according to some embodiments.

FIG. 102 is a longitudinal cross-sectional view of a needle proximal member (50"). The needle proximal member (50") includes two distal longitudinal channels (90) formed in approximately opposite surfaces of the needle proximal member (50"). As shown in FIG. 99, when the needle proximal member (50") is partially disposed in the needle joining member (83'), the distal longitudinal channels (90) form two flow paths from outside of the needle assembly (76") into the needle joining member (83'), then into the needle distal member (78), and out of the sharp distal end (81) of the needle distal member (78).

FIG. 99 depicts the needle assembly (76") fully assembled with the distal end of the needle proximal member (50") inserted into the needle joining member (83') until only a proximal end of the distal longitudinal channel (90) remains outside of the needle joining member (83'). This proximal end of the distal longitudinal channel (90) forms the middle opening (80') in the needle assembly (76"), which fluidly couples the interior and exterior of the needle assembly (76").

FIGS. 103A and 103B are axial cross-sections of respective distal ends of needle proximal members (50", 50B) according to some embodiments. The distal end of the needle proximal member (50") depicted in FIG. 103A has a dumbbell shaped cross-section, similar to the needle proximal member (50") depicted in FIGS. 101 and 16. The distal end of the needle proximal member (50B) depicted in FIG. 103B has a crescent shaped cross-section. The dumbbell and crescent shapes define two and one distal longitudinal channels (90, 90B) respectively. The distal longitudinal channels (90, 90B) have a rounded/circular cross-section, which minimizes fluid flow restriction through the distal longitudinal channels (90, 90B). A circular cross-section is a highly efficient cross-section for fluid flow due to its minimization of fluid interaction with the wall of the channel, which would otherwise impart a zero velocity boundary condition on the flowing fluid. Minimizing wall exposure thus minimizes the amount of shear resistance the fluid experiences during flow. A single round channel (90B) (see FIG. 103B) may have a lower fluid flow resistance compared to a double channel (90) (see FIG. 103A), even when cross-sectional area is preserved, because the resistance of a theoretical pipe is inversely proportional to $R^4$, (the radius of the cross-sectional area), according to the Hagen-Poisseuille formula:

$$\Delta P = \frac{8\mu LQ}{\pi R^4}.$$

Even with the distal longitudinal channels (90, 90B) formed therein, the needle proximal members (50", 50B) have sufficient bending moments of inertia for improved rigidity and resistance to bending. In fact, the needle proximal members (50", 50B) resemble steel I-beams and have similar rigidity characteristics. Resistance to bending is particularly important as the needle proximal members (50", 50B) puncture through the stopper member 640. Minimizing bending of the needle proximal members (50", 50B) as they puncture through the stopper member 640, improves the probability of capture of the proximal tip (84) of the needle proximal member (50") to enable retraction of the needle assembly (76").

The diameters of the needle proximal members (50", 50B) are also relatively large (e.g., about 0.026" compared to cold-formed proximal members, which have a diameter of about 0.020"). The larger diameter of the needle proximal member (50") results in a higher overall bending moment of inertia, and more resistance to bending, which also improves the probability of capture. The needle proximal members (50", 50B) are also quite close in diameter to the needle joining member (83'), which may have a diameter of about 0.036". The similarity in diameters renders the needle assembly (76") easier to retract through stopper members during retraction, as compared to a needle assembly made with a cold formed proximal member, because the needle joining member (83') is less likely to snag the stopper member during retraction due to the diameter difference between the needle joining member (83') and the needle proximal member (50") being relatively small.

Figure 104:
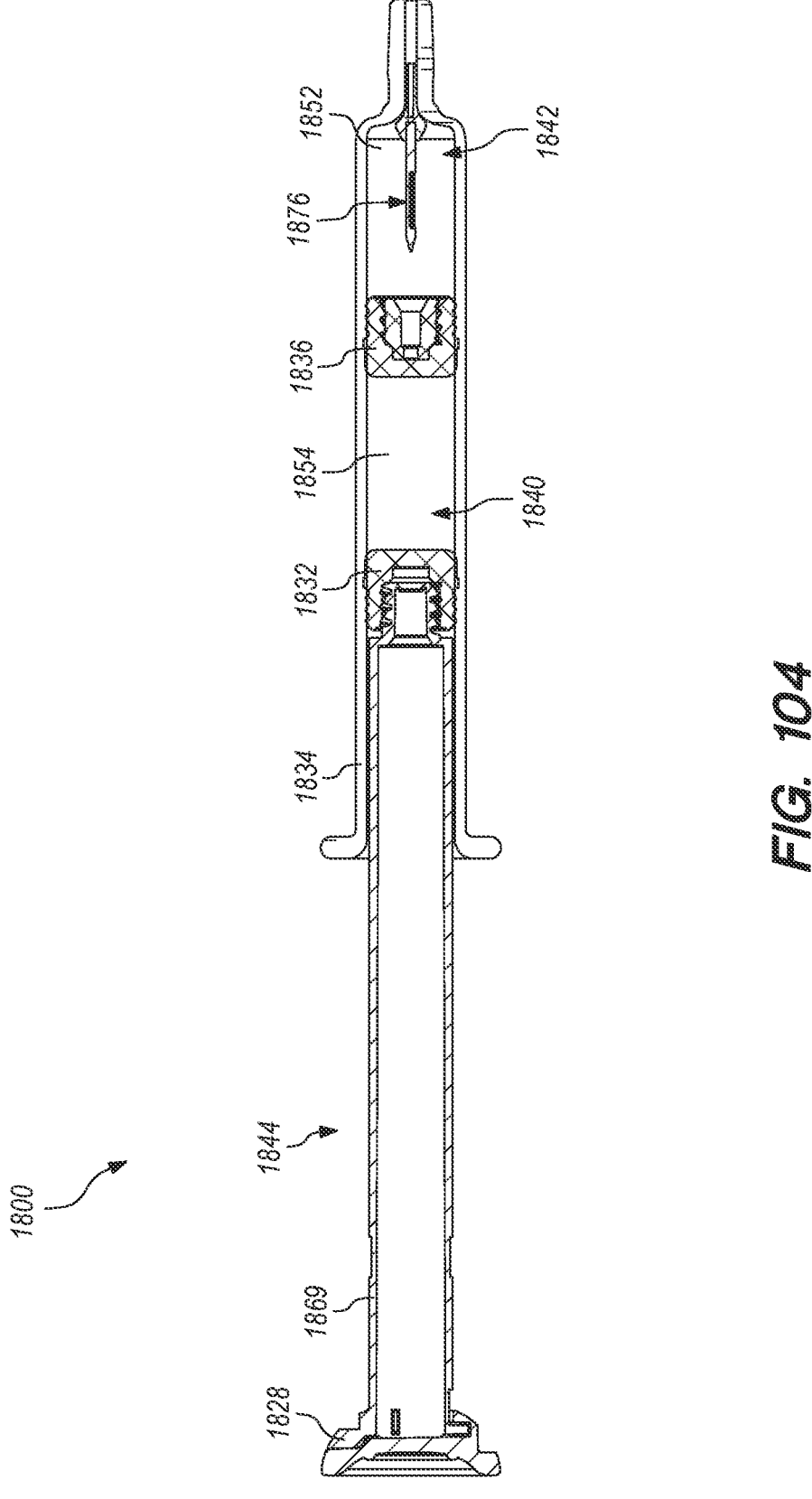
FIGS. 104 to 109 are longitudinal cross-sectional views of various degrees of detail illustrating a sequential injection method using a prefilled needleless dual chamber serial injection system according to some embodiments.
Figure 105:
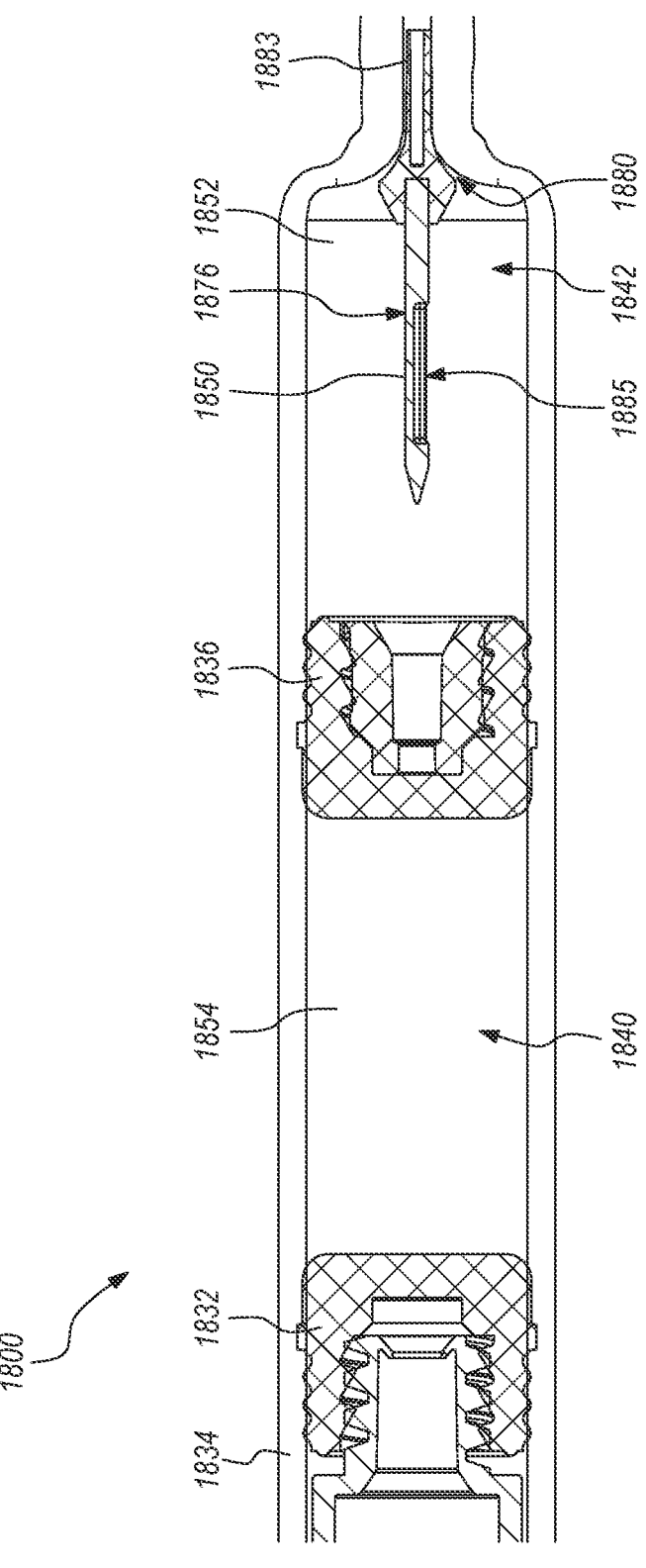
Figure 106:
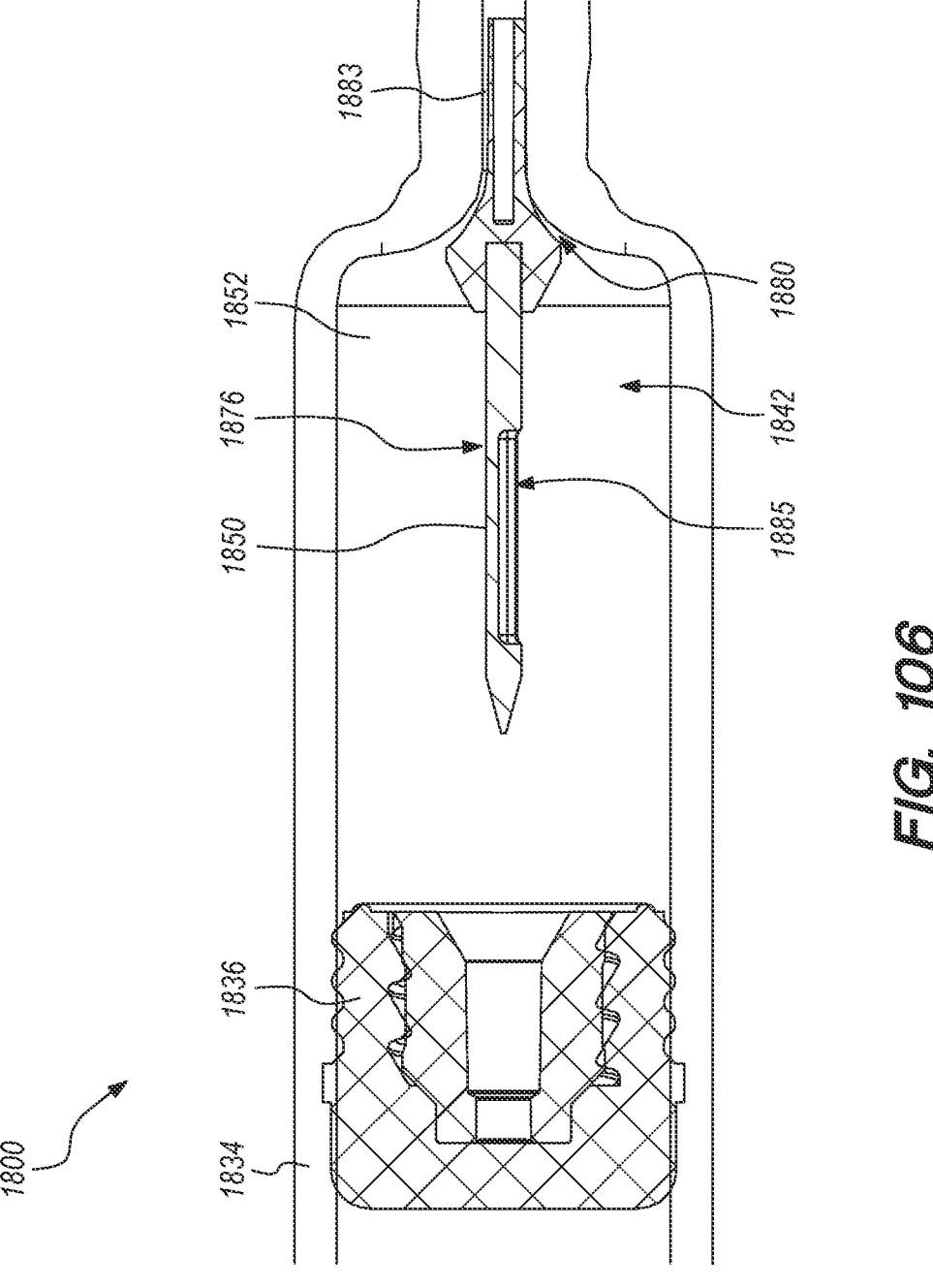

IX. Exemplary Prefilled Needleless Dual Chamber Sequential Injection Systems and Methods FIGS. 104 to 106 are a longitudinal cross-sectional view and two increasingly detailed longitudinal cross-sectional views depicting a prefilled needleless dual chamber serial injection system (1800) according to some embodiments. The prefilled needleless dual chamber serial safe injection system (1800) is similar to the prefilled dual chamber serial injection system (100) depicted in FIGS. 92 to 94. There are two main differences between the systems (1800, 100). First, the dual chamber serial injection system (1800) depicted in FIGS. 104 to 106 does not include a "needle" extending outside of the syringe body (1834) like the needle distal member (78) in the dual chamber serial injection system (100) depicted in FIGS. 92 to 94. Second, the dual chamber serial injection system (1800) depicted in FIGS. 104 to 106 does not include a needle retraction system like one in the dual chamber serial injection system (100) depicted in FIGS. 92 to 94. Accordingly, the dual chamber serial injection system (1800) is not a "safe" injection system.

The prefilled needleless dual chamber serial injection system (1800) includes a conventional off-the-shelf prefilled syringe body (1834) with conventional off-the-shelf proximal and distal stopper members (1832, 1836) disposed therein. The proximal and distal stopper members (1832, 1836) together with the syringe body (1834) define proximal and distal chambers (1840, 1842). First and second liquids (1852, 1854) are contained in the distal and proximal chambers (1842, 1840) respectively. The proximal and distal stopper members (1832, 1836) occlude the proximal and distal ends of the proximal chamber (1840). The distal stopper member (1836) occludes a proximal end of the distal chamber (1842). In some embodiments, the distal surface of the proximal stopper member (1832) and the proximal surface of the distal stopper member (1836) are each coated with a lubricious polymer coating (e.g., PTFE or ETFE), the first and second polymer coatings of the proximal and distal stopper members (1832, 1836), together with the syringe body (1834) define the proximal chamber (1840). The lubricious polymer coating also serves to isolate the rubber of the proximal and distal stopper members (1832, 1836) from the second liquid (1854). The proximal and distal stopper members (1832, 1836) may be oriented as shown in FIGS. 104 to 106 or the distal stopper (1836) may be flipped so the lubricious coating faces the distal chamber (1842) such that the first liquid (1852) in the distal chamber (1842) contacts the lubricious coating for storage.

The dual chamber serial injection system (1800) depicted in FIGS. 104 to 106 does not include a "needle" extending outside of the syringe body (1834). Instead, the dual chamber serial injection system (1800) includes a fluid transfer assembly (1876). The fluid transfer assembly (1876) of the prefilled needleless dual chamber serial injection system (1800) facilitates sequential injection of the first liquid (1852) from the distal chamber (1842) followed by injection of the second liquid (1854) from the proximal chamber (1840) subject to sequential insertion of a plunger assembly (1844) relative to the syringe body (1834) to various degrees by a user. The plunger assembly (1844) includes a plunger housing member (1869) coupled to the proximal stopper member (1832) and a plunger manipulation interface (1828). The first and second liquids (1852, 1854) located in the distal and proximal chambers (1842, 1840) respectively may be any liquid or gel, such as aqueous or oil based medicine solutions.

The fluid transfer assembly (1876) of the prefilled needleless dual chamber serial injection system (1800) is configured for use with connectors (e.g., Luer lock or Luer slip interfaces coupled to needles with sharpened ends or fluid transfer tubes (not shown)).

The fluid transfer assembly (1876) includes a fluid transfer proximal member (1850; see FIGS. 105 and 106) coupled to a proximal end of a fluid transfer joining member (1883; see FIGS. 105 and 106). The fluid transfer proximal member (1850) is a metal spike with a proximal channel (1885) formed therein. The fluid transfer joining member (1883) is configured to be coupled to a distal end of the fluid transfer proximal member (1850) and to secure the fluid transfer assembly (1876) in a distal opening of the syringe body (1834). The fluid transfer joining member (1883) includes a fluid transfer distal anchor (1891), which includes an open core (1892) to provide compliance to the fluid transfer distal anchor (1891). The fluid transfer joining member (1883) may be coupled to the fluid transfer proximal member (1850) with a mechanical fit. The fluid transfer joining member (1883) may secure the fluid transfer assembly (1876) to the syringe body (1834) with a mechanical fit between the fluid transfer distal anchor (1891) and a distal end of the syringe body (1834). The fluid transfer joining member (1883) may define one or more channels therein to provide a middle opening (1880) between an interior of the syringe body (1834)/distal chamber (42) and an exterior. The middle opening (1880) is disposed adjacent a distal end of the syringe body (1834). The proximal longitudinal channel (1885) is defined by the proximal fluid transfer member (1850). In some embodiments, the fluid transfer proximal member (1850) is a solid proximal end feature.

In some embodiments, the fluid transfer proximal member (1850) is formed by stamping a piece of flat sheet metal, or a metal wire to form the various features of the fluid transfer proximal member (1850). Forming a fluid transfer proximal member (1850) by stamping reduces manufacturing complexity and costs.

Other details regarding the prefilled needleless dual chamber serial injection system (1800) are described in U.S. Provisional Patent Application Ser. No. 63/156,264, which was previously incorporated by reference herein.

FIGS. 104 to 109 illustrate a safe sequential injection method using the prefilled needleless dual chamber serial injection system (1800) described herein according to some embodiments.

FIGS. 104 to 106 depict the prefilled needleless dual chamber serial injection system (1800) in a first/ready to use configuration. The only difference between the first/ready to use configuration and a shipping configuration (not shown) is that a syringe body cap (not shown) present in the shipping configuration has been removed in the first/ready to use configuration.

In the first/ready to use configuration, the proximal longitudinal channel (1885) is disposed in the distal chamber (1842), along with the middle opening (1880). As such, there is no flow path between the proximal chamber (1840), and the distal opening (1882). Therefore, any distally directed force applied to the plunger manipulation interface (1828) is transferred through the plunger member (1844), the proximal stopper member (1832), and the incompressible second liquid (1854) in the proximal chamber (1840) to move the distal stopper member (1836) distally relative to the syringe body (1834). Moving the distal stopper member (1836) distally relative to the syringe body (1834) increases a pressure in the distal chamber (1842), which drives the first liquid (1852) from the distal chamber (1842) through the middle opening (1880) formed between the fluid transfer joining member (1883) and the distal end of the syringe body (1834), and out the distal end of the syringe body (1834) (e.g., into a Luer connector).

Figure 107:
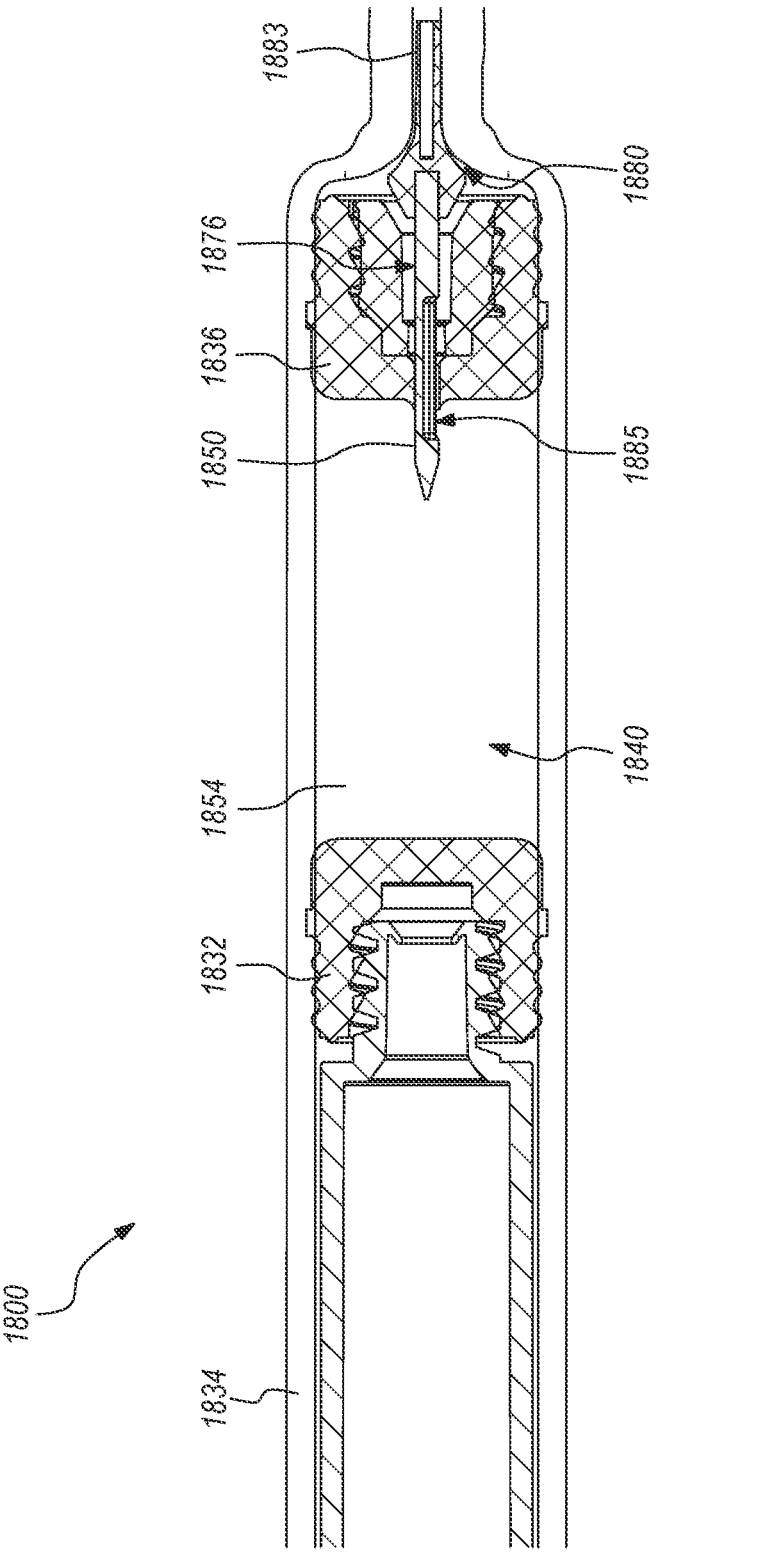
Figure 108:
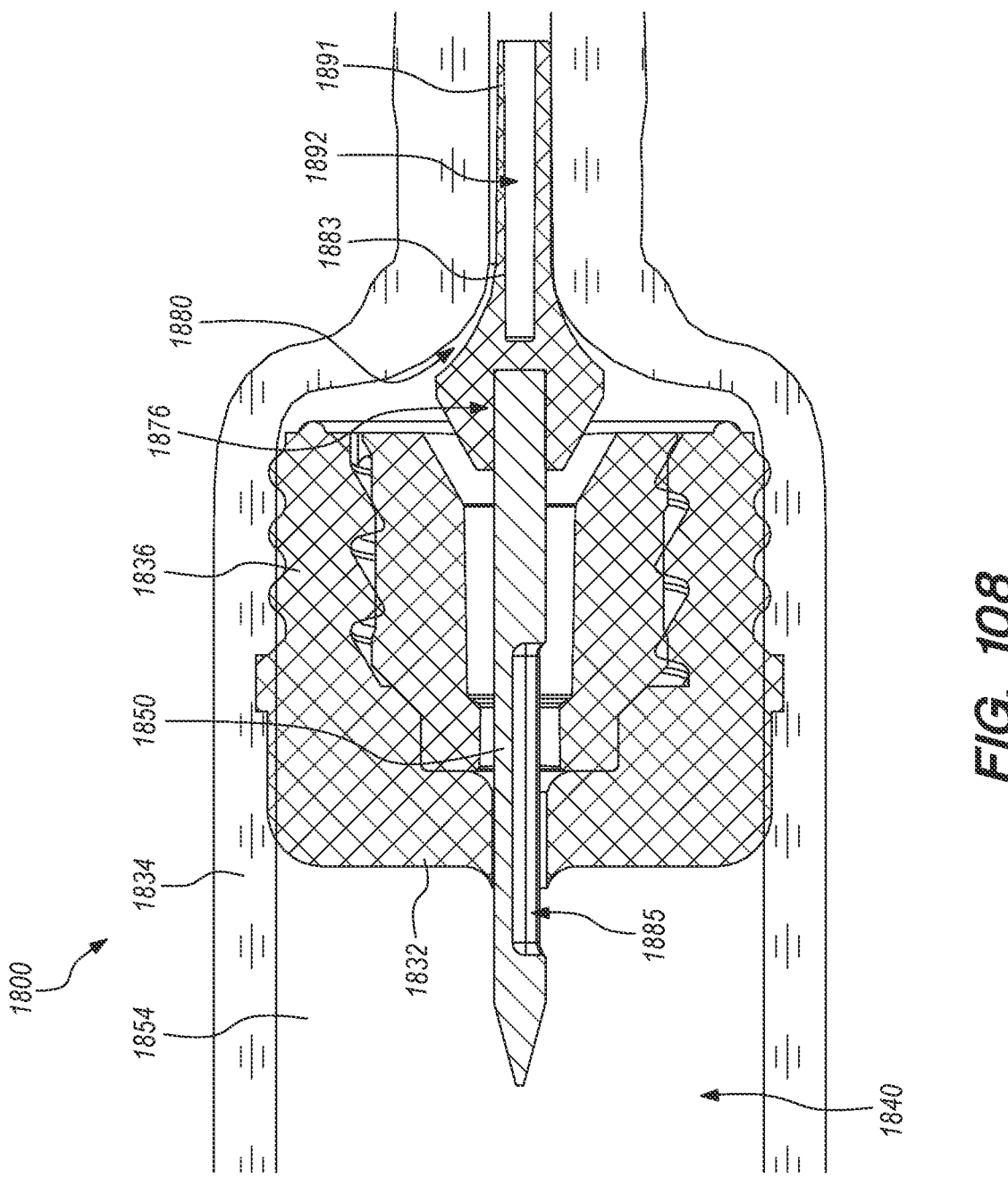

FIGS. 107 and 108 depict the prefilled needleless dual chamber serial injection system (1800) after the distal stopper member (1836) has been moved distally relative to the syringe body (1834) until the distal stopper member (1836) is almost in contact with the distal end of the syringe body (1836). The distal chamber (1842, see FIG. 105) has almost fully collapsed/been almost completely eliminated, and most of the first liquid (1852, see FIG. 105) has been ejected from the prefilled needleless dual chamber serial injection system (1800) through the distal end of the syringe body (1836). Moving the distal stopper member (1836) distally relative to the syringe body (1834) has also caused the fluid transfer proximal member (1850) of the fluid transfer assembly (1876) to penetrate the distal stopper member (1836). With penetration of the fluid transfer proximal member (1850) of the fluid transfer assembly (1876), the proximal longitudinal channel (1885) is now disposed in the proximal chamber (1840). Accordingly, there is now a flow path between the proximal chamber (1840) and the middle opening (1880), and distally directed force applied to the plunger manipulation interface (1828) now moves the proximal stopper member (1832) distally relative to the syringe body (1834) and the distal stopper member (1836) to eject the second liquid (1854) from the proximal chamber (1840). Opening of the flow path between the proximal chamber (1840) and the distal opening (1882) places the prefilled needleless dual chamber serial injection system (1800) in a second configuration in which the second liquid (1854) may be ejected from the proximal chamber (1840) in sequence after the first liquid (1852) is mostly ejected from the distal chamber (1842).

Figure 109:
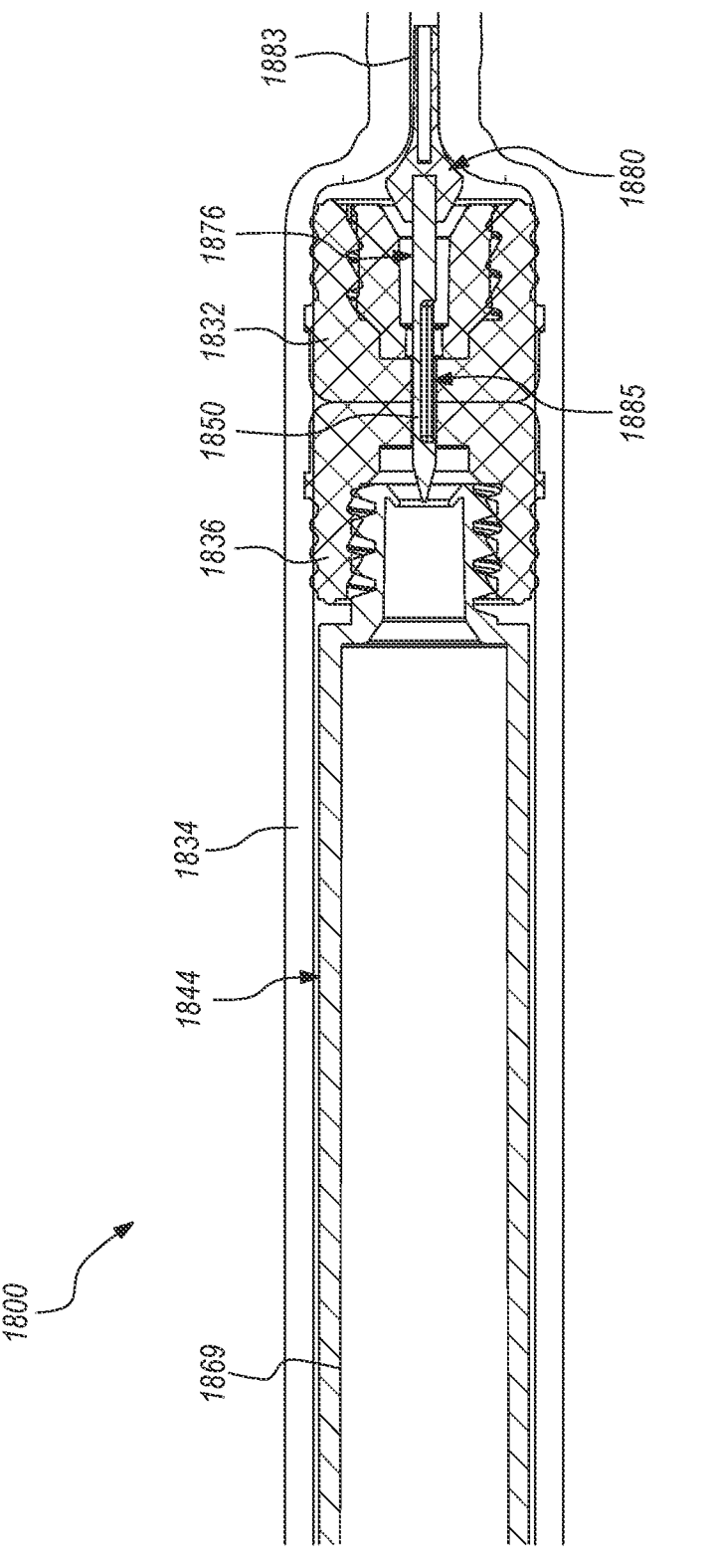

FIG. 109 depicts the prefilled needleless dual chamber serial injection system (1800) after the second liquid (1854, see FIG. 107) has been substantially ejected from the proximal chamber (1840, see FIG. 96) with distal movement of the proximal stopper member (1832) with the prefilled needleless dual chamber serial injection system (1800) in the second configuration.

Exemplary Fluid Transfer Assemblies

FIGS. 110 to 112C depict a fluid transfer assembly (1876) for use with the prefilled needleless dual chamber serial injection system (1800) according to some embodiments.

Figure 110:
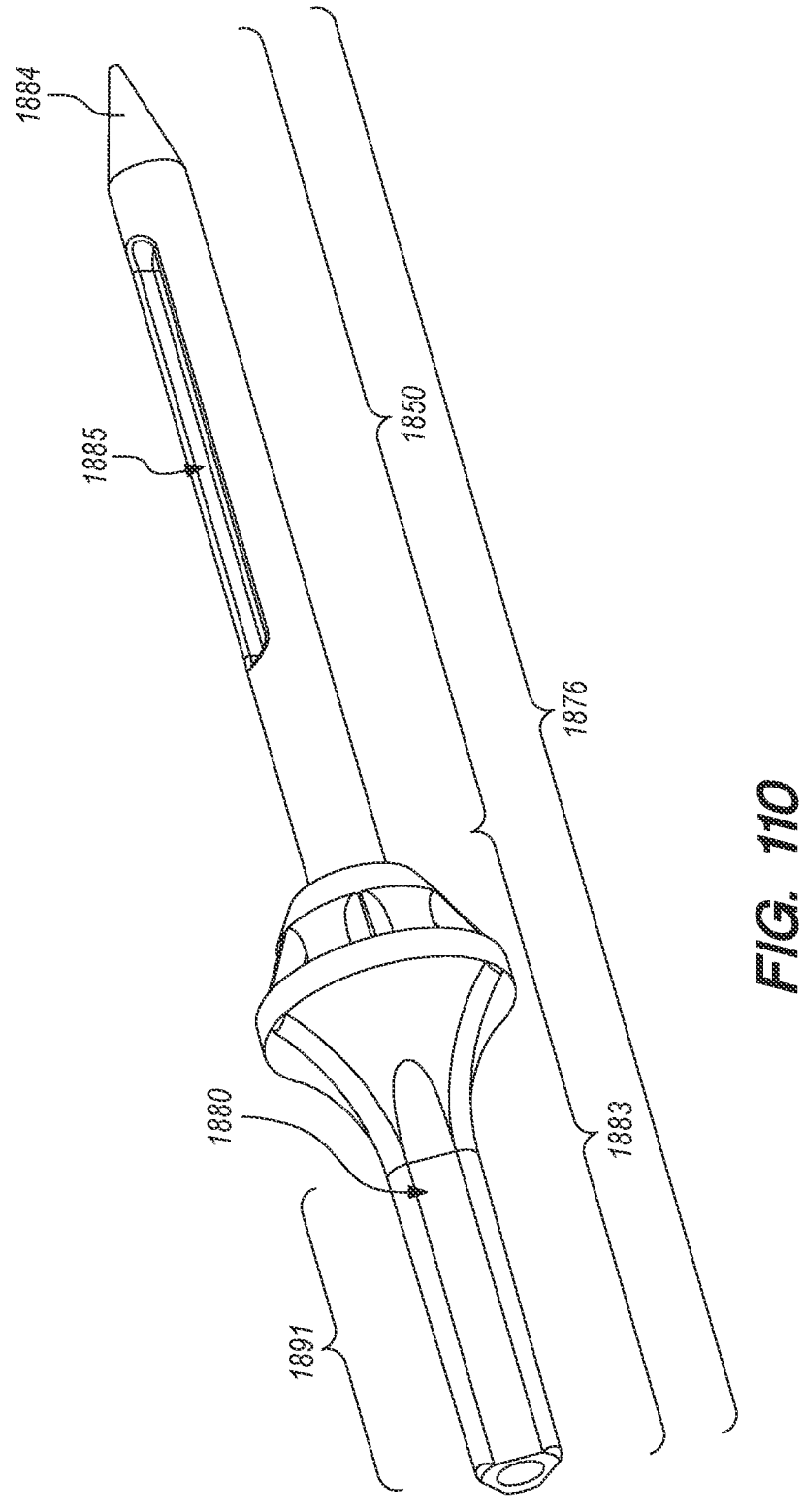
FIGS. 110 and 111 are perspective and exploded perspective views of a fluid transfer assembly according to some embodiments.
Figure 111:
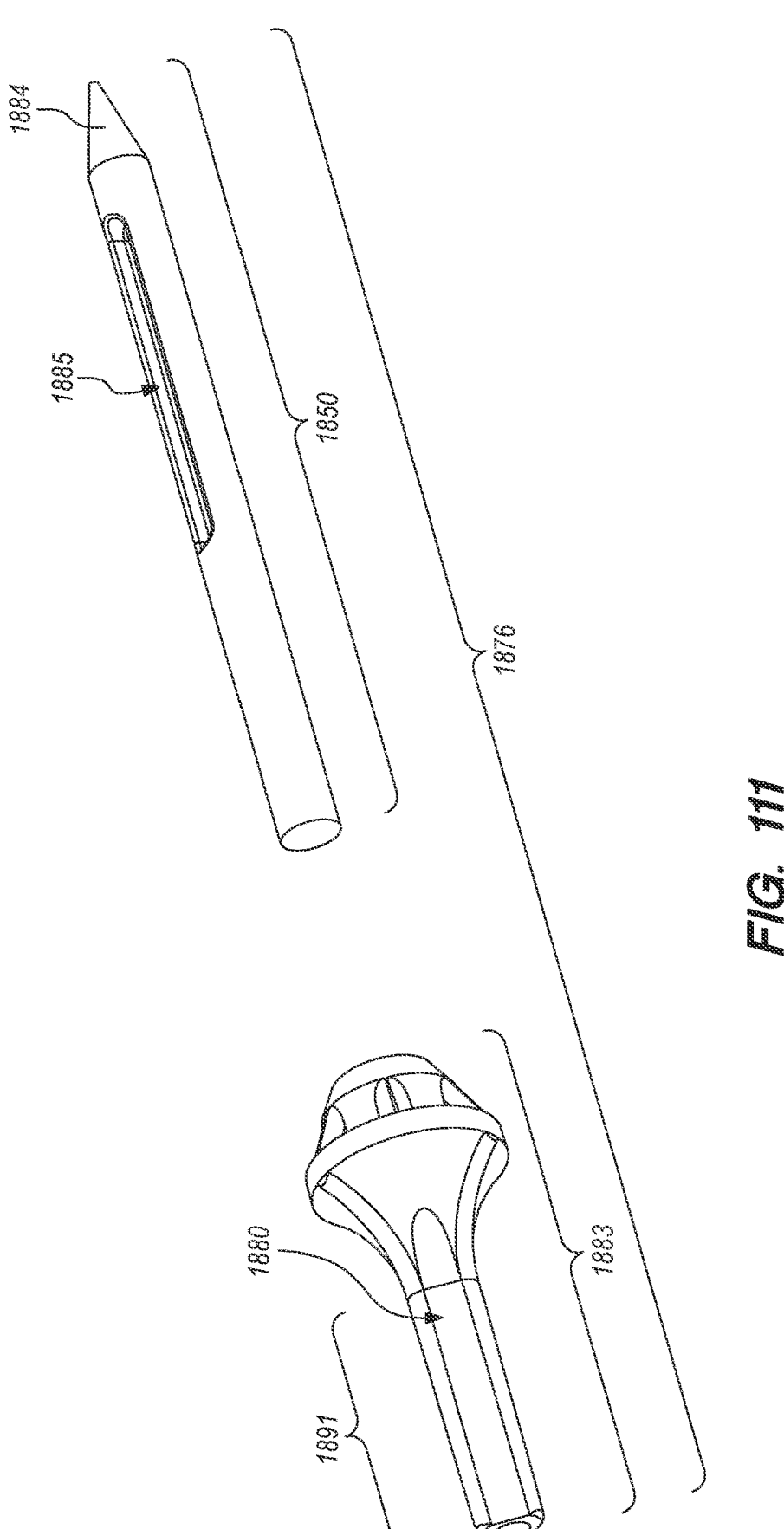

FIGS. 110 and 111 are perspective and exploded views of a fluid transfer assembly (1876) according to some embodiments. The fluid transfer assembly (1876) includes a fluid transfer proximal member (1850) configured to be partially disposed in and coupled to a proximal end of a fluid transfer joining member (1883). The fluid transfer proximal member (1850) includes a proximal piercing tip (1884) at a proximal end thereof configured to pierce the distal stopper member (1836). The fluid transfer joining member (1883) includes a fluid transfer distal anchor (1891) configured to secure the fluid transfer assembly (1876) to a distal opening in the syringe body (1834) with an interference fit.

Figure 112A:
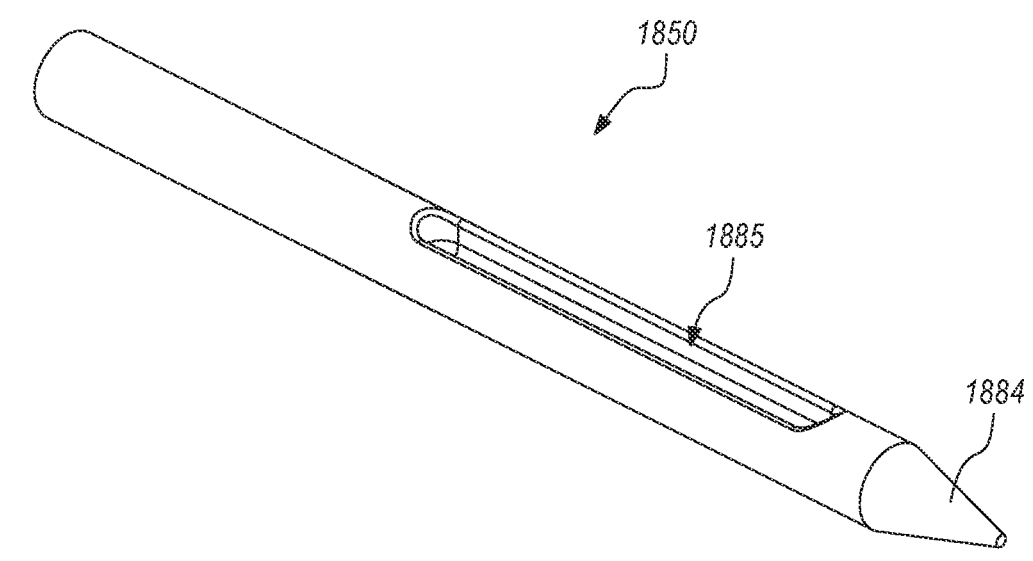
FIGS. 112A to 112C are perspective, longitudinal cross-sectional, and axial cross-sectional views of a fluid transfer proximal member according to some embodiments.
Figure 112B:
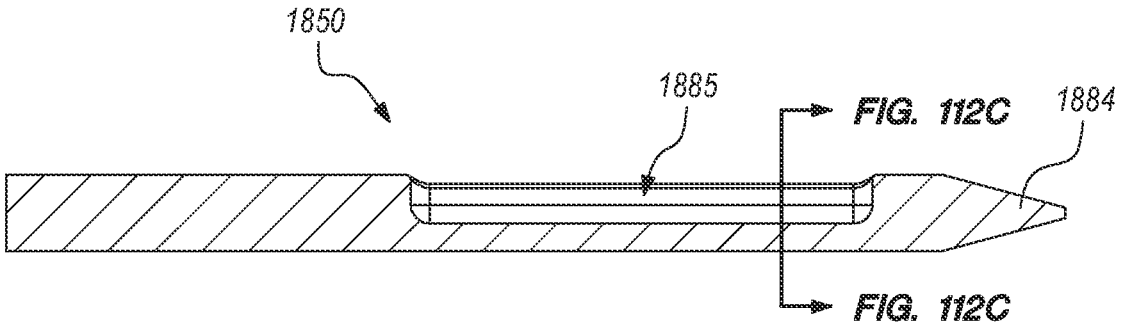
Figure 112C:
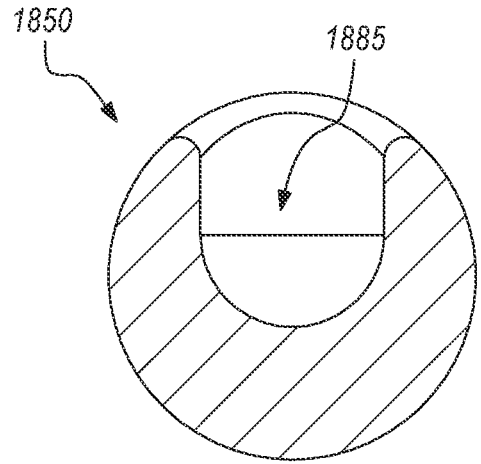

FIGS. 112A to 112C are perspective, longitudinal cross-sectional, and axial cross-sectional views of a fluid transfer proximal member (1850) according to some embodiments. The fluid transfer proximal member (1850) includes a proximal piercing tip (1884) at a proximal end thereof and a proximal longitudinal channel (1885) between the proximal and distal ends thereof The diameters of the fluid transfer proximal member (1850) are also relatively large (e.g., about 0.026" to about 0.040" compared to cold-formed proximal members, which have a diameter of about 0.020"). The larger diameter of the fluid transfer proximal member (1850) results in a higher overall bending moment of inertia, and more resistance to bending, which also improves the probability of capture. Due to its relatively large diameter and solid construction, the fluid transfer proximal member (1850) has sufficient bending moments of inertia for improved rigidity and resistance. Resistance to bending is particularly important as the fluid transfer proximal member (1850) punctures through the distal stopper member (1836). Minimizing bending of the fluid transfer proximal member (1850) as it punctures through the distal stopper member (1836), facilitates proper functioning of the prefilled needleless dual chamber serial injection system (1800) during serial injection.

FIGS. 113 to 121C depict a prefilled needleless dual chamber serial injection system (2700) and a fluid transfer assembly (2776) for use therewith according to some embodiments. The prefilled needleless dual chamber serial injection system (2700) and the fluid transfer assembly (2776) are similar to the prefilled needleless dual chamber serial injection system (1800) and the fluid transfer assembly (1876) depicted in FIGS. 104 to 112C. The difference between these two systems (2700, 1800) and assemblies (2776, 1876) is that the fluid transfer assembly (2776) depicted in FIGS. 113 to 121C is molded or formed as a single piece (e.g., from a polymer or a metal sheet or wire). The fluid transfer assembly (2776) still includes a fluid transfer proximal portion (2750) and a fluid transfer joining portion (2783). Molding or forming the fluid transfer assembly (2776) as a single piece simplifies system manufacturing and assembling. Forming the fluid transfer assembly (2776), including the fluid transfer joining portion (2783), from metal minimizes system failure from stress-induced cracking of the fluid transfer distal anchor portion (2791) of the fluid transfer joining portion (2783), which may occur in structures formed from polymers.

Figure 113:
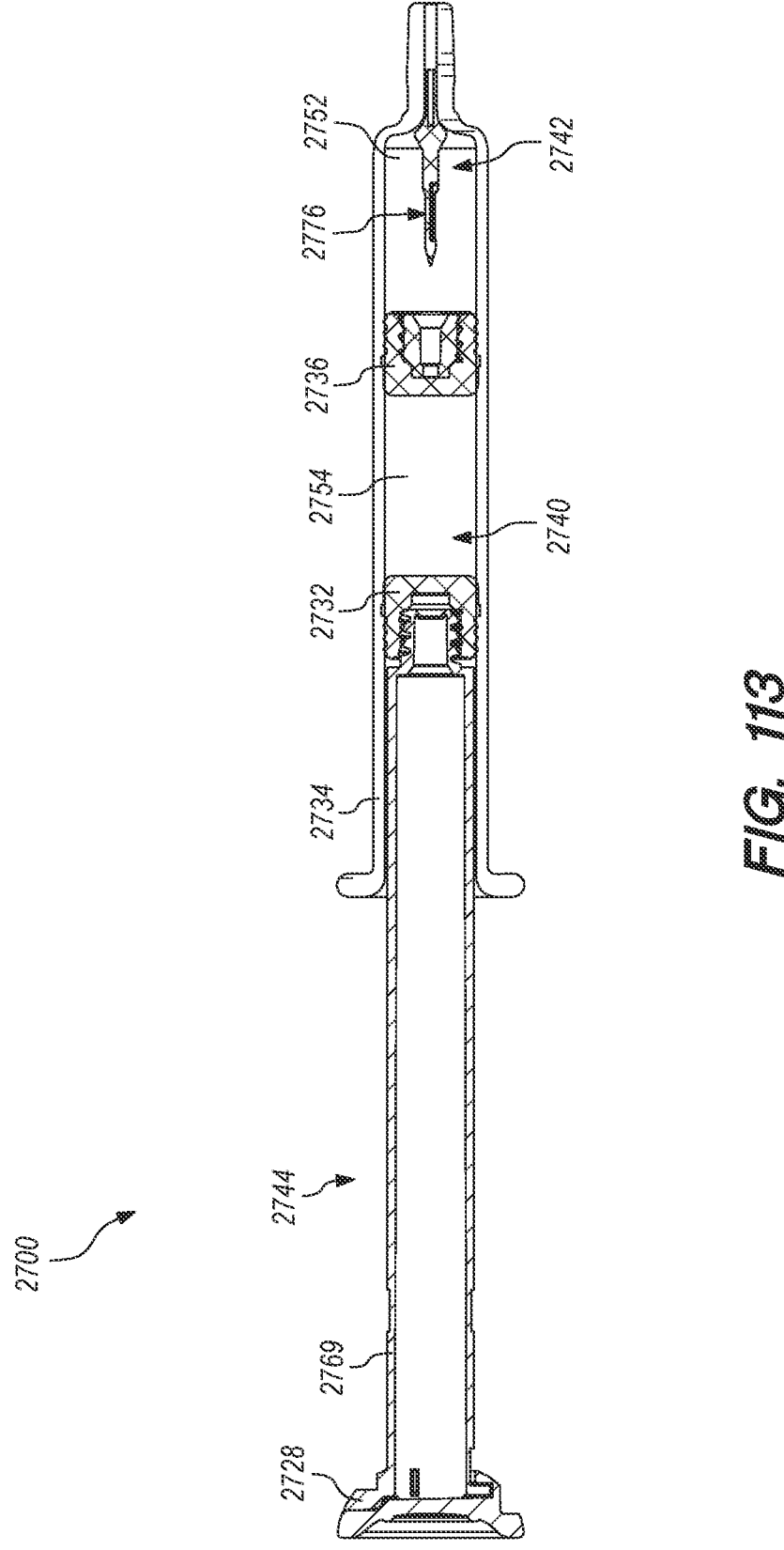
FIGS. 113 to 118 are longitudinal cross-sectional views of various degrees of detail illustrating a sequential injection method using a prefilled needleless dual chamber serial injection system according to some embodiments.
Figure 114:
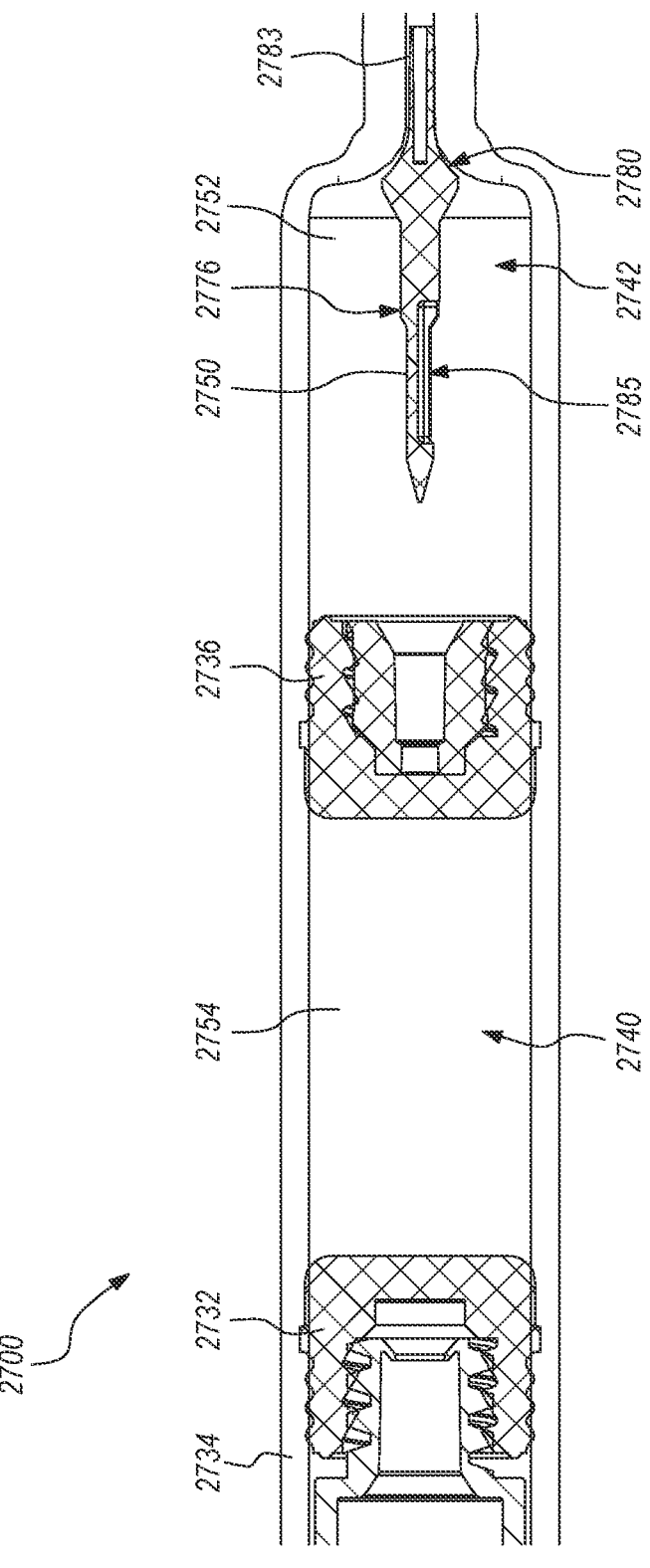
Figure 115:
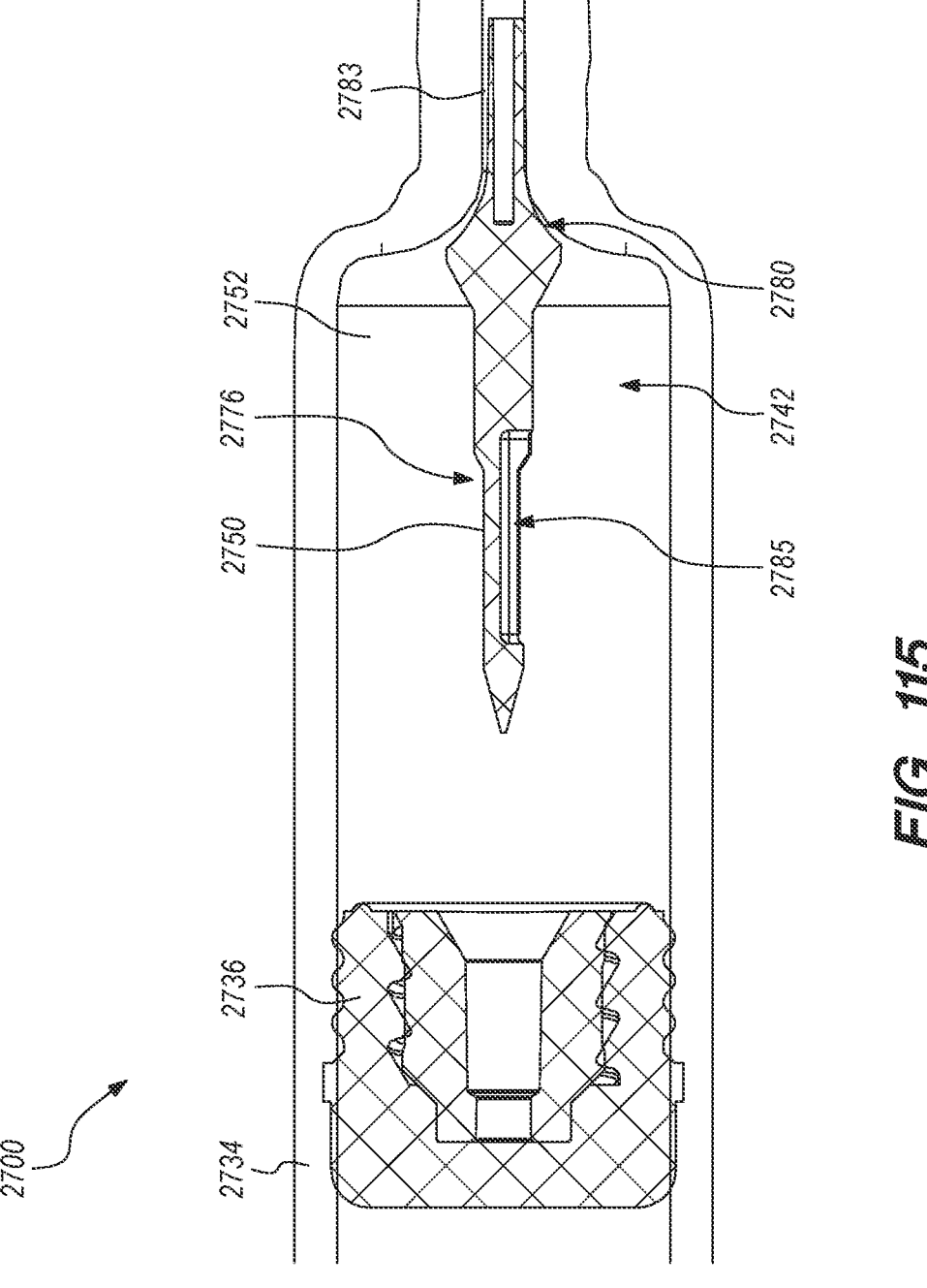

FIGS. 113 to 115 are a longitudinal cross-sectional view and two increasingly detailed longitudinal cross-sectional views depicting a prefilled needleless dual chamber serial injection system (2700) according to some embodiments. The prefilled needleless dual chamber serial safe injection system (2700) is similar to the prefilled dual chamber serial injection system (100) depicted in FIGS. 92 to 94. The prefilled needleless dual chamber serial injection system (2700) includes a conventional off-the-shelf prefilled syringe body (2734) with conventional off-the-shelf proximal and distal stopper members (2732, 1836) disposed therein. The proximal and distal stopper members (2732, 1836) together with the syringe body (2734) define proximal and distal chambers (2740, 1842). First and second liquids (2752, 1854) are contained in the distal and proximal chambers (2742, 1840) respectively. The proximal and distal stopper members (2732, 1836) occlude the proximal and distal ends of the proximal chamber (2740). The distal stopper member (2736) occludes a proximal end of the distal chamber (2742). In some embodiments, the distal surface of the proximal stopper member (2732) and the proximal surface of the distal stopper member (2736) are each coated with a lubricious polymer coating (e.g., PTFE or ETFE), the first and second polymer coatings of the proximal and distal stopper members (2732, 1836), together with the syringe body (2734) define the proximal chamber (2740). The lubricious polymer coating also serves to isolate the rubber of the proximal and distal stopper members (2732, 1836) from the second liquid (2754). The proximal and distal stopper members (2732, 1836) may be oriented as shown in FIGS. 104 to 106 or the distal stopper (2736) may be flipped so the lubricious coating faces the distal chamber (2742) such that the first liquid (2752) in the distal chamber (2742) contacts the lubricious coating for storage.

The dual chamber serial injection system (2700) depicted in FIGS. 113 to 115 does not include a "needle" extending outside of the syringe body (2734). Instead, the dual chamber serial injection system (2700) includes a fluid transfer assembly (2776), which as described above is molded or formed as a single piece. The fluid transfer assembly (2776) of the prefilled needleless dual chamber serial injection system (2700) facilitates sequential injection of the first liquid (2752) from the distal chamber (2742) followed by injection of the second liquid (2754) from the proximal chamber (2740) subject to sequential insertion of a plunger assembly (2744) relative to the syringe body (2734) to various degrees by a user. The plunger assembly (2744) includes a plunger housing member (2769) coupled to the proximal stopper member (2732) and a plunger manipulation interface (2728). The first and second liquids (2752, 1854) located in the distal and proximal chambers (2742, 1840) respectively may be any liquid or gel, such as aqueous or oil based medicine solutions.

The fluid transfer assembly (2776) of the prefilled needleless dual chamber serial injection system (2700) is configured for use with connectors (e.g., Luer lock or Luer slip interfaces coupled to needles with sharpened ends or fluid transfer tubes (not shown)).

The fluid transfer assembly (2776) includes a fluid transfer proximal portion (2750; see FIGS. 114 and 115) and a fluid transfer joining member (2783; see FIGS. 114 and 115). The fluid transfer proximal portion (2750) has a proximal channel (2785) molded or formed therein. The fluid transfer joining portion (2783) is configured to secure the fluid transfer assembly (2776) in a distal opening of the syringe body (2734). The fluid transfer joining portion (2783) includes a fluid transfer distal anchor (2791), which includes a cylindrical open core (2792) to provide compliance to the fluid transfer distal anchor (2791). The fluid transfer joining portion (2783) may secure the fluid transfer assembly (2776) to the syringe body (2734) with an interference fit between the fluid transfer distal anchor (2791) and a distal end of the syringe body (2734). The fluid transfer joining portion (2783) may define one or more channels therein to provide a middle opening (2780) between an interior of the syringe body (2734)/distal chamber (2742) and an exterior. The middle opening (2780) is disposed adjacent a distal end of the syringe body (2734). The proximal longitudinal channel (2785) is defined by the proximal fluid transfer portion (2750).

Other details regarding the prefilled needleless dual chamber serial injection system (2700) are described in U.S. Provisional Patent Application Ser. No. 63/156,264, which was previously incorporated by reference herein.

FIGS. 113 to 118 illustrate a safe sequential injection method using the prefilled needleless dual chamber serial injection system (2700) described herein according to some embodiments.

FIGS. 113 to 115 depict the prefilled needleless dual chamber serial injection system (2700) in a first/ready to use configuration. The only difference between the first/ready to use configuration and a shipping configuration (not shown) is that a syringe body cap (not shown) present in the shipping configuration has been removed in the first/ready to use configuration.

In the first/ready to use configuration, the proximal longitudinal channel (2785) is disposed in the distal chamber (2742), along with the middle opening (2780). As such, there is no flow path between the proximal chamber (2740), and the distal opening (2782). Therefore, any distally directed force applied to the plunger manipulation interface (2728) is transferred through the plunger member (2744), the proximal stopper member (2732), and the incompressible second liquid (2754) in the proximal chamber (2740) to move the distal stopper member (2736) distally relative to the syringe body (2734). Moving the distal stopper member (2736) distally relative to the syringe body (2734) increases a pressure in the distal chamber (2742), which drives the first liquid (2752) from the distal chamber (2742) through the middle opening (2780), formed between the tubular fluid transfer joining portion (2783) and the distal end of the syringe body (2734), and out the distal end of the syringe body (2734) (e.g., into a Luer connector).

Figure 116:
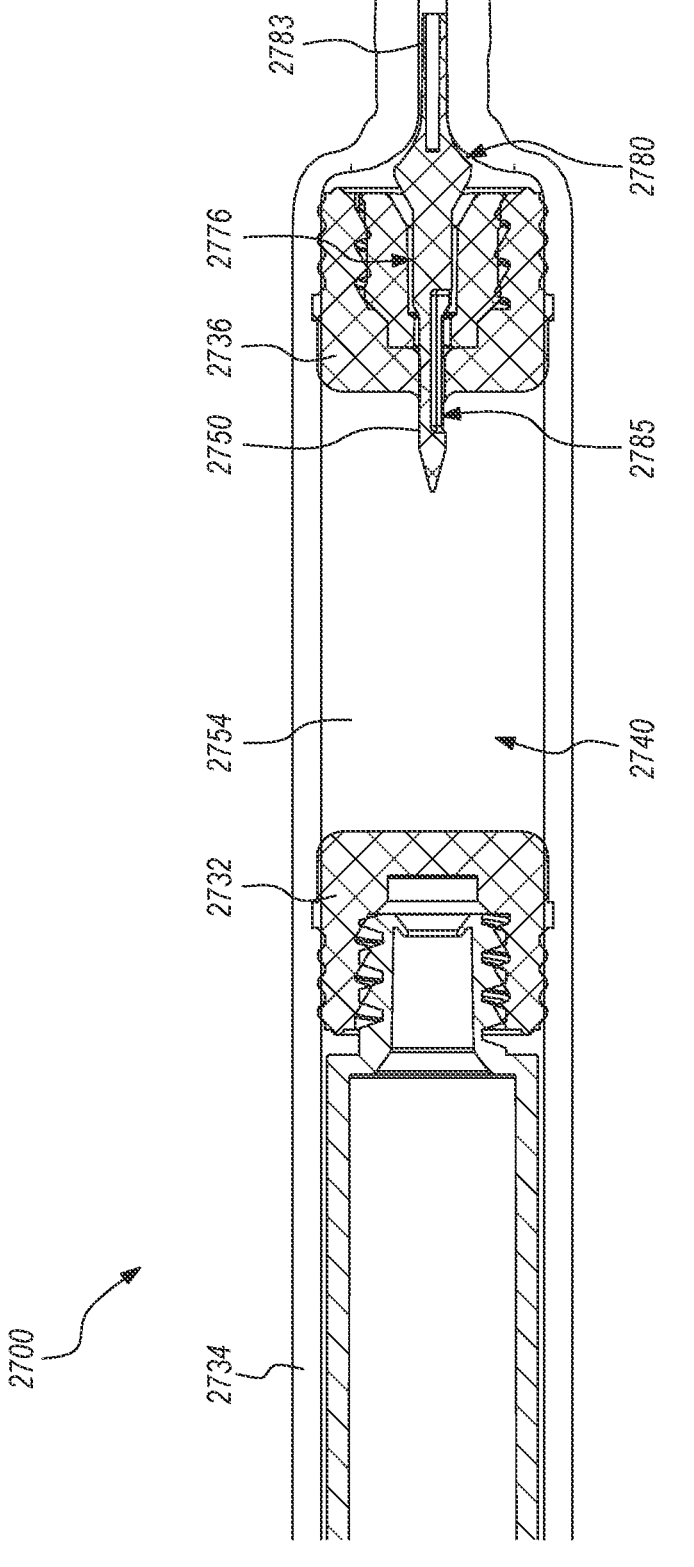
Figure 117:
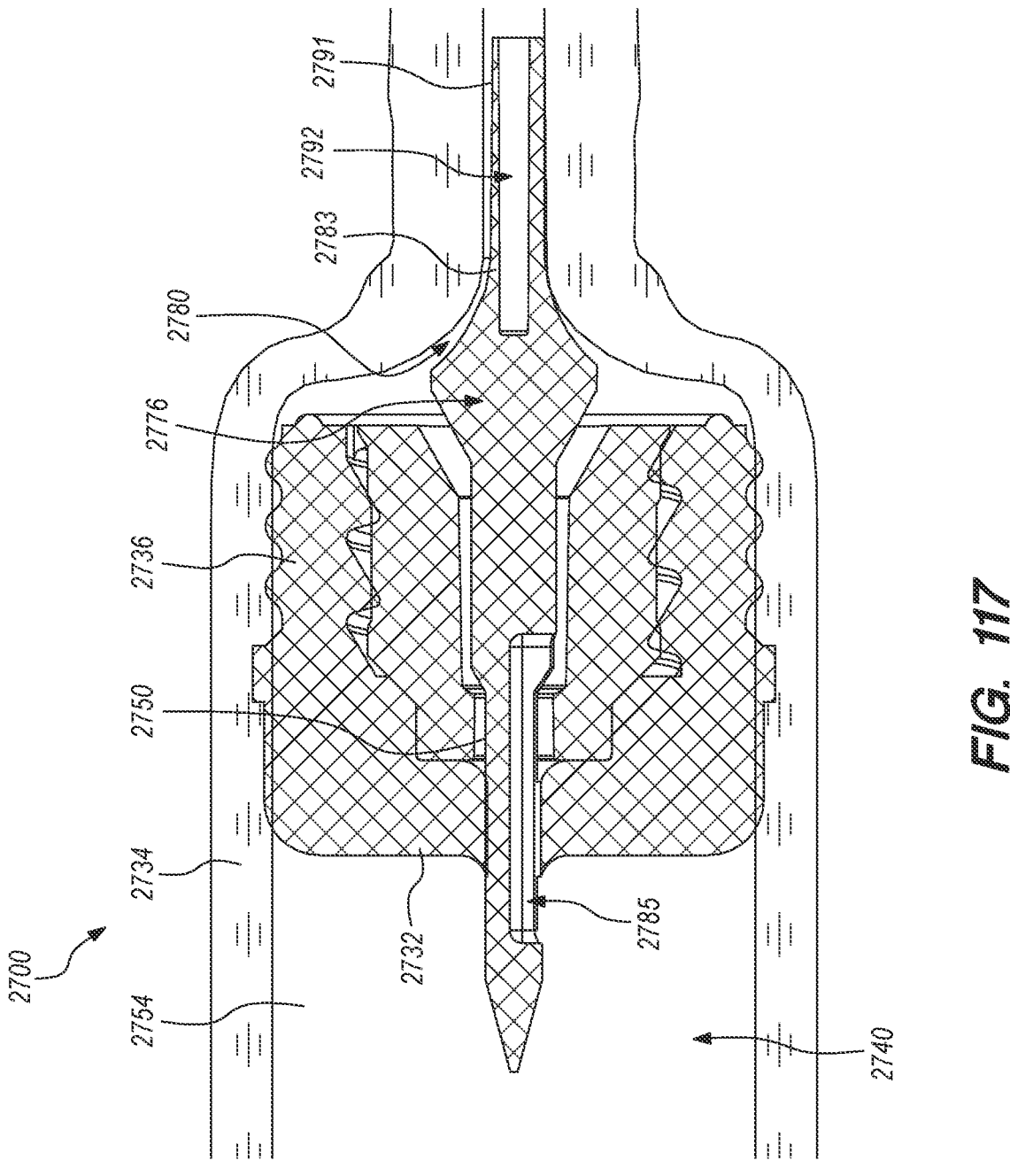

FIGS. 116 and 117 depict the prefilled needleless dual chamber serial injection system (2700) after the distal stopper member (2736) has been moved distally relative to the syringe body (2734) until the distal stopper member (2736) is almost in contact with the distal end of the syringe body (2736). The distal chamber (2742, see FIG. 114) has almost fully collapsed/been almost completely eliminated, and most of the first liquid (2752, see FIG. 114) has been ejected from the prefilled needleless dual chamber serial injection system (2700) through the distal end of the syringe body (2736). Moving the distal stopper member (2736) distally relative to the syringe body (2734) has also caused the fluid transfer proximal portion (2750) of the fluid transfer assembly (2776) to penetrate the distal stopper member (2736). With penetration of the fluid transfer proximal portion (2750) of the fluid transfer assembly (2776), the proximal longitudinal channel (2785) is now disposed in the proximal chamber (2740). Accordingly, there is now a flow path between the proximal chamber (2740) and the middle opening (2780), and distally directed force applied to the plunger manipulation interface (2728) now moves the proximal stopper member (2732) distally relative to the syringe body (2734) and the distal stopper member (2736) to eject the second liquid (2754) from the proximal chamber (2740). Opening of the flow path between the proximal chamber (2740) and the distal opening (2782) places the prefilled needleless dual chamber serial injection system (2700) in a second configuration in which the second liquid (2754) may be ejected from the proximal chamber (2740) in sequence after the first liquid (2752) is mostly ejected from the distal chamber (2742).

Figure 118:
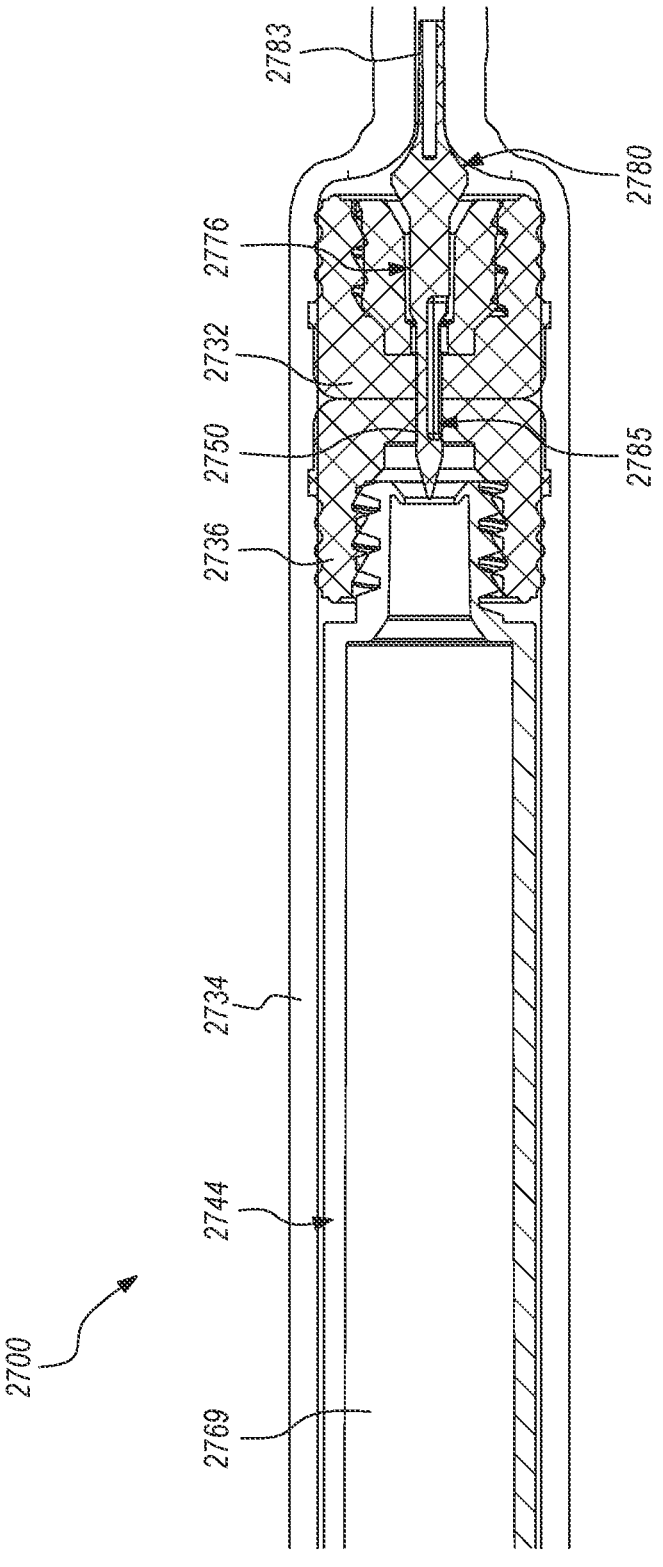

FIG. 118 depicts the prefilled needleless dual chamber serial injection system (2700) after the second liquid (2754, see FIG. 107) has been substantially ejected from the proximal chamber (2740, see FIG. 96) with distal movement of the proximal stopper member (2732) with the prefilled needleless dual chamber serial injection system (2700) in the second configuration.

FIGS. 119 to 121C depict a fluid transfer assembly (2776) for use with the prefilled needleless dual chamber serial injection system (2700) according to some embodiments.

Figure 119:
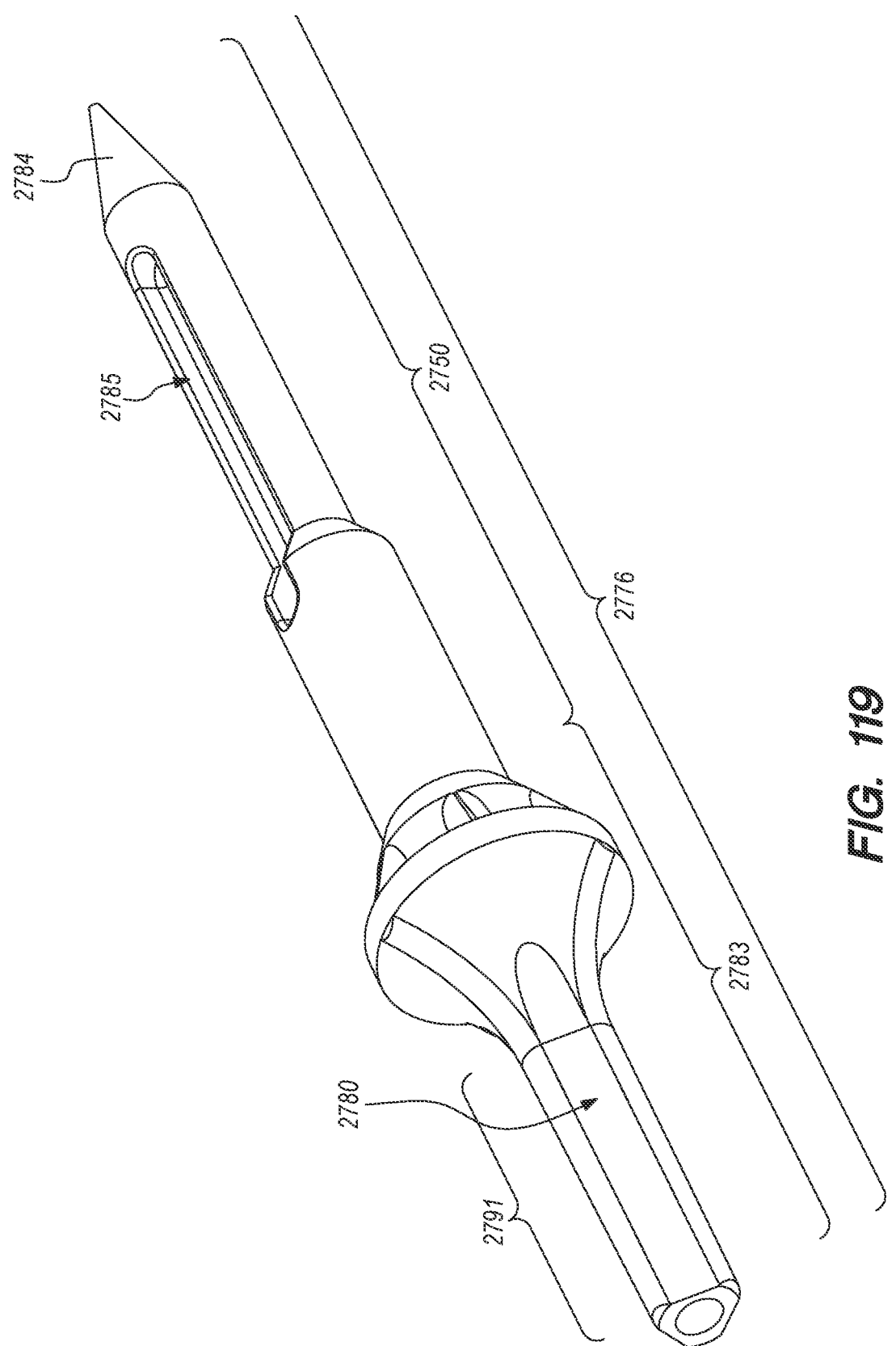
FIGS. 119 and 120 are perspective views of a fluid transfer assembly according to some embodiments.
Figure 120:
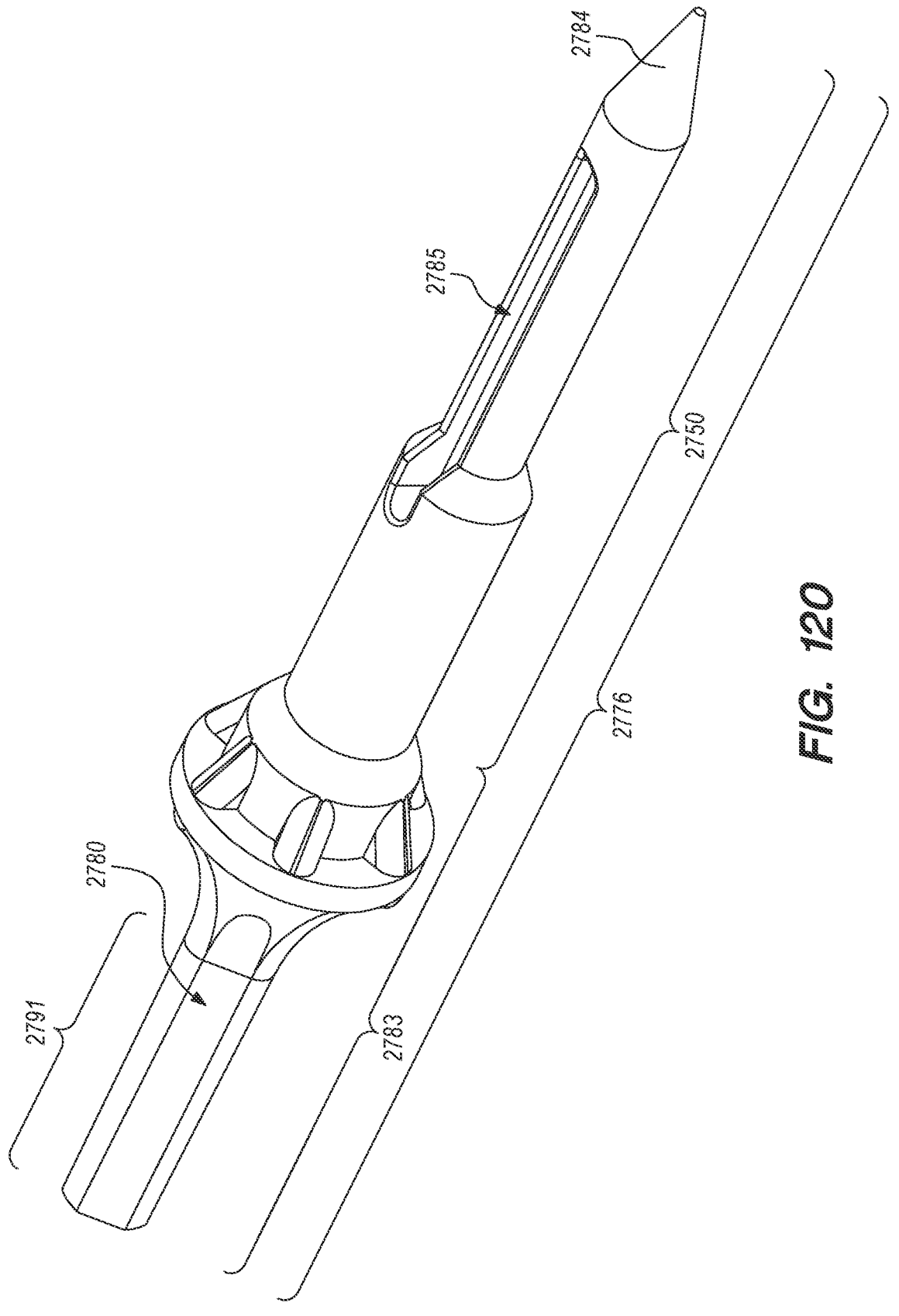

FIGS. 119 and 120 are perspective views of a fluid transfer assembly (2776) according to some embodiments. The fluid transfer assembly (2776) includes a fluid transfer proximal portion (2750) and a fluid transfer joining portion (2783). The fluid transfer proximal portion (2750) includes a proximal piercing tip (2784) at a proximal end thereof configured to pierce the distal stopper member (2736). The fluid transfer joining portion (2783) includes a fluid transfer distal anchor (2791) configured to secure the fluid transfer assembly (2776) to a distal opening in the syringe body (2734) with an interference fit.

FIGS. 121A to 121C are perspective and axial cross-sectional views of a fluid transfer assembly (2776) according to some embodiments. The fluid transfer proximal portion (2750) includes a proximal piercing tip (2784) at a proximal end thereof and a proximal longitudinal channel (2785) between the proximal and distal ends thereof. The fluid transfer distal anchor (2791) has a triangular cross-sectional shape to provide flow channels leading from the middle opening (2780) to an exterior of the syringe body (2734). The fluid transfer distal anchor (2791) also defines a cylindrical open core (2792) to provide compliance to the fluid transfer distal anchor (2791), which allows the fluid transfer distal anchor (2791) to deform slightly to generate an interference fit with a distal opening of the syringe body (2734).

The diameter of the fluid transfer proximal portion (2750) is also relatively large (e.g., about 0.026" to about 0.040" compared to cold-formed proximal portions, which have a diameter of about 0.020"). The larger diameter of the fluid transfer proximal portion (2750) results in a higher overall bending moment of inertia, and more resistance to bending, which also improves the probability of capture. Due to its relatively large diameter and solid construction, the fluid transfer proximal portion (2750) has sufficient bending moments of inertia for improved rigidity and resistance. Resistance to bending is particularly important as the fluid transfer proximal portion (2750) punctures through the distal stopper member (2736). Minimizing bending of the fluid transfer proximal portion (2750) as it punctures through the distal stopper member (2736) facilitates proper functioning of the prefilled needleless dual chamber serial injection system (2700) during serial injection.

Figure 122:
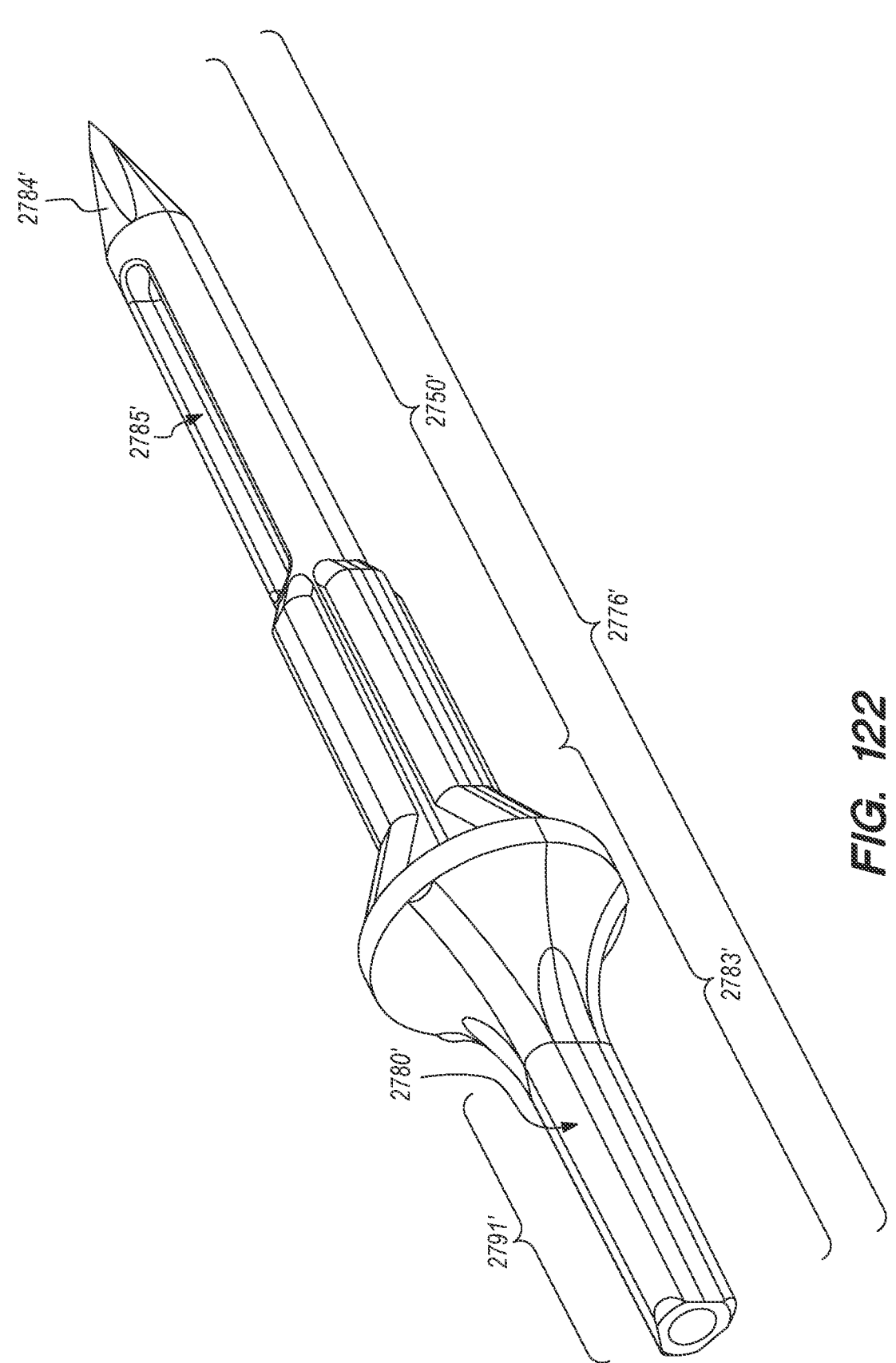
FIGS. 122 and 123 are perspective views of a fluid transfer assembly according to some embodiments.
Figure 123:
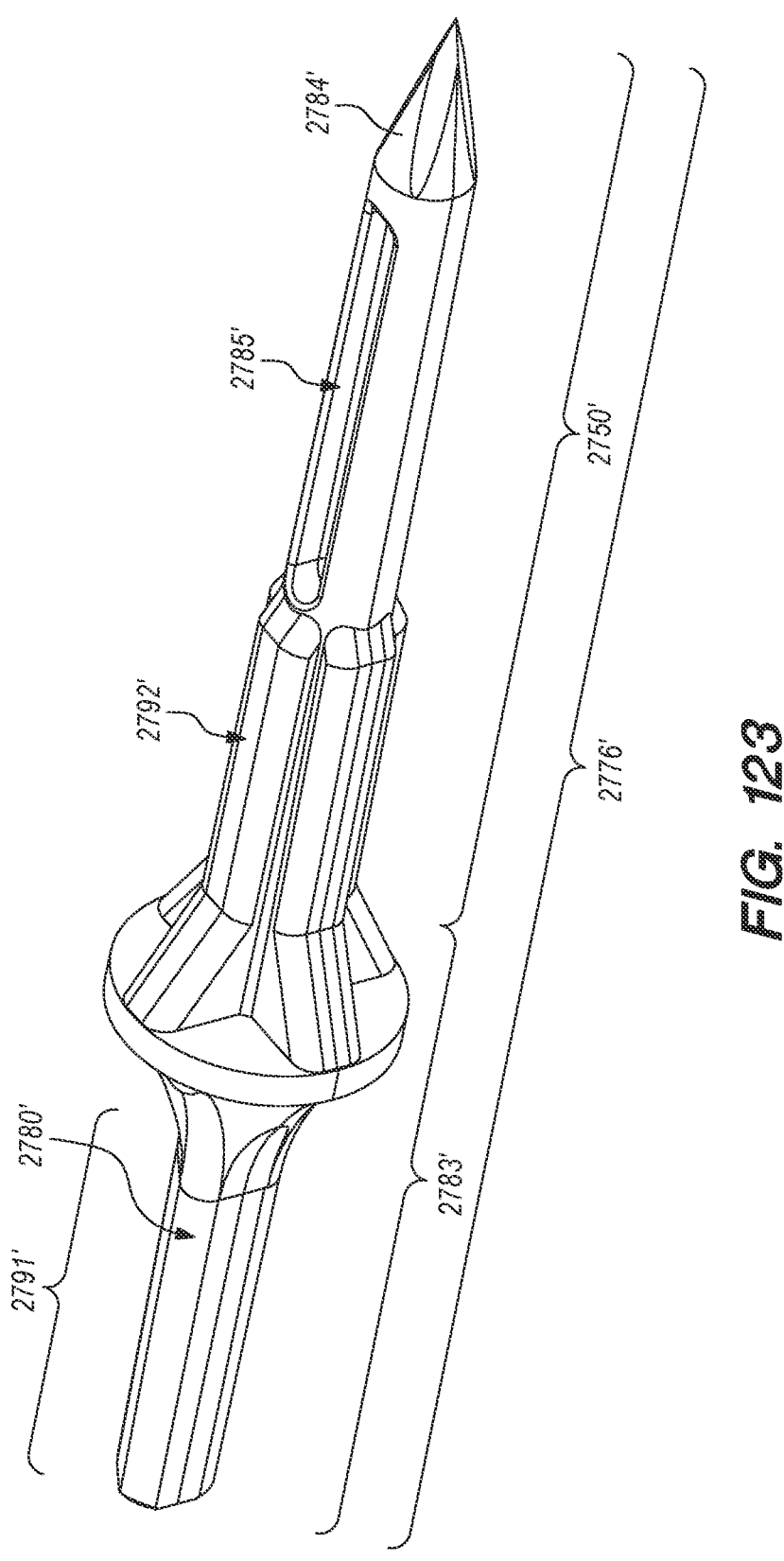
Figure 124:
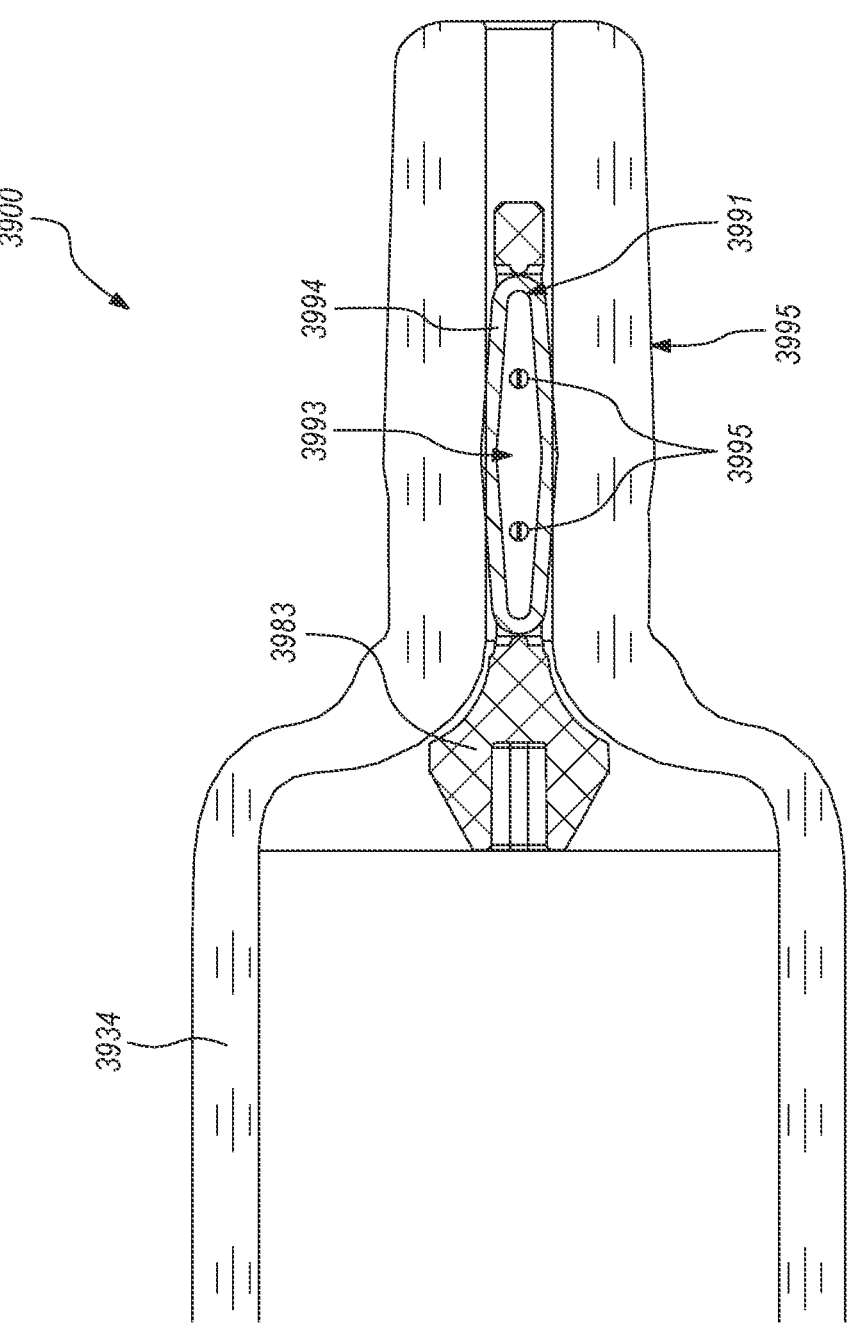
FIG. 124 is a detailed longitudinal cross-sectional view of an injection system including a fluid transfer joining member/portion according to some embodiments.
Figure 125A:
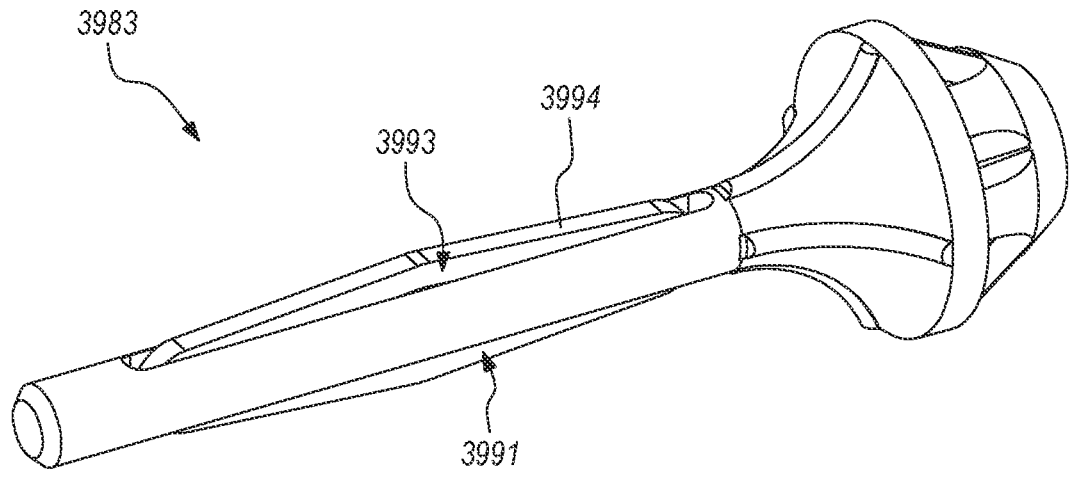
FIGS. 125A and 125B are perspective and exploded perspective views of a fluid transfer joining member/portion according to some embodiments.
Figure 125B:
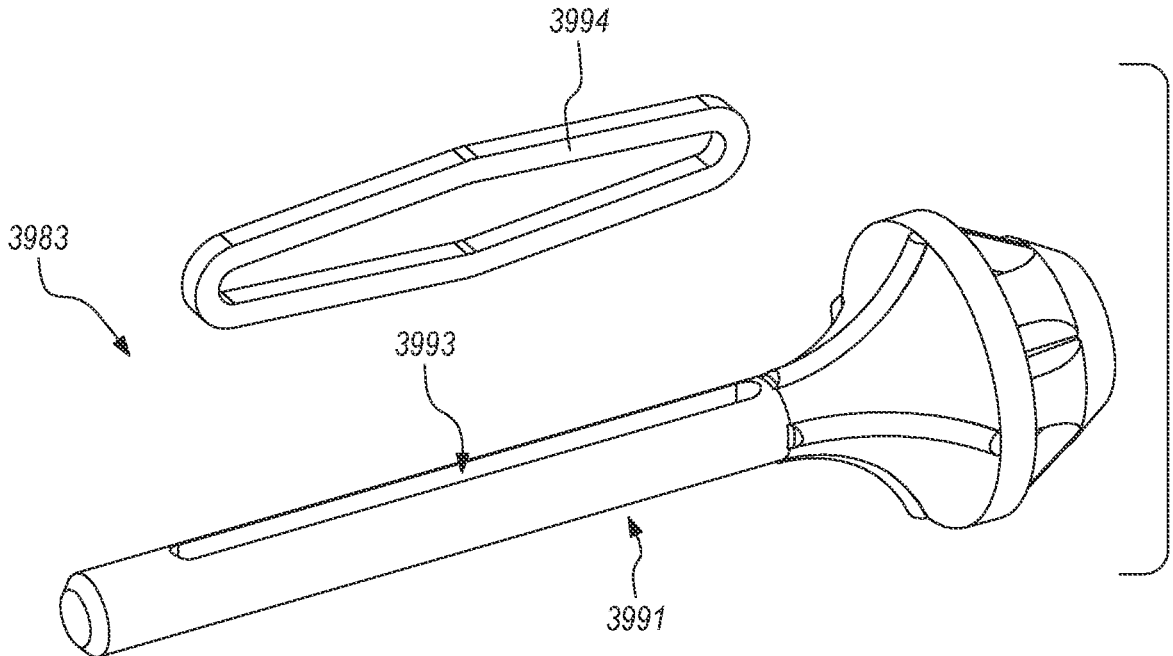
Figure 126A:
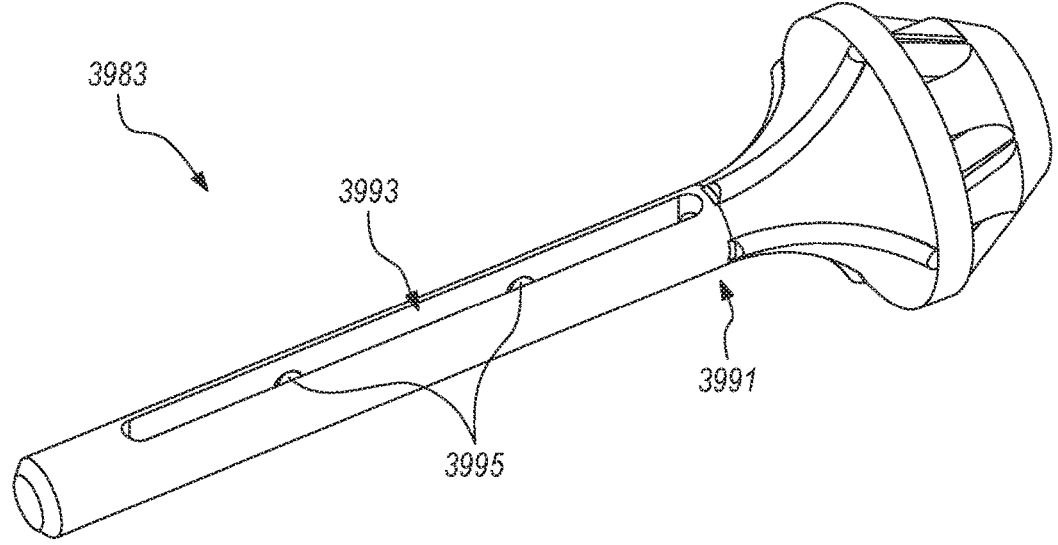
FIGS. 126A and 126B are perspective and top views of a fluid transfer distal anchor of a fluid transfer joining member/portion according to some embodiments.
Figure 126B:
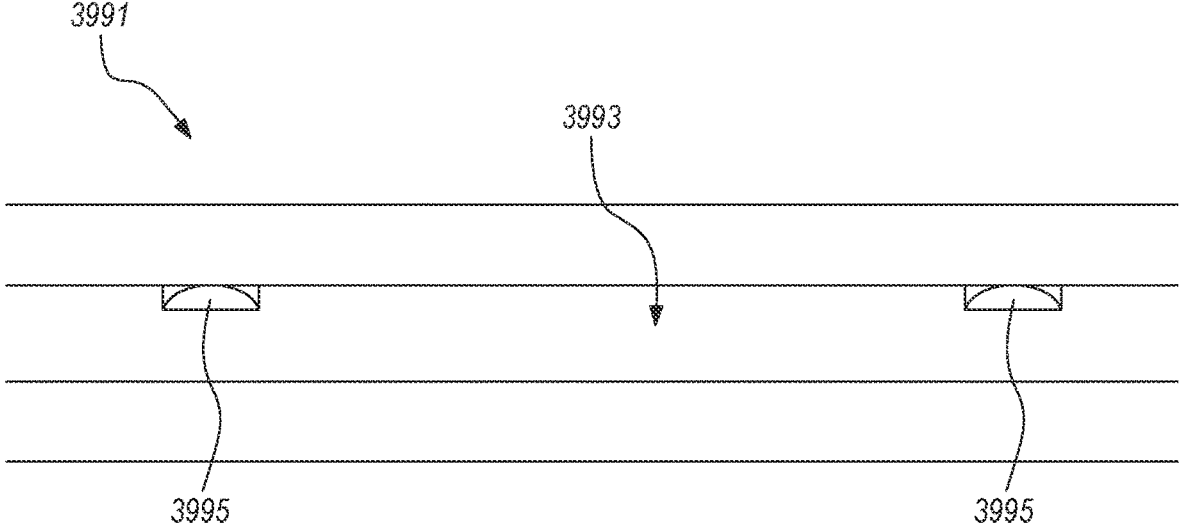
Figure 127A:
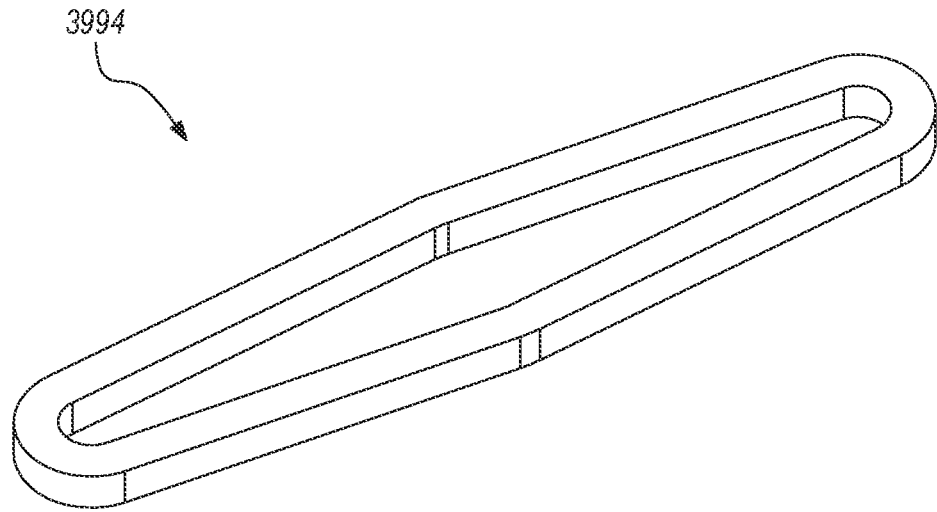
FIGS. 127A and 127B are perspective and side views of a biasing member of a fluid transfer joining member/portion according to some embodiments.
Figure 127B:
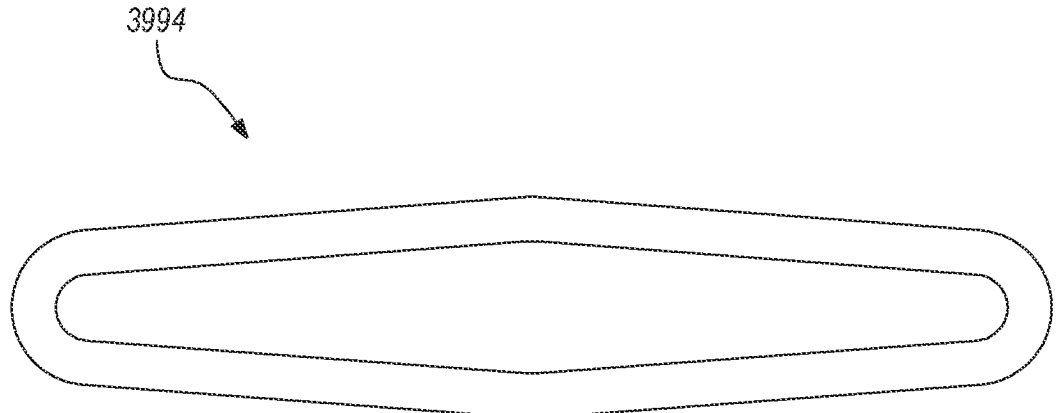

FIGS. 122 and 123 are perspective views of a fluid transfer assembly (2776') for use with the prefilled needleless dual chamber serial injection system (2700) according to some embodiments. The fluid transfer assembly (2776') is similar to the fluid transfer assembly (2776) depicted in FIGS. 119 to 121C. A difference between the two fluid transfer assemblies (2776', 2776) is the addition of ribs and drafts (2792') at a distal end of the fluid transfer proximal portion (2750'), which facilitate penetration of the distal stopper member (2736). Another difference is that the proximal piercing tip (2784') is faceted to facilitate penetration of the distal stopper member (2736).

Exemplary Fluid Transfer Distal Anchors

While fluid transfer assemblies (1876, 2776, 2776') have been described herein with a simple triangular cross-section fluid transfer distal anchor (1891, 2791, 2791'), fluid transfer assemblies according to some embodiments may be used with other fluid transfer distal anchors configured to secure the fluid transfer assemblies to a distal opening of a syringe body. The fluid transfer distal anchors described herein may be used with any fluid transfer assembly, including the fluid transfer assemblies (1876, 2776, 2776') described herein.

FIGS. 124 to 127B depict an injection system (3900) including a fluid transfer joining member/portion (3983) according to some embodiments. The remainder of the fluid transfer assembly has been omitted for clarity. The fluid transfer joining member/portion (3983) includes a fluid transfer distal anchor (3991) at a distal end thereof.

The fluid transfer distal anchor (3991) defines a slot (3993) and includes a biasing member (3994) disposed in the slot (3993). The fluid transfer distal anchor (3991) also defines two pegs (3995) (see FIGS. 124, 126A, and 126B) configured to retain the biasing member (3994) in the slot (3993). The biasing member (3994) (see FIGS. 127A and 127B) is a spring-like metal loop configured to interfere with an inner diameter of the distal end (3995) of the syringe body (3934) (see FIG. 124) to generate an interference fit holding the fluid transfer distal anchor (3991) in the distal end (3995) of the syringe body (3934) while minimizing stress on the remainder of the fluid transfer distal anchor (3991).

Figure 128:
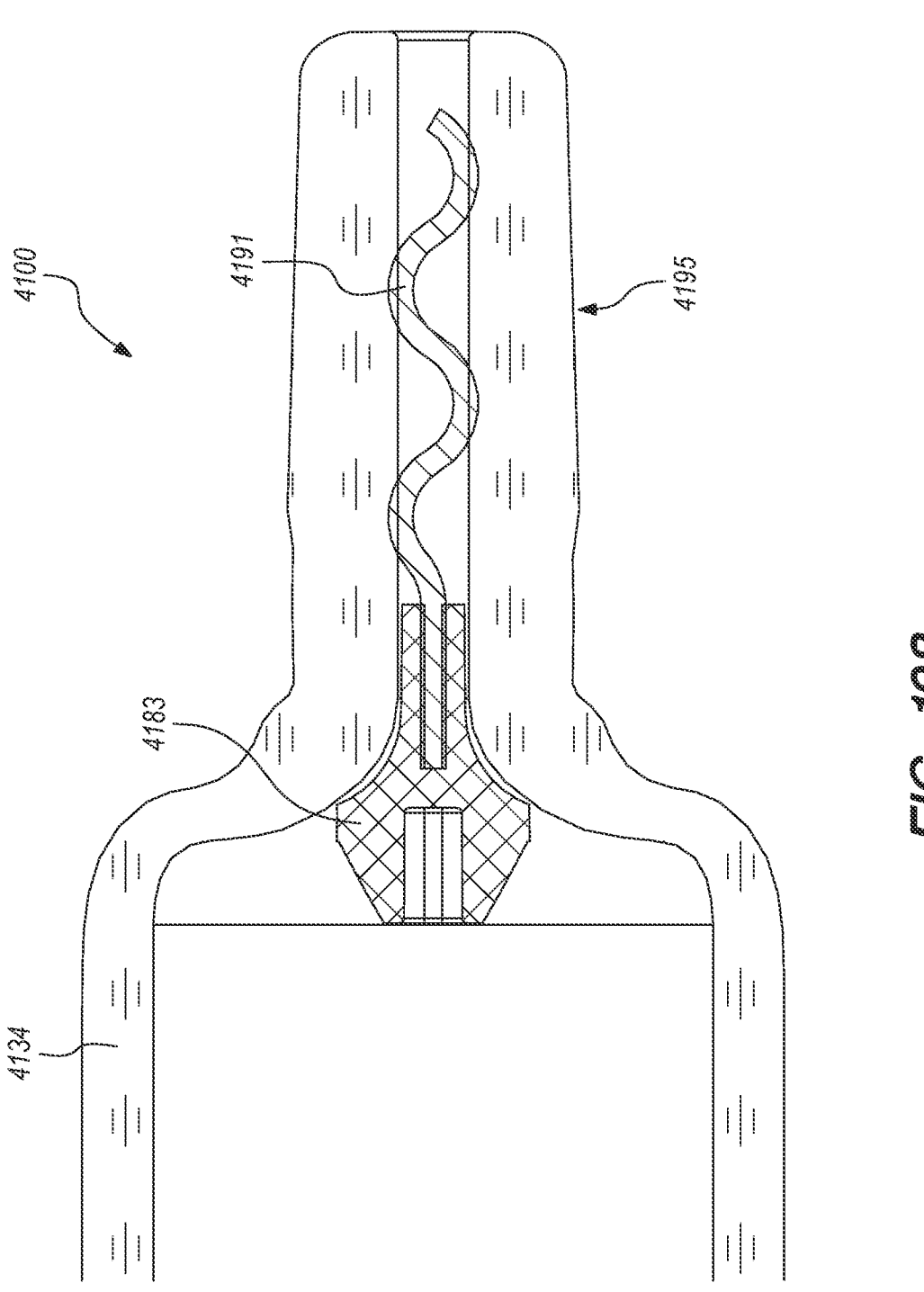
FIG. 128 is a detailed longitudinal cross-sectional view of an injection system including a fluid transfer joining member/portion according to some embodiments.
Figure 129A:
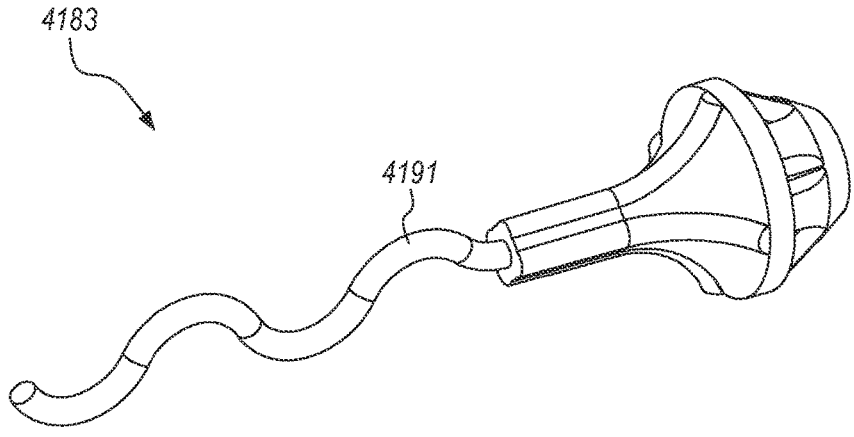
FIGS. 129A, 129B and 130 are perspective, exploded perspective, and exploded side views of a fluid transfer joining member/portion according to some embodiments.
Figure 129B:
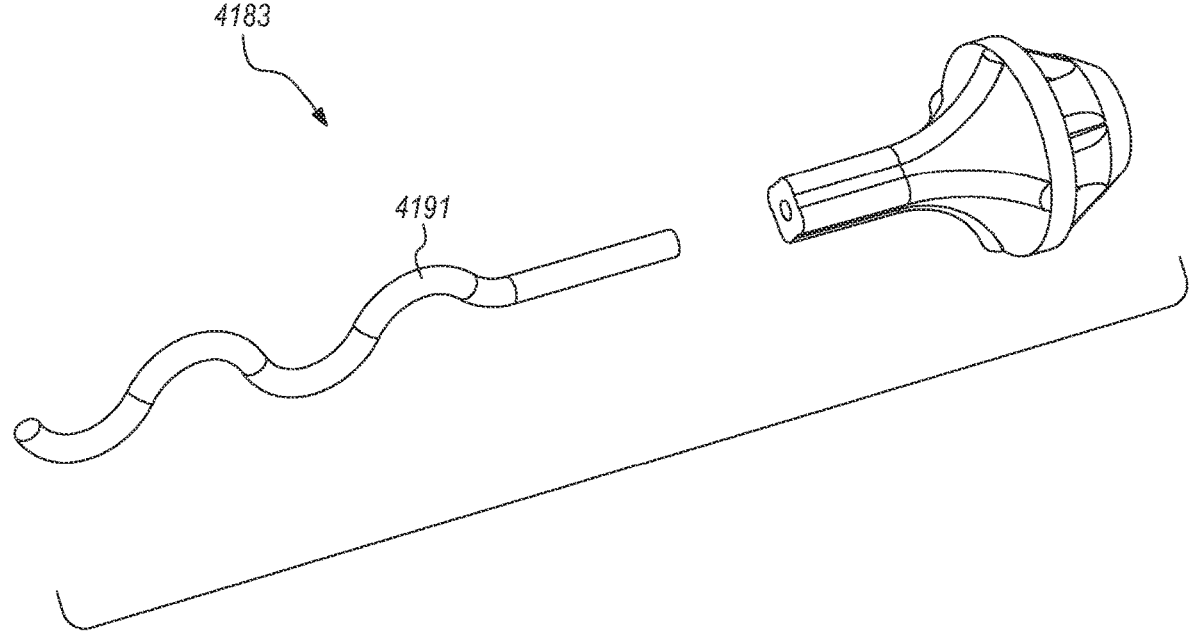
Figure 130:
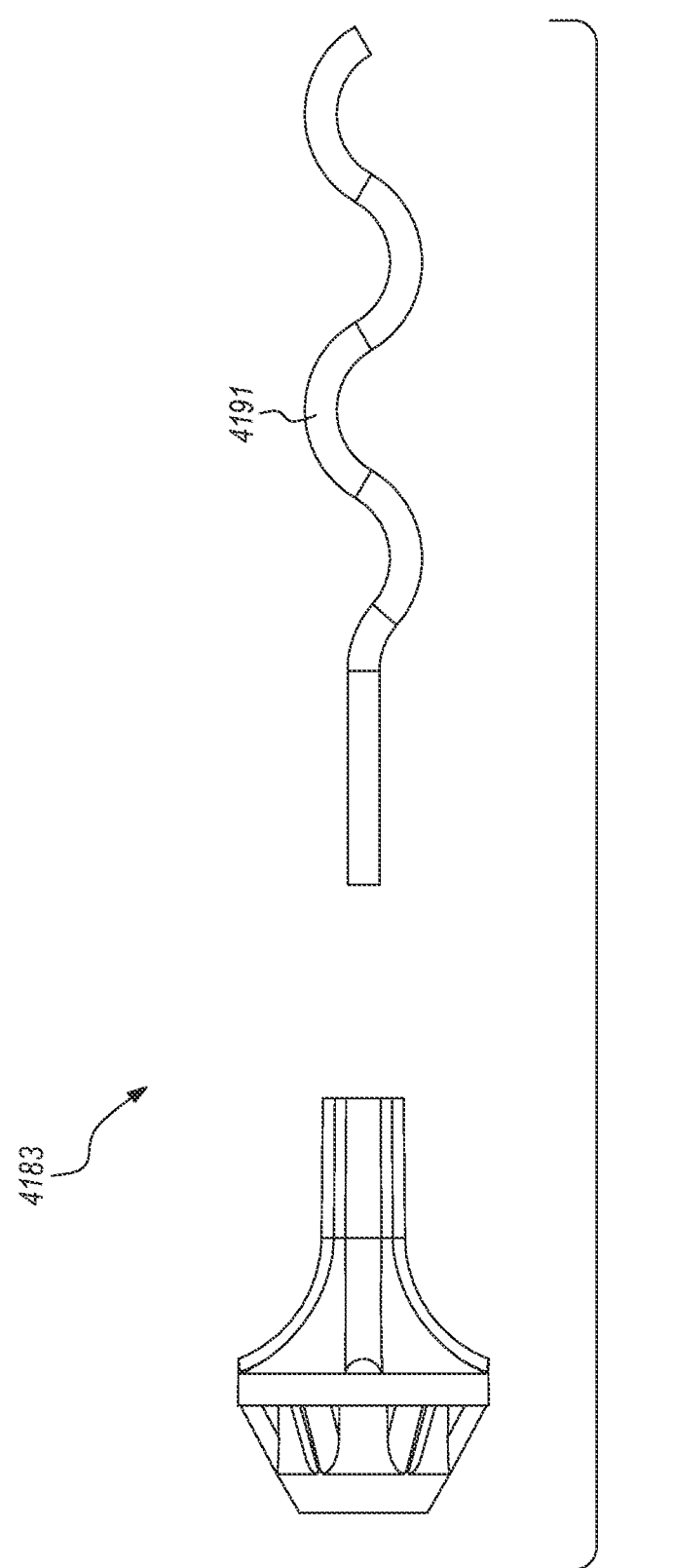

FIGS. 128 to 130 depict an injection system (4100) including a fluid transfer joining member/portion (4183) according to some embodiments. The remainder of the fluid transfer assembly has been omitted for clarity. The fluid transfer joining member/portion (4183) includes a fluid transfer distal anchor (4191) at a distal end thereof.

The fluid transfer distal anchor (4191) takes the form of a wavy wire segment configured to interfere with an inner diameter of the distal end (4195) of the syringe body (4134) (see FIG. 128) to generate an interference fit holding the fluid transfer distal anchor (4191) in the distal end (4195) of the syringe body (4134). The wavy wire fluid transfer distal anchor (4191) may be press fit into the remainder of the fluid transfer joining member/portion (4183).

Figure 131:
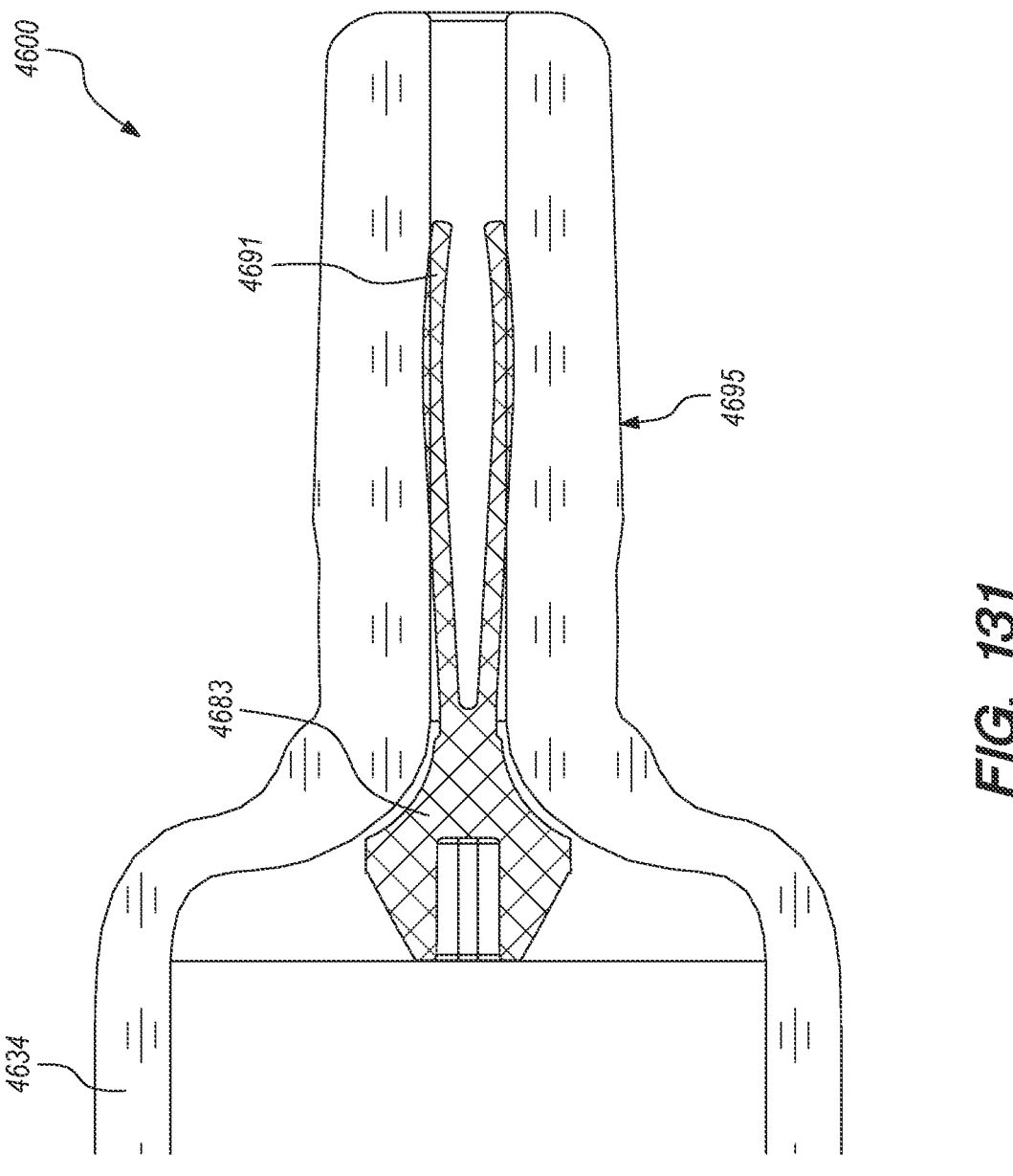
FIG. 131 is a detailed longitudinal cross-sectional view of an injection system including a fluid transfer joining member/portion according to some embodiments.
Figure 132A:
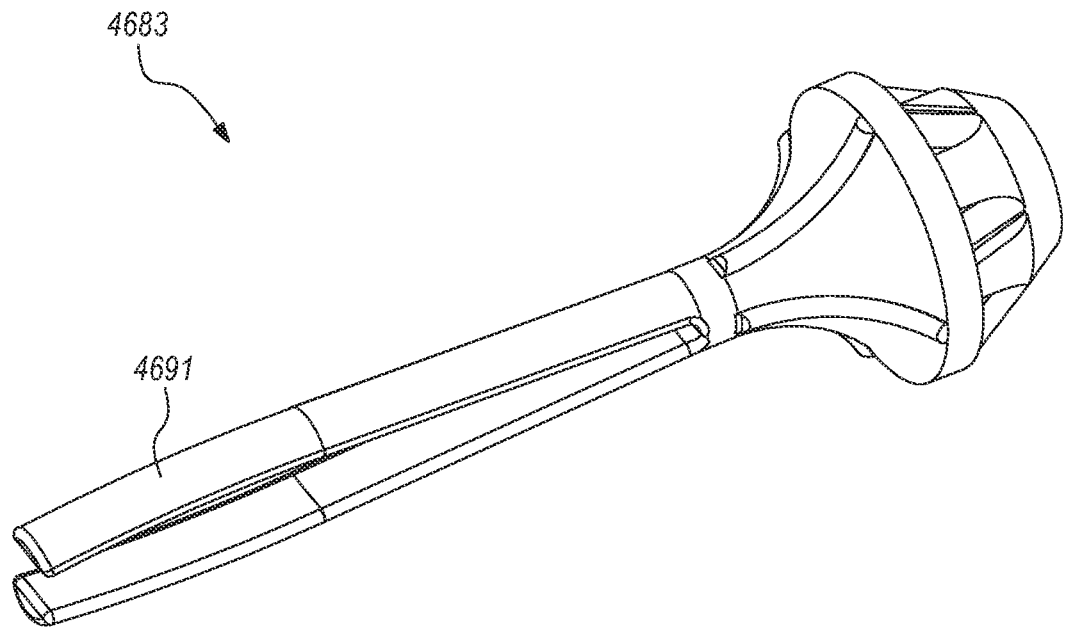
FIGS. 132A and 132B are perspective and side views of a fluid transfer joining member/portion according to some embodiments.
Figure 132B:
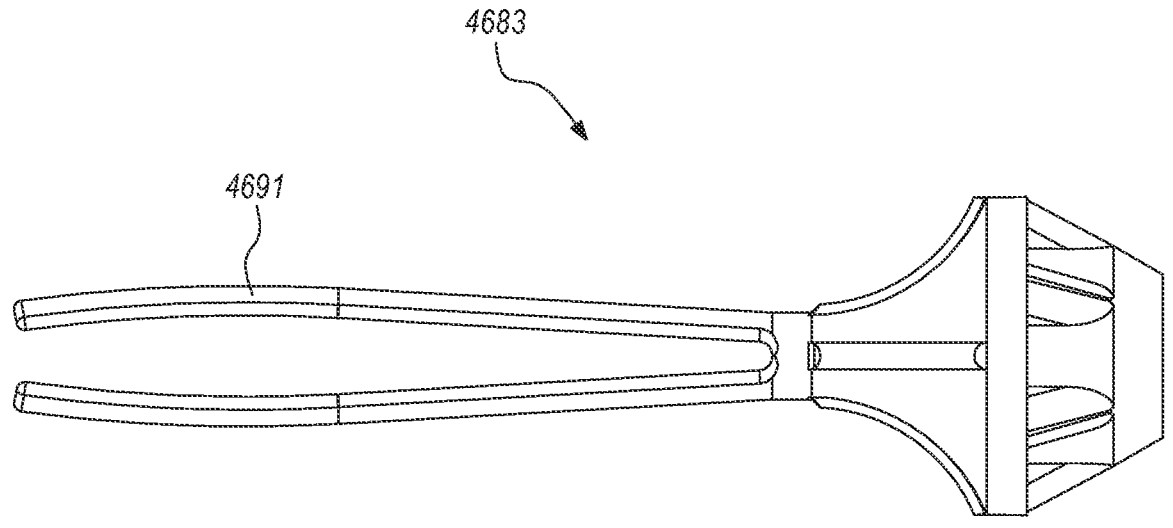

FIGS. 131 to 132B depict an injection system (4600) including a fluid transfer joining member/portion (4683) according to some embodiments. The remainder of the fluid transfer assembly has been omitted for clarity. The fluid transfer joining member/portion (4683) includes a fluid transfer distal anchor (4691) at a distal end thereof.

The fluid transfer distal anchor (4691) takes the form of a pair of long, flexible plastic arms configured to interfere with an inner diameter of the distal end (4695) of the syringe body (4634) (see FIG. 131) to generate an interference fit holding the fluid transfer distal anchor (4691) in the distal end (4695) of the syringe body (4634) with very low resting stress. The length of the flexible plastic arms (4691) and relatively small interference with the inner diameter of the distal end (4695) of the syringe body (4634) allow the flexible plastic arms (4691) to operate in the elastic region, which ensures an applied radial spring force while minimizing resting stresses and the risk of stress cracking of the glass distal end (4695) of the syringe body (4634) and in the body of the fluid transfer distal anchor (4691).

Figure 133:
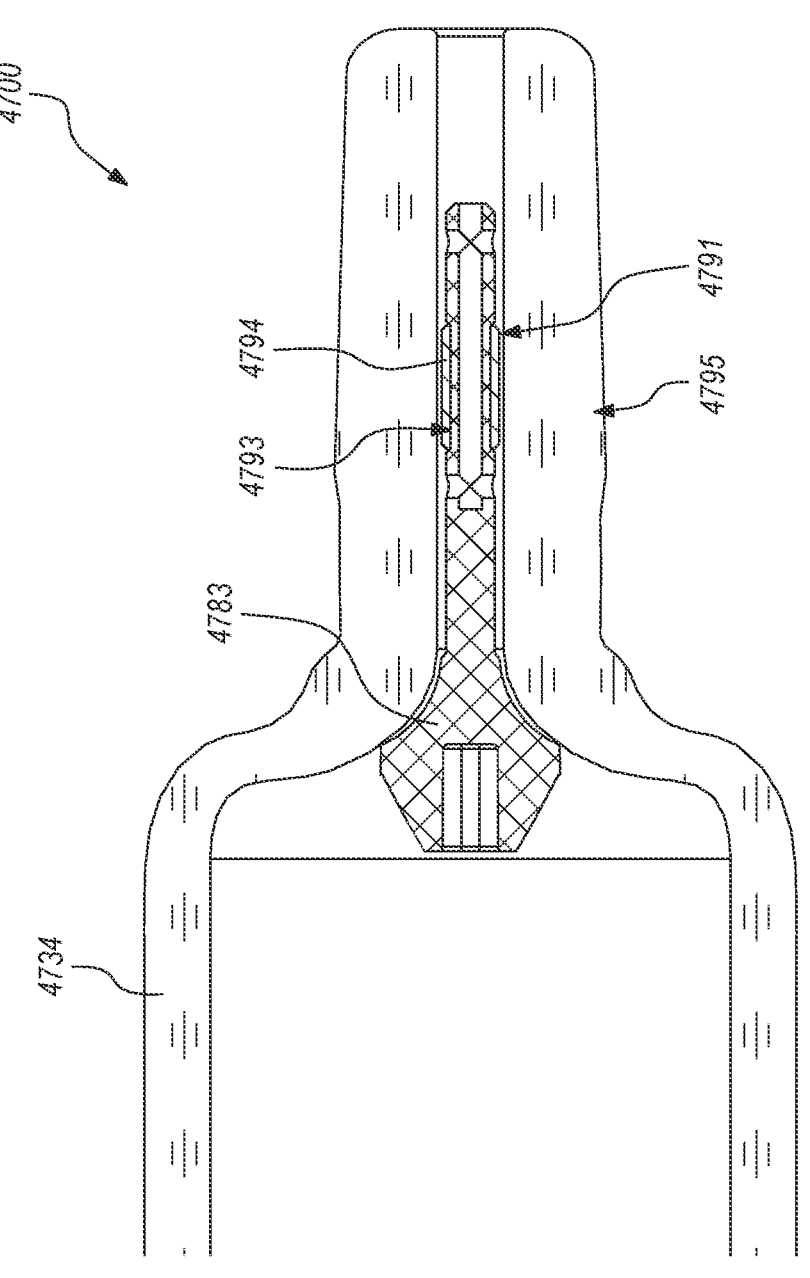
FIG. 133 is a detailed longitudinal cross-sectional view of an injection system including a fluid transfer joining member/portion according to some embodiments.
Figure 134A:
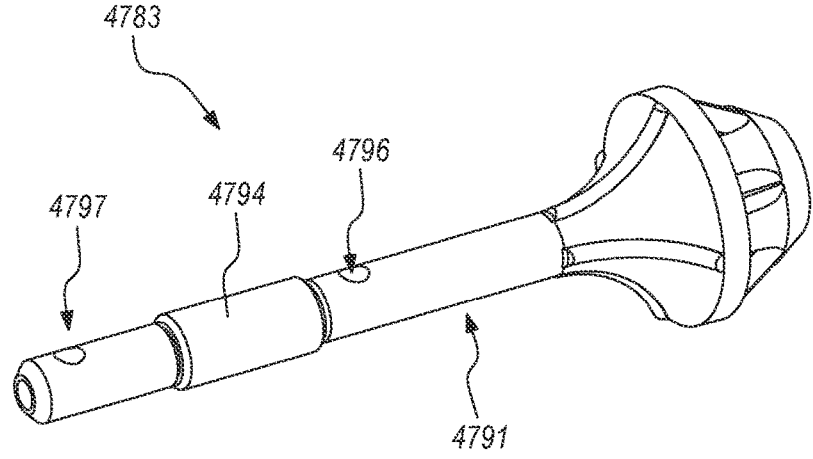
FIGS. 134A, 134B, and 135 are perspective, exploded perspective, and longitudinal cross-sectional views of a fluid transfer joining member/portion according to some embodiments.
Figure 134B:
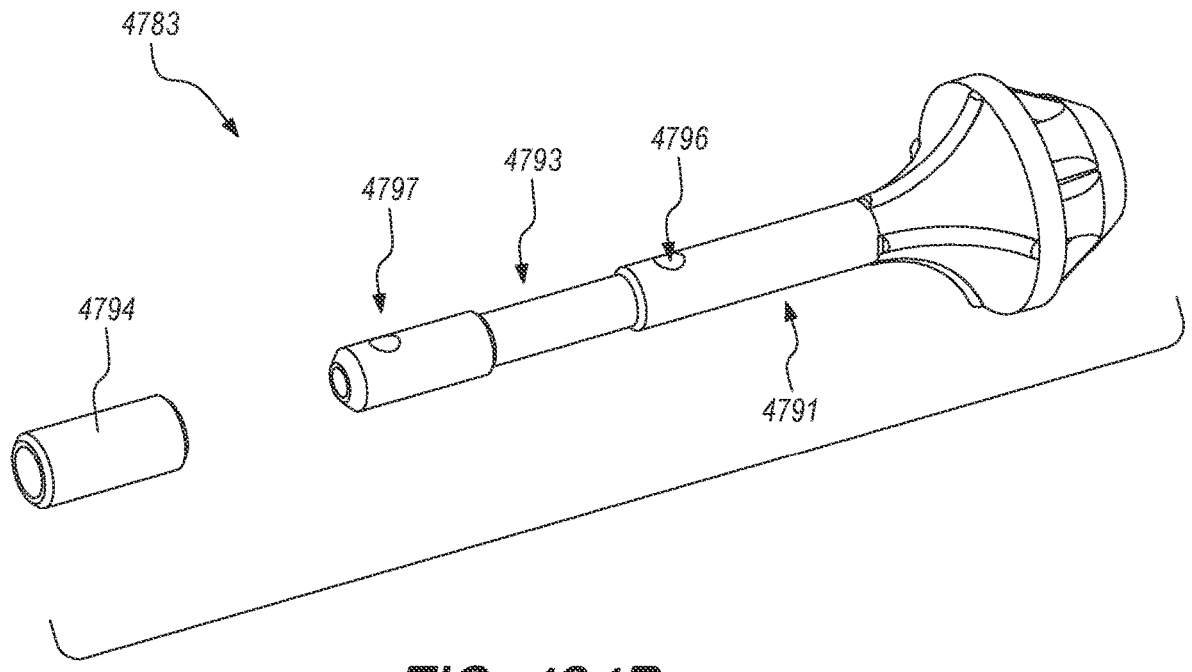
Figure 135:
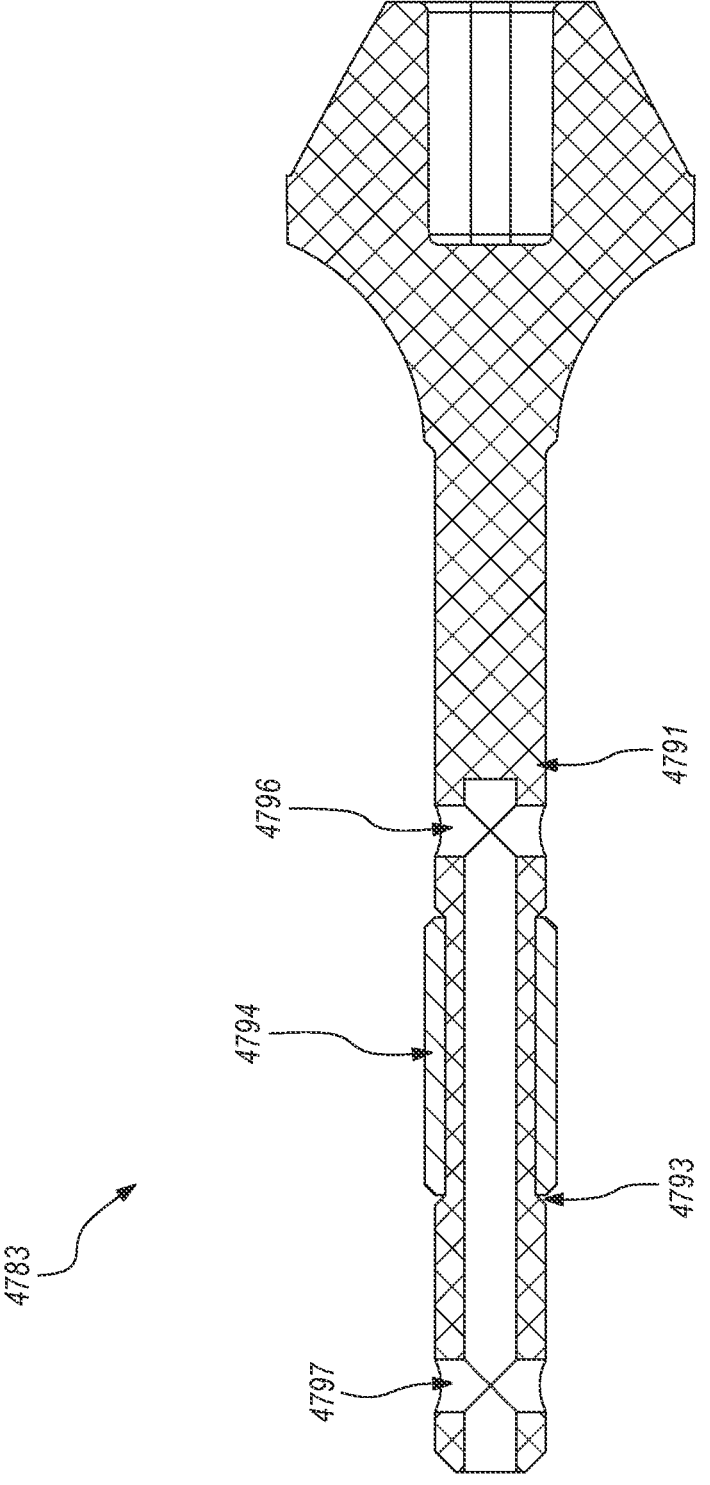

FIGS. 133 to 135 depict an injection system (4700) including a fluid transfer joining member/portion (4783) according to some embodiments. The remainder of the fluid transfer assembly has been omitted for clarity. The fluid transfer joining member/portion (4783) includes a fluid transfer distal anchor (4791) at a distal end thereof.

The fluid transfer distal anchor (4791) includes a recessed portion (4793) and a rubber sleeve (4794) disposed in the recessed portion (4793) and configured to interfere with an inner diameter of the distal end (4795) of the syringe body (4734) (see FIG. 133) to generate an interference fit holding the fluid transfer distal anchor (4791) in the distal end (4795) of the syringe body (4734). The fluid transfer distal anchor (4791) also includes proximal and distal openings (4796, 4797) to bypass the seal generated by the rubber sleeve (4794) and the distal end (4795) of the syringe body (4734) (see FIG. 145).

Exemplary Fluid Transfer Assemblies

Figure 136:
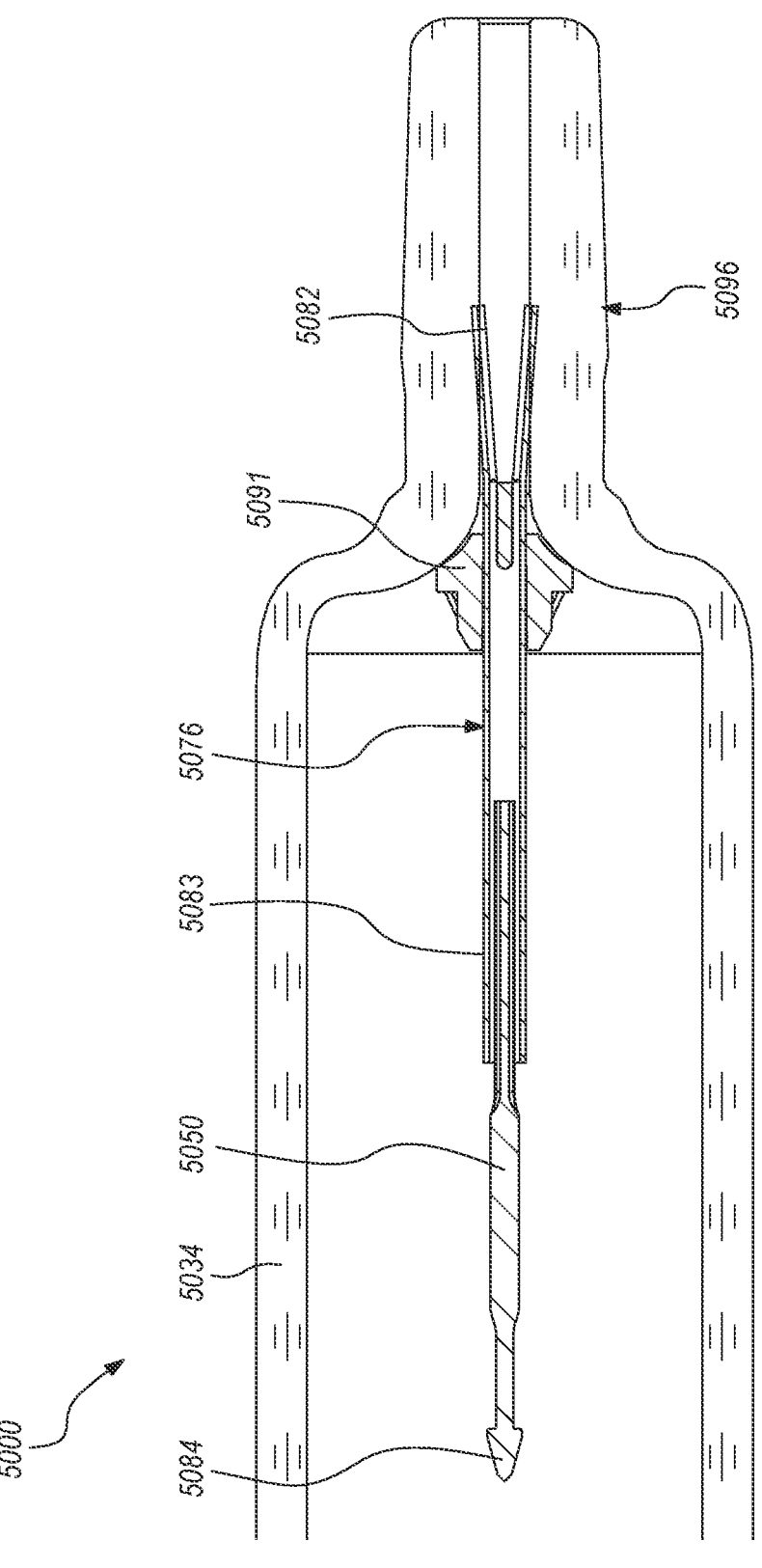
FIG. 136 is a longitudinal cross-sectional view of a fluid transfer assembly installed in a syringe body according to some embodiments.

FIGS. 136 to 140 depict a fluid transfer assembly 5076 according to some embodiments. FIG. 136 is a longitudinal cross-sectional view depicting a fluid transfer assembly 5076 installed in a syringe body 5034 according to some embodiments. The fluid transfer assembly 5076 may be used in a prefilled needleless dual chamber serial injection system according to some embodiments such as the prefilled needleless dual chamber serial injection systems 1800, 2700 depicted in FIGS. 104 to 109 and 113 to 118, respectively. Like the fluid transfer assemblies 1876, 2776, the fluid transfer assembly 5076 is configured for use with a dual chamber serial injection system that does not include a "needle" extending outside of the syringe body 5034. Further, the fluid transfer assembly 5076 is not configured for use with a needle retraction system like one in the dual chamber serial injection system 100 depicted in FIGS. 92 to 94.

The fluid transfer assembly 5076 is configured for use with a conventional off-the-shelf prefilled syringe body 5034 and conventional off-the-shelf proximal and distal stopper members (not shown) disposed therein.

The fluid transfer assembly 5076 of facilitates sequential injection of a first liquid from a distal chamber followed by injection of a second liquid from a proximal chamber in a prefilled needleless dual chamber serial injection system subject to sequential insertion of a plunger assembly relative to the syringe body 5034 to various degrees by a user. The sequential injection system and various system components are similar to those in the prefilled needleless dual chamber serial injection systems 1800, 2700 depicted in FIGS. 104 to 109 and 113 to 118, respectively.

The fluid transfer assembly 5076 is configured for use with connectors (e.g., Luer lock or Luer slip interfaces coupled to needles with sharpened ends or fluid transfer tubes (not shown)). The fluid transfer assembly 5076 includes a fluid transfer proximal member 5050 coupled to a proximal end of a fluid transfer distal anchor 5091.

Figure 137:
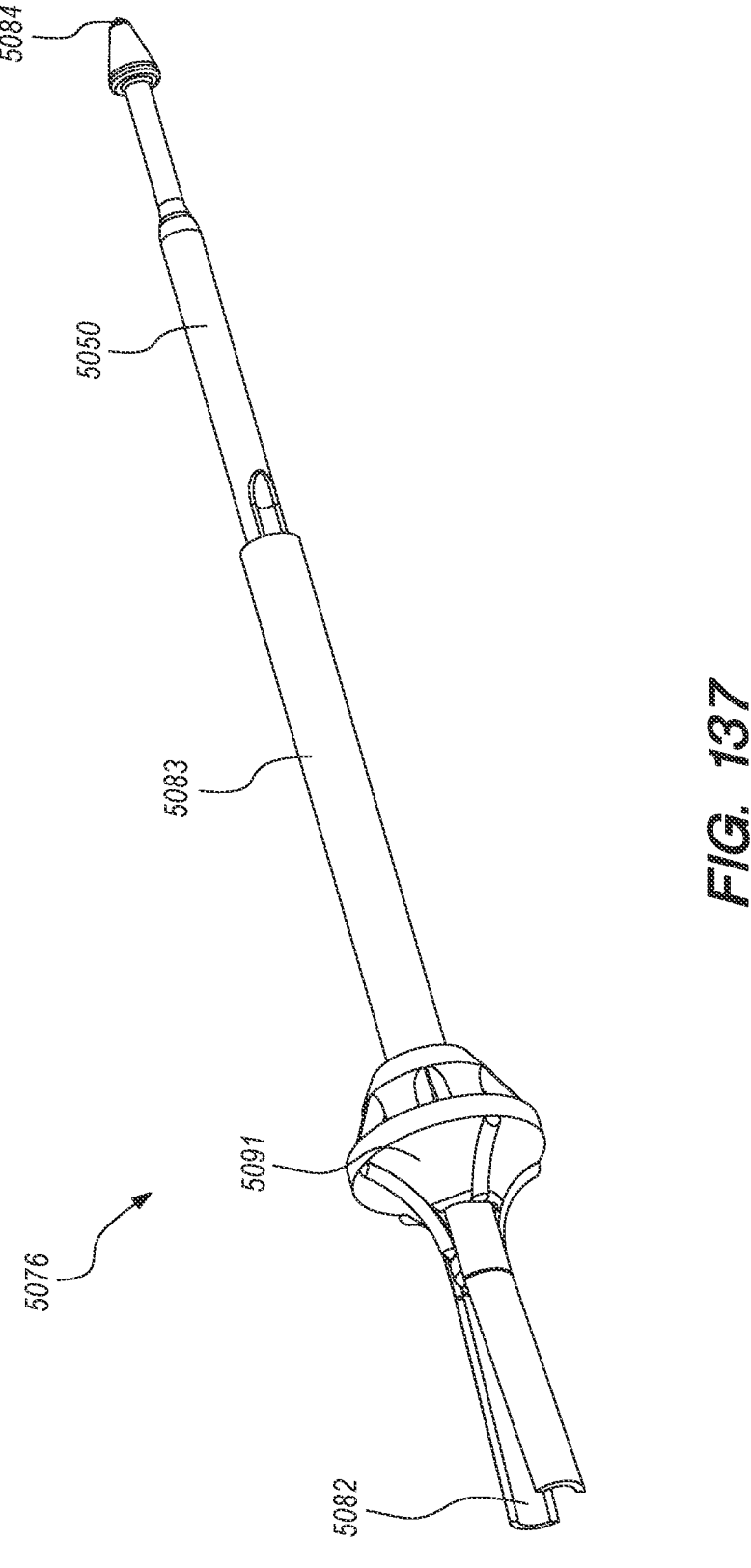
FIGS. 137 and 138 are perspective and longitudinal cross-sectional views of a fluid transfer assembly according to some embodiments.
Figure 138:
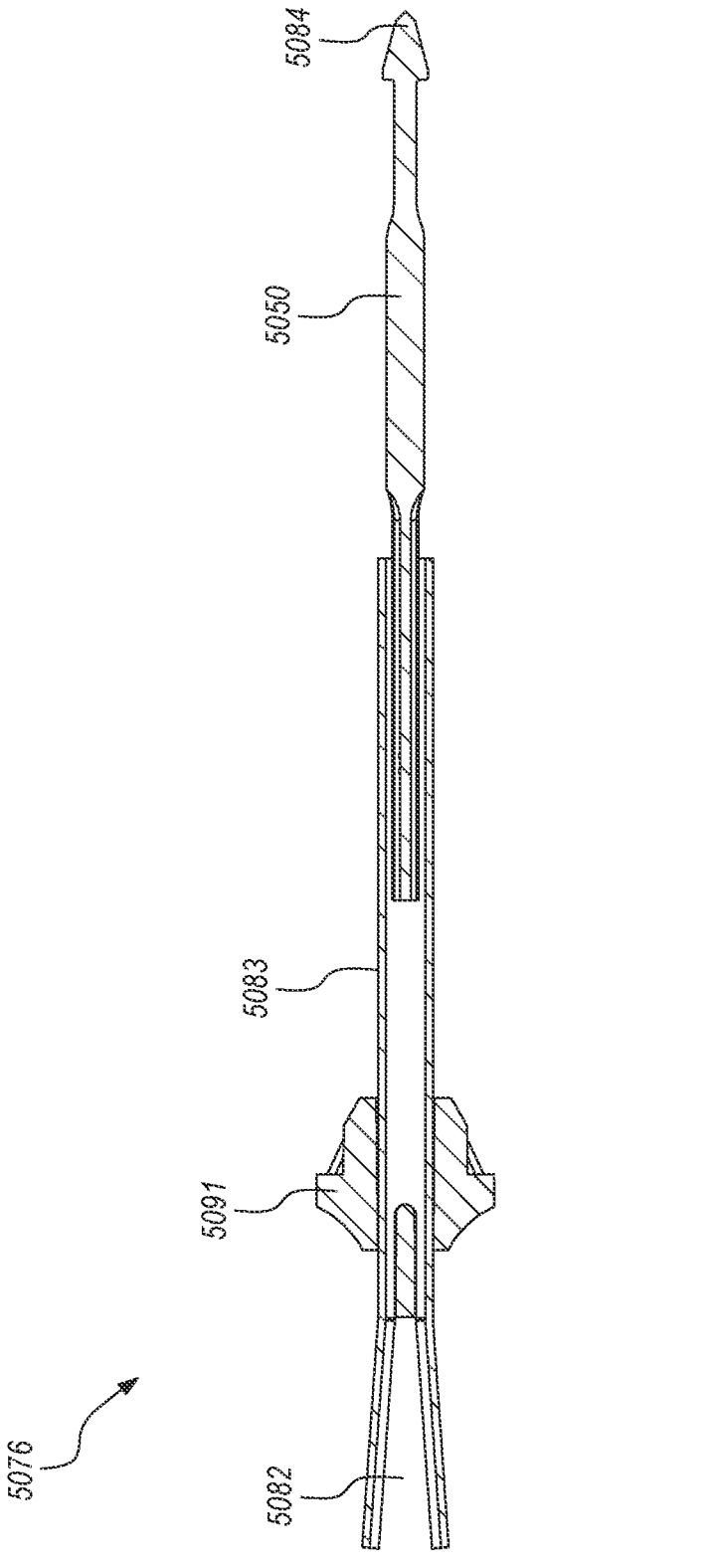

FIGS. 137 and 138 depict a fluid transfer assembly 5076 according to some embodiments. The fluid transfer assembly 5076 includes a fluid transfer proximal member 5050 partially disposed in a proximal end of the fluid transfer joining member 5083, which is in turn partially disposed in a proximal end of a fluid transfer distal anchor 5091. The fluid transfer proximal member 5050 includes a proximal tip 5084 at a proximal end thereof configured to penetrate a distal stopper member during sequential injection. The fluid transfer proximal member 5050 may be a solid metal body, and the fluid transfer joining member 5083 may be a metal tube. The fluid transfer proximal member 5050 may be coupled to the fluid transfer joining member 5083 by welding.

The proximal end of the fluid transfer joining member 5083 is a split tube, which defines two arms 5082 that both couple the fluid transfer joining member 5083 to the fluid transfer distal anchor 5091 and couple the fluid transfer assembly 5076 to the syringe body 5034.

Figures 139A, 139B, 139C:
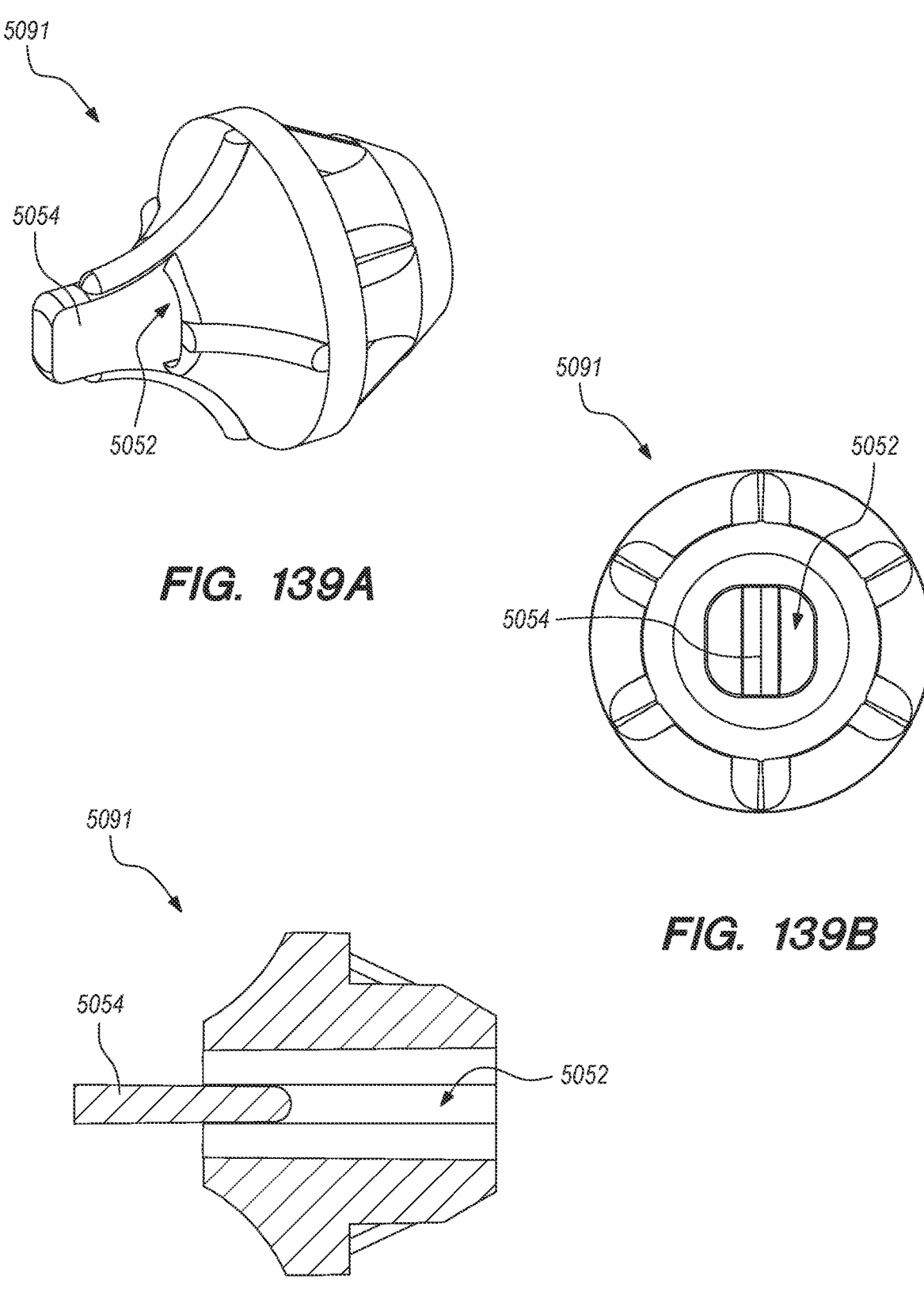
FIGS. 139A to 139C are perspective, axial, and longitudinal cross-sectional views of a fluid transfer proximal member according to some embodiments.
Figure 140:
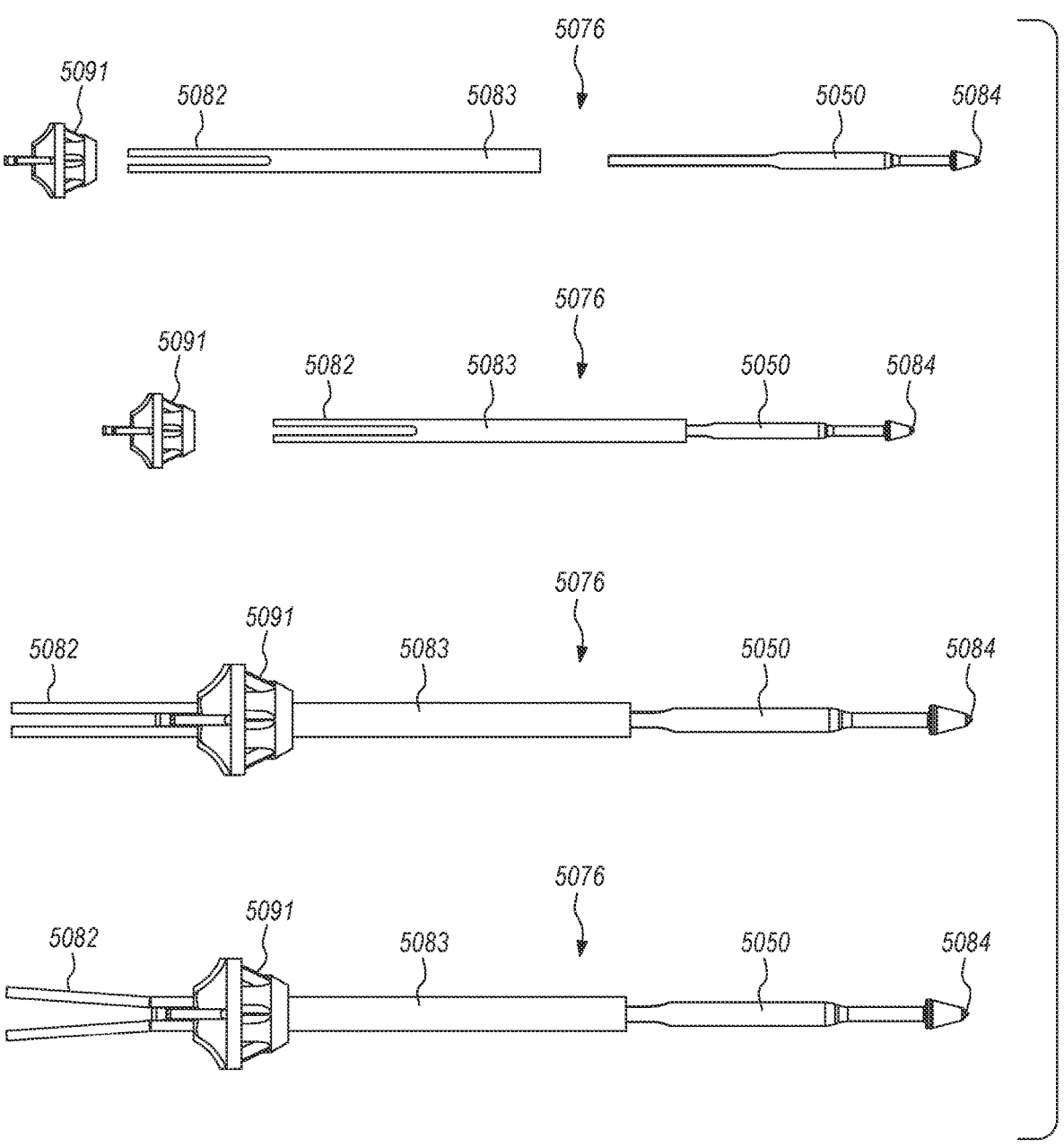
FIG. 140 is a series of side views depicting steps in assembly of a fluid transfer assembly according to some embodiments.

As shown in FIGS. 139A to 139C, the fluid transfer proximal member 5050 includes a longitudinal opening 5052 and a crossbeam 5054 defined partially therein. The longitudinal opening 5052 is configured to receive the two arms 5082 on either side of the crossbeam 5054 during assembly as shown in FIG. 140. After the arms 5082 are inserted past the crossbeam 5054, the arms 5082 are plastically deformed outward to couple the fluid transfer joining member 5083 to the fluid transfer distal anchor 5091 and prevent disassembly of the two components without introducing resting stresses to the fluid transfer distal anchor 5091. The outward plastic deformation of the two arms 5082 mechanically prevents disassembly of the fluid transfer joining member 5083 and the fluid transfer distal anchor 5091, without introducing resting stress on the fluid transfer distal anchor 5091. The outwardly deformed arms 5082 interfere with an inner diameter of a distal end 5096 of the syringe body 5034 (see FIG. 136) to generate an interference fit coupling the fluid transfer assembly 5076 to the distal end 5096 of the syringe body 5034 while minimizing stress on the remainder of the fluid transfer distal anchor 5091, which may be formed from a polymer.

Figure 141:
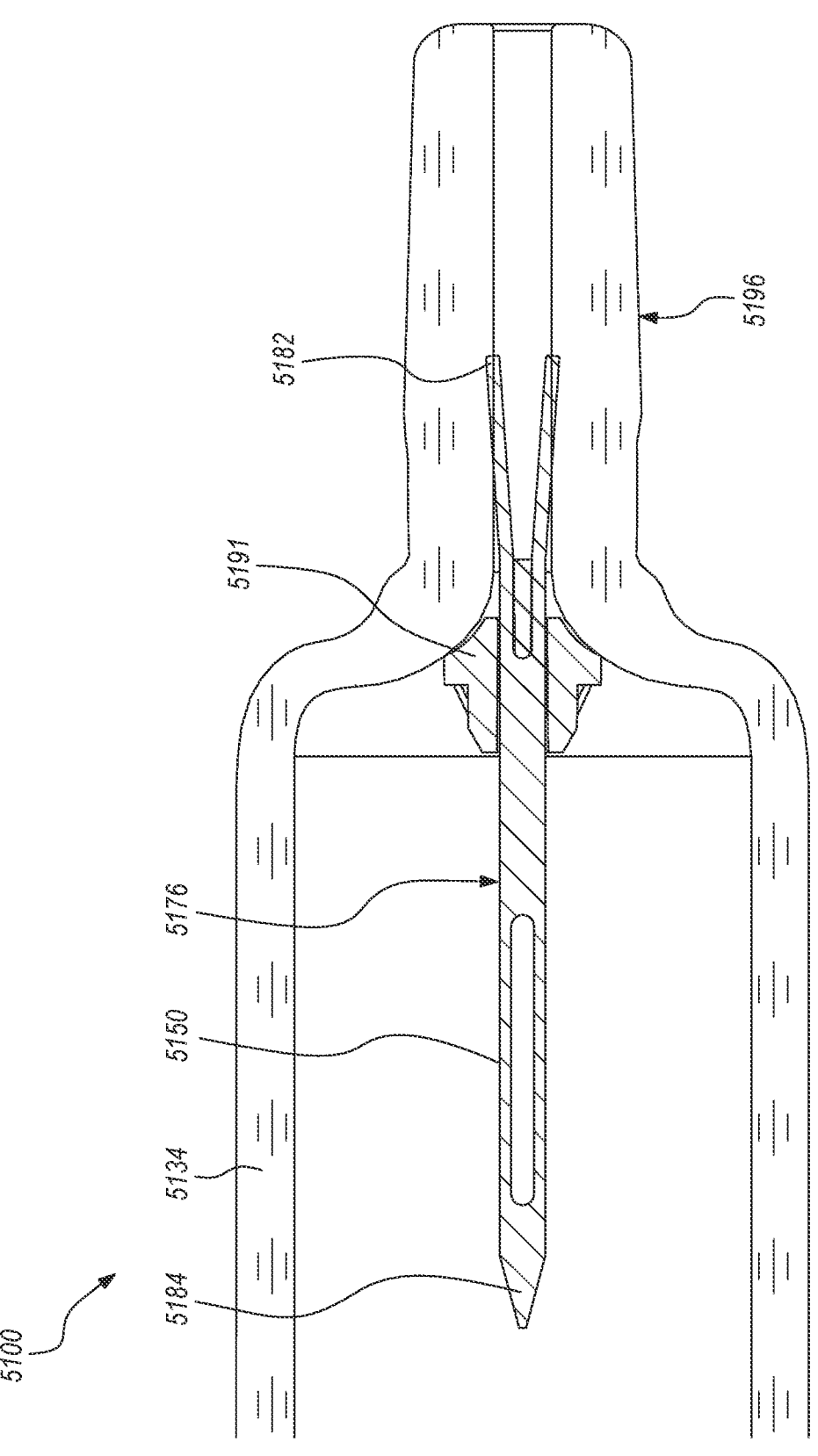
FIG. 141 is a longitudinal cross-sectional view of a fluid transfer assembly installed in a syringe body according to some embodiments.
Figure 142:
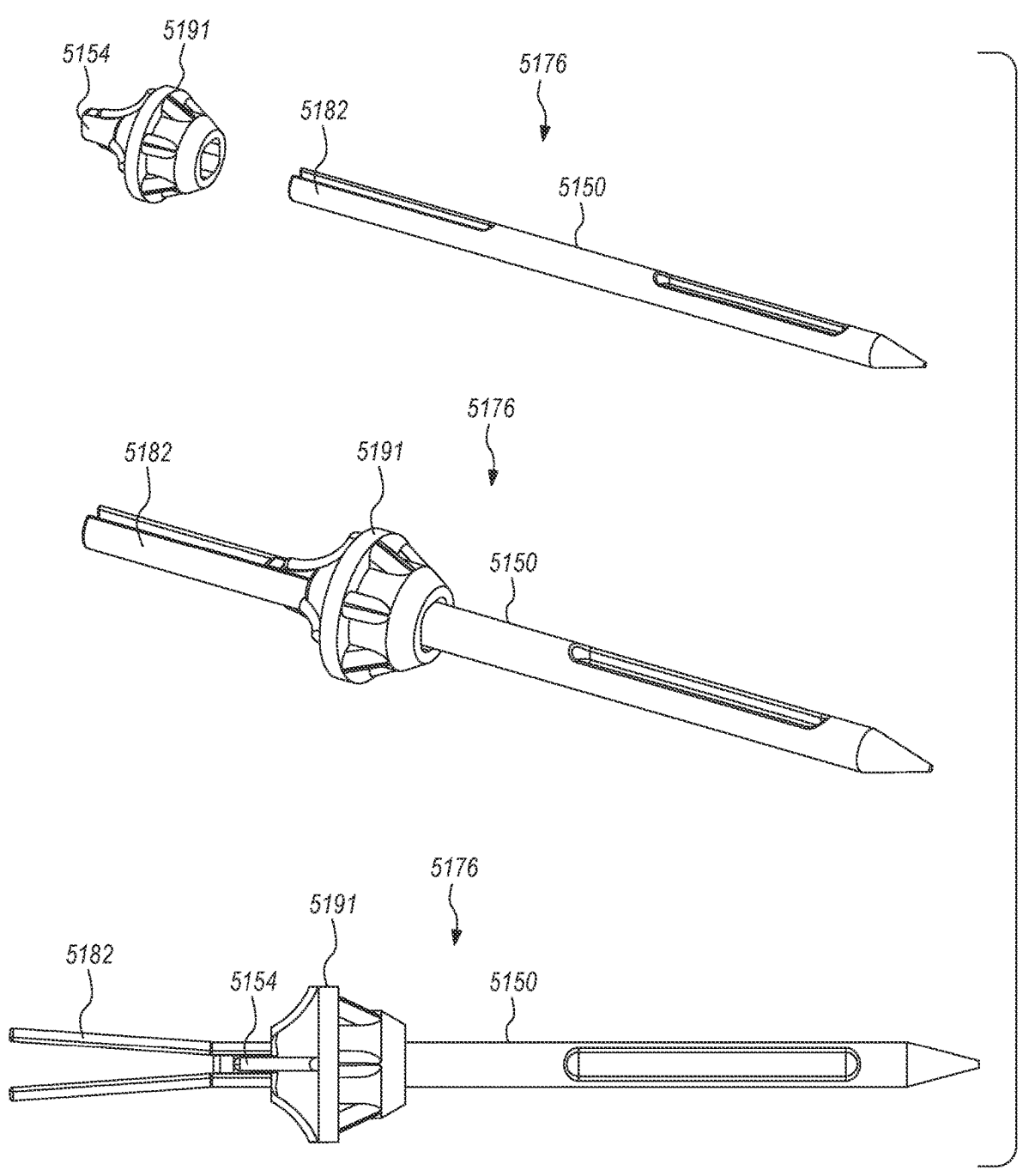
FIG. 142 includes three perspective views depicting steps in assembly of a fluid transfer assembly according to some embodiments.

FIGS. 141 and 142 depict a fluid transfer assembly 5176 according to some embodiments. FIG. 141 is a longitudinal cross-sectional view depicting a fluid transfer assembly 5176 installed in a syringe body 5134 according to some embodiments. The fluid transfer assembly 5176 is similar to the fluid transfer assembly 5076 depicted in FIGS. 136 to 140 in that it is configured for use with a dual chamber serial injection system that does not include a "needle" extending outside of the syringe body 5134 and that it is configured for use with a non-retracting system. The fluid transfer assembly 5176 also includes a fluid transfer proximal member 5150 coupled to a proximal end of a fluid transfer distal anchor 5191. The difference between the fluid transfer assemblies 5076, 5176 depicted in FIGS. 136 and 141 is that the fluid transfer proximal member 5150 extends distally to define a pair of arms 5182 instead of being connected to a tubular member that splits distally.

The fluid transfer distal anchor 5191 depicted in FIG. 141 is identical to the fluid transfer distal anchor 5091 depicted in FIG. 136. During assembly, the arms 5182 are inserted past the crossbeam 5154, the arms 5182 are plastically deformed outward to couple the fluid transfer proximal member 5150 to the fluid transfer distal anchor 5191 and prevent disassembly of the two components without introducing resting stress to the fluid transfer distal anchor 5191. The outwardly deformed arms 5182 also interfere with an inner diameter of a distal end 5196 of the syringe body 5134 (see FIG. 141) to generate an interference fit coupling the fluid transfer assembly 5176 to the distal end 5196 of the syringe body 5134 while minimizing stress on the remainder of the fluid transfer distal anchor 5191, which may be formed from plastic and a polymer.

Exemplary Fluid Transfer Distal Anchors

Figure 143:
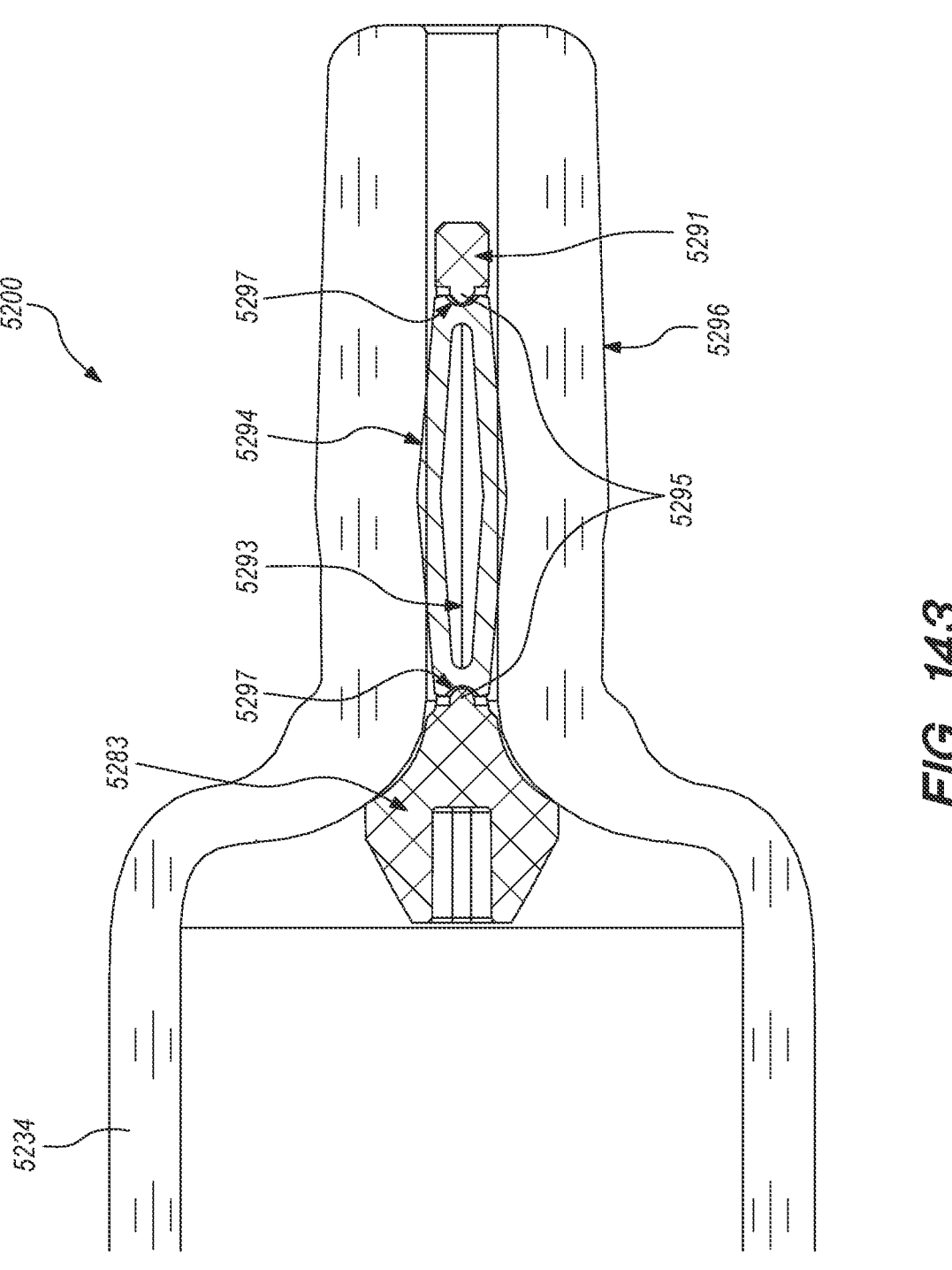
FIG. 143 is a longitudinal cross-sectional view of a fluid transfer joining member/portion installed in a syringe body according to some embodiments.

FIGS. 143 to 145C depict an injection system 5200 including a fluid transfer joining member/portion 5283 according to some embodiments. The remainder of the fluid transfer assembly has been omitted for clarity. As shown in FIGS. 143 and 144A, the fluid transfer joining member/portion 5283 includes a fluid transfer distal anchor 5291 at a distal end thereof.

The fluid transfer distal anchor 5291 defines a slot 5293 and the fluid transfer joining member/portion 5283 includes a rhomboidal biasing member 5294 disposed in the slot 5293. The fluid transfer distal anchor 5291 also defines two bumps 5295 (see FIGS. 143 and 145A to 145C) and the biasing member 5294 defines two notches 5297 configured to receive the two bumps 5295 to retain the biasing member 5294 in the slot 5293 (see FIGS. 143 and 145B to C). The biasing member 5294 (see FIGS. 144B and 145A) is a spring-like, rhomboidal metal loop configured to interfere with an inner diameter of the distal end 5296 of the syringe body 5234 (see FIG. 143) to generate an interference fit holding the fluid transfer distal anchor 5291 in the distal end 5296 of the syringe body 5234 while minimizing stress on the remainder of the fluid transfer distal anchor 5291.

Figure 144A:
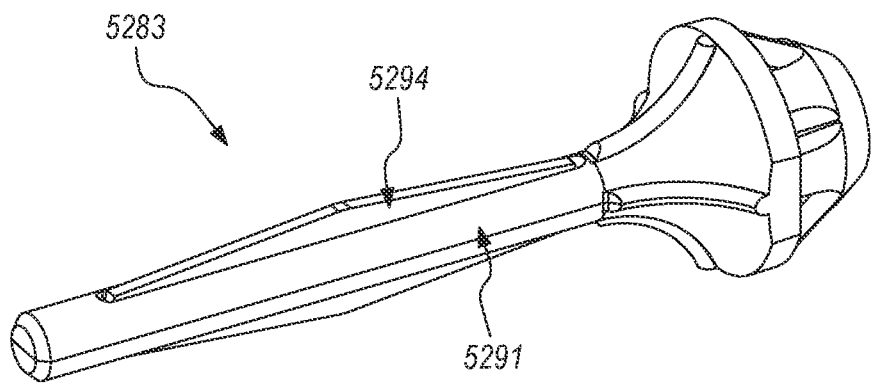
FIGS. 144A to 145C is a series of perspective and longitudinal cross-sectional views depicting steps in assembly of a fluid transfer joining member/portion according to some embodiments.
Figure 144B:
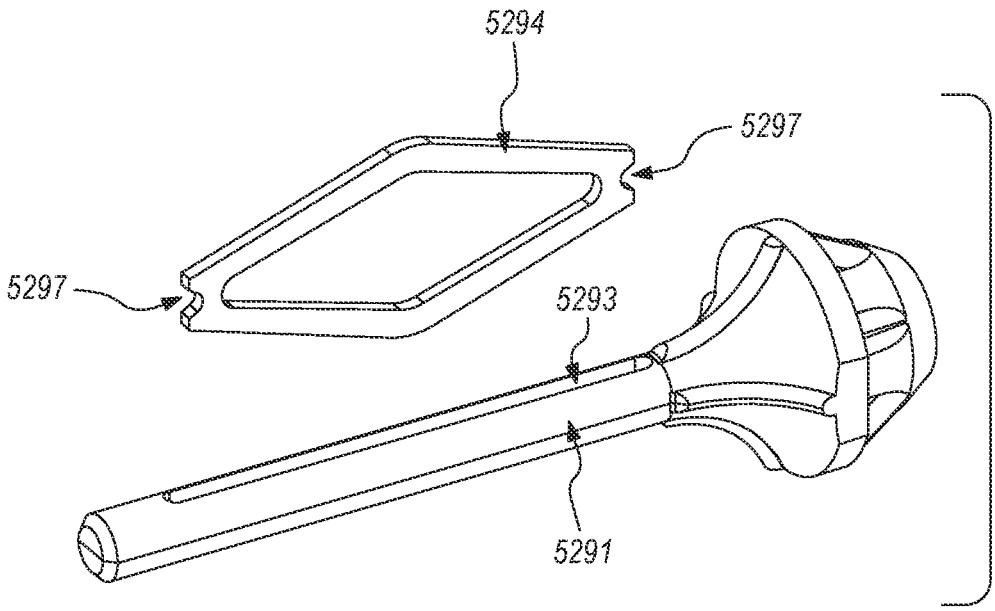
Figure 145A:
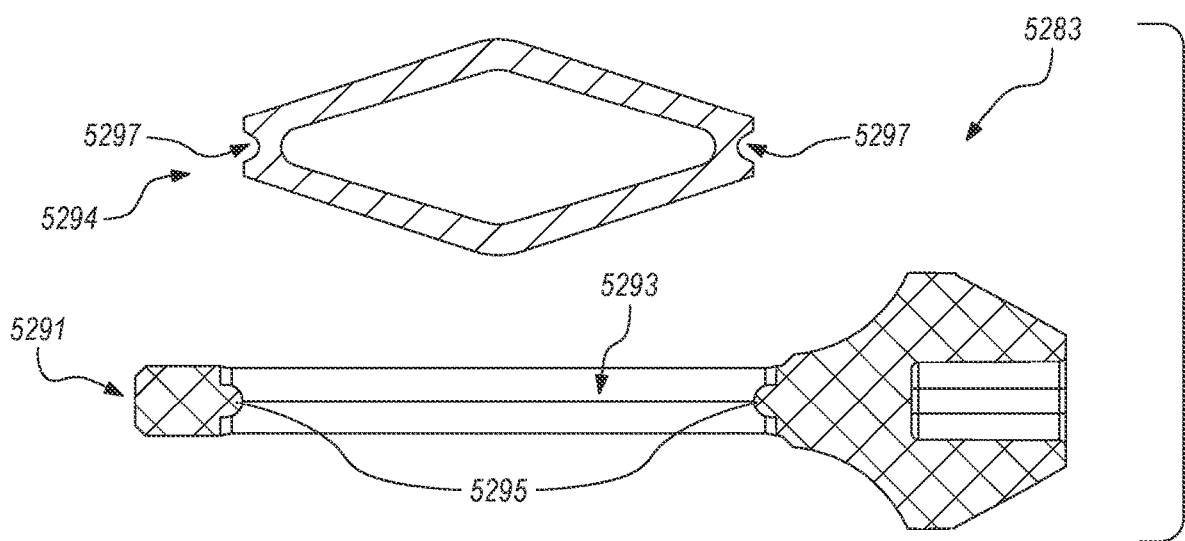
Figure 145B:
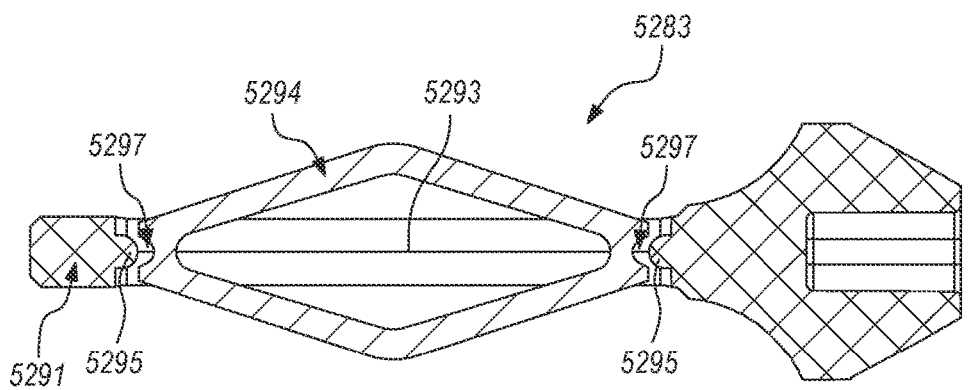

FIGS. 144B and 145A depict the rhomboidal biasing member 5294 before it is installed in the slot 5293 defined by the fluid transfer distal anchor 5291. FIG. 145B shows insertion of the rhomboidal biasing member 5294 into the slot 5293 defined by the fluid transfer distal anchor 5291. In FIG. 145b, the rhomboidal biasing member 5294 is in a "free" state in which it can pass between the two bumps 5295 defined by the fluid transfer distal anchor 5291.

Figure 145C:
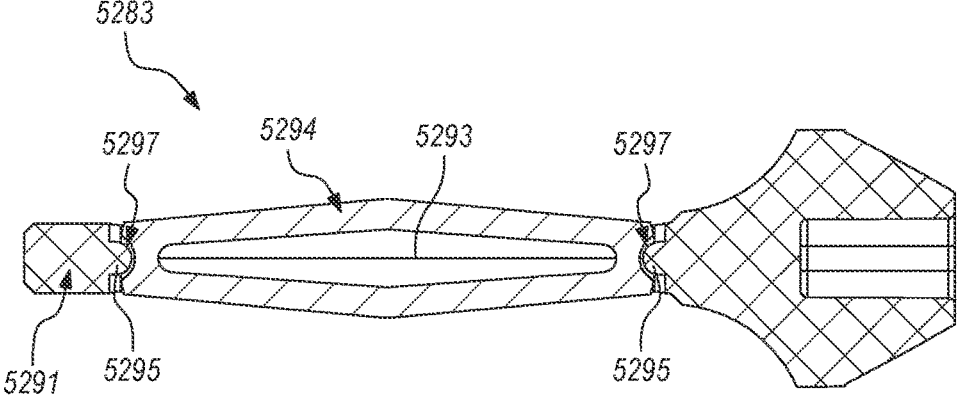
Figure 146:
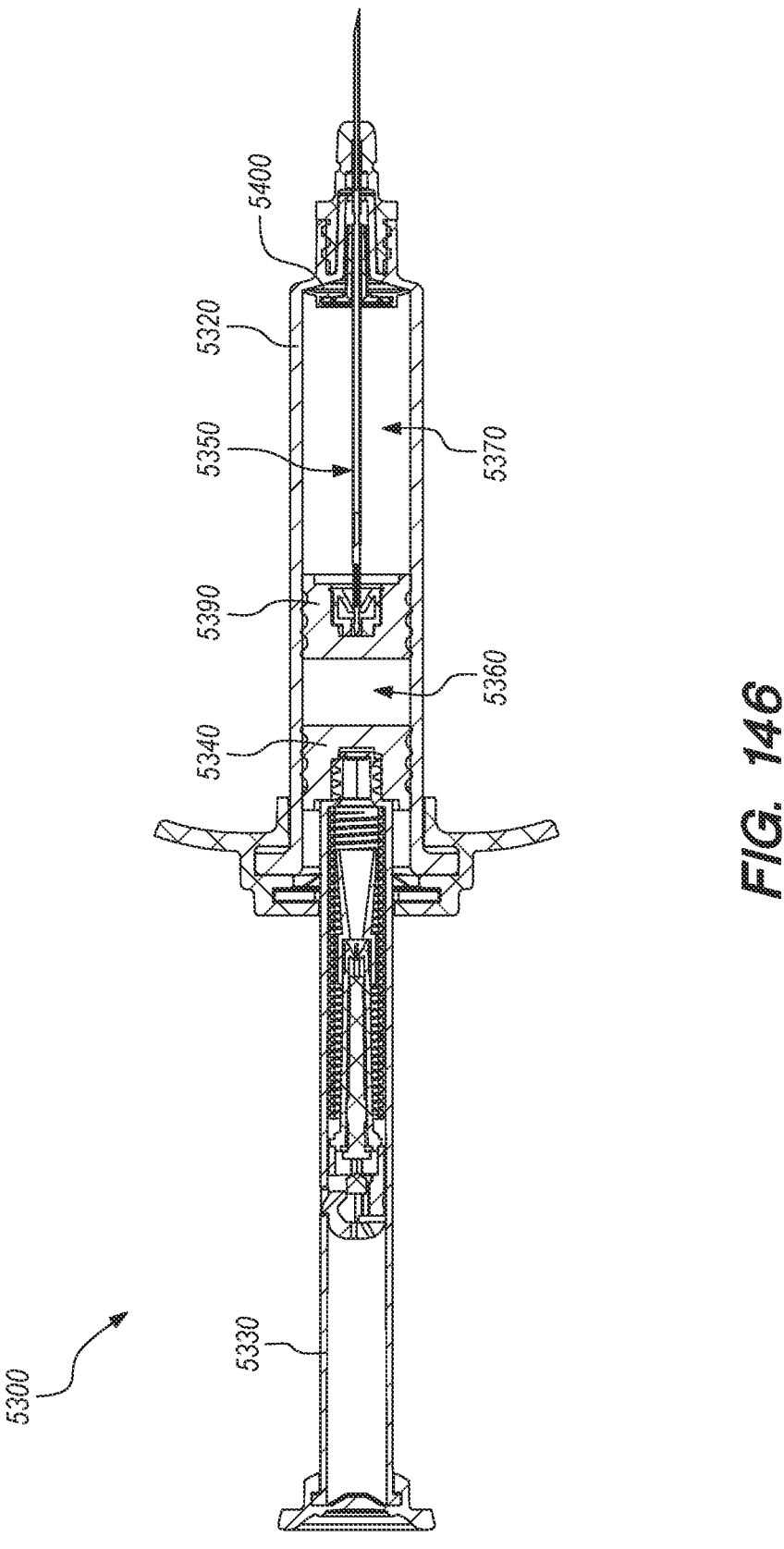
FIGS. 146 and 147 are longitudinal cross-sectional and detailed longitudinal cross-sectional views of a dual chamber safe injection system including a one-way valve according to some embodiments.

In FIG. 145C, after the rhomboidal biasing member 5294 is inserted into the slot 5293 defined by the fluid transfer distal anchor 5291, the rhomboidal biasing member 5294 is squeezed/crimped to plastically deform the rhomboidal biasing member 5294 such that the pair of notches 5297 engage the pair of bumps 5295. Engagement of the notches 5297 with the pair of bumps 5295 mechanically couples the rhomboidal biasing member 5294 to the fluid transfer distal anchor 5291 without introducing any resting stresses to the fluid transfer distal anchor 5291. FIG. 145C shows the fluid transfer joining member/portion 5283 completely assembled as shown in FIG. 144A.

When the fluid transfer joining member/portion 5283 is inserted into the distal end 5296 of the syringe body 5234 (see FIG. 143), the rhomboidal biasing member 5294 interferes with an inner diameter of the distal end 5296 of the syringe body 5234 to generate an interference fit holding the fluid transfer distal anchor 5291 in the distal end 5296 of the syringe body 5234.

X. Exemplary Dual Chamber Injection System

FIGS. 146 to 148C depict a dual chamber safe injection system 5300 having a syringe body 5320 with a one-way valve 5400 disposed in a distal end thereof according to some embodiments. The dual chamber safe injection system 5300 also includes a needle assembly 5350 extending through the one-way valve 5400, and proximal and distal stopper members 5340, 5390 disposed in an interior of the syringe body 5320. The proximal and distal stopper members 5340, 5390 define proximal and distal chambers 5360, 5370 in the interior of the syringe body 5320. The dual chamber safe injection system 5300 also includes a plunger member 5330, which includes a needle retraction system such as those described in U.S. patent application Ser. Nos. 14/696,342, 14/543,787, 14/321,706, 15/801,239, 15/801,259, 15/801,281, 15/801,304, 16/908,531, 17/031,108, and 63/094,313, the contents of which have been previously Incorporated by reference herein. The needle retraction system is mostly disposed in an interior of the plunger member 5330.

In some embodiments, a liquid drug component is disposed in the proximal chamber 5360 and a powder (e.g., lyophilized) drug component is disposed in the distal chamber 5370. The dual chamber safe injection system 5300 is configured such that applying distally directed force to the plunger member 5330 moves the proximal stopper member 5340 distally transferring the liquid drug component from the proximal chamber 5360 to the distal chamber 5370. The dual chamber safe injection system 5300 can then be agitated (e.g., inverted) to mix the liquid and powder drug components to form a mixed liquid drug. Then continued application of distally directed force to the plunger member 5330 moves the proximal and distal stopper members 5340, 5390 distally to eject the mixed liquid drug from the distal chamber 5370 through the needle assembly 5350. After the mix liquid drug is ejected from the distal chamber 5370, the needle retraction system in the plunger member 5330 retracts the needle assembly 5350 at least partially inside of the plunger member 5330 to position the sharp distal end of the needle assembly 5350 inside of the syringe body 5320. Further details about such dual chamber mixed drug injection systems are described in U.S. patent application Ser. Nos. 15/801,259, 16/435,429, 16/798,188, 16/908,531, and 63/046,517, the contents of which have been previously Incorporated by reference herein.

The one-way valve 5400 is depicted in detail in FIGS. 148A to 148C. As shown in FIG. 148C, the one-way valve 5400 includes a rigid (e.g., plastic) proximal portion 5410 with a circular base 5412 defining a pair of side openings 5414 and having a sleeve 5416 extending distally from the center thereof. The sleeve 5416 includes defines a plurality of longitudinal channels 5418 on an outer surface thereof.

Figure 147:
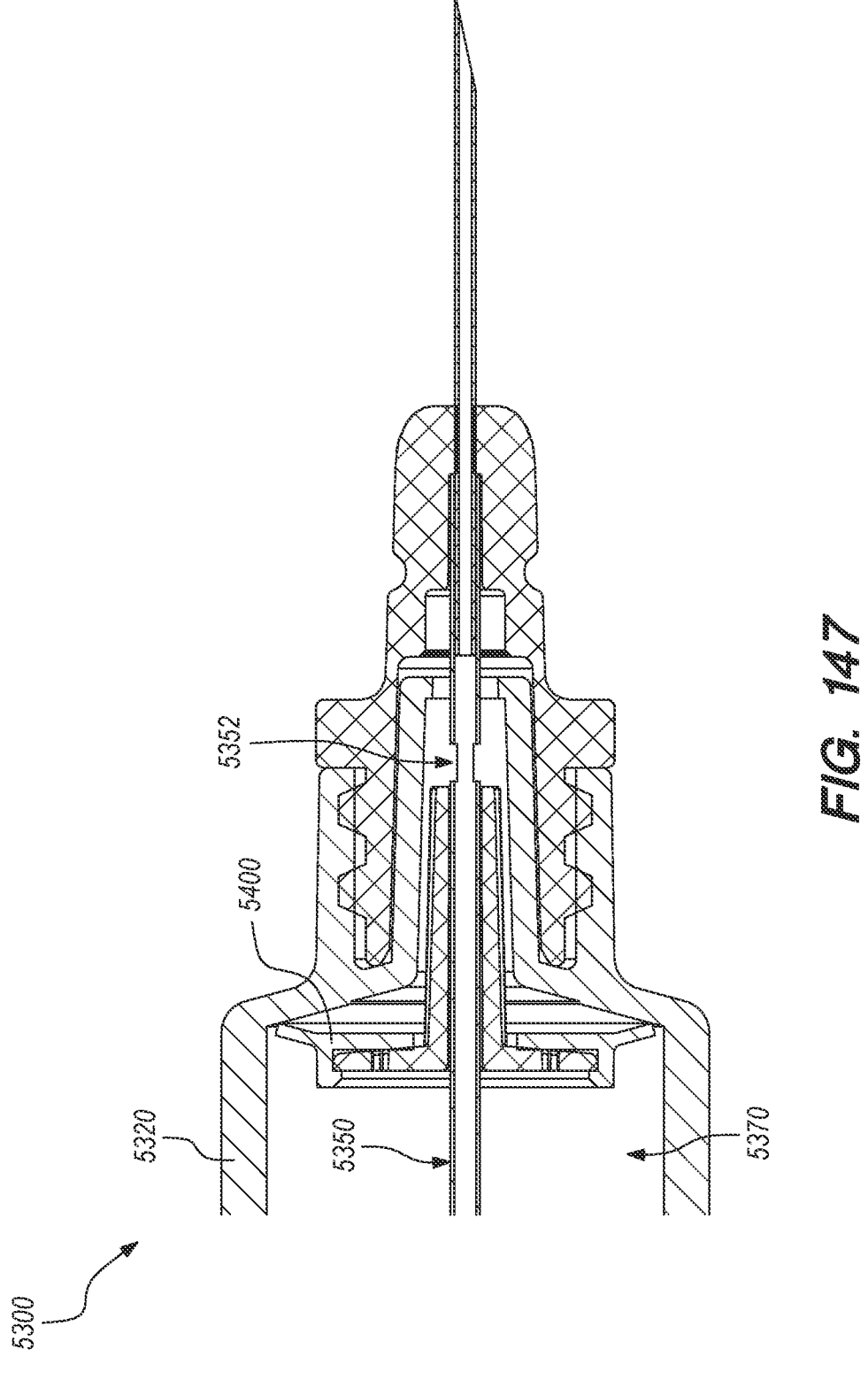

The one-way valve 5400 also includes a compliant/pliable (e.g., rubber) distal portion 5420 with a center opening 5422 configured receive the sleeve 5416. As shown in FIG. 147, the sleeve 5416 has an inner diameter only slightly larger than the outer diameter of the portion of the needle assembly 5350 passing therethrough. This tight tolerance prevents powder drug component from inadvertently passing through the one-way valve 5400 and entering and clogging the needle assembly 5350. The tolerance between the side openings 5414 and the proximal and distal portions 5410, 5420 of the one-way valve 5400 is also tight enough to prevent the powder drug component from passing through. The compliant distal portion 5420 stretches around the circular base 5412 of the rigid proximal portion 5410 fitting snugly and blocking the two side openings 5414, and preventing any powder drug component from passing therethrough. On the other hand, the one-way valve 5400 allows the mixed liquid drug to pass under pressure (described below) through the side openings 5414, between the proximal and distal portions 5410, 5420 of the one-way valve 5400, along the plurality of longitudinal channels 5418 on the sleeve 5416, and into the needle assembly 5350 through a middle opening 5352 (see FIG. 147) and out of the dual chamber safe injection system 5300. Accordingly, the one-way valve 5400 prevents powder drug component from passing therethrough and entering and clogging the needle assembly 5350, while allowing liquids (e.g., mixed liquid drug) to pass (e.g., under pressure exerted by a plunger member) through and exit the dual chamber safe injection system 5300 through the needle assembly 5350.

The proximal and distal portions 5410, 5420 of the one-way valve 5400 in their default assembled state are in contact with one another at the distal face of the circular base 5412, and close off the two side openings 5414, preventing powder drug component from exiting the distal chamber 5370. However, after liquid drug is mixed and ready for injection, distally directed force applied to the plunger member 5330 generates pressure in the distal chamber 5370 in turn, which ejects the mixed liquid drug under pressure. The pressure in the distal chamber causes the compliant distal portion 5420 of the one-way valve 5400 to separate from the rigid proximal portion 5410 of the one-way valve 5400, thereby un-blocking the two side openings 5414 and allowing the mixed liquid drug to transfer through the one-way valve 5400 under pressure, along the plurality of longitudinal channels 5418 on the sleeve 5416, and into the needle assembly 5350 through a middle opening 5352 (see FIG. 147) and out of the dual chamber safe injection system 5300.

While the prefilled dual chamber safety injection systems depicted and described herein include syringes with staked needles, the various configurations/embodiments described herein (e.g., serial injection, detent dual chamber, threaded plunger member, and shielded and vented needle cover) can be used with cartridges an auto injector, and injection systems with Luer connectors, transfer pipes, and no needles such as those described in U.S. Utility patent application Ser. Nos. 15/801,281 and 15/801,259, which were previously incorporated by reference herein.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, ETFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A system for serially injecting liquids, comprising:
a syringe body defining a syringe proximal opening and a distal needle interface at a distal end thereof;
proximal and distal stopper members disposed in the syringe body, forming a proximal chamber between the proximal and distal stopper members and a distal chamber between the distal stopper member and the distal end of the syringe body;
a first liquid in the distal chamber;
a second liquid in the proximal chamber;
a plunger configured to be manually manipulated to insert the proximal stopper member distally relative to the syringe body; and
a needle hub assembly coupled to the distal needle interface of the syringe body, the needle assembly including a needle,
wherein the needle defines a needle interior, a distal end opening, a middle opening, and a proximal channel,
wherein the distal end opening and the middle opening are fluidly coupled through the needle interior,
wherein manipulating the plunger member to insert the proximal stopper member distally relative to the syringe body initially expels the first liquid from the distal chamber through the needle, then serially expels the second liquid from the proximal chamber through the needle,
wherein the needle comprises
a distal portion having a sharp distal tip defining the distal end opening,
a tubular middle connecting member having middle connecting member proximal and distal ends and defining a portion of the needle interior, and
a solid and monolithic proximal end feature having a proximal end feature distal end coupled to the middle connecting member proximal end and defining the middle opening with the middle connecting member proximal end,
wherein the proximal end feature distal end of the solid and monolithic proximal end feature has a crescent or dumbbell shaped cross-section,
wherein the tubular middle connecting member has a continuous external surface with no side openings along its entire length, and
wherein a distal end of the solid and monolithic proximal end feature is disposed in an open proximal end of the tubular middle connecting member.

2. The system of claim 1, wherein the solid and monolithic proximal end feature is coupled to the tubular member with a weld.

3. The system of claim 2, wherein the weld is a fillet weld configured to reduce cutting of the proximal stopper member when the needle penetrates the proximal stopper member compared to a needle without a fillet weld.

4. The system of claim 2, wherein the weld tapers in a proximal direction.

5. The system of claim 2, wherein the middle opening is adjacent to the weld.

6. The system of claim 1, wherein the solid and monolithic proximal end feature is cold formed.

7. The system of claim 1, wherein a distal end of the solid and monolithic proximal end feature is disposed in a proximal end of the tubular member.

8. The system of claim 1, wherein the middle opening has a rounded edge configured to reduce cutting of the proximal stopper member when the needle penetrates the proximal stopper member compared to a needle without a rounded edge.

9. The system of claim 1, wherein the middle opening is an elongated slot.

10. The system of claim 9, wherein a length of the elongated slot provides a tolerance for a variability relating to the proximal and distal stopper members.

11. The system of claim 10, wherein the variability relating to the proximal and distal stopper members is selected from a group consisting of distortion of a proximal surface of the distal stopper member, a position of the proximal stopper member relative to the elongated slot, and a position of the distal stopper member relative to the elongated slot.

12. The system of claim 10, wherein the length of the elongated slot is between about ⅟₃₂ inch to about ⅟₁₆ inch.

13. The system of claim 9, wherein a distance between the elongated slot and the solid and monolithic proximal end feature minimizes retrograde leaking of the first and second liquids into the plunger.

14. The system of claim 9, wherein the elongated slot is formed using a grinding wheel.

15. The system of claim 1, wherein first and second sizes of the respective distal and proximal chambers can be modified by movement of the proximal and distal stopper members relative to the syringe body.

16. The system of claim 1, wherein the plunger member comprises:

a needle retention feature disposed in the plunger interior;

an energy-storage member disposed in the plunger interior; and an energy-storage member latching member disposed in the plunger interior, wherein the needle hub assembly comprises:

a hub; and a needle holding member configured to couple the needle to the hub wherein the needle is at least partially retractable into plunger interior upon manipulation of the plunger member relative to the syringe body to transform the energy-storage member latching member from a latched state to an unlatched state.

17. The system of claim 16, wherein the needle is configured to pierce entirely through at least the distal stopper member to be retracted at least partially into the plunger interior.

18. The system of claim 16, wherein the energy-storage member latching member is configured to transform from the latched state to the unlatched state at least partially retracting the needle into plunger interior after the second liquid has been expelled from the proximal chamber through the needle.

19. The system of claim 16, wherein the needle retention feature is configured to actuate transformation of the energy-storage member latching member from the latched state to the unlatched state upon manipulation of the plunger member to insert the proximal stopper member to the distal end of the syringe body.

20. The system of claim 1, the proximal and distal stopper members comprising respective first and second polymer coatings on respective distal and proximal surfaces thereof, such that the proximal chamber is defined by the syringe body and the first and second polymer coatings.

21. The system of claim 1, the distal stopper member having a funnel that tapers in a proximal direction, and a space disposed at a tapered proximal end of the funnel.

22. The system of claim 1, wherein the middle opening is adjacent the distal end of the syringe body.

* * * * *